Figure 1A:
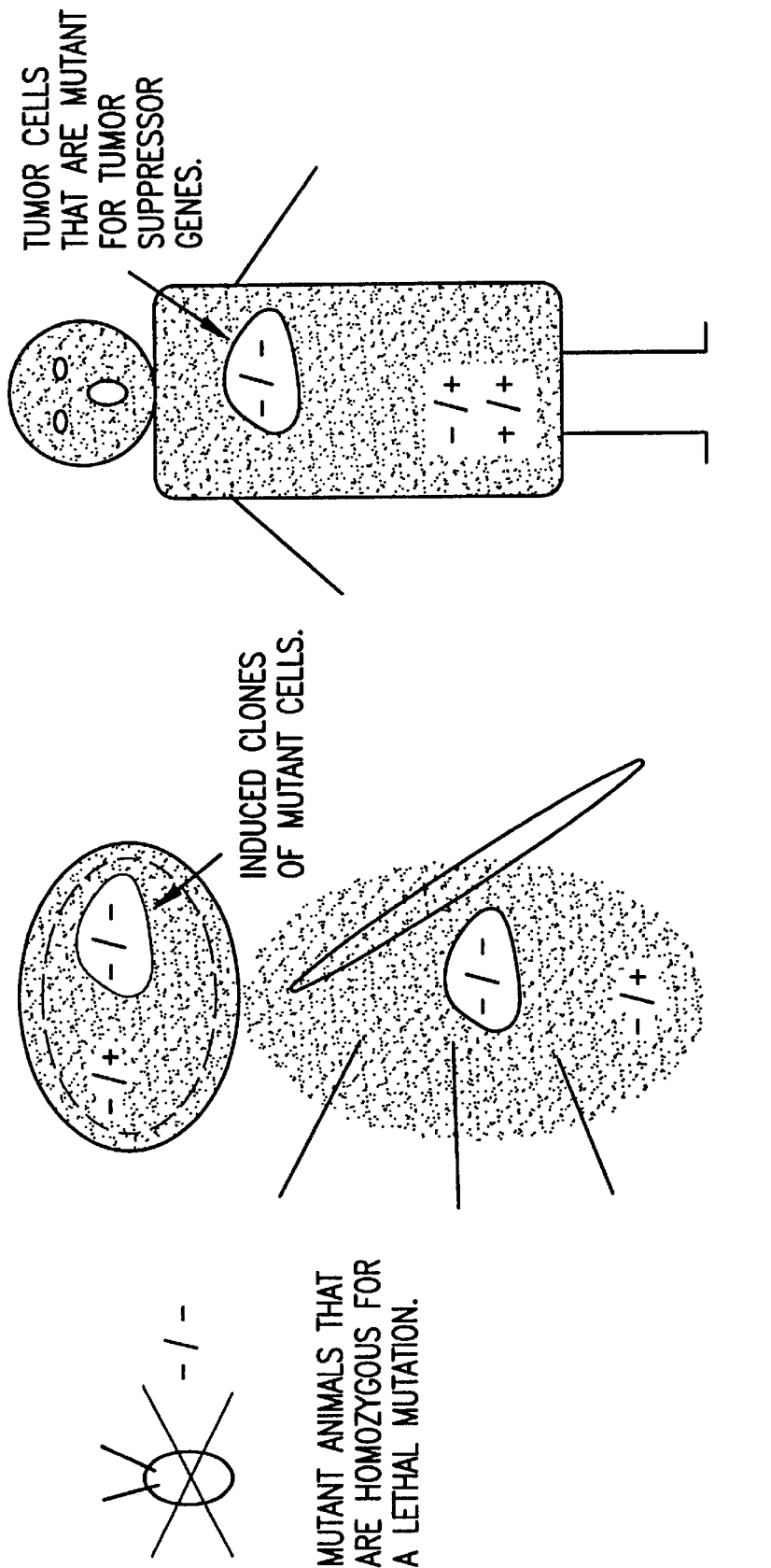

United States Patent [19]
Xu et al.

[11] Patent Number: 5,994,503
[45] Date of Patent: *Nov. 30, 1999

[54] NUCLEOTIDE AND PROTEIN SEQUENCES OF LATS GENES AND METHODS BASED THEREON

[75] Inventors: Tian Xu, Guilford; Wufan Tao, Branford; Weiyi Wang; Sheng Zhang, both of New Haven; Wan Yu, Guilford, all of Conn.

[73] Assignee: Yale University, New Haven, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/411,111

[22] Filed: Mar. 27, 1995

[51] Int. Cl.$^6$ .................. C07K 14/435; C07K 14/46; C07K 7/08; G01N 33/53

[52] U.S. Cl. .................. 530/350; 530/300; 530/324; 530/325; 530/326; 435/7.1; 435/194; 435/925; 424/185

[58] Field of Search .................. 530/350, 300, 530/324–326; 514/2; 435/69.1, 69.2, 69.7, 194, 7.1, 925; 930/10; 424/185

[56] References Cited

PUBLICATIONS

Bier et al., 1989, "Searching for pattern and mutation in the Drosophila genome with a P–lacZ vector," Genes Dev. 3:1273–1287.

Bishop, 1991, "Molecular themes in oncogenesis," Cell 64:235–248.

Boedigheimer et al., 1993, "Expanded, a negative regulator of cell proliferation in Drosophila, shows homology to the NF2 tumor suppressor," Mechan. Dev. 44:83–84.

Boedigheimer and Laughton, 1993, "Expanded: a gene involved in the control of cell proliferation in imaginal discs," Development 118:1291–1301.

Brook et al., 1992, "Molecular basis of myotonic dystrophy: expansion of a trinucleotide (CTG) repeat at the 3' end of a transcript encoding a protein kinase family member," Cell 68:799–808.

Bryant, 1987, "Experimental and genetic analysis of growth and cell proliferation in Drosophila imaginal discs," in *Genetic Regulation of Development*, A.R. Liss, NY, pp. 339–372.

Bryant, 1993, "Towards the cellular functions of tumor suppressors," Trends Cell. Biol. 3:31–35.

Capecchi, 1989, "Altering the genome by homologous recombination," Science 244:1288–1292.

Fearon and Vogelstein, 1990, "A genetic model for colorectal tumorigenesis," Cell 61:759–767.

Featherstone and Russell, 1991, "Fission yeast p107$^{wee1}$ mitotic inhibitor is a tyrosine/serine kinase," Nature 349:808–811.

Fiering et al., 1993, "An "in–out" strategy using gene targeting and FLP recombinase for the functional dissection of complex DNA regulatory elements: analysis of the β–globin locus control region," Proc. Natl. Acad. Sci. USA 90:8469–8473.

Fortini et al., 1991, "The Drosophila zfh–1 and zfh–2 genes encode novel proteins containing both zinc–finger and homeodomain motifs," Mechan. Dev. 34:113–122.

Fu et al., 1993, "Decreased expression of myotonin–protein kinase messenger RNA and protein in adult form of myotonic dystrophy," Science 260:235–238.

Galsworthy, 1966, "Biochemical aspects of temperature sensitivity in neurospora," Diss. Abstr. 26:6348.

Gateff, 1978, "Malignant neoplasms of genetic origin in *Drosophila melanogaster*," Science 200:1448–1459.

Gateff and Mechler, 1989, "Tumor–suppressor genes of *Drosophila melanogaster*," CRC Crit. Rev. Oncogen 1:221–245.

Golic, 1991, "Site–specific recombination between homologous chromosomes in Drosophila," Science 252:958–961.

Golic and Lindquist, 1989, "The FLP recombinase of yeast catalyzes site–specific recombination in the Drosophila genome," Cell 59:499–509.

Hanks et al., 1988, "The protein kinase family: conserved features and deduced phylogeny of the catalytic domains," Science 241:42–52.

Hartl et al., 1994, "Genome structure and evolution in Drosophila: applications of the framework P1 map," Proc. Natl. Acad. Sci. USA 91:6824–6829.

Jacob et al., 1987, "Structure of the l(2)gl gene of Drosophila and delimitation of its tumor suppressor domain," Cell 50:215–225.

Johnston and Thomas, 1982, "The isolation of new DNA synthesis mutants in the beast *Saccharomyces cerevisiae*," Mol. Gen. Genet. 186:439–444.

(List continued on next page.)

*Primary Examiner*—Mary E. Mosher
*Attorney, Agent, or Firm*—Pennie & Edmonds LLP

[57] ABSTRACT

The present invention relates to a tumor suppressor gene, termed large tumor suppressor (lats), and methods for identifying tumor suppressor genes. The method provides nucleotide sequences of lats genes, and amino acid sequences of their encoded proteins, as well as derivatives (e.g., fragments) and analogs thereof. In a specific embodiment, the lats protein is a human protein. The invention further relates to fragments (and derivatives and analogs thereof) of lats which comprise one or more domains of a lats protein. Antibodies to lats, its derivatives and analogs, are additionally provided. Methods of production of the lats proteins, derivatives and analogs, e.g., by recombinant means, are also provided. Therapeutic and diagnostic methods and pharmaceutical compositions are provided. The invention also relates to recombinant plants and animals and methods of increasing the growth of edible plants and animals. In specific examples, isolated lats genes, from Drosophila, mouse, and human, and the sequences thereof, are provided.

67 Claims, 43 Drawing Sheets

PUBLICATIONS

Johnston et al., 1990, "The product of the *Saccharomyces cerevisiae* cell cycle gene DBF2 has homology with protein kinases and is periodically expressed in the cell cycle," Mol. Cell. Biol. 10(4):1358–1366.

Karpen and Spradling, 1992, "Analysis of subtelomeric heterochromatin in the Drosophila minichromosome Dp1187 by single P element insertional mutagenesis," Genetics 132:737–753.

Knudson, 1971, "Mutation and cancer: statistical study of retinoblastoma," Proc. Natl. Acad. Sci. USA 68(4):820–823.

Lai et al., 1993, "Loss of function of the Drosophila zfh–1 gene results in abnormal development of mesodermally derived tissues," Proc. Natl. Acad. Sci. USA 90:4122–4126.

Lützelschwab et al., 1987, "A protein product of the Drosophila recessive tumor gene, l(2) giant gl, potentially has cell adhesion properties," EMBO J. 6(6):1791–1797.

Mahadevan et al., 1993, "Structure and genomic sequence of the myotonic dystrophy (DM kinase) gene," Hum. Mol. Genet. 2(3):299–304.

Mahoney et al., 1991, "The fat tumor suppressor gene in Drosophila encodes a novel member of the cadherin gene superfamily," Cell 67:853–868.

Mansfield et al., 1994, "Genetic and molecular analysis of hyperplastic discs, a gene whose product is required for regulation of cell proliferation in *Drosophila melanogaster* imaginal discs and germ cells," Dev. Biol. 165:507–526.

Mitchell and Mitchell, 1954, "A partial map of linkage group D in neurospora crassa," Proc. Natl. Acad. Sci. USA 40:436–440.

Ponder, 1990, "Inherited predisposition to cancer," Trends Genet. 6(7):213–218.

Ren et al., 1993, "Identification of a ten–amino acid proline–rich SH3 binding site," Science 259:1157–1161.

Robertson et al., 1988, "A stable genomic source of P element transposase in *Drosophila melanogaster*," Genetics 118:461–470.

Rooke et al., 1994, "Molecular and genetic characterization of a novel gene which plays an essential role during bristle and photoreceptor development," EMBL Intl. Conf. on Drosophila Development, Crete, Greece, Jun. 19–25, 1994.

Russell and Nurse, 1987, "Negative regulation of mitosis by wee1$^+$, a gene encoding a protein kinase homolog," Cell 49:559–567.

Sanger et al., 1977, "DNA sequencing with chain–terminating inhibitors," Proc. Natl. Acad. Sci. USA 74(12):5463–5467.

Sauer and Henderson, 1988, "Site–specific DNA recombination in mammalian cells by the Cre recombinase of bacteriophage P1," Proc. Natl. Acad. Sci. USA 85:5166–5170.

Shortridge et al., 1991, "A Drosophila phospholipase C gene that is expressed in the central nervous system," J. Biol. Chem. 266(19):12474–12480.

Stewart and Denell, 1993, "Mutations in the Drosophila gene encoding ribosomal protein S6 cause tissue overgrowth," Mol. Cell. Biol. 13:2524–2535.

Tao et al., 1994, "Facilitating genetic analysis in mammalian systems using the FLP/FRT recombination system," EMBL Intl. Conf. on Drosophila Development, Crete, Greece, Jun. 19–25, 1994.

Thummel and Pirrotta, 1992, "New pCaSpeR P element vectors," Dros. Inf. Svc. 71:150.

Tomlinson and Ready, 1987, "Cell fate in the Drosophila ommatidium," Dev. Biol. 123:264–275.

Török et al., 1993, "P–lacW insertional mutagenesis on the second chromosome of *Drosophila melanogaster*: isolation of lethals with different overgrowth phenotypes," Genetics 135:71–80.

Toyn and Johnston, 1994, "The Dbf2 and Dbf20 protein kinases of budding yeast are activated after the metaphase to anaphase cell cycle transition," EMBO J. 13(5):1103–1113.

Toyn et al., 1991, "The cell–cycle–regulated budding yeast gene DBF2, encoding a putative protein kinase, has a homologue that is not under cell–cycle control," Gene 104:63–70.

Vogelstein and Kinzler, 1993, "The multistep nature of cancer," Trends Genet. 9:138–141.

Wang et al., 1994, "Identification and characterization of tumor suppressor genes in Drosophila," EMBL Int. Conf. on Drosophila Development, Crete, Greece, Jun. 19–25, 1994.

Watson et al., 1992, "Drosophila homolog of the human S6 ribosomal protein is required for tumor suppression in the hematopoietic system," Proc. Natl. Acad. Sci. USA 89:11302–11306.

Weinberg, 1991, "Tumor suppressor genes," Science 254:1138–1146.

Wharton et al., 1985, "opa: a novel family of transcribed repeats shared by the Notch locus and other developmentally regulated Loci in *D. melanogaster*," Cell 40:55–62.

Woods and Bryant, 1989, "Molecular cloning of the lethal(1)Discs large–1 oncogene of Drosophila," Dev. Biol. 134:222–235.

Woods and Bryant, 1991, "The discs–large tumor suppressor gene of Drosophila encodes a guanylate kinase homolog–localized at septate junctions," Cell 66:451–464.

Woods and Bryant, 1993, "ZO–1, DlgA and PSD–95/SAP90: homologous proteins in tight, septate and synaptic cell junctions," Mechan. Dev. 44:85–89.

Xu and Artavanis–Tsakonas, 1990, "deltex, a locus interacting with the neurogenic genes, Notch, Delta, and mastermind in *Drosophila melanogaster*," Genetics 126:665–677.

Xu and Harrison, 1994, "Mosaic analysis using FLP recombinase," Meth. Cell Biol. 44:655–682.

Xu and Rubin, 1993, "Analysis of genetic mosaics in developing and adult Drosophila tissues," Development 117:1223–1237.

Yarden et al., 1992, "cot–1, a gene required for hyphal elongation in *Neurospora crassa*, encodes a protein kinase," EMBO J. 11(6):2159–2166.

Yavari et al., 1994, "Isolation of genes whose expression is regulated by the Drosophila mutant tumor suppressor gene lats," EMBL Intl. Conf. on Drosophila Development, Crete, Greece, Jun. 19–25, 1994.

Xu, T. et al., 1995, "Identifying tumor suppressors in genetic mosaics: the Drosophila lats gene encodes a putative protein kinase", Development 121: 1053–1063.

Sanders, Peter G., 1990, "Protein Production by Genetically Engineered Mammalian Cell Lines", Animal Cell Biotechnology, vol. 4, pp. 16–70.

Rudinger In "Peptide Hormones," (Jun. 1976), ed. J.A. Parsons, University Park Press, Baltimore, pp. 1–7.

Hopp et al. Proc. Natl. Acad. Sci. 78(1981)3824–3828.

Gibco BRL Catalogue and Reference Guide,(1992) p. 296.

Justice et al. Genes and Development 9 (1995) 534–546.

```
GENOMIC
cDNA    1   ATCTAGCACGACGGCAGCAACAAAACCACGAATTAATTTTACTAAATTTAAGCCAAACGCGCATCGGAAATGCCT
                         A
                         ˇ
        76  GAAAATGCGATTGAATGCACGCGAAAAGTGATGGGTTGCGAACGCGAGTGAATCAAGTGAAAATACGTCGGCAAA
                                                     ┌─►A2 START
       151  TATCAGCGAATTGTCGTCAAAAGGCAAGGAAAAACGGAGAAAAAGAGGAAAAGCAATAAGTGCCGTGTGTGGGAA

226  ACGCGAAAAAGGCGAGAACAAAGAGGCGAAAAGCGAGGAAATTGCGTGGAAAACGTGGAAAACGCGAAGAAGCGA
            INTRON 1                   T
               ↓
       301  AGCTCCAAGTTGGCCGCCATCGATTCGTGCGTAGGATCAATTAAGATTCCGAGTGGTCGAGAATCGGCTCAAATC

376  AAATTAAAATCAACTAATATTTTGGTATTCAGATATTCAAATGGAATTCATTCATCGCCTGCGACTTTTATTCGG

451  ATCTGCCAACTATTTTTGAATTTGAATTGTGTGTCTGCGGCTGGCGCAGAATCTCTGATAAAGCAGAGGAATAAA

526  ATCGGAAGAACAACAAATACAAATACAAATGAAATGCGGGGAGCAGTATTTACATGCCAAATGAATGCTGGATAG
                         GGA
                         ˇ
       601  GCGAAAGGGGGGGTTTCTCTTATAATGCAAATGTGAATGTGAATGCGAATGCGAATGCGAGTGGAAGAATTCCCG

676  GCGCGAGTGATAAATAATCCGACGACAAACAAAGCAGAAGCCTACACCGCGAGAAAGAGCAGCGCAAACACAATT
                                                                                    G
       751  ATCTTTATTGAGAGCAACAATATCAAGATCGAGATAATAAAGCATCCTAAAACCCGCGCCTTAGTTCGTTTTAGT
                A
       826  CTCGCCACGGATATAGATATTCAAAGGCAAAAAGGTGGTGTCGGCATCGCCAGACAAACAAGTAAAGCATCTATT

901  TCATACAAAACAACCAATTAAATAATAATAAAAATAATAATAATCGTAGAGAGGCAGAGCCAAATCAAATTCCCG

976  GCCGCCGATGTGCCCCAGTGTGTGTGCGTGTGTGTGTGTGTGTGCTGTGCTGTGCTGTGCGAGTGTTAGTGTGCG

1051  GAGCATTTCTGTGATATGAGTGCTAAATGCCACAGGGCGAAGCAGCAGCATCATGCATCCAGCGGCCGAAAAAAG
A.A.     1                                                    M  H  P  A  G  E  K  R
      1126  GGGCGGTCGCCCCAATGATAAATACACGGCGGAAGCCCTCGAGAGCATCAAGCAGGACCTAACCCGATTTGAAGT
         8   G  G  R  P  N  D  K  Y  T  A  E  A  L  E  S  I  K  Q  D  L  T  R  F  E  V
                                                      INTRON 2
                                                          ↓
      1201  ACAAAATAACCATAGGAATAATCAGAATTACACACCTCTGCGATACACGGCGACCAACGGACGCAACGATGCACT
        34   Q  N  N  H  R  N  N  Q  N  Y  T  P  L  R  Y  T  A  T  N  G  R  N  D  A  L
      1276  TACTCCTGACTATCACCACGCCAAGCAGCCGATGGAGCCGCCACCCTCCGCCTCTCCTGCTCCGGACGTGGTCAT
        59   T  P  D  Y  H  H  A  K  Q  P  M  E  P  P  P  S  A  S  P  A  P  D  V  V  I
                                           ┌─►LATS-AL DELETION
      1351  ACCGCCGCCGCCCGCCATTGTAGGTCAGCCCGGAGCCGGCTCCATATCCGTATCCGGTGTGGGCGTTGGAGTGGT
        84   P  P  P  P  A  I  V  G  Q  P  G  A  G  S  I  S  V  S  G  V  G  V  G  V  V
                                                                    C
      1426  GGGTGTGGCGAACGGACGTGTGCCAAAGATGATGACGGCCCTAATGCCAAACAAACTGATCCGGAAGCCGAGCAT
       109   G  V  A  N  G  R  V  P  K  M  M  T  A  L  M  P  N  K  L  I  R  K  P  S  I
      1501  CGAACGGGACACGGCGAGCAGTCACTACCTGCGCTGCAGTCCGGCTCTGGACTCCGGAGCCGGTAGCTCCCGATC
       134   E  R  D  T  A  S  S  H  Y  L  R  C  S  P  A  L  D  S  G  A  G  S  S  R  S
      1576  GGACAGCCCCCATTCGCACCACACCCACCAGCCGAGCTCGAGGACGGTGGGTAATCCAGGTGGAAATGGTGGATT
       159   D  S  P  H  S  H  H  T  H  Q  P  S  S  R  T  V  G  N  P  G  G  N  G  G  F
```

FIG.5A

```
                                                                        G
1651 TTCTCCGTCGCCAAGCGGTTTCAGTGAGGTGGCTCCACCGGCGCCGCCGCCACGCAATCCCACCGCCTCCAGCGC
 184   S P S P S G F S E V A P P A P P P R N P T A S S A
1726 GGCCACGCCCCCACCGCCAGTGCCGCCCACCAGCCAGGCGTACGTGAAGCGGCGATCACCGGCCCTGAACAACCG
 209   A T P P P P V P P T S Q A Y V K R R S P A L N N R
     lat-al deletion
1801 CCCGCCGGCGATAGCGCCACCCCACTCAGCGGAGGCAACTCACCTGTSATAACCCAAAACGGGCTGAAGAACCCGC
 234   P P A I A P P T Q R G N S P V I T Q N G L K N P Q
                                              T
1876 GCAGCAGTTGACGCAGCAGCTGAAGTCCCTGAACCTATACCCAGGCGGAGGCAGTGGAGCAGTGGTGGAGCCACC
 259   Q Q L T Q Q L K S L N L Y P G G G S G A V V E P P
1951 GCCGCCCTACCTAATTCAAGGCGGAGCCGGAGGAGCAGCACCGCCGCCGCCACCACCCAGTTACACGGCCTCCAT
 284   P P Y L I Q G G A G G A A P P P P P P S Y T A S M
2026 GCAGTCGCGGCAGTCGCCCACACAATCCCAACAATCGGACTACAGGAAATCCCCGAGCAGTGGGATATACTCGGC
 309   Q S R Q S P T Q S Q Q S D Y R K S P S S G I Y S A
                                  C
2101 CACCTCGGCGGGCTCGCCGAGCCCCATAACTGTGTCGCTGCCGCCGGCGCCGCTGGCGAAGCCACAACCACGAGT
 334   T S A G S P S P I T V S L P P A P L A K P Q P R V
2176 CTACCAGGCCAGGAGTCAGCAGCCGATCATCATGCAGAGTGTGAAGAGCACGCAGGTCCAAAAGCCCGTGCTGCA
 359   Y Q A R S Q Q P I I M Q S V K S T Q V Q K P V L Q
2251 AACAGCAGTGGCGCCCCAATCGCCCATCGAGTGCCTCGGCCAGCAATTCACCAGTCCACGTGCTGGCCGCTCCACC
 384   T A V A P Q S P S S A S A S N S P V H V L A A P P
2306 CTCTTACCCTCAGAAGTCCGCCGGCAGTGGTGCAGCAGCAGCAACAGGCAGCAGCGGCGGCCCACCAGCAGCAGCA
 409   S Y P Q K S A A V V Q Q Q Q Q A A A A A H Q Q Q H
                              C                              T
2401 TCAGCACCAGCAATCCAAACCACCAACGCCAACCACACCGCCCTTGGTGGGTCTGAACAGCAAGCCCAATTGCCT
 434   Q H Q Q S K P P T P T T P P L V G L N S K P N C L
2476 GGAGCCACCGTCCTATGCCAAGAGCATGCAGGCCAAGGCGGCCACGGTGGTACAGCAGCAGCAACAGCAGCAGCA
 459   E P P S Y A K S M Q A K A A T V V Q Q Q Q Q Q Q Q
                 AAC
     G G A                           G
2551 ACAACAGCAGGTCCAGCAGCAGCAGGTGCAACAGCAGCAGCAACAGCAGCAACAGCAACTGCAGGCCTTGAGGGT
 484     Q Q Q V Q Q Q Q V Q Q Q Q Q Q Q Q L Q A L R V GGGAGCGGGATCAAC
                        ˅
2626 GCTCCAGGCACAGGCTCAGAGGGAGCGGGATCAACGGGAGCGGGAACGGGATCAGCAGAAGCTGGCCAACGGAAA
 559    L Q A Q A Q R E R D Q R E R E R D Q Q K L A N G N
2701 TCCTGGCCGGCAGATGCTTCCGCCGCCGCCCTATCAGAGCAACAACAACAACAGCGAGATCAAACCGCCGAG
 534    P G R Q M L P P P P Y Q S N N N N S E I K P P S
2776 CTGCAACAACAACAACATACAGATAAGCAACAGCAACCTGGCGACGACACCACCCATTCCGCCTGCCAAATACAA
 559     C N N N N I Q I S N S N L A T T P P I P P A K Y N
2851 TAACAACTCCTCCAACACGGGCGCGAATAGCTCGGGCGGCAGCAACGGATCCACCGGCACCACCGCCTCCTCGTC
 584     N N S S N T G A N S S G G S N G S T G T T A S S S
2926 GACCAGCTGCAAGAAGATCAAGCACGCCTCGCCCATCCCGGAGCGCAAGAAGATCTCCAAGGAGAAGGAGGAGGA
 609    T S C K K I K H A S P I P E R K K I S K E K E E E
```

FIG.5B

```
3001  GCGCAAGGAGTTCCGCATCAGGCAGTACTCGCCGCAAGCCTTCAAGTTCTTCATGGAGCAGCACATAGAGAACGT
634     R  K  E  F  R  I  R  Q  Y  S  P  Q  A  F  K  F  F  M  E  Q  H  I  E  N  V

3076  GATCAAGTCGTATCGCCAGCGCACGTATCGCAAGAATCAGCTGGAGAAGGAGATGCACAAAGTGGGACTGCCCGA
709     I  K  S  Y  R  Q  R  T  Y  R  K  N  Q  L  E  K  E  M  H  K  V  G  L  P  D

3151  TCAGACCCAAATCGAGATGAGGAAAATGCTGAACCAAAAGGAGAGCAACTACATTCGATTGAAGCGCGCCAAGAT
684     Q  T  Q  I  E  M  R  K  M  L  N  Q  K  E  S  N  Y  I  R  L  K  R  A  K  M

3226  GGACAAGAGCATGTTCGTCAAACTGAAGCCCAATTGGAGTGGGTGCATTTGGCGAGGTAACGCTGGTGAGCAAAT
759     D  K  S  M  F  V  K  L  K  P  I  G  V  G  A  F  G  E  V  T  L  V  S  K  I
3301  CGATACCTCGAACCATTTGTATGCGATGAAAACCCTGCGGAAAGCGGACGTTCTCAAGCGGAATCAGGTGGCACA
734     D  T  S  N  H  L  Y  A  M  K  T  L  R  K  A  D  V  L  K  R  N  Q  V  A  H

3376  CGTGAAGGCCGAGAGGGATATCCTCGCGGAAGCCGACAATAACTGGGTGGTGAAGTTGTACTACAGCTTCCAGGA
809     V  K  A  E  R  D  I  L  A  E  A  D  N  N  W  V  V  K  L  Y  Y  S  F  Q  D
                                                    Intron 3
                                                       ↓
3451  CAAGGATAATCTGTACTTTGTGATGGACTACATACCAGGTGGTGATCTGATGTCTCTGCTCATCAAACTGGGCAT
784     K  D  N  L  Y  F  V  M  D  Y  I  P  G  G  D  L  M  S  L  L  I  K  L  G  I 3526  TTTCGAGGAGGAACTGGCCAGATTCTACATCGCCGAGGTCACCTGCGCCGTGGACAGCGTTCACAAAATFFFCTT
809F    F  E  E  E  L  A  R  F  Y  I  A  E  V  T  C  A  V  D  S  V  H  K  M  G  F
            Intron 4
                ↓
3601  CATTCACAGAGACATCAAGCCTGACAACATACTCATCGATAGGGACGGACACATAAAGCTCACCGACTTTGGCCT
834     I  H  R  D  I  K  P  D  N  I  L  I  D  R  D  G  H  I  K  L  T  D  F  G  L
                                                              Intron 5
                                                                ↓
3676  GTGCACGGGATTCCGATGGACGCACAACTCGAAGTACTACCAGGAGAACGGCAATCACTCGCGCCAGGACTCGAT
859     C  T  G  F  R  W  T  H  N  S  K  Y  Y  Q  E  N  G  N  H  S  R  Q  D  S  M
                                                                   Intron 6
                                                                      ↓
3751  GGAGCCCTGGGAGGAATACTCCGAGAACGGACCGAAGCCCACCGTGCTGGAGAGGCGACGGATGCGCGATCACCA
884     E  P  W  E  E  Y  S  E  N  G  P  K  P  T  V  L  E  R  R  R  M  R  D  H  Q
                                                                              A
3826  AAGAGTCCTGGCCCACTCGCTGGTGGGCACCCCGAACTACATAGCTCCCGAGGTGCTGGAGAGGAGTGGGTACAC
909     R  V  L  A  H  S  L  V  G  T  P  N  Y  I  A  P  E  V  L  E  R  S  G  Y  T
                                                    C  T
3901  GCAGCTGTGCCGACTACTGGAGCGTGGGCGTCATCCTTTACGAGATGCTGGTGGGTCAGCCGCCCTTTCTGGCCAA
934     Q  L  C  D  Y  W  S  V  G  V  I  L  Y  E  M  L  V  G  Q  P  P  F  L  A  N
                           Intron 7                C
                              ↓
3976  CAGTCCGCTGGAAACGCAACAAAAGGTCATCAACTGGGAGAAAAACGCTGCATATTCCGCCGCAGGCCGAGTTATC
959     S  P  L  E  T  Q  Q  K  V  I  N  W  E  K  T  L  H  I  P  P  Q  A  E  L  S 4051  CCGCGAGGCTACGGACTTGATAAGGAGGCTCTGTGCCGTCGGCTGACAAGCGGCTGGGCAAGAGCGTGGACGAGGT
984     R  E  A  T  D  L  I  R  R  L  C  A  S  A  D  K  R  L  G  K  S  V  D  E  V 4126  CAAGAGCCACGACTTCTTCAAGGGCATCGACTTTGCGGACATGCGGAAGCAGAAAGCGCCCTACATACCGGAAAT
1059    K  S  H  D  F  F  K  G  I  D  F  A  D  M  R  K  Q  K  A  P  Y  I  P  E  I
```

FIG.5C

```
                    G
4201  CAAGCACCCAACGGACACATCCAACTTTGATCCCGTGGATCCGGAGAAGCTGCGCTCGAATGACTCCACCATGAG
1034    K  H  P  T  D  T  S  N  F  D  P  V  D  P  E  K  L  R  S  N  D  S  T  M  S
                          C                C
4276  CAGCGGCGATGATGTCGATCAGAATGACCFCACTTTCCACGGCTTTTTCGAATTTACCTTCCGTCGCTTCTTCGA
1059    S  G  D  D  V  D  Q  N  D  R  T  F  H  G  F  F  E  F  T  F  R  R  F  F  D

4351  CGACAAGCAGCCGCCGGATATGACGGACGATCAGGCGCCGGTTTACGTCTGAAATGGATGCTCTCCATGTGCCCA
1084    D  K  Q  P  P  D  M  T  D  D  Q  A  P  V  Y  V

4426  ACACCAACACCCCGCCCCCGAATCATTGTTAGTCAAATAGTCACAAAAAGGGGATAGAAACCATTGAGTGGGCTT

4501  GCATTGTAAAGGAAGCCTGGGTATAGAATGAAACTATCTATATACATTATATAAATTATAGGAGACAGTAGAGGC

4576  GGGAGCTACGTATATACATACAAATAATATACATATATTTGATATATATATATATATATATGCCGTAGGGCATGA

4651  ACTGAATAAATATAAAACGGAGCCGAGTAGAGATGAAACGAGAGGAGCGAGTCAGGACCTTCGACCTTTAACTGA
      ‾‾‾‾‾
      Poly A                                                                    G
4726  ACATAGTATATCCTTGTGCACTACTACTCCACAACAAATATATATTTTTAAATTGTTAGAATTCAAAAGGGACCA
                              ┌─delete─┐                                         C
4801  ACTGGAAATCGAACCTTTCTGGTGCTCAAAGCAAAGCAAAGCAAAGCAAAACAAAACGCCTTAAACTAAATGAGA 4876  CGCGAATTTACCCAACCACTTCACTCCTCTCCTTTCTCCACCTCCGATCGGTGGCCGGATTCGAACTCAGCAGGC
                                           T
4951  TGGTTGCATCCGGCCATCCCATTGACTTCCCATTCAGAATTGAGATTGCGAGGTGTGCGATGGAGAACGAACGGA
                                                                 ‾‾‾‾‾‾‾‾‾‾‾‾‾‾‾
5026  GACCAAAAGTCGCACGGCAGCGATATAAGCGGGTCTTATAAGCCTAATCTAAATCTAAACTGGGAGAACAGGACC
      ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                                                    GTGGCCCCCCTCCCTCCCTCCTCAT
       C   TGTAATTAGTG                 A    A      \                         /
5101  TATGTATGTCCTGCTATCCAATTCGTCTATCACTGCTCTTCATCTGTGTACGACCCCCACCCCCCCCCTCCCCAT Identical to the 1-141 n.t. of the Drosophila plc-21 transcript
5176  CCAAAAGAACAAACTTAGACGTAGCCTATGTGAAAAGCTAGCAATGTTAGACCAACTTGTTGAATGCCAAATGAA
                                                                                del
5251  ATTGTTTAGCCCCATGAGGAAAAACGCGGGGGAAATTCAACACTTATTCTCTGATAGCAAACGGAAAAGAAAGAAA
      ete
5326  GAAAAAAAAAAAACAGAAACAGTACGAGAAAATTGTAATCTTCTTAATGTAATATTGTAAAFAACACFRRAARRGT 5401  AATCTATGCTAGAGTTGTGTAGCGCCCTAAGATGTTTTTTAGTTTATAGACCGCTAACCGTAATCTAGTTTAATT 5476  CCTAACACTAAGCGAGAGTACAGTACATTGGTTTTTTTGTTTGTCGTAGGTTCGTTGGAAAATGCTTAACGGGAA 5551  ACGATTTGTTTTTCTCTTTAATTAGCTTCAGTTTGTATGTGCCGTGTGTTTTTATTATGACTTATATATAGTCCAT 5626  CTGAATATTCGTGGATGGAGCCTATTTTAAATGTGAGATCGAGCTAATTGAAGGAAATACAAACAAACTCTGTGT
                            AAAAGCAAATTAATAAAT
                            ‾‾‾‾‾‾‾‾‾‾‾‾‾‾‾‾‾‾
5701  GCCTAGGCCAATTAGTTAT                Poly A
```

FIG.5D

FIG.6B

```
          10         20         30         40         50         60         70         80
          *          *          *          *          *          *          *          *
GTGCAACATT CAATTAACCG AAAACAAAGC TGGAAAGGTT CTAAAGAGTC TCTAGTTCCT CAGAGACACG GCCCATCTCT
 V  Q  H   S  I  N  R  K  Q  S   W  K  G    S  K  E  S  L  V  P   Q  R  H   G  P  S  L
          90        100        110        120        130        140        150        160
          *          *          *          *          *          *          *          *
AGGAGAAAAT GTGGTTTATC GTTCTGAAAG CCCCAACTCA CAGGCGGATG TAGGAAGACC TCTGTCTGGA TCCGGCATTG
 G  E  N   V  V  Y    R  S  E  S  P  N  S   Q  A  D    V  G  R  P  L  S  G   S  G  I
         170        180        190        200        210        220        230        240
          *          *          *          *          *          *          *          *
CAGCATTTGC TCAAGCTCAC CCAAGCAATG GACAGAGAGT GAACCCCCCA CCACCACCTC AAGTTAGGAG TGTTACTCCT
 A  A  F  A  Q  A  H   P  S  N   G  Q  R  V  N  P  P   P  P  P    Q  V  R  S  V  T  P
         250        260        270        280        290        300        310        320
          *          *          *          *          *          *          *          *
CCACCACCTC CGAGAGGCCA GACCCCACCT CCCGAGGCA CCACTCCCCC TCCCCCTCA TGGAACCAA GCTCTCAGAC
 P  P  P  P  R  G  Q   T  P  P    P  R  G  T  T  P    P  P  P  S  W  E  P  S  S  Q  T
         330        340        350        360        370        380        390        400
          *          *          *          *          *          *          *          *
AAAGGCTAC TCTGGAACA TGGAGTACGT AATCTCCCGA ATCTCCCCTG TTCCACTGG GGCGTGGCAG GAGGGGTACC
 K  R  Y   S  G  N   M  E  Y  V  I  S  R   I  S  P   V  P  P  G   A  W  Q   E  G  Y
         410        420        430        440        450        460        470        480
          *          *          *          *          *          *          *          *
CTCCACCACC TCTTACCACT TCTCCCATGA ATCCCCCTAG CCAGGCTCAG AGGGCCATTA GTTCTGTTCC AGTTGGTAGA
 P  P  P  P  L  T  T   S  P  M   N  P  P  S  Q  A  Q   R  A  I   S  S  V  P  V  G  R
         490        500        510        520        530        540        550        560
          *          *          *          *          *          *          *          *
CAACCCATCA TCATGCAGAG TACTAGCAAA TTTAACTTTA CCACCAGGGCG ACCTGGAGTT CAGAATGGTG GTGGTCAGTC
 Q  P  I   I  M  Q  S  T  S  K   F  N  F  T  P  G  R   R  P  G  V  Q  N  G   G  G  Q  S
```

FIG. 7A

```
          570        580        590        600        610        620        630        640
            *          *          *          *          *          *          *          *
TGATTTTATC GTGCACCAAA ATGTCCCCAC TGGTTCTGTG ACTCGGCAGC CACCACCTCC ATATCCTCTG ACCCCAGCTA
 D  F  I    V  H  Q   N  V  P  T  G  S  V   T  R  Q    P  P  P    Y  P  L    T  P  A 650        660        670        680        690        700        710        720
            *          *          *          *          *          *          *          *
ATGGACAAAG CCCCTCTGCT TTACAAACAG GGGCTTCTGC TGCTCCACCA TCATTCGCCA ATGGAAACGT TCCTCAGTCG
 N  G  Q  S  P  S  A   L  Q  T   G  A  S  A  A  P  P   S  F  A    N  G  N  V  P  Q  S 730        740        750        760        770        780        790        800
            *          *          *          *          *          *          *          *
ATGATGGTGC CCAACAGGAA CAGTCATAAC ATGGAGCTTT ATAATATTAA TGTCCCTGGA CTGCAAACAG CCTGGCCCCA
 M  M  V    P  N  R  N  S  H  N   M  E  L   Y  N  I  N  V  P  G   L  Q  T    A  W  P  Q 810        820        830        840        850        860        870        880
            *          *          *          *          *          *          *          *
GTCGTCTTCT GCTCCTGCGC AGTCATCCCC AAGCGGGTGG GAGCAAGTCA CTCTGCTAAT CATGAAATTC CCAGTGAGGT
 S  S  S    A  P  A   Q  S  S  P  S  G  G    R  A  S  H  S  A  N   H  E  I    P  V  R 890        900        910        920        930        940        950        960
            *          *          *          *          *          *          *          *
CAAAATTCTT TAATAACCCA TTAGGAAGTA AAAAGCATGC AAAAGCATGC CTCTGCTAAT TCTCAGCCTT CTGCCACTAC AGTCACTGCC
 S  N  S  F  N  N  P   L  G  S   R  A  S  H  S  A  N   S  Q  P    S  A  T  T  V  T  A 970        980        990       1000       1010       1020       1030       1040
            *          *          *          *          *          *          *          *
ATCACACCCG CTCCTATTCA ACAGCCCGTG AAAAGCATGC GCGTCCTGAA ACCAGAGCTG CAGACTGCTY TAGCCCCAAC
 I  T  P   A  P  I  Q  Q  P  V   K  S  M    R  V  L  K  P  E  L    Q  T  A    L  A  P  T 1050       1060       1070       1080       1090       1100       1110       1120
            *          *          *          *          *          *          *          *
CCATCCTTCT TGGATGCCAC AGCCAGTTCA GACTGTTCAG CCTACCCCTT TTTCTGAGGG TACAGCTTCA AGTGTGCCTG
 H  P  S   W  M  P   Q  P  V  Q   T  V  Q    P  T  P    F  S  E  G  T  A  S   S  V  P
```

FIG. 7B

```
     1130       1140       1150       1160       1170       1180       1190       1200
       *          *          *          *          *          *          *          *
TCATCCCACC TGTTGCTGAA GCTCCAAGCT ATCAAGGTCC ACCACCGCCT TATCCAAAAC ATCTGCTACA CCAAAACCCA
 V  I  P  P   V  A  E    A  P  S   Y  Q  G  P   P  P  P    Y  P  K   H  L  L  H   Q  N  P
     1210       1220       1230       1240       1250       1260       1270       1280
       *          *          *          *          *          *          *          *
TCTGTCCCTC CATATGAGTC AGTAAGTAAG CCCTGCAAAG ATGAACAGCC TAGCTTACCC AAGGAAGATG ATAGTGAGAA
 S  V  P    P  Y  E  S   V  S  K   P  C  K   D  E  Q  P    S  L  P    K  E  D   D  S  E  K
     1290       1300       1310       1320       1330       1340       1350       1360
       *          *          *          *          *          *          *          *
GAGTGCGGAC AGTGGTGACT CTGGGGATAA AGAAAAGAAA CAGATTACAA CTTCACCTAT CACTGTTCGG AAAAACAAGA
 S  A  D    S  G  D   S  G  D  K   E  K  K    Q  I  T    T  S  P  I    T  V  R    K  N  K
     1370       1380       1390       1400       1410       1420       1430       1440
       *          *          *          *          *          *          *          *
AAGATGAAGA ACGAAGAGAG TCTCGGATTC AGAGTTACTC CCCACAGGCC TTTAAGTTCT TCATGGAGCA GCACGTAGAG
 K  D  E  E    R  R  E    S  R  I   Q  S  Y  S    P  Q  A    F  K  F    F  M  E  Q   H  V  E
     1450       1460       1470       1480       1490       1500       1510       1520
       *          *          *          *          *          *          *          *
AACGTCCTGA AGTCTCATCA GCAGGCGTCTG AGTCTAGA AGCAGCTAGA AAATGAAATG ATGCGGGGTTG GATTATCTCA
 N  V  L    K  S  H  Q    Q  R  L    H  R  K   Q  L  E    N  E  M    M  R  V   G  L  S  Q
     1530       1540       1550       1560       1570       1580       1590       1600
       *          *          *          *          *          *          *          *
AGATGCCCAG GATCAAATGA GAAAGATGCT TTGCCAGAAA GAGTCTAACT ATATTCGTCT TAAAAGGGCT AAAATGGACA
 D  A  Q    D  Q  M   R  K  M  L    C  Q  K   E  S  N    Y  I  R  L    K  R  A    K  M  D
     1610       1620       1630       1640       1650       1660       1670       1680
       *          *          *          *          *          *          *          *
AGTCTATGTT TGTAAAGATA AAGACATTAG GAATAGGAGC GTTTGGTGAA GTCTGTCTAG CAAGAAAAGT CGATACTAAA
 K  S  M  F   V  K  I   K  T  L   G  I  G  A    F  G  E   V  C  L   A  R  K  V   D  T  K
```

FIG. 7C

```
      1690        1700        1710        1720        1730        1740        1750        1760
        *           *           *           *           *           *           *           *
GCTTTGTATG CAACAAAGAC TCTTCGAAAG AAAGACGTTC TGCTCCGAAA TCAGGTGGCT CATGTGAAAG CGGAGAGGGA
 A   L   Y     Q   Q   R   T     L   R   K     K   D   V     L   L   R   N     Q   V   A     H   V   K     A   E   R   D
      1770        1780        1790        1800        1810        1820        1830        1840
        *           *           *           *           *           *           *           *
TATCCTAGCA GAAGCCGACA ATGAGTGGGT GGTCCGCCTG TACTACTCTT TCCAGGACAA GGACAACTTG TACTTTGTGA
 I   L   A     E   A   D     N   E   W   V     V   R   L     Y   Y   S     F   Q   D   K     D   N   L     Y   F   V
      1850        1860        1870        1880        1890        1900        1910        1920
        *           *           *           *           *           *           *           *
TGGACTACAT TCCTGGGGGG GATATGATGA GCCTATTAAT TAGAATGGGC ATCTTTCCTG AAAATCTGGC ACGATTCTAC
 M   D   Y   I     P   G   G     D   M   M     S   L   L   I     R   M   G     I   F   P     E   N   L   A     R   F   Y
      1930        1940        1950        1960        1970        1980        1990        2000
        *           *           *           *           *           *           *           *
ATAGCAGAAC TTACCTGTGC AGTTGAAAGT GTTCATAAAA TGGGTTTTAT TCATAGAGAT ATTAAACCTG ATAACATTTT
 I   A   E     L   T   C   A     V   E   S     V   H   K     M   G   F   I     H   R   D     I   K   P     D   N   I   L
      2010        2020        2030        2040        2050        2060        2070        2080
        *           *           *           *           *           *           *           *
GATTGACCGT GATGGCCATA TTAAATTGAC TGACTTTGGC TTGTGCACTG GCTTCAGATC CAGTAACGAA TGGGGAGATC
 I   D   R     D   G   H     I   K   L   T     D   F   G     L   C   T     G   F   R   W     T   H   D     S   K   Y
      2090        2100        2110        2120        2130        2140        2150        2160
        *           *           *           *           *           *           *           *
ACCAGAGTGG GGATCACCCA CGGCAAGATA GCATGGATTT CAGTAACGAA TGGGGAGATC CTTCCAATTG TCGGTGTGGG
 Y   Q   S   G     D   H   P     R   Q   D     S   M   D   F     S   N   E     W   G   D     P   S   N   C     R   C   G
      2170        2180        2190        2200        2210        2220        2230        2240
        *           *           *           *           *           *           *           *
GACAGACTGA AGCCACTGGA GCGGAGAGCT GCTCGCCAGC ACCAGCGATG TCTAGCCCAT TCTCTGGTTG GGACTCCCAA
 D   R   L     K   P   L   E     R   R   A     A   R   Q     H   Q   R   C     L   A   H     S   L   V     G   T   P   N
```

FIG. 7D

```
         2250       2260       2270       2280       2290       2300       2310       2320
           *          *          *          *          *          *          *          *
TTATATTGCA CCTGAAGTGC TACTGCGAAC AGGATATACA CAGCTGTGTG ACTGGTGGAG TGTTGGTGTT ATTCTTTGTG
 Y  I  A    P  E  V    L  L  R  T  G  Y  T    Q  L  C    D  W  W  S    V  G  V   I  L  C
             2330       2340       2350       2360       2370       2380       2390       2400
               *          *          *          *          *          *          *          *

AAATGTTGGT GGGACAACCT CCTTTCTTGG CACAAACCCC ATTAGAAACA CAAATGAAGG TTATCATCTG GCAAACTTCT
 K  M  L  V  G  Q  P    P  F  L    A  Q  T  P    L  E  T    Q  M  K   V  I  I  W   Q  T  S
E
             2410       2420       2430       2440       2450       2460       2470       2480
               *          *          *          *          *          *          *          *

CTACACATCC CTCCTCAAGC TAAGCTGAGT CCTGAAGCCT CTGACCTCAT TATCAAACTG TGTCGAGGAC CAGAAGACCG
 L  H  I    P  P  Q  A   K  L  S    P  E  A    S  D  L  I    I  K  L    C  R  G    P  E  D  R
             2490       2500       2510       2520       2530       2540       2550       2560
               *          *          *          *          *          *          *          *

CCTCGGCAAG AACGGTGCTG ATGAGATAAA GGCTCATCCA TTTTTTAAGA CCATCGATTT CTCTAGTGAT CTGAGACAGC
 L  G  K    N  G  A    D  E  I  K   A  H  P    F  F  K    T  I  D  F    S  S  D    L  R  Q
             2570       2580       2590       2600       2610       2620       2630       2640
               *          *          *          *          *          *          *          *

AGTCTGCTTC ATACATCCCT AAAATCACGC ATCCAACAGA TACATCCAAT TTCGACCCTG TTGATCCTGA TAAAATTGTGG
 Q  S  A  S   Y  I  P    K  I  T    H  P  T  D   T  S  N    F  D  P    V  D  P  D    K  L  W
             2650       2660       2670       2680       2690       2700       2710       2720
               *          *          *          *          *          *          *          *

AGGGATGGCA GCGAGGAGGA AAATATCAGT GACACTCTGA GCGGATGGTA TAAAAATGGG AAGCACCCCG AGCACGCTTT
 S  D  G    S  E  E  E   N  I  S    D  T  L    S  G  W  Y    K  N  G    K  H  P    E  H  A  F
             2730       2740       2750       2760       2770       2780       2790       2800
               *          *          *          *          *          *          *          *

CTATGAGTTC ACCTTTCGGA GGTTTTTTGA TGACAATGGC TACCCATATA ATTATCCAAA GCCTATTGAG TATGAATACA
 Y  E  F    T  F  R    R  F  F  D   D  N  G    Y  P  Y    N  Y  P  K    P  I  E    Y  E  Y
```

FIG. 7E

```
         2810       2820       2830       2840       2850       2860       2870       2880
           *          *          *          *          *          *          *          *
TTCATTCACA GGGCTCAGAA CAACAGTCTG ATGAAGATGA TCAACACACA AGCTCCGATG GAAACAACCG AGATCTAGTG
 I  H  S  Q  G  S  E  Q  Q  S  D  E  D  D  Q  H  T  S  S  D  G  N  N  R  D  L  V
         2890       2900       2910       2920       2930       2940       2950       2960
           *          *          *          *          *          *          *          *
TATGTTTAAT AAACTAGGAG ATCATTGTAA GAATTGCAA GAGGCCTGAA GTGCAGGGGT TTTTGAAGTT TTGAGARAAT
 Y  V  *
         2970       2980       2990       3000       3010       3020       3030       3040
           *          *          *          *          *          *          *          *
TATGCAAATG TGACAGAGTT TGTGTGCTCT GTGTACAATA TTTTATTTTC CTAAGTTATG GGAAATTGTT TTAAAATGTT
         3050       3060       3070       3080       3090       3100       3110       3120
           *          *          *          *          *          *          *          *
AATTTATTCC ACCCTTTTAA TTCAGTAATT TAGAAAAAAT TGTTATAAGG AAAGTAAATT ATGAACTGAG TATTATAGTC
         3130       3140       3150       3160       3170       3180       3190       3200
           *          *          *          *          *          *          *          *
AATTCTTGGT ACTTAAAGTA CTTAAAAAGA GAAGCCTGGT ATCTTTTGTA TATATAATAA ATAATTTTAA AATCCCAAAA
         3210
           *
AAAAAAAAAA AAA
```

FIG. 7F

FIG. 8A

```
         10         20         30         40         50         60         70         80
          *          *          *          *          *          *          *          *
ATGAGAGCCA CCCCGAAGTT TGGACCTTAT CAAAAAGCTC TCAGGGAAAT CCGATATTCC CTCCTGCCTT TTGCCAACGA
 M  R  A    T  P  K  F   G  P  Y   Q  K  A   L  R  E  I   R  Y  S    L  L  P    A  N  E
         90        100        110        120        130        140        150        160
          *          *          *          *          *          *          *          *
GTCAGGCACT TCGGCAGCTG CAGAGGTGAA CCGGCAGATG CTTCAGGAGT TGGTGAATGC GGCATGTGAC CAGGAGATGG
 S  G  T    S  A  A    A  E  V  N   R  Q  M   L  Q  E    L  V  N  A   A  C  D   Q  E  M
        170        180        190        200        210        220        230        240
          *          *          *          *          *          *          *          *
CTGGCAGAGC GCTCACGCAG ACGGGCAGTA GGAGTATCGA AGCTGCCTTG GAGTACATCA GTAAGATGGG CTACCTGGAC
 A  G  R    A  L  T  Q   T  G  S    R  S  I  E   A  A  L   E  Y  I    S  K  M  G   Y  L  D
        250        260        270        280        290        300        310        320
          *          *          *          *          *          *          *          *
CCCAGGAATG AGCAGATTGT GCGAGTCATC AAGCAGACCT CCCCAGGAAA GGGCCTGGCG TCCACCCCGG TGACTCGGCG
 P  R  N    E  Q  I  V   R  V  I    K  Q  T    S  P  G  K   G  L  A    S  T  P    V  T  R  R
        330        340        350        360        370        380        390        400
          *          *          *          *          *          *          *          *
GCCCAGTTTC GAGGGCACAG GGGAAGCACT CCCATCCTAC TTCTCTTCCC TGGAGCCGGA GCCCGGCACC ACGGTGCCCA GGCTCACCAG
 P  S  F    E  G  T    G  E  A  L   P  S  Y    F  L  F  P   G  A  G    A  G  T    H  G  A    Q  H  Q
        410        420        430        440        450        460        470        480
          *          *          *          *          *          *          *          *
TGGAGGAGAT GCCCGGGCAA TATTTAGACT TTCTCTTCCC TGGAGCCGGA GCCCGGCACC ACGGTGCCCA GGCTCACCAG
 L  E  E  M   P  R  Q    Y  L  D    F  L  F  P    G  A  G    A  G  T    H  G  A    Q  H  Q
        490        500        510        520        530        540        550        560
          *          *          *          *          *          *          *          *
CATCCTCCCA AAGGGTACAG CACAGCAGTA GAGCCAAGTG CGCACTTTCC GGGCACACAC TATGGTCGTG GTCATCTACT
 H  P  P    K  G  Y  S   T  A  V    E  P  S    A  H  F  P    G  T  H    Y  G  R    G  H  L  L
```

```
             570         580         590         600         610         620         630         640
              *           *           *           *           *           *           *           *
        ATCGGAGCAG TCTGGGTATG GGGTGCAGCG CAGTTCCTCC TTCCAGAACA AGACGCCACC AGATGCCTAT TCCAGCATGG
         S  E  Q   S  G  Y   G  V  Q  R  Q  V  P  P  F  Q  N  K  T  P  P  D  A  Y   S  S  M
             650         660         670         680         690         700         710         720
              *           *           *           *           *           *           *           *
        CCAAGGCCCA GGGTGGCCCT CCCGCCAGCC TCACCTTTCC TGCCCATGCT GGGCTGTACA CTGCCTCGCA CCACAAGCCG
         A  K  A  Q  G  G  P  P  A  S   L  T  F  P   A  H  A   G  L  Y   T  A  S  H  H  K  P
             730         740         750         760         770         780         790         800
              *           *           *           *           *           *           *           *
        GCGGCTACCC CACCTGGGGC CCACCCATTA CATGTGTTGG GCACCCGGGG TCCCACGTTT ACTGGGGAAA GCTCTGCACA
         A  A  T   P  P  G  A  H  P  L   H  V  L   G  T  R  G  P  T  F   T  G  E   S  S  A  Q
             810         820         830         840         850         860         870         880
              *           *           *           *           *           *           *           *
        GGCTGTGCTG GCACCGTCCA GGAACAGCCT CAATGCTGAC TTGTACGAGC TGGGCTCCAC GGTGCCCTGG TCTGCAGCTC
         A  V  L   A  P  S   R  N  S  L  N  A  D   L  Y  E   L  G  S  T  V  P  W   S  A  A
             890         900         910         920         930         940         950         960
              *           *           *           *           *           *           *           *
        CACTGGCACG CCGGACTCG CTGCAGAAGC AGGGTCTAGA GAGCCCTCGG CCGCATGTGG CTTTTCGGGC TGGCCCCAGC
         P  L  A  R  R  D  S  L  Q  K   Q  G  L  E  E  P  S  R  P  H  V  A  F  R  A  G  P  S
             970         980         990         1000        1010        1020        1030        1040
              *           *           *           *           *           *           *           *
        AGGACCAACT CCTTCAACAA CCCACACCT GAGCCCTCAC TGCCCGCCC CAACACGGTC ACCGCCGTGA CGGCCGCACA
         R  T  N   S  F  N  N  P  Q  P   E  P  S   L  P  A  P  N  T  V  T  A  V  T  A  A  H
             1050        1060        1070        1080        1090        1100        1110        1120
              *           *           *           *           *           *           *           *
        CATCCTTCAC CCTGTGAAGA GCGTGCGTGT GCTGCGGCCC GAGCCCCAGA CAGCCGTGGG GCCCTCGCAC CCCGCCTGGG
         I  L  H   P  V  K   S  V  R  V  L  R  P   E  P  Q   T  A  V  G  P  S  H   P  A  W
```

FIG. 8B

```
        1130           1140           1150           1160           1170           1180           1190           1200
          *              *              *              *              *              *              *              *
TGGCTGCGCC CACAGCACCT GCCACTGAGA GCCTGGAGAC GAAGGAGGGC AGGGCAGGCC CACACCCGCT GGATGTGGAC
         1210           1220           1230           1240           1250           1260           1270           1280
           *              *              *              *              *              *              *              *
 V  A  A  P  T  A  P  A  T  E  S  L  E  T  K  E  G  S  A  G  P  H  P  L  D  V  D 1290           1300           1310           1320           1330           1340           1350           1360
          *              *              *              *              *              *              *              *
TATGGCGGCT CCGAGCGCAG GTGCCACCCG CCTCCGTATC CAAAGCACTT GCTGCTGCCC AGTAAGTCTG AGCAGTACAG
 Y  G  G  S  E  R  R  C  P  P  P  P  Y  P  K  H  L  L  L  P  S  K  S  E  Q  Y  S 1370           1380           1390           1400           1410           1420           1430           1440
          *              *              *              *              *              *              *              *
CGTGGACCTG GACAGCCTGT GCACCAGTGT GCAGCAGAGT CTGCGAGGGG GCACTGATCT AGACGGGAGT GACAAGAGCC
 V  D  L  D  S  L  C  T  S  V  Q  Q  S  L  R  G  G  T  D  L  D  G  S  D  K  S 1450           1460           1470           1480           1490           1500           1510           1520
          *              *              *              *              *              *              *              *
ACAAAGGTGC GAAGGGAGAC AAAAGCTGGCA GAGACAAAAA GCAGATTCAG ACCTCCCCGG TGCCTGTCCG CAAGAATAGC
 H  K  G  A  K  G  D  K  A  G  R  D  K  K  Q  I  Q  T  S  P  V  P  V  R  K  N  S 1530           1540           1550           1560           1570           1580           1590           1600
          *              *              *              *              *              *              *              *
AGAGATGAAG AGAAGAGAGA GTCTCGCATC AAGAGTTACT CCCCTTATGC CTTCAAATTC TTCATGGAGC AACACGTGGA
 R  D  E  E  K  R  E  S  R  I  K  S  Y  S  P  Y  A  F  K  F  F  M  E  Q  H  V  E 1610           1620           1630           1640           1650           1660           1670           1680
          *              *              *              *              *              *              *              *
GAATGTCATC AAAACCTACC AGCAGAAGGT CAGCCGGAGG CTACAGCTGG AGCAGGAAAT GGCCAAAGCT GGGCTCTGTG
 N  V  I  K  T  Y  Q  Q  K  V  S  R  R  L  Q  L  E  Q  E  M  A  K  A  G  L  C

AGGCCGAGCA GGAGCAGATG AGGAAGATCC TCTACCAGAA GGAGTCTAAC TACAACCGGC TGAAGAGGGC CAAGATGGAC
 E  A  E  Q  E  Q  M  R  K  I  L  Y  Q  K  E  S  N  Y  N  R  L  K  R  A  K  M  D
```

FIG. 8C

```
     1690       1700       1710       1720       1730       1740       1750       1760
       *          *          *          *          *          *          *          *
AAGTCCATGT TTGTGAAAAT CAAGACTCTA GGCATCGGTG CCTTTGGGGA AGTGTGCCTC GCTTGTAAGC TGGACACTCA
 K  S  M   F  V  K  I   K  T  L   G  I  G    A  F  G  E   V  C  L   A  C  K   L  D  T  H
      1770       1780       1790       1800       1810       1820       1830       1840
        *          *          *          *          *          *          *          *
CGCTCTGTAC GCCATGAAGA CTCTCAGGAA GAAGGATGTC CTGAACCGGA ATCAAGTGGC CCATGTCAAG GCTGAGAGGG
 A  L  Y   A  M  K  T   L  R  K   K  D  V    L  N  R   N  Q  V  A   H  V  K   A  E  R
      1850       1860       1870       1880       1890       1900       1910       1920
        *          *          *          *          *          *          *          *
ACATCCTGGC TGAAGCAGAC AATGAGTGGG TGGTCAAACT CTACTACTCC TTCCAGGACA AGGACAGCCT GTACTTTGTG
 D  I  L  A   E  A  D   N  E  W    V  V  K  L   Y  Y  S   F  Q  D    K  D  S  L   Y  F  V
      1930       1940       1950       1960       1970       1980       1990       2000
        *          *          *          *          *          *          *          *
ATGGACTACA TACCAGGCGG GGATATGATG AGCCTGCTGA TCAGGATGGA GGTCTTCCCT GAGCACTTCT CCCGCTTCTA
 M  D  Y    I  P  G  G   D  M  M   S  L  L   I  R  M  E   V  F  P   E  H  L    A  R  F  Y
      2010       2020       2030       2040       2050       2060       2070       2080
        *          *          *          *          *          *          *          *
CATTGCAGAG TTGACCCTGG CCATTGAAAG ATTAAGCTGA CAGATTTTGG CCCTCTGCACT GGATTCAGGT GGACTCACAA TTCCAAGTAC
 I  A  E    L  T  L    A  I  E  S   V  H  K   M  G  F    I  H  R  D   I  K  P   D  N  I
      2090       2100       2110       2120       2130       2140       2150       2160
        *          *          *          *          *          *          *          *
TCATCGACCT GGATGGTCAT ATTAAGCTGA CAGATTTTGG CCCTCTGCACT GGATTCAGGT GGACTCACAA TTCCAAGTAC
 L  I  D  L   D  G  H    I  K  L    T  D  F  G    L  C  T    G  F  R    W  T  H   N  S  K  Y
      2170       2180       2190       2200       2210       2220       2230       2240
        *          *          *          *          *          *          *          *
TACCAGAAAG GGAACCACAT GAGACAGGAC AGCATGGAGC CCGGTGACCT CTGGACGAT GTTCCAACT GTCGCTGTGG
 Y  Q  K    G  N  H  M   R  Q  D   S  M  E    P  G  D  L   W  D  D   V  S  N    C  R  C  G
```

FIG. 8D

```
              2250        2260        2270        2280        2290        2300        2310        2320
                *           *           *           *           *           *           *           *
AGACAGGTTA AAGACCCTGG AGCAGAGGGC AGCAGAAGCAG CACCAGAGGT GCCTGGCACA TTCTCTTGTC GGGACACCAA
 D  R  L    K  T  L    E  Q  R  A    Q  K  Q     H  Q  R     C  L  A  H     S  L  V    G  T  P
              2330        2340        2350        2360        2370        2380        2390        2400
                *           *           *           *           *           *           *           *
ATTACATCGC TCCGGAGGTG CTTCTCCGCA AAGGGTACAC GCAGCTCTGT GACTGGTGGA GCGTCGGTGT GATTCTCTTT
 N  Y  I  A   P  E  V    L  L  R     K  G  Y  T    Q  L  C      D  W  W     S  V  G  V    I  L  F
              2410        2420        2430        2440        2450        2460        2470        2480
                *           *           *           *           *           *           *           *
GAGATGCTGG TTGGGCAGCC GCCTTTCTTG GCCCCCCACCC CCACAGAGAC GCAGCTGAAG GTGATCAACT GGGAGAGCAC
 E  M  L     V  G  Q  P   P  F  L     A  P  T     P  T  E  T      Q  L  K     V  I  N     W  E  S  T
              2490        2500        2510        2520        2530        2540        2550        2560
                *           *           *           *           *           *           *           *
GCTGCATATC CCTACGCAGC TGAGGCTCAG CGCTGAGGCC CGAGACCTCA TCACGAAGCT GTGCTGCGCG GCTGACTGCC
 L  H  I     P  T  Q    V  R  L  S     A  E  A     R  D  L      I  T  K  L     C  C  A     A  D  C
              2570        2580        2590        2600        2610        2620        2630        2640
                *           *           *           *           *           *           *           *
GCCTGGGCAG GGATGGGGCA GATGACCTCA AGGCACACCC GTTCTTCAAC ACCATCGACT TTTCCCGTGA CATCCGAAAG
 A  W  A     D  G  A    D  D  L     K  A  H  P     F  F  N      T  I  D      F  S  R  D     I  R  K
              2650        2660        2670        2680        2690        2700        2710        2720
                *           *           *           *           *           *           *           *
CAGGCTGCAC CCTACGTCCC CACCATCAGC CACCCCATGG ACACCTCCAA TTTTGACCCG GTGGATGAAG AAAGCCCCTG
 Q  A  A     P  Y  V  P    T  I  S     H  P  M     D  T  S  N     F  D  P     V  D  E    E  S  P  W
              2730        2740        2750        2760        2770        2780        2790        2800
                *           *           *           *           *           *           *           *
GCACGAGGCC AGCGGAGAGA GCGCCAAGGC CTGGGACACG CTGGCCTCCC CCAGCAGCAA GCATCCAGAG CACGCCTTCT
 H  E  A     S  G  E    S  A  K  A    W  D  T  L    A  S     P  S  S  K     H  P  E  H     A  F
```

FIG. 8E

```
                  2810        2820        2830        2840        2850        2860        2870        2880
                    *           *           *           *           *           *           *           *
            ATGAGTTCAC CTTCCGCAGG TTCTTCGATG ACAACGGCTA TCCCTTCCGG TGCCCGAAGC CCTCAGAGCC CGCAGAGAGT
             Y  E  F   T   F  R   R   F  F   D   D  N   G  Y   P   F  R   C    P  K   P   S  E  P    A  E  S 2890        2900        2910        2920        2930        2940        2950        2960
                    *           *           *           *           *           *           *           *
            GCAGACCCAG GGGATGCGGA CTTGGAAGGT GCGGGCCGAGG GCTGCCAGCC GGTGTACGTG TAAGCCTCAG TTAACCACAA
             A  D  P   G   D  A   D   L  E   G   A  A   E   G  C    Q  P   V   Y   V   *

2970        2980        2990        3000        3010        3020        3030        3040
                    *           *           *           *           *           *           *           *
            CTCGAGGAAA CCCAAAATGA GATTTCTTTT CAGAAGACAA ACTCAAGCTT AGGAATCCTT CATTTTTAGT TCTGGTAAAT 3050        3060        3070        3080        3090        3100        3110        3120
                    *           *           *           *           *           *           *           *
            GGGCAACAGG AAGAGTCAAC ATGATTTCAA ATTAGCCCTC TGAGGACCTT CACTGCATTA AAACAGTATT TTTTAAAAAA 3130        3140        3150
                    *           *           *
            TTAGTACAGT ATGGAAAGAG CACTTATTTT GGGGG
```

FIG. 8F

```
           10         20         30         40         50         60         70         80
            *          *          *          *          *          *          *          *
ACCTTTGGGT TGCTGGGACG GACTCTGGCC GCCTCAGCGT CCGCCCTCAG GCCCGTGGCC GCTGTCCAGG AGCTCTGCTC
           90        100        110        120        130        140        150        160
            *          *          *          *          *          *          *          *
TCCCCTCCAG AGTTAATTAT TTATATTGTA AAGAATTTTA ACAGTCCTGG GGACTTCCTT GAAGGATCAT TTTCACTTTT
          170        180        190        200        210        220        230        240
            *          *          *          *          *          *          *          *
GCTCAGAAGA AAGCTCTGGA TCTATCAAAT AAAGAAGTCC TTCGTGTGGG CTACATATAT AGATGTTTTC ATGAAGAGGA
                                                                              M  K  R
          250        260        270        280        290        300        310        320
            *          *          *          *          *          *          *          *
GTGAAAAGCC AGAAGGATAT AGACAAATGA GGCCTAAGAC CTTTCCTGCC AGTAACTATA CTGTCAGTAG CCGGCAAATG
 S  E  K  P  E  G  Y  R  Q  M  R  P  K  T  F  P  A  S  N  Y  T  V  S  S  R  Q  M
          330        340        350        360        370        380        390        400
            *          *          *          *          *          *          *          *
TTACAAGAAA TTCGGGAATC CCTTAGGAAT TTATCTAAAC CATCTGATGC TGCTAAGGCT GAGCATAACA TGAGTAAAAT
 L  Q  E  I  R  E  S  L  R  N  L  S  K  P  S  D  A  A  K  A  E  H  N  M  S  K  M
          410        420        430        440        450        460        470        480
            *          *          *          *          *          *          *          *
GTCAACGAAA GATCCTCGAC AAGTCAGAGA AACCCACCCAAA TCCACCCAAA TTTGGGACGC ATCATAAAGC CTTGCAGGAA ATTCGAAACT
 S  T  E  D  P  R  Q  V  R  N  P  P  K  F  G  T  H  H  K  A  L  Q  E  I  R  N
          490        500        510        520        530        540        550        560
            *          *          *          *          *          *          *          *
CTCTGCTTCC ATTTGCAAAT GAAACAAATT CTTCTCGGAG TACTTCAGAA GTTAATCCAC AAATGCTTCA AGACTTGCAA
 S  L  L  P  F  A  N  E  T  N  S  S  R  S  T  S  E  V  N  P  Q  M  L  Q  D  L  Q

FIG. 9A
```

```
        570         580         590         600         610         620         630         640
         *           *           *           *           *           *           *           *
GCTGCTGGAT TTGATGAGGA TATGGTTATA CAAGCTCTTC AGAAAACTAA CAACAGAAGT ATAGAAGCAG CAATTGAATT
 A  A  G    F  D  E  D    M  V  I    Q  A  L    Q  K  T  N    N  R  S    I  E  A    A  I  E  F
        650         660         670         680         690         700         710         720
         *           *           *           *           *           *           *           *
CATTAGTAAA ATGAGTTACC AAGATCCTCG ACGAGAGCAG ATGGCTGCAG CAGCTGCCAG ACCTATTAAT GCCAGCATGA
 I  S  K    M  S  Y    Q  D  P  R    R  E  Q    M  A  A    A  A  A  R    P  I  N    A  S  M
        730         740         750         760         770         780         790         800
         *           *           *           *           *           *           *           *
AACCAGGGAA TGTGCAGCAA TCAGTTAACC GCAAACAGAG CTGGAAAGGT TCTAAAGAAT CCTTAGTTCC TCAGAGGCAT
 K  P  G  N    V  Q  Q    S  V  N    R  K  Q  S    W  K  G    S  K  E    S  L  V  P    Q  R  H
        810         820         830         840         850         860         870         880
         *           *           *           *           *           *           *           *
GGCCCGCCAC TAGGAGAAAG TGTGGCCTAT CATTCTGAGA GTCCCAACTC ACAGACAGAT GTAGGAAGAC CTTTGTCTGG
 G  P  P    L  G  E  S    V  A  Y    H  S  E    S  P  N  S    Q  T  D    V  G  R    P  L  S  G
        890         900         910         920         930         940         950         960
         *           *           *           *           *           *           *           *
ATCTGGTATA TCAGCATTTG TTCAAGCTCA CCCTAGCAAC AGACTCCCCC TCCAAGAGGT ACAACTCCAC CAAGTAAGGA
 S  G  I    S  A  F    V  Q  A  H    P  S  N    G  Q  R    V  N  P  P    P  P  P    Q  V  R
        970         980         990        1000        1010        1020        1030        1040
         *           *           *           *           *           *           *           *
GTGTTACTCC TCCACCACCT CCAAGAGGGC AGACTCCCCG AGACTCCCCC TCCAAGAGGT ACAACTCCAC CTCCCCCTTC ATGGAACCA
 S  V  T  P    P  P  P    P  R  G    Q  T  P  P    P  R  G    T  T  P    P  P  P  S    W  E  P
       1050        1060        1070        1080        1090        1100        1110        1120
         *           *           *           *           *           *           *           *
AACTCTCAAA CAAAGGCGCTA TTCTGGAAAC ATGGAATACG TAATCTCCCG AATCTCTCCT GTCCCACCTG GGGCATGGCA
 N  S  Q    T  K  R  Y    S  G  N    M  E  Y    V  I  S  R    I  S  P    V  P  P    G  A  W  Q
```

FIG. 9B

```
              1130         1140         1150         1160         1170         1180         1190         1200
               *            *            *            *            *            *            *            *
           AGAGGGCTAT CCTCCACCAC CTCTCAACAC TTCCCCCATG AATCCTCCTA ATCAAGGACA GAGAGGCATT AGTTCTGTTC
            E  G  Y    P  P  P   P  L  N  T   S  P  M   N  P  P   N  Q  G  Q   R  G  I   S  S  V
              1210         1220         1230         1240         1250         1260         1270         1280
               *            *            *            *            *            *            *            *
           CTGTTGGCAG ACAACCAATC ATCATGCAGA GTTCTAGCAA ATTTAACTTT CCATCAGGGA GACCTGGAAT GCAGAATGGT
            P  V  G  R   Q  P  I   I  M  Q   S  S  S  K   F  N  F   P  S  G   R  P  G  M   Q  N  G
              1290         1300         1310         1320         1330         1340         1350         1360
               *            *            *            *            *            *            *            *
           ACTGGACAAA CTGATTTCAT GATACACCAA AATGTTGTCC CTGCTGGCAC ACAGGGGGAT CTGCTGCTCC TTCGTCATAT ACAAATGGAA
            T  G  Q    T  D  F  M   I  H  Q   N  V  V   P  A  G  T   V  N  R   Q  P  P   P  P  Y  P
              1370         1380         1390         1400         1410         1420         1430         1440
               *            *            *            *            *            *            *            *
           TCTGACAGCA GCTAATGGAC AAAGCCCTTC TGCTTTACAA ACAGGGGGAT CTGCTGCTCC TTCGTCATAT ACAAATGGAA
            L  T  A    A  N  G    Q  S  P  S   A  L  Q   T  G  G   S  A  A  P   S  S  Y   T  N  G
              1450         1460         1470         1480         1490         1500         1510         1520
               *            *            *            *            *            *            *            *
           GTATTCCTCA GTCTATGATG GTGCCAAACA GAAATAGTCA TAACATGGAA CCCCGAGCAG TGGGCATGAA ATCCCTACAT GGCAACCTAA
            S  I  P  Q   S  M  M   V  P  N   R  N  S  H   N  M  E   L  Y  N   I  S  V  P   G  L  Q
              1530         1540         1550         1560         1570         1580         1590         1600
               *            *            *            *            *            *            *            *
           ACAAATTGGC CTCAGTCATC TTCTGCTCCA GCCCAGTCAT CCCCGAGCAG TGGGCATGAA ATCCCTACAT GGCAACCTAA
            T  N  W    P  Q  S  S   S  A  P   A  Q  S   S  P  S  S   G  H  E   I  P  T   W  Q  P  N
              1610         1620         1630         1640         1650         1660         1670         1680
               *            *            *            *            *            *            *            *
           CATACCAGTG AGGTCAAATT CTTTTAATAA CCCATTAGGA AATAGAGCAA GTCACTCTGC TAATTCTCAG CCTTCTGCTA
            I  P  V  R   S  N     S  F  N  N   P  L  G   N  R  A   S  H  S  A   N  S  Q   P  S  A

FIG. 9C
```

```
           1690       1700       1710       1720       1730       1740       1750       1760
            *          *          *          *          *          *          *          *
CAACAGTCAC TGCAATTACA CCAGCTCCTA TTCAACAGCC TGTGAAAAGT ATGCGTGTAT TAAAACCAGA GCTACAGACT
 T T V T    A I T      P A P      I Q Q P    V K S      M R V      L K P E    L Q T
            1770       1780       1790       1800       1810       1820       1830       1840
             *          *          *          *          *          *          *          *
GCTTTAGCAC CTACACACCC TTCTTGGATA CCAGCAGCCAA TTCAAACTGT TCAACCCAGT CCTTTTCCTG AGGGAACCGC
 A L A      P T H P    S W I      P Q P      I Q T V    Q P S      P F P      E G T A
            1850       1860       1870       1880       1890       1900       1910       1920
             *          *          *          *          *          *          *          *
TTCAAATGTG ACTGTGATGC CACCTGTTGC TGAAGCTCCA AACTATCAAG GACCACCACC ACCCTACCCA AAACATCTGC
 S N V      T V M      P P V A    E A P      N Y Q      G P P P    P Y P      K H L
            1930       1940       1950       1960       1970       1980       1990       2000
             *          *          *          *          *          *          *          *
TGCACCAAAA CCCATCTGTT CCTCCATACG AGTCAATCAG TAAGCCTAGC AAAGAGGATC AGCCAAGCTT GCCCAAGGAA
 L H Q N    P S V      P P Y      E S I S    K P S      K E D      Q P S L    P K E
            2010       2020       2030       2040       2050       2060       2070       2080
             *          *          *          *          *          *          *          *
GATGAGAGTG AAAAGAGTTA TGAAAATGTT GATAGTGGGG ATAAAGAAAA GAAACAGATT ACAACTTCAC CTATTACTGT
 D E S      E K S Y    E N V      D S G      D K E K    K Q I      T T S      P I T V
            2090       2100       2110       2120       2130       2140       2150       2160
             *          *          *          *          *          *          *          *
TAGGAAAAAC AAGAAAGATG AAGAGGGAAG GGAATCTCGT ATTCAAAGTT ATTCCCCTCA AGCATTTAAA TTCTTTATGG
 R K N      K K D      E E R R    E S R      I Q S      Y S P Q    A F K      F F M
            2170       2180       2190       2200       2210       2220       2230       2240
             *          *          *          *          *          *          *          *
AGCAACATGT AGAAAATGTA CTCAAATCTC ATCAGCAGCG TCTACATCGT AAAAAACAAT TAGAGAATGA AATGATGCGG
 E Q H V    E N V      L K S      H Q Q R    L H R      K K Q      L E N E    M M R
```

FIG. 9D

```
          2250       2260       2270       2280       2290       2300       2310       2320
            *          *          *          *          *          *          *          *
GTTGGATTAT CTCAAGATGC CCAGGATCAA ATGAGAAAGA TGCTTTGCCA AAAAGAATCT AATTACATCC GTCTTAAAAG
 V  G  L    S  Q  D  A    Q  D  Q    M  R  K    M  L  C  Q    K  E  S    N  Y  I    R  L  K  R
          2330       2340       2350       2360       2370       2380       2390       2400
            *          *          *          *          *          *          *          *
GGCTAAAATG GACAAGTCTA TGTTTGTGAA GATAAAGACA CTAGGAATAG GAGCATTTGG TGAAGTCTGT CTAGCAAGAA
 A  K  M    D  K  S    M  F  V  K    I  K  T    L  G  I    G  A  F  G    E  V  C    L  A  R
          2410       2420       2430       2440       2450       2460       2470       2480
            *          *          *          *          *          *          *          *
AAGTAGATAC TAAGGCTTTG TATGCAACAA AAACTCTTCG AAAGAAAGAT GTTCTTCTTC GAAATCAAGT CGCTCATGTT
 K  V  D  T    K  A  L    Y  A  T    K  T  L  R    K  K  D    V  L  L    R  N  Q  V    A  H  V
          2490       2500       2510       2520       2530       2540       2550       2560
            *          *          *          *          *          *          *          *
AAGGCTGAGA GAGATATCCT GGCTGAAGCT GACAATGAAT GGGTAGTTCG TCTATATTAT TCATTCCAAG ATAAGGACAA
 K  A  E    R  D  I  L    A  E  A    D  N  E    W  V  V  R    L  Y  Y    S  F  Q    D  K  D  N
          2570       2580       2590       2600       2610       2620       2630       2640
            *          *          *          *          *          *          *          *
TTTATACTTT GTAATGGACT ACATTCCTGG GGGTGATATG ATGAGCCTAT TAATTAGAAT GGGCATCTTT CCAGAAAGTC
 L  Y  F    V  M  D    Y  I  P  G    G  D  M    M  S  L    L  I  R  M    G  I  F    P  E  S
          2650       2660       2670       2680       2690       2700       2710       2720
            *          *          *          *          *          *          *          *
TGGCACGATT CTACATAGCA GAACTTACCT GTGCAGTTGA AAGTGTTCAT AAAATGGGTT TTATTCATAG AGATATTAAA
 L  A  R  F    Y  I  A    E  L  T    C  A  V  E    S  V  H    K  M  G    F  I  H  R    D  I  K
          2730       2740       2750       2760       2770       2780       2790       2800
            *          *          *          *          *          *          *          *
CCTGATAATA TTTTGATTGA TCGTGATGGT CATATTAAAT TGACTGACTT TGGCCTCTGC ACTGGCTTCA GATGGACACA
 P  D  N    I  L  I  D    R  D  G    H  I  K    L  T  D  F    G  L  C    T  G  F  R    W  T  H
```

FIG. 9E

```
          2810       2820       2830       2840       2850       2860       2870       2880
           *          *          *          *          *          *          *          *
CGATTCTAAG TACTATCAGA GTGGTGACCA TCCACGGCAA GATAGCATGG ATTTCAGTAA TGAATGGGGG GATCCCTCAA
 D  S  K    Y  Y  Q    S  G  D  H  P  R  Q    D  S  M    D  F  S  N    E  W  G    D  P  S
          2890       2900       2910       2920       2930       2940       2950       2960
           *          *          *          *          *          *          *          *
GCTGTCGATG TGGAGACAGA CTGAAGCCAT TAGAGCGGAG AGCTGCACGC CAGCACCAGC GATGTCTAGC ACATTCTTTG
 S  C  R  C  G  D  R    L  K  P    L  E  R  R    A  A  R    Q  H  Q    R  C  L  A    H  S  L
          2970       2980       2990       3000       3010       3020       3030       3040
           *          *          *          *          *          *          *          *
GTTGGGACTC CCAATTATAT TGCACCTGAA GTGTTGCTAC GAACAGGATA CACACAGTTG TTGGCACAAA CACCATTAGA
 V  G  T    P  N  Y  I    A  P  E    V  L  L    R  T  G  Y    T  Q  L    T  P  L  E
          3050       3060       3070       3080       3090       3100       3110       3120
           *          *          *          *          *          *          *          *
TGTTATTCTT TTTGAAATGT TGGTGGGACA ACCTCCTTTC CAGGCTAAACT CAGTCCTGAA GCTTCTGATC TTATTATTAA ACTTTGCCGA
 V  I  L    F  E  M    L  V  G  Q    P  P  F    Q  A  K  L    S  P  E    A  S  D    L  I  I  K    L  C  R
          3130       3140       3150       3160       3170       3180       3190       3200
           *          *          *          *          *          *          *          *
ACTGGCAAAC ATCTCTTCAC ATTCCACCAC AAGCTAAACT CAGTCCTGAA GCTTCTGATC TTATTATTAA ACTTTGCCGA
 N  W  Q  T    S  L  H    I  P  P    Q  A  K  L    S  P  E    A  S  D    L  I  I  K    L  C  R
          3210       3220       3230       3240       3250       3260       3270       3280
           *          *          *          *          *          *          *          *
GGACCCGAAG ATCGCTTAGG CAAGAATGGT GCTGATGAAA TAAAAGCTCA TCCATTTTTT AAAAACAATTG ACTTCTCCAG
 G  P  E    D  R  L  G    K  N  G    A  D  E    I  K  A  H    P  F  F    K  T  I    D  F  S  S
          3290       3300       3310       3320       3330       3340       3350       3360
           *          *          *          *          *          *          *          *
TGACCTGAGA CAGCAGTCTG CTTCATACAT TCCTAAAATC ACACACCCAA CAGATACATC AAATTTTGAT CCTGTTGATC
 D  L  R    Q  Q  S    A  S  Y  I    P  K  I  T    H  P  T  D  T  S    N  F  D    P  V  D
```

FIG.9F

```
         3370       3380       3390       3400       3410       3420       3430       3440
           *          *          *          *          *          *          *          *
CTGATAAATT ATGGAGTGAT GATAACGAGG AAGAAAATGT AAATGACACT CTCAATGGAT GGTATAAAAA TGGAAAGCAT
 P  D  K  L  W  S  D  D  N  E  E  E  N  V  N  D  T  L  N  G  W  Y  K  N  G  K  H
         3450       3460       3470       3480       3490       3500       3510       3520
           *          *          *          *          *          *          *          *
CCTGAACATG CATTCTATGA ATTTACCTTC CGAAGGTTTT TTGATGACAA TGGCTACCCA TATAATTATC CGAAGCCTAT
 P  E  H  A  F  Y  E  F  T  F  R  R  F  F  D  D  N  G  Y  P  Y  N  Y  P  K  P  I
         3530       3540       3550       3560       3570       3580       3590       3600
           *          *          *          *          *          *          *          *
TGAATATGAA TACATTAATT CACAAGGCTC AGAGCAGCAG TCGGATGAAG ATGATCAAAA CACAGGCTCA GAGATTAAAA
 E  Y  E  Y  I  N  S  Q  G  S  E  Q  Q  S  D  E  D  D  Q  N  T  G  S  E  I  K
         3610       3620       3630       3640       3650       3660       3670       3680
           *          *          *          *          *          *          *          *
ATCGCGATCT AGTATATGTT TAACACACTA GTAATAAAAT GTAATGAGGA TTTGTAAAAG GGCCTGAAAT GCGAGGTGTG
 N  R  D  L  V  Y  V  *
         3690       3700       3710       3720       3730       3740       3750       3760
           *          *          *          *          *          *          *          *
TTGAGGTTCT GAGAGTAAAA TTATGCAAAT ATGACAGAGC TATATATGTG TGCTCTGTGT ACAATATTTT ATTTTCCTAA
         3770       3780       3790       3800       3810       3820       3830       3840
           *          *          *          *          *          *          *          *
ATTATGGGAA ATCCTTTTAA AATGTTAATT TATTCCAGCC GTTTAAATCA GTATTTAGAA AAAAATTGTT ATAAGGAAAG
         3850       3860       3870       3880       3890       3900       3910       3920
           *          *          *          *          *          *          *          *
TAAATTATGA ACTGAATATT ATAGTCAGTT CTTGGTACTT AAAGTACTTA AAATAAGTAG TGCTTTGTTT AAAAGGAGAA
         3930       3940       3950       3960       3970       3980
           *          *          *          *          *          *
ACCTGGTATC TATTTGTATA TATGCTAAAT AATTTTAAAA TACAAGAGTT TTTGAAATTT TTTT
```

FIG. 9G

```
hLATS  MKRSEKPEGYRQMRPKTFPASNYTVSSRQMLQEIRESLRNLSKPSDAAKAEHNMSKMSTEDPRQVRNPPK  70 hLATS  FGTHHKALQEIRNSLLPFANETNSSRSTSEVNPQMLQDLQAAGFDEDMVIQALQRTNNRSIEAAIEFISK  140 hLATS  MSYQDPRREQMAAAARPINASMKPGNVQQSVNRKQSWKGSKESLVPQRHGPPLGESVAYHSESPNSQTD   210
mLATS  .........................h.i.................s..n.v.r........a.      45 hLATS  VGRPLSGSGISAFVQAHPSNGQRVNPPPPQVRSVTPPPPPRGTTPPPPSWEPNSQTKRYSGN         280
mLATS  ............a..a..............t.....s.a.a.................s..         117 hLATS  MEYVISRISPVPPGAWQEGYPPPLNTSPMNPPNQGQRGISSVPVGRQPIIMQSSSRFNFPSGRPGMQNG  350
mLATS  ..........................................t.......tP....v...         187 hLATS  TGQTDFMIHQNVVPAGTVNRQPPPPYPLTAANGQSPSALQTGGSAAPSSYTNGSIPQSMMVPNRNSHME  420
mLATS  g..s..iv...-..t.s.t...........p..........a...p.fa.nv.............    256 hLATS  LYNISVPGLQTNWPQSSSAPAQSSPSSGHEIPTWQPNIPVRSNSFNNPLGNRASHSANSQPSATTVTAIT 490
mLATS  ...n..a..............g.........................s...................  326 hLATS  PAPIQQPVKSMRVLKPELQTALAPTHPSWIPQPIQTVQPSPFPEGTASNVTVMPPVAEAPNYQGPPPPYP 560
mLATS  ............m..v....t.s.....s.p.i.......s...........                 396 hLATS  KHLLHQNPSVPPYESISKPSKEDQPSLPKEDESEKSYENVDSGDKEKKQITTSPITVRKNKDEERRESR  630
mLATS  ........v...c.de......d......adsg...                                 466 hLATS  IQSYSPQAFKFFMEQHVENVLKSHQQRLHRKKQLENEMMRVGLSQDAQDQMRKMLCQKESNYIRLKRAKM 700
mLATS  .....................................................................  536
```

FIG. 11A

```
hLATS  DKSMFVKIKTLGIGAFGEVCLARKVDTKALYATKTLRKKDVLLRNQVAHVKAERDILAEADNEWVVRLYY  770
mLATS  .................................................................n.  606 hLATS  SFQDKDNLYFVMDYIPGGDMMSLLIRMGIFPESLARFYIAELTCAVESVHKMGFIHRDIKPDNILIDRDG  840
mLATS  .................................................................n.  676 hLATS  HIKLTDFGLCTGFRWTHDSKYYQSGDHPRQDSMDFSNEWGDPSSCRCGDRLKPLERRAARQHQRCLAHSL  910
mLATS  ........................................................n...........  746 hLATS  VGTPNYIAPEVLLRTGYTQLCDWWSVGVILFEMLVGQPPFLAQTPLETQMKVINWQTSLHIPPQAKLSPE  980
mLATS  ..........c..................................i......................  816 hLATS  ASDLIIKLCRGPEDRLGKNGADEIKAHPFFKTIDFSSDLRQQSASYIPKITHPTDTSNFDPVDPDKLWSD  1050
mLATS  .....................................................................  886 hLATS  DNEEENVNDTLNGWYKNGKHPEHAFYEFTFRRFFDDNGYPYNYPKPIEYEYINSQGSEQQSDEDDQNTGS  1120
mLATS  gs....is...s.........................................h.........h.s.  966 hLATS  EIKNRDLVYV  1130
mLATS  dgn.......
```

FIG. 11B

```
hLATS   MKRSEKPEGYRQMRPKTFPASNYTVSSRQMLQEIRESLRNLSKPSDAAKAEHNMSKMSTEDPRQVRNPPK    70
mLATS2                                                                   m.at..   45 hLATS   FGTHHKALQEIRNSLLPFANETNSSRSTSEVNPQMLQDLQAAGFDEDMVIQALQKTMNRSIEAAIEFISK   140
mLATS2  ..pyq...r..y......sgt.-aaa...r....e.vn.ac.qe.agr..tq.gs.........y...    114

150       160       170       180       190       200       210
hLATS   MSYQDPRREQMAAAAARPINASMKPGNVQQSVNRKQSWKGSKESLVPQRHGPPLGESVAYHSESPNSQTD   210
mLATS2  .g.l....n...i-vrvikqtspg-..lastp.t.rp.fe.tg.a..-sy..-q..-gan.--.g.aalee  175 hLATS   VGRPLSGSGISAFVQAHPSNGQRVNPPPPPPQVRSVTPPPPPRGQTPPPPRGTTPPPPSWEPNSQTKRYSGN   280
mLATS2  mp.qy-------------------------------------------------------ldflfpgag hLATS   MEYVISRISPVPPGAWQEGYPPPLNTSPMNPPNQGQRGISSVPVGRQPIIMQSSSKFNFPSGRPGMQNG   350
mLATS2  agthgaqahqh..----k....-stave.sahfpgthy.rghllseqsgygv.r..s.q-nktp.dayss  251 hLATS   TGQTDFMIHQNVVPAGTVNRQPPPPYPLTAANGQSPSALQTGGSAAPSSYTNGSIPQSMMVPNRNSHNME   420
mLATS2  makaqgppasltfpahaglytashhk-p..tppgahp.hvl.trg.-tf.ge.sa.avla.s...l.ad   319 hLATS   LYNISVPGLQTNWPQSSSAPAQSSPSSGHEIPTWQPNIPVRSNSFNNPLGNRASHSANSQPSATTVTAIT   490
mLATS2  ..elg-stv--p.saapl.rrd.lqkq...-asr-.hvaf.agp-srtnsfnnpqpep.l.apn....v.  383 hLATS   PAPIQQPVKSMRVLKPELQTALAPTHPSWIPQPIQTVQPSPFPEGTASNVTVMPPVAEAPNYQGPPPPYP   560
mLATS2  a.h.lh....v...r..pQ..v.g.s..a.vaa.tapate.letkegsagphpldvdyggserrc......  453 hLATS   RHLLHQNPSVP---PYESISKPSKEDQPSLPKEDESEKSYENVDSGDKEKKQITTSPITVRKNKKDEERRESR 630
mLATS2  ....lpSk.eqySvdld.lCtsvqqslrggtdl.g.d..hakg.kagrd....q....vp....sr....k....  528
```

FIG. 12A

```
hLATS   IQSYSPQAFKFFMEQHVENVLKSHQQRLHRKKQLENEMMRVGLSQDAQDQMRKMLCQKESNYIRLKRAKM    700
mLATS2  .k...y.............i.ty..kvs.rl...q..aka..ceae.e....i.y......n.........    598 hLATS   DKSMFVKIKTLGIGAFGEVCLARKVDTKALYATKTLRKKDVLLRNQVAHVXAERDILAEADNEWVVRLYY      770
mLATS2  ....................c.l..h...m.......n....................k...            668 hLATS   SFQDKDNLYFVMDYIPGGDMMSLLIRMGIFPESLARFYIAELTCAVESVHKMGFIHRDIKPDNILIDRDG      840
mLATS2  .......s..................ev..h............l.i........................    738 hLATS   HIKLTDFGLCTGFRWTHDSKYYQ-SGDHPRQDSMDFSNEWGDPSSCRCGDRLKPLERRAARQHQRCLAHSL     910
mLATS2  .................n.......-k.n.m.....epgdl.d.v.n........t.q..qk........    808 hLATS   VGTPNYIAPEVLLRTGYTQLCDWWSVGVILFEMLVGQPPFLAQTPLETQMKVINWQTSLHIPPQAKLSPE      980
mLATS2  ........................k..........................p..t..l....est....t.vr..a.   878 hLATS   ASDLIIKLCRGPEDRLGKNGADEIKAHPFFKTIDFSSDLRQQSASYIPKITHPTDTSNFDPVDPDICLWSD    1050
mLATS2  .r..t...caadc...rd....dl......n.....r.i.k.a.p.v.t.s..m.........eesp.he      948 hLATS   DNEEENVN-DTLNGWYKNGKHPEHAFYEFTFRRFFDDNGYPYNYPKPIEYEYINSQGSEQQSDEDDQNTGS    1120
mLATS2  asg.sakaw...as--pss...........................frc...s.paesadpgdadleg -------  1009 hLATS   EIKNRDLVYV 1130
mLATS2  aaegcqp... 1119
```

FIG. 12B

```
                       LSD2a
h-LATS  MKRSEKPEGYRQMRPKTFPASNYTVSS|RQML|QEIRESLRNLSKPSDAAKAEHNMSKMSTEDPRQVRNPPK-     70
LATS    _____Mh.agekrggrpnd.yta.alesikqdltr                  30 h-LATS  FGTHHKALQEIRNSLLPFANETNSSRSTSEVNPQMLQDLQAAGFDEDMVIQALQKTNNRSIEAAIEFISK         140
LATS    .evqnnhrnnq-.ytp.ryta..grndaltpdyhhakqpmepppsaspapdvv-ippppa.vgqpgag.-         97 h-LATS  MSYQDPRREQMAAAAARPINASMKPGNVQQSVNRKQSWKGSKESLVPQRHGPPLGESVAYHSE-SPNSQTD        210
LATS    i..vsgvgvgvvgv.ng.-v-p-.mtalmpnkli..p.ierdta.shyl.cs.a.dsgagssrsd..h.h-h      165
                                                   SH3-BINDING
h-LATS  VGRPLSGSGISAFVQAHPSNGQRVNPPPPPQVRSVT|PPPPPRGQTPPPRGTTPPPPSW|EPNSQTKRYSGN       280
LATS    thq.----s.rt.gnpgg..g-fs.s.sgfsevap|.a....np.assaa.p...vpp|tsqayv...r.pa      229
                                                       LSD1a
h-LATS  MEYVISRISPVPPGAWQEGYPPPPLNTSPMNPPNQGQRGISSVPVGR|QP|IMQS|SSKFNFPSGRPGMQNG       350
LATS    lnnrppa.a.ptqrgnspvitqng.k-n.qqqlt.qlksInly.g.gsgavvepppypyliqg.ag.aapp       298 h-LATS  TGQTDFMIHQNVVPAGTVNRQPPPPYPLTAANGQSPSALQTGGSAAPSSYTNGSIPQSMMVPNRNSHNME         420
LATS    ppppsytasmqsrqsp.qsq.s--d.rkspss.iy-..-tsa..ps.itvslppa.lakpq.rvyqarsq        364 h-LATS  LYNISVPGLQTNWPQSSSA--PAQSSPSSGHEIPTWQPNIPVRSNSFNNPLGNRASHSANSQPSATTVTAIT       490
LATS    |qpi.mqs|vks.qvqkpvIqtav.pq...|.asasnspvhvlsappsypqksaavvqqqqqaaaaahqqqhqhq  436
         LSD1a      LSD1p                                          LSD2a    LSD2p
h-LATS  PAPIQQP|VKSMRVLKPELQTALAPTHPSW|IPQPIQTVQPSPFPEGTASNVTVMPPVAEAPNYQG|PPPPY|p     560
LATS    qskppt.ttppl.glnskpnc.e.psyaksm.akaatvv erdqrerrerdqqklangnpg|rqml|.....q    545
``` qqqqqqqqqqqvqqqqvqqqqqqqqql qalrvlqaqaqr        snnnnnseikppscnnnni

FIG.13A

```
                                                           ┌─ LFD
h-LATS  KHLLHQNPSVPYESISKPSKEDQPSLPKEDESEKS-YENVDSGDKEKKQITTSPITVRKN—K-KDEERRESR  630
LATS    qisnsnlott..ipvkynnnssntgonssgg.ng.tgttos.stsc..ikho...pe..kis.e.e...k.f.  638 h-LATS  IQSYSPQAFKFFMEQHVENVLKSHQQRLHRKKQLENEMMRVGLSQDAQDQMRKMLCQKESNYIRLKRAKM  700
LATS    .rq.............i...i..yr..ty..n...k..hk...pdgt.ie.....n..............  708

LFD ┬─ KINASE DOMAIN
h-LATS  DKSMFVKIKTLGIGAFGEVCLARKVDT-KALYATKTLRKKDVLLRNQVAHVKAERDILAEADNEWVVRLYY  770
LATS    .........pi.v......t.vs.i..snh...m.....o...k................n...k....  779 h-LATS  SFQDKDNLYFVMDYIPGGDMMSLLIRMGIFPESLARFYIAELTCAVESVHKMGFIHRDIKPDNILIDRDG  840
LATS    ....................l.....kl...e.e........v....d....................  849 h-LATS  HIKLTDFGLCTGFRWTHDSKYYQ-SGDHPRQDSMDFSNEWGDPSSCRCGDRLKPLERRAARQHQRCLAHSL  910
LATS    ..................n.....en.n.s.....e-p—..eey.e-n-.pkptv....rm.d...v.....  915 h-LATS  VGTPNYIAPEVLLRTGYTQLCKWWSVGVILFEMLVGQPPFLAQTPLETQMKVINWQTSLHIPPQAKLSPE  980
LATS    ............e.s.......y........y............ns.....q.....ekt........e..r.  985

KINASE DOMAIN ┐
h-LATS  ASDLIIKLCRGPEDRLGKNGADEIKAHPFFKTIDFSSDLRQQSASYIPKIT│HPTDTSNFDPVDP│DKLWSD  1050
LATS    .t...rr..osodk....-sv..v.s.d...g...-o.m.k.k.p...e.k│.............│e..r.n  1053
                                                                LCD1
h-LATS  DNEEENVNDTLNGWYKNGKHPEHAF│YEFTFRRFFDD│NGYPYNYPKPIEYEYINSQGSEQQSDEDDQNTGS  1120
LATS    .stmssgd.-vd---q.dr-tf.g.f│...........│kqp.dmt---------------...op--  1096
                                  LCD2
h-LATS  EIKNRDL│VYV│  1130
LATS    -----│...│  1099
          LCD3
```

FIG. 13B

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 5720 base pairs
      (B) TYPE: nucleic acid
      (C) STRANDEDNESS: double
      (D) TOPOLOGY: unknown (ii) MOLECULE TYPE: cDNA (ix) FEATURE:
      (A) NAME/KEY: CDS
      (B) LOCATION: 1103..4402

(xi) SEQUENCE DESCRIPTION: SEQ ID NO:1:

```
ATCTAGCACG ACGGCAGCAA CAAAACCACG AATTAATTTT ACTAAATTTA AGCCAAACGC      60

GCATCGGAAA TGCCTGAAAA TGCGATTGAA TGCACGCGAA AAGTGATGGG TTGCGAACGC     120

GAGTGAATCA AGTGAAAATA CGTCGGCAAA TATCAGCGAA TTGTCGTCAA AAGGCAAGGA     180
```

-continued

```
AAAACGGAGA AAAAGAGGAA AAGCAATAAG TGCCGTGTGT GGGAAACGCG AAAAAGGCGA        240

GAACAAAGAG GCGAAAAGCG AGGAAATTGC GTGGAAAACG TGGAAAACGC GAAGAAGCGA        300

AGCTCCAAGT TGGCCGCCAT CGATTCGTGC GTAGGATCAA TTAAGATTCC GAGTGGTCGA        360

GAATCGGCTC AAATCAAATT AAAATCAACT AATATTTTGG TATTCAGATA TTCAAATGGA        420

ATTCATTCAT CGCCTGCGAC TTTTATTCGG ATCTGCCAAC TATTTTTGAA TTTGAATTGT        480

GTGTCTGCGG CTGGCGCAGA ATCTCTGATA AAGCAGAGGA ATAAAATCGG AAGAACAACA        540

AATACAAATA CAAATGAAAT GCGGGGAGCA GTATTTACAT GCCAAATGAA TGCTGGATAG        600

GCGAAAGGGG GGGTTTCTCT TATAATGCAA ATGTGAATGT GAATGCGAAT GCGAATGCGA        660

GTGGAAGAAT TCCCGGCGCG AGTGATAAAT AATCCGACGA CAAACAAAGC AGAAGCCTAC        720

ACCGCGAGAA AGAGCAGCGC AAACACAATT ATCTTTATTG AGAGCAACAA TATCAAGATC        780

GAGATAATAA AGCATCCTAA AACCCGCGCC TTAGTTCGTT TTAGTCTCGC CACGGATATA        840

GATATTCAAA GGCAAAAAGG TGGTGTCGGC ATCGCCAGAC AAACAAGTAA AGCATCTATT        900

TCATACAAAA CAACCAATTA AATAATAATA AAAATAATAA TAATCGTAGA GAGGCAGAGC        960

CAAATCAAAT TCCCGGCCGC CGATGTGCCC CAGTGTGTGT GCGTGTGTGT GTGTGTGTGC       1020

TGTGCTGTGC TGTGCGAGTG TTAGTGTGCG GAGCATTTCT GTGATATGAG TGCTAAATGC       1080

CACAGGGCGA AGCAGCAGCA TC ATG CAT CCA GCG GGC GAA AAA AGG GGC GGT       1132
                         Met His Pro Ala Gly Glu Lys Arg Gly Gly
                         1               5                   10

CGC CCC AAT GAT AAA TAC ACG GCG GAA GCC CTC GAG AGC ATC AAG CAG        1180
Arg Pro Asn Asp Lys Tyr Thr Ala Glu Ala Leu Glu Ser Ile Lys Gln
            15                  20                  25

GAC CTA ACC CGA TTT GAA GTA CAA AAT AAC CAT AGG AAT AAT CAG AAT        1228
Asp Leu Thr Arg Phe Glu Val Gln Asn Asn His Arg Asn Asn Gln Asn
        30                  35                  40

TAC ACA CCT CTG CGA TAC ACG GCG ACC AAC GGA CGC AAC GAT GCA CTT        1276
Tyr Thr Pro Leu Arg Tyr Thr Ala Thr Asn Gly Arg Asn Asp Ala Leu
    45                  50                  55

ACT CCT GAC TAT CAC CAC GCC AAG CAG CCG ATG GAG CCG CCA CCC TCC        1324
Thr Pro Asp Tyr His His Ala Lys Gln Pro Met Glu Pro Pro Pro Ser
60                  65                  70

GCC TCT CCT GCT CCG GAC GTG GTC ATA CCG CCG CCG GCC ATT GTA            1372
Ala Ser Pro Ala Pro Asp Val Val Ile Pro Pro Pro Ala Ile Val
75                  80                  85                  90

GGT CAG CCC GGA GCC GGC TCC ATA TCC GTA TCC GGT GTG GGC GTT GGA        1420
Gly Gln Pro Gly Ala Gly Ser Ile Ser Val Ser Gly Val Gly Val Gly
                95                  100                 105

GTG GTG GGT GTG GCG AAC GGA CGT GTG CCA AAG ATG ATG ACG GCC CTA        1468
Val Val Gly Val Ala Asn Gly Arg Val Pro Lys Met Met Thr Ala Leu
            110                 115                 120

ATG CCA AAC AAA CTG ATC CGG AAG CCG AGC ATC GAA CGG GAC ACG GCG        1516
Met Pro Asn Lys Leu Ile Arg Lys Pro Ser Ile Glu Arg Asp Thr Ala
        125                 130                 135

AGC AGT CAC TAC CTG CGC TGC AGT CCG GCT CTG GAC TCC GGA GCC GGT        1564
Ser Ser His Tyr Leu Arg Cys Ser Pro Ala Leu Asp Ser Gly Ala Gly
    140                 145                 150

AGC TCC CGA TCG GAC AGC CCC CAT TCG CAC CAC ACC CAC CAG CCG AGC        1612
Ser Ser Arg Ser Asp Ser Pro His Ser His His Thr His Gln Pro Ser
155                 160                 165                 170

TCG AGG ACG GTG GGT AAT CCA GGT GGA AAT GGT GGA TTT TCT CCG TCG        1660
Ser Arg Thr Val Gly Asn Pro Gly Gly Asn Gly Gly Phe Ser Pro Ser
                175                 180                 185

CCA AGC GGT TTC AGT GAG GTG GCT CCA CCG GCG CCG CCG CCA CGC AAT        1708
```

```
            Pro Ser Gly Phe Ser Glu Val Ala Pro Pro Ala Pro Pro Arg Asn
                        190                 195                 200

CCC ACC GCC TCC AGC GCG GCC ACG CCC CCA CCG CCA GTG CCG CCC ACC            1756
Pro Thr Ala Ser Ser Ala Ala Thr Pro Pro Pro Pro Val Pro Pro Thr
            205                 210                 215

AGC CAG GCG TAC GTG AAG CGG CGA TCA CCG GCC CTG AAC AAC CGC CCG            1804
Ser Gln Ala Tyr Val Lys Arg Arg Ser Pro Ala Leu Asn Asn Arg Pro
            220                 225                 230

CCG GCG ATA GCG CCA CCC ACT CAG CGA GGC AAC TCA CCT GTA ATA ACC            1852
Pro Ala Ile Ala Pro Pro Thr Gln Arg Gly Asn Ser Pro Val Ile Thr
235                 240                 245                 250

CAA AAC GGG CTG AAG AAC CCG CAG CAG CAG TTG ACG CAG CAG CTG AAG            1900
Gln Asn Gly Leu Lys Asn Pro Gln Gln Gln Leu Thr Gln Gln Leu Lys
            255                 260                 265

TCC CTG AAC CTA TAC CCA GGC GGA GGC AGT GGA GCA GTG GTG GAG CCA            1948
Ser Leu Asn Leu Tyr Pro Gly Gly Gly Ser Gly Ala Val Val Glu Pro
            270                 275                 280

CCG CCG CCC TAC CTA ATT CAA GGC GGA GCC GGA GGA GCA GCA CCG CCG            1996
Pro Pro Pro Tyr Leu Ile Gln Gly Gly Ala Gly Gly Ala Ala Pro Pro
            285                 290                 295

CCG CCA CCA CCC AGT TAC ACG GCC TCC ATG CAG TCG CGG CAG TCG CCC            2044
Pro Pro Pro Ser Tyr Thr Ala Ser Met Gln Ser Arg Gln Ser Pro
            300                 305                 310

ACA CAA TCC CAA CAA TCG GAC TAC AGG AAA TCC CCG AGC AGT GGG ATA            2092
Thr Gln Ser Gln Gln Ser Asp Tyr Arg Lys Ser Pro Ser Ser Gly Ile
315                 320                 325                 330

TAC TCG GCC ACC TCG GCC GGC TCG CCG AGC CCC ATA ACT GTG TCG CTG            2140
Tyr Ser Ala Thr Ser Ala Gly Ser Pro Ser Pro Ile Thr Val Ser Leu
            335                 340                 345

CCG CCG GCG CCG CTG GCG AAG CCA CAA CCA CGA GTC TAC CAG GCC AGG            2188
Pro Pro Ala Pro Leu Ala Lys Pro Gln Pro Arg Val Tyr Gln Ala Arg
            350                 355                 360

AGT CAG CAG CCG ATC ATC ATG CAG AGT GTG AAG AGC ACG CAG GTC CAA            2236
Ser Gln Gln Pro Ile Ile Met Gln Ser Val Lys Ser Thr Gln Val Gln
            365                 370                 375

AAG CCC GTG CTG CAA ACA GCA GTG GCG CGC CAA TCG CCA TCG AGT GCC            2284
Lys Pro Val Leu Gln Thr Ala Val Ala Arg Gln Ser Pro Ser Ser Ala
            380                 385                 390

TCG GCC AGC AAT TCA CCA GTC CAC GTG CTG GCC GCT CCA CCC TCT TAC            2332
Ser Ala Ser Asn Ser Pro Val His Val Leu Ala Ala Pro Pro Ser Tyr
395                 400                 405                 410

CCT CAG AAG TCC GCG GCA GTG GTG CAG CAG CAG CAA CAG GCA GCA GCG            2380
Pro Gln Lys Ser Ala Ala Val Val Gln Gln Gln Gln Gln Ala Ala Ala
            415                 420                 425

GCG GCC CAC CAG CAG CAG CAT CAG CAC CAG CAA TCC AAA CCA CCA ACG            2428
Ala Ala His Gln Gln Gln His Gln His Gln Gln Ser Lys Pro Pro Thr
            430                 435                 440

CCA ACC ACA CCG CCC TTG GTG GGT CTG AAC AGC AAG CCC AAT TGC CTG            2476
Pro Thr Thr Pro Pro Leu Val Gly Leu Asn Ser Lys Pro Asn Cys Leu
            445                 450                 455

GAG CCA CCG TCC TAT GCC AAG AGC ATG CAG GCC AAG GCG GCC ACG GTG            2524
Glu Pro Pro Ser Tyr Ala Lys Ser Met Gln Ala Lys Ala Ala Thr Val
            460                 465                 470

GTA CAG CAG CAG CAA CAG CAG CAG CAA CAA CAG CAG GTC CAG CAG CAG            2572
Val Gln Gln Gln Gln Gln Gln Gln Gln Gln Gln Gln Val Gln Gln Gln
475                 480                 485                 490

CAG GTG CAA CAG CAG CAG CAA CAG CAG CAA CAG CAA CTG CAG GCC TTG            2620
Gln Val Gln Gln Gln Gln Gln Gln Gln Gln Gln Leu Gln Ala Leu
            495                 500                 505

AGG GTG CTC CAG GCA CAG GCT CAG AGG GAG CGG GAT CAA CGG GAG CGG            2668
```

-continued

```
                Arg Val Leu Gln Ala Gln Ala Gln Arg Glu Arg Asp Gln Arg Glu Arg
                                510                 515                 520

GAA CGG GAT CAG CAG AAG CTG GCC AAC GGA AAT CCT GGC CGG CAG ATG           2716
Glu Arg Asp Gln Gln Lys Leu Ala Asn Gly Asn Pro Gly Arg Gln Met
            525                 530                 535

CTT CCG CCG CCG CCC TAT CAG AGC AAC AAC AAC AAC AAC AGC GAG ATC           2764
Leu Pro Pro Pro Pro Tyr Gln Ser Asn Asn Asn Asn Asn Ser Glu Ile
540                 545                 550

AAA CCG CCG AGC TGC AAC AAC AAC AAC ATA CAG ATA AGC AAC AGC AAC           2812
Lys Pro Pro Ser Cys Asn Asn Asn Asn Ile Gln Ile Ser Asn Ser Asn
555                 560                 565                 570

CTG GCG ACG ACA CCA CCC ATT CCG CCT GCC AAA TAC AAT AAC AAC TCC           2860
Leu Ala Thr Thr Pro Pro Ile Pro Pro Ala Lys Tyr Asn Asn Asn Ser
                575                 580                 585

TCC AAC ACG GGC GCG AAT AGC TCG GGC GGC AGC AAC GGA TCC ACC GGC           2908
Ser Asn Thr Gly Ala Asn Ser Ser Gly Gly Ser Asn Gly Ser Thr Gly
                590                 595                 600

ACC ACC GCC TCC TCG TCG ACC AGC TGC AAG AAG ATC AAG CAC GCC TCG           2956
Thr Thr Ala Ser Ser Ser Thr Ser Cys Lys Lys Ile Lys His Ala Ser
                605                 610                 615

CCC ATC CCG GAG CGC AAG AAG ATC TCC AAG GAG AAG GAG GAG GAG CGC           3004
Pro Ile Pro Glu Arg Lys Lys Ile Ser Lys Glu Lys Glu Glu Glu Arg
620                 625                 630

AAG GAG TTC CGC ATC AGG CAG TAC TCG CCG CAA GCC TTC AAG TTC TTC           3052
Lys Glu Phe Arg Ile Arg Gln Tyr Ser Pro Gln Ala Phe Lys Phe Phe
635                 640                 645                 650

ATG GAG CAG CAC ATA GAG AAC GTG ATC AAG TCG TAT CGC CAG CGC ACG           3100
Met Glu Gln His Ile Glu Asn Val Ile Lys Ser Tyr Arg Gln Arg Thr
                655                 660                 665

TAT CGC AAG AAT CAG CTG GAG AAG GAG ATG CAC AAA GTG GGA CTG CCC           3148
Tyr Arg Lys Asn Gln Leu Glu Lys Glu Met His Lys Val Gly Leu Pro
                670                 675                 680

GAT CAG ACC CAA ATC GAG ATG AGG AAA ATG CTG AAC CAA AAG GAG AGC           3196
Asp Gln Thr Gln Ile Glu Met Arg Lys Met Leu Asn Gln Lys Glu Ser
                685                 690                 695

AAC TAC ATT CGA TTG AAG CGC GCC AAG ATG GAC AAG AGC ATG TTC GTC           3244
Asn Tyr Ile Arg Leu Lys Arg Ala Lys Met Asp Lys Ser Met Phe Val
700                 705                 710

AAA CTG AAG CCC ATT GGA GTG GGT GCA TTT GGC GAG GTA ACG CTG GTG           3292
Lys Leu Lys Pro Ile Gly Val Gly Ala Phe Gly Glu Val Thr Leu Val
715                 720                 725                 730

AGC AAA ATC GAT ACC TCG AAC CAT TTG TAT GCG ATG AAA ACC CTG CGG           3340
Ser Lys Ile Asp Thr Ser Asn His Leu Tyr Ala Met Lys Thr Leu Arg
                735                 740                 745

AAA GCG GAC GTT CTC AAG CGG AAT CAG GTG GCA CAC GTG AAG GCC GAG           3388
Lys Ala Asp Val Leu Lys Arg Asn Gln Val Ala His Val Lys Ala Glu
                750                 755                 760

AGG GAT ATC CTC GCG GAA GCC GAC AAT AAC TGG GTG GTG AAG TTG TAC           3436
Arg Asp Ile Leu Ala Glu Ala Asp Asn Asn Trp Val Val Lys Leu Tyr
                765                 770                 775

TAC AGC TTC CAG GAC AAG GAT AAT CTG TAC TTT GTG ATG GAC TAC ATA           3484
Tyr Ser Phe Gln Asp Lys Asp Asn Leu Tyr Phe Val Met Asp Tyr Ile
                780                 785                 790

CCA GGT GGT GAT CTG ATG TCG CTG CTC ATC AAA CTG GGC ATT TTC GAG           3532
Pro Gly Gly Asp Leu Met Ser Leu Leu Ile Lys Leu Gly Ile Phe Glu
795                 800                 805                 810

GAG GAA CTG GCC AGA TTC TAC ATC GCC GAG GTC ACC TGC GCC GTG GAC           3580
Glu Glu Leu Ala Arg Phe Tyr Ile Ala Glu Val Thr Cys Ala Val Asp
                815                 820                 825

AGC GTT CAC AAA ATG GGC TTC ATT CAC AGA GAC ATC AAG CCT GAC AAC           3628
```

```
Ser Val His Lys Met Gly Phe Ile His Arg Asp Ile Lys Pro Asp Asn
        830             835             840

ATA CTC ATC GAT AGG GAC GGA CAC ATA AAG CTC ACC GAC TTT GGC CTG      3676
Ile Leu Ile Asp Arg Asp Gly His Ile Lys Leu Thr Asp Phe Gly Leu
            845             850             855

TGC ACG GGA TTC CGA TGG ACG CAC AAC TCG AAG TAC TAC CAG GAG AAC      3724
Cys Thr Gly Phe Arg Trp Thr His Asn Ser Lys Tyr Tyr Gln Glu Asn
860             865             870

GGC AAT CAC TCG CGC CAG GAC TCG ATG GAG CCC TGG GAG GAA TAC TCC      3772
Gly Asn His Ser Arg Gln Asp Ser Met Glu Pro Trp Glu Glu Tyr Ser
875             880             885             890

GAG AAC GGA CCG AAG CCC ACC GTG CTG GAG AGG CGA CGG ATG CGC GAT      3820
Glu Asn Gly Pro Lys Pro Thr Val Leu Glu Arg Arg Arg Met Arg Asp
                895             900             905

CAC CAA AGA GTC CTG GCC CAC TCG CTG GTG GGC ACC CCG AAC TAC ATA      3868
His Gln Arg Val Leu Ala His Ser Leu Val Gly Thr Pro Asn Tyr Ile
            910             915             920

GCT CCC GAG GTG CTG GAG AGG AGT GGG TAC ACG CAG CTG TGC GAC TAC      3916
Ala Pro Glu Val Leu Glu Arg Ser Gly Tyr Thr Gln Leu Cys Asp Tyr
            925             930             935

TGG AGC GTG GGC GTC ATC CTT TAC GAG ATG CTG GTG GGT CAG CCG CCC      3964
Trp Ser Val Gly Val Ile Leu Tyr Glu Met Leu Val Gly Gln Pro Pro
940             945             950

TTT CTG GCC AAC AGT CCG CTG GAA ACG CAA CAA AAG GTC ATC AAC TGG      4012
Phe Leu Ala Asn Ser Pro Leu Glu Thr Gln Gln Lys Val Ile Asn Trp
955             960             965             970

GAG AAA ACG CTG CAT ATT CCG CCG CAG GCC GAG TTA TCC CGC GAG GCT      4060
Glu Lys Thr Leu His Ile Pro Pro Gln Ala Glu Leu Ser Arg Glu Ala
                975             980             985

ACG GAC TTG ATA AGG AGG CTC TGT GCG TCG GCT GAC AAG CGG CTG GGC      4108
Thr Asp Leu Ile Arg Arg Leu Cys Ala Ser Ala Asp Lys Arg Leu Gly
            990             995             1000

AAG AGC GTG GAC GAG GTC AAG AGC CAC GAC TTC TTC AAG GGC ATC GAC      4156
Lys Ser Val Asp Glu Val Lys Ser His Asp Phe Phe Lys Gly Ile Asp
        1005            1010            1015

TTT GCG GAC ATG CGG AAG CAG AAA GCG CCC TAC ATA CCG GAA ATC AAG      4204
Phe Ala Asp Met Arg Lys Gln Lys Ala Pro Tyr Ile Pro Glu Ile Lys
        1020            1025            1030

CAC CCA ACG GAC ACA TCC AAC TTT GAT CCC GTG GAT CCG GAG AAG CTG      4252
His Pro Thr Asp Thr Ser Asn Phe Asp Pro Val Asp Pro Glu Lys Leu
1035            1040            1045            1050

CGC TCG AAT GAC TCC ACC ATG AGC AGC GGC GAT GAT GTC GAC CAG AAT      4300
Arg Ser Asn Asp Ser Thr Met Ser Ser Gly Asp Asp Val Asp Gln Asn
                1055            1060            1065

GAC CGC ACT TTC CAC GGC TTT TTC GAA TTT ACC TTC CGT CGC TTC TTC      4348
Asp Arg Thr Phe His Gly Phe Phe Glu Phe Thr Phe Arg Arg Phe Phe
            1070            1075            1080

GAC GAC AAG CAG CCG CCG GAT ATG ACG GAC GAT CAG GCG CCG GTT TAC      4396
Asp Asp Lys Gln Pro Pro Asp Met Thr Asp Asp Gln Ala Pro Val Tyr
        1085            1090            1095

GTC TGA AATGGATGCT CTCCATGTGC CCAACACCAA CACCCCGCCC CCGAATCATT        4452
Val *
    1100

GTTAGTCAAA TAGTCACAAA AAGGGGATAG AAACCATTGA GTGGGCTTGC ATTGTAAAGG    4512

AAGCGTGGCT ATAGAATGAA ACTATCTATA TACATTATAT AAATTATAGG AGACAGTAGA    4572

GGCGGGAGCT ACGTATATAC ATACAAATAA TATACATATA TTTGATATAT ATATATATAT    4632

ATATGCCGTA GGGCATGAAC TGAATAAATA TAAAACGGAG CCGAGTAGAG ATGAAACGAG    4692

AGGAGCGAGT CAGGACCTTC GACCTTTAAC TGAACATAGT ATATCCTTGT GCACTACTAC    4752
```

```
TCCACAACAA ATATATATTT TTAAATTGTT AGAATTCAAA AGGGACCAAC TGGAAATCGA    4812

ACCTTTCTGG TGCTCAAAGC AAAGCAAAGC AAAGCAAAAC AAAACGCCTT AAACTAAATG    4872

AGACGCGAAT TTACCCAACC ACTTCACTCC TCTCCTTTCT CCACCTCCGA TCGGTGGCCG    4932

GATTCGAACT CAGCAGGCTG GTTGCATCCG GCCATCCCAT TGACTTCCCA TTCAGAATTG    4992

AGATTGCGAG GTGTGCGATG GAGAACGAAC GGAGACCAAA AGTCGCACGG CAGCGATATA    5052

AGCGGGTCTT ATAAGCCTAA TCTAAATCTA AACTGGGAGA ACAGGACCTA TGTATGTCCT    5112

GCTATCCAAT TCGTCTATCA CTGCTCTTCA TCTGTGTACG ACCCCACCC CCCCCCTCCC     5172

CATCCAAAAG AACAAACTTA GACGTAGCCT ATGTGAAAAG CTAGCAATGT TAGACCAACT    5232

TGTTGAATGC CAAATGAAAT TGTTTAGCCC CACGAGGAAA ACGCGGGGGA AATTCAACAC    5292

TTATTCTCTG ATAGCAAACG GAAAGAAAG AAAGAAAAAA AAAAACAGAA ACAGTACGAG     5352

AAAATTGTAA TCTTCTTAAT GTAATATTGT AAAGAACACG TTAATTGTAA TCTATGCTAG    5412

AGTTGTGTAG CGCCCTAAGA TGTTTTTTAG TTTATAGACC GCTAACCGTA ATCTAGTTTA    5472

ATTCCTAACA CTAAGCGAGA GTACAGTACA TTGGTTTTTT TGTTTGTCGT AGGTTCGTTG    5532

GAAAATGCTT AACGGAAAC GATTTGTTTT TCTCTTTAAT TAGCTTCAGT TTGTATGTGC     5592

GTGTGTTTTT ATTATGACTT ATATATAGTC CATCTGAATA TTCGTGGATG GAGCCTATTT    5652

TAAATGTGAG ATCGAGCTAA TTGAAGGAAA TACAAACAAA CTCTGTGTGC CTTGGCCAAT    5712

TAGTTTAC                                                             5720
```

(2) INFORMATION FOR SEQ ID NO:2:

(i) SEQUENCE CHARACTERISTICS:
        (A) LENGTH: 1099 amino acids
        (B) TYPE: amino acid
        (D) TOPOLOGY: unknown (ii) MOLECULE TYPE: protein (xi) SEQUENCE DESCRIPTION: SEQ ID NO:2:

```
Met His Pro Ala Gly Glu Lys Arg Gly Gly Arg Pro Asn Asp Lys Tyr
 1               5                  10                  15

Thr Ala Glu Ala Leu Glu Ser Ile Lys Gln Asp Leu Thr Arg Phe Glu
            20                  25                  30

Val Gln Asn Asn His Arg Asn Asn Gln Asn Tyr Thr Pro Leu Arg Tyr
        35                  40                  45

Thr Ala Thr Asn Gly Arg Asn Asp Ala Leu Thr Pro Asp Tyr His His
    50                  55                  60

Ala Lys Gln Pro Met Glu Pro Pro Ser Ala Ser Pro Ala Pro Asp
65                  70                  75                  80

Val Val Ile Pro Pro Pro Ala Ile Val Gly Gln Pro Gly Ala Gly
                85                  90                  95

Ser Ile Ser Val Ser Gly Val Gly Val Val Gly Val Ala Asn
                100                 105                 110

Gly Arg Val Pro Lys Met Met Thr Ala Leu Met Pro Asn Lys Leu Ile
            115                 120                 125

Arg Lys Pro Ser Ile Glu Arg Asp Thr Ala Ser Ser His Tyr Leu Arg
        130                 135                 140

Cys Ser Pro Ala Leu Asp Ser Gly Ala Gly Ser Ser Arg Ser Asp Ser
145                 150                 155                 160

Pro His Ser His His Thr His Gln Pro Ser Ser Arg Thr Val Gly Asn
                165                 170                 175
```

-continued

```
Pro Gly Gly Asn Gly Gly Phe Ser Pro Ser Pro Ser Gly Phe Ser Glu
            180                 185                 190

Val Ala Pro Ala Pro Pro Arg Asn Pro Thr Ala Ser Ser Ala
        195                 200                 205

Ala Thr Pro Pro Pro Val Pro Pro Thr Ser Gln Ala Tyr Val Lys
    210                 215                 220

Arg Arg Ser Pro Ala Leu Asn Asn Arg Pro Pro Ala Ile Ala Pro Pro
225                 230                 235                 240

Thr Gln Arg Gly Asn Ser Pro Val Ile Thr Gln Asn Gly Leu Lys Asn
                245                 250                 255

Pro Gln Gln Gln Leu Thr Gln Leu Lys Ser Leu Asn Leu Tyr Pro
                260                 265                 270

Gly Gly Gly Ser Gly Ala Val Val Glu Pro Pro Pro Tyr Leu Ile
            275                 280                 285

Gln Gly Gly Ala Gly Ala Ala Pro Pro Pro Pro Ser Tyr
        290                 295                 300

Thr Ala Ser Met Gln Ser Arg Gln Ser Pro Thr Gln Ser Gln Gln Ser
305                 310                 315                 320

Asp Tyr Arg Lys Ser Pro Ser Ser Gly Ile Tyr Ser Ala Thr Ser Ala
                325                 330                 335

Gly Ser Pro Ser Pro Ile Thr Val Ser Leu Pro Pro Ala Pro Leu Ala
            340                 345                 350

Lys Pro Gln Pro Arg Val Tyr Gln Ala Arg Ser Gln Gln Pro Ile Ile
        355                 360                 365

Met Gln Ser Val Lys Ser Thr Gln Val Gln Lys Pro Val Leu Gln Thr
    370                 375                 380

Ala Val Ala Arg Gln Ser Pro Ser Ser Ala Ser Ala Ser Asn Ser Pro
385                 390                 395                 400

Val His Val Leu Ala Ala Pro Pro Ser Tyr Pro Gln Lys Ser Ala Ala
                405                 410                 415

Val Val Gln Gln Gln Gln Ala Ala Ala Ala His Gln Gln Gln
            420                 425                 430

His Gln His Gln Gln Ser Lys Pro Pro Thr Pro Thr Thr Pro Pro Leu
        435                 440                 445

Val Gly Leu Asn Ser Lys Pro Asn Cys Leu Glu Pro Pro Ser Tyr Ala
    450                 455                 460

Lys Ser Met Gln Ala Lys Ala Ala Thr Val Val Gln Gln Gln Gln
465                 470                 475                 480

Gln Gln Gln Gln Gln Gln Val Gln Gln Gln Val Gln Gln Gln
                485                 490                 495

Gln Gln Gln Gln Gln Leu Gln Ala Leu Arg Val Leu Gln Ala Gln
            500                 505                 510

Ala Gln Arg Glu Arg Asp Gln Arg Glu Arg Asp Gln Gln Lys
        515                 520                 525

Leu Ala Asn Gly Asn Pro Gly Arg Gln Met Leu Pro Pro Pro Tyr
    530                 535                 540

Gln Ser Asn Asn Asn Asn Ser Glu Ile Lys Pro Pro Ser Cys Asn
545                 550                 555                 560

Asn Asn Asn Ile Gln Ile Ser Asn Ser Asn Leu Ala Thr Thr Pro Pro
                565                 570                 575

Ile Pro Pro Ala Lys Tyr Asn Asn Asn Ser Ser Asn Thr Gly Ala Asn
            580                 585                 590

Ser Ser Gly Gly Ser Asn Gly Ser Thr Gly Thr Thr Ala Ser Ser Ser
        595                 600                 605
```

-continued

| | | | | | | | | | | | |
|---|---|---|---|---|---|---|---|---|---|---|---|
|Thr|Ser|Cys|Lys|Lys|Ile|Lys|His|Ala|Ser|Pro|Ile|Pro|Glu|Arg|Lys|
| |610| | | |615| | | |620| | | | | | |

Lys Ile Ser Lys Glu Lys Glu Glu Arg Lys Glu Phe Arg Ile Arg
625             630             635             640

Gln Tyr Ser Pro Gln Ala Phe Lys Phe Phe Met Glu Gln His Ile Glu
            645             650             655

Asn Val Ile Lys Ser Tyr Arg Gln Arg Thr Tyr Arg Lys Asn Gln Leu
            660             665             670

Glu Lys Glu Met His Lys Val Gly Leu Pro Asp Gln Thr Gln Ile Glu
675             680             685

Met Arg Lys Met Leu Asn Gln Lys Glu Ser Asn Tyr Ile Arg Leu Lys
    690             695             700

Arg Ala Lys Met Asp Lys Ser Met Phe Val Lys Leu Lys Pro Ile Gly
705             710             715             720

Val Gly Ala Phe Gly Glu Val Thr Leu Val Ser Lys Ile Asp Thr Ser
                725             730             735

Asn His Leu Tyr Ala Met Lys Thr Leu Arg Lys Ala Asp Val Leu Lys
            740             745             750

Arg Asn Gln Val Ala His Val Lys Ala Glu Arg Asp Ile Leu Ala Glu
    755             760             765

Ala Asp Asn Asn Trp Val Val Lys Leu Tyr Tyr Ser Phe Gln Asp Lys
770             775             780

Asp Asn Leu Tyr Phe Val Met Asp Tyr Ile Pro Gly Gly Asp Leu Met
785             790             795             800

Ser Leu Leu Ile Lys Leu Gly Ile Phe Glu Glu Glu Leu Ala Arg Phe
                805             810             815

Tyr Ile Ala Glu Val Thr Cys Ala Val Asp Ser Val His Lys Met Gly
            820             825             830

Phe Ile His Arg Asp Ile Lys Pro Asp Asn Ile Leu Ile Asp Arg Asp
    835             840             845

Gly His Ile Lys Leu Thr Asp Phe Gly Leu Cys Thr Gly Phe Arg Trp
850             855             860

Thr His Asn Ser Lys Tyr Tyr Gln Glu Asn Gly Asn His Ser Arg Gln
865             870             875             880

Asp Ser Met Glu Pro Trp Glu Tyr Ser Glu Asn Gly Pro Lys Pro
                885             890             895

Thr Val Leu Glu Arg Arg Arg Met Arg Asp His Gln Arg Val Leu Ala
            900             905             910

His Ser Leu Val Gly Thr Pro Asn Tyr Ile Ala Pro Glu Val Leu Glu
    915             920             925

Arg Ser Gly Tyr Thr Gln Leu Cys Asp Tyr Trp Ser Val Gly Val Ile
930             935             940

Leu Tyr Glu Met Leu Val Gly Gln Pro Pro Phe Leu Ala Asn Ser Pro
945             950             955             960

Leu Glu Thr Gln Gln Lys Val Ile Asn Trp Glu Lys Thr Leu His Ile
                965             970             975

Pro Pro Gln Ala Glu Leu Ser Arg Glu Ala Thr Asp Leu Ile Arg Arg
            980             985             990

Leu Cys Ala Ser Ala Asp Lys Arg Leu Gly Lys Ser Val Asp Glu Val
    995             1000            1005

Lys Ser His Asp Phe Phe Lys Gly Ile Asp Phe Ala Asp Met Arg Lys
1010            1015            1020

Gln Lys Ala Pro Tyr Ile Pro Glu Ile Lys His Pro Thr Asp Thr Ser

-continued

```
           1025                1030                1035                1040
Asn Phe Asp Pro Val Asp Pro Glu Lys Leu Arg Ser Asn Asp Ser Thr
                    1045                1050                1055

Met Ser Ser Gly Asp Asp Val Asp Gln Asn Asp Arg Thr Phe His Gly
            1060                1065                1070

Phe Phe Glu Phe Thr Phe Arg Arg Phe Phe Asp Asp Lys Gln Pro Pro
        1075                1080                1085

Asp Met Thr Asp Asp Gln Ala Pro Val Tyr Val
    1090                1095                1100
```

(2) INFORMATION FOR SEQ ID NO:3:

(i) SEQUENCE CHARACTERISTICS:
        (A) LENGTH: 3983 amino acids
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 231..3623

(xi) SEQUENCE DESCRIPTION: SEQ ID NO:3:

```
ACCTTTGGGT TGCTGGGACG GACTCTGGCC GCCTCAGCGT CCGCCCTCAG GCCCGTGGCC    60

GCTGTCCAGG AGCTCTGCTC TCCCCTCCAG AGTTAATTAT TTATATTGTA AAGAATTTTA   120

ACAGTCCTGG GGACTTCCTT GAAGGATCAT TTTCACTTTT GCTCAGAAGA AAGCTCTGGA   180

TCTATCAAAT AAAGAAGTCC TTCGTGTGGG CTACATATAT AGATGTTTTC ATG AAG      236
                                                      Met Lys
                                                        1

AGG AGT GAA AAG CCA GAA GGA TAT AGA CAA ATG AGG CCT AAG ACC TTT    284
Arg Ser Glu Lys Pro Glu Gly Tyr Arg Gln Met Arg Pro Lys Thr Phe
      5                  10                  15

CCT GCC AGT AAC TAT ACT GTC AGT AGC CGG CAA ATG TTA CAA GAA ATT    332
Pro Ala Ser Asn Tyr Thr Val Ser Ser Arg Gln Met Leu Gln Glu Ile
 20                  25                  30

CGG GAA TCC CTT AGG AAT TTA TCT AAA CCA TCT GAT GCT GCT AAG GCT    380
Arg Glu Ser Leu Arg Asn Leu Ser Lys Pro Ser Asp Ala Ala Lys Ala
 35                  40                  45                  50

GAG CAT AAC ATG AGT AAA ATG TCA ACC GAA GAT CCT CGA CAA GTC AGA    428
Glu His Asn Met Ser Lys Met Ser Thr Glu Asp Pro Arg Gln Val Arg
                 55                  60                  65

AAT CCA CCC AAA TTT GGG ACG CAT CAT AAA GCC TTG CAG GAA ATT CGA    476
Asn Pro Pro Lys Phe Gly Thr His His Lys Ala Leu Gln Glu Ile Arg
         70                  75                  80

AAC TCT CTG CTT CCA TTT GCA AAT GAA ACA AAT TCT TCT CGG AGT ACT    524
Asn Ser Leu Leu Pro Phe Ala Asn Glu Thr Asn Ser Ser Arg Ser Thr
     85                  90                  95

TCA GAA GTT AAT CCA CAA ATG CTT CAA GAC TTG CAA GCT GCT GGA TTT    572
Ser Glu Val Asn Pro Gln Met Leu Gln Asp Leu Gln Ala Ala Gly Phe
100                 105                 110

GAT GAG GAT ATG GTT ATA CAA GCT CTT CAG AAA ACT AAC AAC AGA AGT    620
Asp Glu Asp Met Val Ile Gln Ala Leu Gln Lys Thr Asn Asn Arg Ser
115                 120                 125                 130

ATA GAA GCA GCA ATT GAA TTC ATT AGT AAA ATG AGT TAC CAA GAT CCT    668
Ile Glu Ala Ala Ile Glu Phe Ile Ser Lys Met Ser Tyr Gln Asp Pro
                135                 140                 145

CGA CGA GAG CAG ATG GCT GCA GCA GCT GCC AGA CCT ATT AAT GCC AGC    716
Arg Arg Glu Gln Met Ala Ala Ala Ala Ala Arg Pro Ile Asn Ala Ser
            150                 155                 160
```

```
ATG AAA CCA GGG AAT GTG CAG CAA TCA GTT AAC CGC AAA CAG AGC TGG      764
Met Lys Pro Gly Asn Val Gln Gln Ser Val Asn Arg Lys Gln Ser Trp
        165                 170                 175

AAA GGT TCT AAA GAA TCC TTA GTT CCT CAG AGG CAT GGC CCG CCA CTA      812
Lys Gly Ser Lys Glu Ser Leu Val Pro Gln Arg His Gly Pro Pro Leu
        180                 185                 190

GGA GAA AGT GTG GCC TAT CAT TCT GAG AGT CCC AAC TCA CAG ACA GAT      860
Gly Glu Ser Val Ala Tyr His Ser Glu Ser Pro Asn Ser Gln Thr Asp
195                 200                 205                 210

GTA GGA AGA CCT TTG TCT GGA TCT GGT ATA TCA GCA TTT GTT CAA GCT      908
Val Gly Arg Pro Leu Ser Gly Ser Gly Ile Ser Ala Phe Val Gln Ala
                215                 220                 225

CAC CCT AGC AAC GGA CAG AGA GTG AAC CCC CCA CCA CCA CCT CAA GTA      956
His Pro Ser Asn Gly Gln Arg Val Asn Pro Pro Pro Pro Pro Gln Val
            230                 235                 240

AGG AGT GTT ACT CCT CCA CCA CCT CCA AGA GGC CAG ACT CCC CCT CCA     1004
Arg Ser Val Thr Pro Pro Pro Pro Pro Arg Gly Gln Thr Pro Pro Pro
            245                 250                 255

AGA GGT ACA ACT CCA CCT CCC CCT TCA TGG GAA CCA AAC TCT CAA ACA     1052
Arg Gly Thr Thr Pro Pro Pro Pro Ser Trp Glu Pro Asn Ser Gln Thr
260                 265                 270

AAG CGC TAT TCT GGA AAC ATG GAA TAC GTA ATC TCC CGA ATC TCT CCT     1100
Lys Arg Tyr Ser Gly Asn Met Glu Tyr Val Ile Ser Arg Ile Ser Pro
275                 280                 285                 290

GTC CCA CCT GGG GCA TGG CAA GAG GGC TAT CCT CCA CCA CCT CTC AAC     1148
Val Pro Pro Gly Ala Trp Gln Glu Gly Tyr Pro Pro Pro Pro Leu Asn
                295                 300                 305

ACT TCC CCC ATG AAT CCT CCT AAT CAA GGA CAG AGA GGC ATT AGT TCT     1196
Thr Ser Pro Met Asn Pro Pro Asn Gln Gly Gln Arg Gly Ile Ser Ser
            310                 315                 320

GTT CCT GTT GGC AGA CAA CCA ATC ATC ATG CAG AGT TCT AGC AAA TTT     1244
Val Pro Val Gly Arg Gln Pro Ile Ile Met Gln Ser Ser Ser Lys Phe
            325                 330                 335

AAC TTT CCA TCA GGG AGA CCT GGA ATG CAG AAT GGT ACT GGA CAA ACT     1292
Asn Phe Pro Ser Gly Arg Pro Gly Met Gln Asn Gly Thr Gly Gln Thr
        340                 345                 350

GAT TTC ATG ATA CAC CAA AAT GTT GTC CCT GCT GGC ACT GTG AAT CGG     1340
Asp Phe Met Ile His Gln Asn Val Val Pro Ala Gly Thr Val Asn Arg
355                 360                 365                 370

CAG CCA CCA CCT CCA TAT CCT CTG ACA GCA GCT AAT GGA CAA AGC CCT     1388
Gln Pro Pro Pro Pro Tyr Pro Leu Thr Ala Ala Asn Gly Gln Ser Pro
                375                 380                 385

TCT GCT TTA CAA ACA GGG GGA TCT GCT GCT CCT TCG TCA TAT ACA AAT     1436
Ser Ala Leu Gln Thr Gly Gly Ser Ala Ala Pro Ser Ser Tyr Thr Asn
            390                 395                 400

GGA AGT ATT CCT CAG TCT ATG ATG GTG CCA AAC AGA AAT AGT CAT AAC     1484
Gly Ser Ile Pro Gln Ser Met Met Val Pro Asn Arg Asn Ser His Asn
            405                 410                 415

ATG GAA CTA TAT AAC ATT AGT GTA CCT GGA CTG CAA ACA AAT TGG CCT     1532
Met Glu Leu Tyr Asn Ile Ser Val Pro Gly Leu Gln Thr Asn Trp Pro
        420                 425                 430

CAG TCA TCT TCT GCT CCA GCC CAG TCA TCC CCG AGC AGT GGG CAT GAA     1580
Gln Ser Ser Ser Ala Pro Ala Gln Ser Ser Pro Ser Ser Gly His Glu
435                 440                 445                 450

ATC CCT ACA TGG CAA CCT AAC ATA CCA GTG AGG TCA AAT TCT TTT AAT     1628
Ile Pro Thr Trp Gln Pro Asn Ile Pro Val Arg Ser Asn Ser Phe Asn
                455                 460                 465

AAC CCA TTA GGA AAT AGA GCA AGT CAC TCT GCT AAT TCT CAG CCT TCT     1676
Asn Pro Leu Gly Asn Arg Ala Ser His Ser Ala Asn Ser Gln Pro Ser
            470                 475                 480
```

```
GCT ACA ACA GTC ACT GCA ATT ACA CCA GCT CCT ATT CAA CAG CCT GTG    1724
Ala Thr Thr Val Thr Ala Ile Thr Pro Ala Pro Ile Gln Gln Pro Val
            485                 490                 495

AAA AGT ATG CGT GTA TTA AAA CCA GAG CTA CAG ACT GCT TTA GCA CCT    1772
Lys Ser Met Arg Val Leu Lys Pro Glu Leu Gln Thr Ala Leu Ala Pro
500                 505                 510

ACA CAC CCT TCT TGG ATA CCA CAG CCA ATT CAA ACT GTT CAA CCC AGT    1820
Thr His Pro Ser Trp Ile Pro Gln Pro Ile Gln Thr Val Gln Pro Ser
515                 520                 525                 530

CCT TTT CCT GAG GGA ACC GCT TCA AAT GTG ACT GTG ATG CCA CCT GTT    1868
Pro Phe Pro Glu Gly Thr Ala Ser Asn Val Thr Val Met Pro Pro Val
                535                 540                 545

GCT GAA GCT CCA AAC TAT CAA GGA CCA CCA CCA CCC TAC CCA AAA CAT    1916
Ala Glu Ala Pro Asn Tyr Gln Gly Pro Pro Pro Pro Tyr Pro Lys His
            550                 555                 560

CTG CTG CAC CAA AAC CCA TCT GTT CCT CCA TAC GAG TCA ATC AGT AAG    1964
Leu Leu His Gln Asn Pro Ser Val Pro Pro Tyr Glu Ser Ile Ser Lys
            565                 570                 575

CCT AGC AAA GAG GAT CAG CCA AGC TTG CCC AAG GAA GAT GAG AGT GAA    2012
Pro Ser Lys Glu Asp Gln Pro Ser Leu Pro Lys Glu Asp Glu Ser Glu
580                 585                 590

AAG AGT TAT GAA AAT GTT GAT AGT GGG GAT AAA GAA AAG AAA CAG ATT    2060
Lys Ser Tyr Glu Asn Val Asp Ser Gly Asp Lys Glu Lys Lys Gln Ile
595                 600                 605                 610

ACA ACT TCA CCT ATT ACT GTT AGG AAA AAC AAG AAA GAT GAA GAG CGA    2108
Thr Thr Ser Pro Ile Thr Val Arg Lys Asn Lys Lys Asp Glu Glu Arg
                615                 620                 625

AGG GAA TCT CGT ATT CAA AGT TAT TCT CCT CAA GCA TTT AAA TTC TTT    2156
Arg Glu Ser Arg Ile Gln Ser Tyr Ser Pro Gln Ala Phe Lys Phe Phe
                630                 635                 640

ATG GAG CAA CAT GTA GAA AAT GTA CTC AAA TCT CAT CAG CAG CGT CTA    2204
Met Glu Gln His Val Glu Asn Val Leu Lys Ser His Gln Gln Arg Leu
            645                 650                 655

CAT CGT AAA AAA CAA TTA GAG AAT GAA ATG ATG CGG GTT GGA TTA TCT    2252
His Arg Lys Lys Gln Leu Glu Asn Glu Met Met Arg Val Gly Leu Ser
660                 665                 670

CAA GAT GCC CAG GAT CAA ATG AGA AAG ATG CTT TGC CAA AAA GAA TCT    2300
Gln Asp Ala Gln Asp Gln Met Arg Lys Met Leu Cys Gln Lys Glu Ser
675                 680                 685                 690

AAT TAC ATC CGT CTT AAA AGG GCT AAA ATG GAC AAG TCT ATG TTT GTG    2348
Asn Tyr Ile Arg Leu Lys Arg Ala Lys Met Asp Lys Ser Met Phe Val
                695                 700                 705

AAG ATA AAG ACA CTA GGA ATA GGA GCA TTT GGT GAA GTC TGT CTA GCA    2396
Lys Ile Lys Thr Leu Gly Ile Gly Ala Phe Gly Glu Val Cys Leu Ala
            710                 715                 720

AGA AAA GTA GAT ACT AAG GCT TTG TAT GCA ACA AAA ACT CTT CGA AAG    2444
Arg Lys Val Asp Thr Lys Ala Leu Tyr Ala Thr Lys Thr Leu Arg Lys
            725                 730                 735

AAA GAT GTT CTT CTT CGA AAT CAA GTC GCT CAT GTT AAG GCT GAG AGA    2492
Lys Asp Val Leu Leu Arg Asn Gln Val Ala His Val Lys Ala Glu Arg
740                 745                 750

GAT ATC CTG GCT GAA GCT GAC AAT GAA TGG GTA GTT CGT CTA TAT TAT    2540
Asp Ile Leu Ala Glu Ala Asp Asn Glu Trp Val Val Arg Leu Tyr Tyr
755                 760                 765                 770

TCA TTC CAA GAT AAG GAC AAT TTA TAC TTT GTA ATG GAC TAC ATT CCT    2588
Ser Phe Gln Asp Lys Asp Asn Leu Tyr Phe Val Met Asp Tyr Ile Pro
                775                 780                 785

GGG GGT GAT ATG ATG AGC CTA TTA ATT AGA ATG GGC ATC TTT CCA GAA    2636
Gly Gly Asp Met Met Ser Leu Leu Ile Arg Met Gly Ile Phe Pro Glu
                790                 795                 800
```

-continued

| | |
|---|---|
| AGT CTG GCA CGA TTC TAC ATA GCA GAA CTT ACC TGT GCA GTT GAA AGT<br>Ser Leu Ala Arg Phe Tyr Ile Ala Glu Leu Thr Cys Ala Val Glu Ser<br>805                    810                    815 | 2684 |
| GTT CAT AAA ATG GGT TTT ATT CAT AGA GAT ATT AAA CCT GAT AAT ATT<br>Val His Lys Met Gly Phe Ile His Arg Asp Ile Lys Pro Asp Asn Ile<br>    820                    825                    830 | 2732 |
| TTG ATT GAT CGT GAT GGT CAT ATT AAA TTG ACT GAC TTT GGC CTC TGC<br>Leu Ile Asp Arg Asp Gly His Ile Lys Leu Thr Asp Phe Gly Leu Cys<br>835                    840                    845                    850 | 2780 |
| ACT GGC TTC AGA TGG ACA CAC GAT TCT AAG TAC TAT CAG AGT GGT GAC<br>Thr Gly Phe Arg Trp Thr His Asp Ser Lys Tyr Tyr Gln Ser Gly Asp<br>                    855                    860                    865 | 2828 |
| CAT CCA CGG CAA GAT AGC ATG GAT TTC AGT AAT GAA TGG GGG GAT CCC<br>His Pro Arg Gln Asp Ser Met Asp Phe Ser Asn Glu Trp Gly Asp Pro<br>    870                    875                    880 | 2876 |
| TCA AGC TGT CGA TGT GGA GAC AGA CTG AAG CCA TTA GAG CGG AGA GCT<br>Ser Ser Cys Arg Cys Gly Asp Arg Leu Lys Pro Leu Glu Arg Arg Ala<br>885                    890                    895 | 2924 |
| GCA CGC CAG CAC CAG CGA TGT CTA GCA CAT TCT TTG GTT GGG ACT CCC<br>Ala Arg Gln His Gln Arg Cys Leu Ala His Ser Leu Val Gly Thr Pro<br>    900                    905                    910 | 2972 |
| AAT TAT ATT GCA CCT GAA GTG TTG CTA CGA ACA GGA TAC ACA CAG TTG<br>Asn Tyr Ile Ala Pro Glu Val Leu Leu Arg Thr Gly Tyr Thr Gln Leu<br>915                    920                    925                    930 | 3020 |
| TGT GAT TGG TGG AGT GTT GGT GTT ATT CTT TTT GAA ATG TTG GTG GGA<br>Cys Asp Trp Trp Ser Val Gly Val Ile Leu Phe Glu Met Leu Val Gly<br>                    935                    940                    945 | 3068 |
| CAA CCT CCT TTC TTG GCA CAA ACA CCA TTA GAA ACA CAA ATG AAG GTT<br>Gln Pro Pro Phe Leu Ala Gln Thr Pro Leu Glu Thr Gln Met Lys Val<br>                    950                    955                    960 | 3116 |
| ATC AAC TGG CAA ACA TCT CTT CAC ATT CCA CCA CAA GCT AAA CTC AGT<br>Ile Asn Trp Gln Thr Ser Leu His Ile Pro Pro Gln Ala Lys Leu Ser<br>        965                    970                    975 | 3164 |
| CCT GAA GCT TCT GAT CTT ATT ATT AAA CTT TGC CGA GGA CCC GAA GAT<br>Pro Glu Ala Ser Asp Leu Ile Ile Lys Leu Cys Arg Gly Pro Glu Asp<br>980                    985                    990 | 3212 |
| CGC TTA GGC AAG AAT GGT GCT GAT GAA ATA AAA GCT CAT CCA TTT TTT<br>Arg Leu Gly Lys Asn Gly Ala Asp Glu Ile Lys Ala His Pro Phe Phe<br>995                    1000                 1005                1010 | 3260 |
| AAA ACA ATT GAC TTC TCC AGT GAC CTG AGA CAG CAG TCT GCT TCA TAC<br>Lys Thr Ile Asp Phe Ser Ser Asp Leu Arg Gln Gln Ser Ala Ser Tyr<br>                  1015                 1020                1025 | 3308 |
| ATT CCT AAA ATC ACA CAC CCA ACA GAT ACA TCA AAT TTT GAT CCT GTT<br>Ile Pro Lys Ile Thr His Pro Thr Asp Thr Ser Asn Phe Asp Pro Val<br>                1030                 1035                1040 | 3356 |
| GAT CCT GAT AAA TTA TGG AGT GAT GAT AAC GAG GAA GAA AAT GTA AAT<br>Asp Pro Asp Lys Leu Trp Ser Asp Asp Asn Glu Glu Glu Asn Val Asn<br>            1045                 1050                1055 | 3404 |
| GAC ACT CTC AAT GGA TGG TAT AAA AAT GGA AAG CAT CCT GAA CAT GCA<br>Asp Thr Leu Asn Gly Trp Tyr Lys Asn Gly Lys His Pro Glu His Ala<br>        1060                 1065                1070 | 3452 |
| TTC TAT GAA TTT ACC TTC CGA AGG TTT TTT GAT GAC AAT GGC TAC CCA<br>Phe Tyr Glu Phe Thr Phe Arg Arg Phe Phe Asp Asp Asn Gly Tyr Pro<br>1075                  1080                 1085                1090 | 3500 |
| TAT AAT TAT CCG AAG CCT ATT GAA TAT GAA TAC ATT AAT TCA CAA GGC<br>Tyr Asn Tyr Pro Lys Pro Ile Glu Tyr Glu Tyr Ile Asn Ser Gln Gly<br>            1095                 1100                1105 | 3548 |
| TCA GAG CAG CAG TCG GAT GAA GAT GAT CAA AAC ACA GGC TCA GAG ATT<br>Ser Glu Gln Gln Ser Asp Glu Asp Asp Gln Asn Thr Gly Ser Glu Ile<br>        1110                 1115                1120 | 3596 |

```
AAA AAT CGC GAT CTA GTA TAT GTT TAA CACACTAGTA AATAAATGTA          3643
Lys Asn Arg Asp Leu Val Tyr Val
        1125            1130

ATGAGGATTT GTAAAAGGGC CTGAAATGCG AGGTGTTTTG AGGTTCTGAG AGTAAAATTA  3703

TGCAAATATG ACAGAGCTAT ATATGTGTGC TCTGTGTACA ATATTTTATT TTCCTAAATT  3763

ATGGAAATC CTTTTAAAAT GTTAATTTAT TCCAGCCGTT TAAATCAGTA TTTAGAAAAA   3823

AATTGTTATA AGGAAAGTAA ATTATGAACT GAATATTATA GTCAGTTCTT GGTACTTAAA  3883

GTACTTAAAA TAAGTAGTGC TTTGTTTAAA AGGAGAAACC TGGTATCTAT TTGTATATAT  3943

GCTAAATAAT TTTAAAATAC AAGAGTTTTT GAAATTTTTT T                      3984
```

(2) INFORMATION FOR SEQ ID NO:4:

(i) SEQUENCE CHARACTERISTICS:
        (A) LENGTH: 1130 amino acids
        (B) TYPE: amino acid
        (D) TOPOLOGY: unknown (ii) MOLECULE TYPE: protein (xi) SEQUENCE DESCRIPTION: SEQ ID NO:4:

```
Met Lys Arg Ser Glu Lys Pro Glu Gly Tyr Arg Gln Met Arg Pro Lys
 1               5                  10                  15

Thr Phe Pro Ala Ser Asn Tyr Thr Val Ser Ser Arg Gln Met Leu Gln
                20                  25                  30

Glu Ile Arg Glu Ser Leu Arg Asn Leu Ser Lys Pro Ser Asp Ala Ala
            35                  40                  45

Lys Ala Glu His Asn Met Ser Lys Met Ser Thr Glu Asp Pro Arg Gln
        50                  55                  60

Val Arg Asn Pro Pro Lys Phe Gly Thr His Lys Ala Leu Gln Glu
 65                  70                  75                  80

Ile Arg Asn Ser Leu Leu Pro Phe Ala Asn Glu Thr Asn Ser Ser Arg
                85                  90                  95

Ser Thr Ser Glu Val Asn Pro Gln Met Leu Gln Asp Leu Gln Ala Ala
            100                 105                 110

Gly Phe Asp Glu Asp Met Val Ile Gln Ala Leu Gln Lys Thr Asn Asn
        115                 120                 125

Arg Ser Ile Glu Ala Ala Ile Glu Phe Ile Ser Lys Met Ser Tyr Gln
130                 135                 140

Asp Pro Arg Arg Glu Gln Met Ala Ala Ala Ala Arg Pro Ile Asn
145                 150                 155                 160

Ala Ser Met Lys Pro Gly Asn Val Gln Gln Ser Val Asn Arg Lys Gln
                165                 170                 175

Ser Trp Lys Gly Ser Lys Glu Ser Leu Val Pro Gln Arg His Gly Pro
            180                 185                 190

Pro Leu Gly Glu Ser Val Ala Tyr His Ser Glu Ser Pro Asn Ser Gln
        195                 200                 205

Thr Asp Val Gly Arg Pro Leu Ser Gly Ser Gly Ile Ser Ala Phe Val
    210                 215                 220

Gln Ala His Pro Ser Asn Gly Gln Arg Val Asn Pro Pro Pro Pro
225                 230                 235                 240

Gln Val Arg Ser Val Thr Pro Pro Pro Pro Arg Gly Gln Thr Pro
                245                 250                 255

Pro Pro Arg Gly Thr Thr Pro Pro Pro Ser Trp Glu Pro Asn Ser
            260                 265                 270
```

-continued

```
Gln Thr Lys Arg Tyr Ser Gly Asn Met Glu Tyr Val Ile Ser Arg Ile
        275                 280                 285

Ser Pro Val Pro Pro Gly Ala Trp Gln Glu Gly Tyr Pro Pro Pro Pro
    290                 295                 300

Leu Asn Thr Ser Pro Met Asn Pro Pro Asn Gln Gly Gln Arg Gly Ile
305                 310                 315                 320

Ser Ser Val Pro Val Gly Arg Gln Pro Ile Ile Met Gln Ser Ser Ser
                325                 330                 335

Lys Phe Asn Phe Pro Ser Gly Arg Pro Gly Met Gln Asn Gly Thr Gly
            340                 345                 350

Gln Thr Asp Phe Met Ile His Gln Asn Val Val Pro Ala Gly Thr Val
        355                 360                 365

Asn Arg Gln Pro Pro Pro Tyr Pro Leu Thr Ala Ala Asn Gly Gln
    370                 375                 380

Ser Pro Ser Ala Leu Gln Thr Gly Gly Ser Ala Ala Pro Ser Ser Tyr
385                 390                 395                 400

Thr Asn Gly Ser Ile Pro Gln Ser Met Met Val Pro Asn Arg Asn Ser
                405                 410                 415

His Asn Met Glu Leu Tyr Asn Ile Ser Val Pro Gly Leu Gln Thr Asn
            420                 425                 430

Trp Pro Gln Ser Ser Ser Ala Pro Ala Gln Ser Ser Pro Ser Ser Gly
        435                 440                 445

His Glu Ile Pro Thr Trp Gln Pro Asn Ile Pro Val Arg Ser Asn Ser
    450                 455                 460

Phe Asn Asn Pro Leu Gly Asn Arg Ala Ser His Ser Ala Asn Ser Gln
465                 470                 475                 480

Pro Ser Ala Thr Thr Val Thr Ala Ile Thr Pro Ala Pro Ile Gln Gln
                485                 490                 495

Pro Val Lys Ser Met Arg Val Leu Lys Pro Glu Leu Gln Thr Ala Leu
            500                 505                 510

Ala Pro Thr His Pro Ser Trp Ile Pro Gln Pro Ile Gln Thr Val Gln
        515                 520                 525

Pro Ser Pro Phe Pro Glu Gly Thr Ala Ser Asn Val Thr Val Met Pro
    530                 535                 540

Pro Val Ala Glu Ala Pro Asn Tyr Gln Gly Pro Pro Pro Tyr Pro
545                 550                 555                 560

Lys His Leu Leu His Gln Asn Pro Ser Val Pro Pro Tyr Glu Ser Ile
                565                 570                 575

Ser Lys Pro Ser Lys Glu Asp Gln Pro Ser Leu Pro Lys Glu Asp Glu
            580                 585                 590

Ser Glu Lys Ser Tyr Glu Asn Val Asp Ser Gly Asp Lys Glu Lys Lys
        595                 600                 605

Gln Ile Thr Thr Ser Pro Ile Thr Val Arg Lys Asn Lys Lys Asp Glu
    610                 615                 620

Glu Arg Arg Glu Ser Arg Ile Gln Ser Tyr Ser Pro Gln Ala Phe Lys
625                 630                 635                 640

Phe Phe Met Glu Gln His Val Glu Asn Val Leu Lys Ser His Gln Gln
                645                 650                 655

Arg Leu His Arg Lys Lys Gln Leu Glu Asn Glu Met Met Arg Val Gly
            660                 665                 670

Leu Ser Gln Asp Ala Gln Asp Gln Met Arg Lys Met Leu Cys Gln Lys
        675                 680                 685

Glu Ser Asn Tyr Ile Arg Leu Lys Arg Ala Lys Met Asp Lys Ser Met
    690                 695                 700
```

```
Phe Val Lys Ile Lys Thr Leu Gly Ile Gly Ala Phe Gly Glu Val Cys
705                 710                 715                 720

Leu Ala Arg Lys Val Asp Thr Lys Ala Leu Tyr Ala Thr Lys Thr Leu
            725                 730                 735

Arg Lys Lys Asp Val Leu Leu Arg Asn Gln Val Ala His Val Lys Ala
                740                 745                 750

Glu Arg Asp Ile Leu Ala Glu Ala Asp Asn Glu Trp Val Val Arg Leu
            755                 760                 765

Tyr Tyr Ser Phe Gln Asp Lys Asp Asn Leu Tyr Phe Val Met Asp Tyr
            770                 775                 780

Ile Pro Gly Gly Asp Met Met Ser Leu Leu Ile Arg Met Gly Ile Phe
785                 790                 795                 800

Pro Glu Ser Leu Ala Arg Phe Tyr Ile Ala Glu Leu Thr Cys Ala Val
                805                 810                 815

Glu Ser Val His Lys Met Gly Phe Ile His Arg Asp Ile Lys Pro Asp
            820                 825                 830

Asn Ile Leu Ile Asp Arg Asp Gly His Ile Lys Leu Thr Asp Phe Gly
            835                 840                 845

Leu Cys Thr Gly Phe Arg Trp Thr His Asp Ser Lys Tyr Tyr Gln Ser
850                 855                 860

Gly Asp His Pro Arg Gln Asp Ser Met Asp Phe Ser Asn Glu Trp Gly
865                 870                 875                 880

Asp Pro Ser Ser Cys Arg Cys Gly Asp Arg Leu Lys Pro Leu Glu Arg
                885                 890                 895

Arg Ala Ala Arg Gln His Gln Arg Cys Leu Ala His Ser Leu Val Gly
                900                 905                 910

Thr Pro Asn Tyr Ile Ala Pro Glu Val Leu Leu Arg Thr Gly Tyr Thr
            915                 920                 925

Gln Leu Cys Asp Trp Trp Ser Val Gly Val Ile Leu Phe Glu Met Leu
            930                 935                 940

Val Gly Gln Pro Pro Phe Leu Ala Gln Thr Pro Leu Glu Thr Gln Met
945                 950                 955                 960

Lys Val Ile Asn Trp Gln Thr Ser Leu His Ile Pro Pro Gln Ala Lys
                965                 970                 975

Leu Ser Pro Glu Ala Ser Asp Leu Ile Ile Lys Leu Cys Arg Gly Pro
            980                 985                 990

Glu Asp Arg Leu Gly Lys Asn Gly Ala Asp Glu Ile Lys Ala His Pro
            995                 1000                1005

Phe Phe Lys Thr Ile Asp Phe Ser Ser Asp Leu Arg Gln Gln Ser Ala
    1010                1015                1020

Ser Tyr Ile Pro Lys Ile Thr His Pro Thr Asp Thr Ser Asn Phe Asp
1025                1030                1035                1040

Pro Val Asp Pro Asp Lys Leu Trp Ser Asp Asp Asn Glu Glu Glu Asn
                1045                1050                1055

Val Asn Asp Thr Leu Asn Gly Trp Tyr Lys Asn Gly Lys His Pro Glu
            1060                1065                1070

His Ala Phe Tyr Glu Phe Thr Phe Arg Arg Phe Phe Asp Asp Asn Gly
        1075                1080                1085

Tyr Pro Tyr Asn Tyr Pro Lys Pro Ile Glu Tyr Glu Tyr Ile Asn Ser
        1090                1095                1100

Gln Gly Ser Glu Gln Gln Ser Asp Glu Asp Gln Asn Thr Gly Ser
1105                1110                1115                1120

Glu Ile Lys Asn Arg Asp Leu Val Tyr Val
```

(2) INFORMATION FOR SEQ ID NO:5:

(i) SEQUENCE CHARACTERISTICS:
        (A) LENGTH: 3212 amino acids
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..2889

(xi) SEQUENCE DESCRIPTION: SEQ ID NO:5:

```
GTG CAA CAT TCA ATT AAC CGA AAA CAA AGC TGG AAA GGT TCT AAA GAG      48
Val Gln His Ser Ile Asn Arg Lys Gln Ser Trp Lys Gly Ser Lys Glu
 1               5                  10                  15

TCT CTA GTT CCT CAG AGA CAC GGC CCA TCT CTA GGA GAA AAT GTG GTT      96
Ser Leu Val Pro Gln Arg His Gly Pro Ser Leu Gly Glu Asn Val Val
             20                  25                  30

TAT CGT TCT GAA AGC CCC AAC TCA CAG GCG GAT GTA GGA AGA CCT CTG     144
Tyr Arg Ser Glu Ser Pro Asn Ser Gln Ala Asp Val Gly Arg Pro Leu
         35                  40                  45

TCT GGA TCC GGC ATT GCA GCA TTT GCT CAA GCT CAC CCA AGC AAT GGA     192
Ser Gly Ser Gly Ile Ala Ala Phe Ala Gln Ala His Pro Ser Asn Gly
     50                  55                  60

CAG AGA GTG AAC CCC CCA CCA CCT CAA GTT AGG AGT GTT ACT CCT         240
Gln Arg Val Asn Pro Pro Pro Pro Gln Val Arg Ser Val Thr Pro
 65                  70                  75                  80

CCA CCA CCT CCG AGA GGC CAG ACC CCA CCT CCC CGA GGC ACC ACT CCC     288
Pro Pro Pro Pro Arg Gly Gln Thr Pro Pro Pro Arg Gly Thr Thr Pro
                 85                  90                  95

CCT CCC CCC TCA TGG GAA CCA AGC TCT CAG ACA AAG CGC TAC TCT GGG     336
Pro Pro Pro Ser Trp Glu Pro Ser Ser Gln Thr Lys Arg Tyr Ser Gly
             100                 105                 110

AAC ATG GAG TAC GTA ATC TCC CGA ATC TCC CCT GTT CCA CCT GGG GCG     384
Asn Met Glu Tyr Val Ile Ser Arg Ile Ser Pro Val Pro Pro Gly Ala
         115                 120                 125

TGG CAG GAG GGG TAC CCT CCA CCA CCT CTT ACC ACT TCT CCC ATG AAT     432
Trp Gln Glu Gly Tyr Pro Pro Pro Pro Leu Thr Thr Ser Pro Met Asn
     130                 135                 140

CCC CCT AGC CAG GCT CAG AGG GCC ATT AGT TCT GTT CCA GTT GGT AGA     480
Pro Pro Ser Gln Ala Gln Arg Ala Ile Ser Ser Val Pro Val Gly Arg
145                 150                 155                 160

CAA CCC ATC ATC ATG CAG AGT ACT AGC AAA TTT AAC TTT ACA CCA GGG     528
Gln Pro Ile Ile Met Gln Ser Thr Ser Lys Phe Asn Phe Thr Pro Gly
                165                 170                 175

CGA CCT GGA GTT CAG AAT GGT GGT GGT CAG TCT GAT TTT ATC GTG CAC     576
Arg Pro Gly Val Gln Asn Gly Gly Gly Gln Ser Asp Phe Ile Val His
            180                 185                 190

CAA AAT GTC CCC ACT GGT TCT GTG ACT CGG CAG CCA CCA CCT CCA TAT     624
Gln Asn Val Pro Thr Gly Ser Val Thr Arg Gln Pro Pro Pro Pro Tyr
        195                 200                 205

CCT CTG ACC CCA GCT AAT GGA CAA AGC CCC TCT GCT TTA CAA ACA GGG     672
Pro Leu Thr Pro Ala Asn Gly Gln Ser Pro Ser Ala Leu Gln Thr Gly
    210                 215                 220

GCT TCT GCT GCT CCA CCA TCA TTC GCC AAT GGA AAC GTT CCT CAG TCG     720
Ala Ser Ala Ala Pro Pro Ser Phe Ala Asn Gly Asn Val Pro Gln Ser
225                 230                 235                 240

ATG ATG GTG CCC AAC AGG AAC AGT CAT AAC ATG GAG CTT TAT AAT ATT     768
```

```
            Met Met Val Pro Asn Arg Asn Ser His Asn Met Glu Leu Tyr Asn Ile
                        245                 250                 255

AAT GTC CCT GGA CTG CAA ACA GCC TGG CCC CAG TCG TCT TCT GCT CCT           816
Asn Val Pro Gly Leu Gln Thr Ala Trp Pro Gln Ser Ser Ser Ala Pro
            260                 265                 270

GCG CAG TCA TCC CCA AGC GGT GGG CAT GAA ATT CCT ACA TGG CAA CCT           864
Ala Gln Ser Ser Pro Ser Gly Gly His Glu Ile Pro Thr Trp Gln Pro
            275                 280                 285

AAC ATA CCA GTG AGG TCA AAT TCT TTT AAT AAC CCA TTA GGA AGT AGA           912
Asn Ile Pro Val Arg Ser Asn Ser Phe Asn Asn Pro Leu Gly Ser Arg
            290                 295                 300

GCA AGT CAC TCT GCT AAT TCT CAG CCT TCT GCC ACT ACA GTC ACT GCC           960
Ala Ser His Ser Ala Asn Ser Gln Pro Ser Ala Thr Thr Val Thr Ala
305                 310                 315                 320

ATC ACA CCC GCT CCT ATT CAA CAG CCC GTG AAA AGC ATG CGC GTC CTG          1008
Ile Thr Pro Ala Pro Ile Gln Gln Pro Val Lys Ser Met Arg Val Leu
            325                 330                 335

AAA CCA GAG CTG CAG ACT GCT TTA GCC CCA ACC CAT CCT TCT TGG ATG          1056
Lys Pro Glu Leu Gln Thr Ala Leu Ala Pro Thr His Pro Ser Trp Met
            340                 345                 350

CCA CAG CCA GTT CAG ACT GTT CAG CCT ACC CCT TTT TCT GAG GGT ACA          1104
Pro Gln Pro Val Gln Thr Val Gln Pro Thr Pro Phe Ser Glu Gly Thr
            355                 360                 365

GCT TCA AGT GTG CCT GTC ATC CCA CCT GTT GCT GAA GCT CCA AGC TAT          1152
Ala Ser Ser Val Pro Val Ile Pro Pro Val Ala Glu Ala Pro Ser Tyr
            370                 375                 380

CAA GGT CCA CCA CCG CCT TAT CCA AAA CAT CTG CTA CAC CAA AAC CCA          1200
Gln Gly Pro Pro Pro Pro Tyr Pro Lys His Leu Leu His Gln Asn Pro
385                 390                 395                 400

TCT GTC CCT CCA TAT GAG TCA GTA AGT AAG CCC TGC AAA GAT GAA CAG          1248
Ser Val Pro Pro Tyr Glu Ser Val Ser Lys Pro Cys Lys Asp Glu Gln
            405                 410                 415

CCT AGC TTA CCC AAG GAA GAT GAT AGT GAG AAG AGT GCG GAC AGT GGT          1296
Pro Ser Leu Pro Lys Glu Asp Asp Ser Glu Lys Ser Ala Asp Ser Gly
            420                 425                 430

GAC TCT GGG GAT AAA GAA AAG AAA CAG ATT ACA ACT TCA CCT ATC ACT          1344
Asp Ser Gly Asp Lys Glu Lys Lys Gln Ile Thr Thr Ser Pro Ile Thr
            435                 440                 445

GTT CGG AAA AAC AAG AAA GAT GAA GAA CGA AGA GAG TCT CGG ATT CAG          1392
Val Arg Lys Asn Lys Lys Asp Glu Glu Arg Arg Glu Ser Arg Ile Gln
450                 455                 460

AGT TAC TCC CCA CAG GCC TTT AAG TTC TTC ATG GAG CAG CAC GTA GAG          1440
Ser Tyr Ser Pro Gln Ala Phe Lys Phe Phe Met Glu Gln His Val Glu
465                 470                 475                 480

AAC GTC CTG AAG TCT CAT CAG CAG CGT CTG CAT CGG AAG AAG CAG CTA          1488
Asn Val Leu Lys Ser His Gln Gln Arg Leu His Arg Lys Lys Gln Leu
            485                 490                 495

GAA AAT GAA ATG ATG CGG GTT GGA TTA TCT CAA GAT GCC CAG GAT CAA          1536
Glu Asn Glu Met Met Arg Val Gly Leu Ser Gln Asp Ala Gln Asp Gln
            500                 505                 510

ATG AGA AAG ATG CTT TGC CAG AAA GAG TCT AAC TAT ATT CGT CTT AAA          1584
Met Arg Lys Met Leu Cys Gln Lys Glu Ser Asn Tyr Ile Arg Leu Lys
            515                 520                 525

AGG GCT AAA ATG GAC AAG TCT ATG TTT GTA AAG ATA AAG ACA TTA GGA          1632
Arg Ala Lys Met Asp Lys Ser Met Phe Val Lys Ile Lys Thr Leu Gly
            530                 535                 540

ATA GGA GCG TTT GGT GAA GTC TGT CTA GCA AGA AAA GTC GAT ACT AAA          1680
Ile Gly Ala Phe Gly Glu Val Cys Leu Ala Arg Lys Val Asp Thr Lys
545                 550                 555                 560

GCT TTG TAT GCA ACA AAG ACT CTT CGA AAG AAA GAC GTT CTG CTC CGA          1728
```

```
                Ala Leu Tyr Ala Thr Lys Thr Leu Arg Lys Lys Asp Val Leu Leu Arg
                                565                 570                 575

AAT CAG GTG GCT CAT GTG AAA GCG GAG AGG GAT ATC CTA GCA GAA GCC              1776
Asn Gln Val Ala His Val Lys Ala Glu Arg Asp Ile Leu Ala Glu Ala
            580                 585                 590

GAC AAT GAG TGG GTG GTC CGC CTG TAC TAC TCT TTC CAG GAC AAG GAC              1824
Asp Asn Glu Trp Val Val Arg Leu Tyr Tyr Ser Phe Gln Asp Lys Asp
        595                 600                 605

AAC TTG TAC TTT GTG ATG GAC TAC ATT CCT GGG GGG GAT ATG ATG AGC              1872
Asn Leu Tyr Phe Val Met Asp Tyr Ile Pro Gly Gly Asp Met Met Ser
    610                 615                 620

CTA TTA ATT AGA ATG GGC ATC TTT CCT GAA AAT CTG GCA CGA TTC TAC              1920
Leu Leu Ile Arg Met Gly Ile Phe Pro Glu Asn Leu Ala Arg Phe Tyr
625                 630                 635                 640

ATA GCA GAA CTT ACC TGT GCA GTT GAA AGT GTT CAT AAA ATG GGT TTT              1968
Ile Ala Glu Leu Thr Cys Ala Val Glu Ser Val His Lys Met Gly Phe
                645                 650                 655

ATT CAT AGA GAT ATT AAA CCT GAT AAC ATT TTG ATT GAC CGT GAT GGC              2016
Ile His Arg Asp Ile Lys Pro Asp Asn Ile Leu Ile Asp Arg Asp Gly
            660                 665                 670

CAT ATT AAA TTG ACT GAC TTT GGC TTG TGC ACT GGC TTC AGA TGG ACA              2064
His Ile Lys Leu Thr Asp Phe Gly Leu Cys Thr Gly Phe Arg Trp Thr
        675                 680                 685

CAT GAC TCC AAG TAC TAC CAG AGT GGG GAT CAC CCA CGG CAA GAT AGC              2112
His Asp Ser Lys Tyr Tyr Gln Ser Gly Asp His Pro Arg Gln Asp Ser
    690                 695                 700

ATG GAT TTC AGT AAC GAA TGG GGA GAT CCT TCC AAT TGT CGG TGT GGG              2160
Met Asp Phe Ser Asn Glu Trp Gly Asp Pro Ser Asn Cys Arg Cys Gly
705                 710                 715                 720

GAC AGA CTG AAG CCA CTG GAG CGG AGA GCT GCT CGC CAG CAC CAG CGA              2208
Asp Arg Leu Lys Pro Leu Glu Arg Arg Ala Ala Arg Gln His Gln Arg
                725                 730                 735

TGT CTA GCC CAT TCT CTG GTT GGG ACT CCC AAT TAT ATT GCA CCT GAA              2256
Cys Leu Ala His Ser Leu Val Gly Thr Pro Asn Tyr Ile Ala Pro Glu
            740                 745                 750

GTG CTA CTG CGA ACA GGA TAT ACA CAG CTG TGT GAC TGG TGG AGT GTT              2304
Val Leu Leu Arg Thr Gly Tyr Thr Gln Leu Cys Asp Trp Trp Ser Val
        755                 760                 765

GGT GTT ATT CTT TGT GAA ATG TTG GTG GGA CAA CCT CCT TTC TTG GCA              2352
Gly Val Ile Leu Cys Glu Met Leu Val Gly Gln Pro Pro Phe Leu Ala
770                 775                 780

CAA ACC CCA TTA GAA ACA CAA ATG AAG GTT ATC ATC TGG CAA ACT TCT              2400
Gln Thr Pro Leu Glu Thr Gln Met Lys Val Ile Ile Trp Gln Thr Ser
                785                 790                 795                 800

CTA CAC ATC CCT CCT CAA GCT AAG CTG AGT CCT GAA GCC TCT GAC CTC              2448
Leu His Ile Pro Pro Gln Ala Lys Leu Ser Pro Glu Ala Ser Asp Leu
            805                 810                 815

ATT ATC AAA CTG TGT CGA GGA CCA GAA GAC CGC CTC GGC AAG AAC GGT              2496
Ile Ile Lys Leu Cys Arg Gly Pro Glu Asp Arg Leu Gly Lys Asn Gly
        820                 825                 830

GCT GAT GAG ATA AAG GCT CAT CCA TTT TTT AAG ACC ATC GAT TTC TCT              2544
Ala Asp Glu Ile Lys Ala His Pro Phe Phe Lys Thr Ile Asp Phe Ser
    835                 840                 845

AGT GAT CTG AGA CAG CAG TCT GCT TCA TAC ATC CCT AAA ATC ACG CAT              2592
Ser Asp Leu Arg Gln Gln Ser Ala Ser Tyr Ile Pro Lys Ile Thr His
850                 855                 860

CCA ACA GAT ACA TCC AAT TTC GAC CCT GTT GAT CCT GAT AAA TTG TGG              2640
Pro Thr Asp Thr Ser Asn Phe Asp Pro Val Asp Pro Asp Lys Leu Trp
865                 870                 875                 880

AGC GAT GGC AGC GAG GAG GAA AAT ATC AGT GAC ACT CTG AGC GGA TGG              2688
```

```
Ser Asp Gly Ser Glu Glu Asn Ile Ser Asp Thr Leu Ser Gly Trp
            885                 890                 895

TAT AAA AAT GGG AAG CAC CCC GAG CAC GCT TTC TAT GAG TTC ACC TTT      2736
Tyr Lys Asn Gly Lys His Pro Glu His Ala Phe Tyr Glu Phe Thr Phe
            900                 905                 910

CGG AGG TTT TTT GAT GAC AAT GGC TAC CCA TAT AAT TAT CCA AAG CCT      2784
Arg Arg Phe Phe Asp Asp Asn Gly Tyr Pro Tyr Asn Tyr Pro Lys Pro
            915                 920                 925

ATT GAG TAT GAA TAC ATT CAT TCA CAG GGC TCA GAA CAA CAG TCT GAT      2832
Ile Glu Tyr Glu Tyr Ile His Ser Gln Gly Ser Glu Gln Gln Ser Asp
        930                 935                 940

GAA GAT GAT CAA CAC ACA AGC TCC GAT GGA AAC AAC CGA GAT CTA GTG      2880
Glu Asp Asp Gln His Thr Ser Ser Asp Gly Asn Asn Arg Asp Leu Val
945                 950                 955                 960

TAT GTT TAA TAAACTAGGA GATCATTGTA AGAATTTGCA AGAGGCCTGA              2929
Tyr Val

AGTGCAGGGG TTTTTGAAGT TTTGAGAAAA TTATGCAAAT GTGACAGAGT TTGTGTGCTC    2989

TGTGTACAAT ATTTTATTTT CCTAAGTTAT GGGAAATTGT TTTAAAATGT TAATTTATTC    3049

CACCCTTTTA ATTCAGTAAT TTAGAAAAAA TTGTTATAAG GAAAGTAAAT TATGAACTGA    3109

GTATTATAGT CAATTCTTGG TACTTAAAGT ACTTAAAAAG AGAAGCCTGG TATCTTTTGT    3169

ATATATAATA AATAATTTTA AAATCCCAAA AAAAAAAAAA AAAA                     3213

(2) INFORMATION FOR SEQ ID NO:6:

(i) SEQUENCE CHARACTERISTICS:
        (A) LENGTH: 962 amino acids
        (B) TYPE: amino acid
        (D) TOPOLOGY: unknown (ii) MOLECULE TYPE: protein (xi) SEQUENCE DESCRIPTION: SEQ ID NO:6:

Val Gln His Ser Ile Asn Arg Lys Gln Ser Trp Lys Gly Ser Lys Glu
  1               5                  10                  15

Ser Leu Val Pro Gln Arg His Gly Pro Ser Leu Gly Glu Asn Val Val
             20                  25                  30

Tyr Arg Ser Glu Ser Pro Asn Ser Gln Ala Asp Val Gly Arg Pro Leu
         35                  40                  45

Ser Gly Ser Gly Ile Ala Ala Phe Ala Gln Ala His Pro Ser Asn Gly
     50                  55                  60

Gln Arg Val Asn Pro Pro Pro Pro Val Arg Ser Val Thr Pro
 65                  70                  75                  80

Pro Pro Pro Arg Gly Gln Thr Pro Pro Arg Gly Thr Thr Pro
             85                  90                  95

Pro Pro Pro Ser Trp Glu Pro Ser Ser Gln Thr Lys Arg Tyr Ser Gly
            100                 105                 110

Asn Met Glu Tyr Val Ile Ser Arg Ile Ser Pro Val Pro Pro Gly Ala
            115                 120                 125

Trp Gln Glu Gly Tyr Pro Pro Pro Leu Thr Thr Ser Pro Met Asn
            130                 135                 140

Pro Pro Ser Gln Ala Gln Arg Ala Ile Ser Ser Val Pro Val Gly Arg
145                 150                 155                 160

Gln Pro Ile Ile Met Gln Ser Thr Ser Lys Phe Asn Phe Thr Pro Gly
                165                 170                 175

Arg Pro Gly Val Gln Asn Gly Gly Gln Ser Asp Phe Ile Val His
            180                 185                 190
```

-continued

```
Gln Asn Val Pro Thr Gly Ser Val Thr Arg Gln Pro Pro Pro Tyr
    195                 200                 205
Pro Leu Thr Pro Ala Asn Gly Gln Ser Pro Ser Ala Leu Gln Thr Gly
    210                 215                 220
Ala Ser Ala Ala Pro Pro Ser Phe Ala Asn Asn Val Pro Gln Ser
225                 230                 235                 240
Met Met Val Pro Asn Arg Asn Ser His Asn Met Glu Leu Tyr Asn Ile
                245                 250                 255
Asn Val Pro Gly Leu Gln Thr Ala Trp Pro Gln Ser Ser Ser Ala Pro
            260                 265                 270
Ala Gln Ser Ser Pro Ser Gly Gly His Glu Ile Pro Thr Trp Gln Pro
        275                 280                 285
Asn Ile Pro Val Arg Ser Asn Ser Phe Asn Asn Pro Leu Gly Ser Arg
    290                 295                 300
Ala Ser His Ser Ala Asn Ser Gln Pro Ser Ala Thr Thr Val Thr Ala
305                 310                 315                 320
Ile Thr Pro Ala Pro Ile Gln Gln Pro Val Lys Ser Met Arg Val Leu
                325                 330                 335
Lys Pro Glu Leu Gln Thr Ala Leu Ala Pro Thr His Pro Ser Trp Met
            340                 345                 350
Pro Gln Pro Val Gln Thr Val Gln Pro Thr Pro Phe Ser Glu Gly Thr
        355                 360                 365
Ala Ser Ser Val Pro Val Ile Pro Pro Val Ala Glu Ala Pro Ser Tyr
    370                 375                 380
Gln Gly Pro Pro Pro Tyr Pro Lys His Leu Leu His Gln Asn Pro
385                 390                 395                 400
Ser Val Pro Pro Tyr Glu Ser Val Ser Lys Pro Cys Lys Asp Glu Gln
                405                 410                 415
Pro Ser Leu Pro Lys Glu Asp Asp Ser Glu Lys Ser Ala Asp Ser Gly
            420                 425                 430
Asp Ser Gly Asp Lys Glu Lys Lys Gln Ile Thr Thr Ser Pro Ile Thr
        435                 440                 445
Val Arg Lys Asn Lys Lys Asp Glu Glu Arg Arg Glu Ser Arg Ile Gln
    450                 455                 460
Ser Tyr Ser Pro Gln Ala Phe Lys Phe Phe Met Glu Gln His Val Glu
465                 470                 475                 480
Asn Val Leu Lys Ser His Gln Gln Arg Leu His Arg Lys Lys Gln Leu
                485                 490                 495
Glu Asn Glu Met Met Arg Val Gly Leu Ser Gln Asp Ala Gln Asp Gln
            500                 505                 510
Met Arg Lys Met Leu Cys Gln Lys Glu Ser Asn Tyr Ile Arg Leu Lys
        515                 520                 525
Arg Ala Lys Met Asp Lys Ser Met Phe Val Lys Ile Lys Thr Leu Gly
    530                 535                 540
Ile Gly Ala Phe Gly Glu Val Cys Leu Ala Arg Lys Val Asp Thr Lys
545                 550                 555                 560
Ala Leu Tyr Ala Thr Lys Thr Leu Arg Lys Lys Asp Val Leu Leu Arg
                565                 570                 575
Asn Gln Val Ala His Val Lys Ala Glu Arg Asp Ile Leu Ala Glu Ala
            580                 585                 590
Asp Asn Glu Trp Val Val Arg Leu Tyr Tyr Ser Phe Gln Asp Lys Asp
        595                 600                 605
Asn Leu Tyr Phe Val Met Asp Tyr Ile Pro Gly Gly Asp Met Met Ser
    610                 615                 620
```

```
Leu Leu Ile Arg Met Gly Ile Phe Pro Glu Asn Leu Ala Arg Phe Tyr
625                 630                 635                 640

Ile Ala Glu Leu Thr Cys Ala Val Glu Ser Val His Lys Met Gly Phe
            645                 650                 655

Ile His Arg Asp Ile Lys Pro Asp Asn Ile Leu Ile Asp Arg Asp Gly
            660                 665                 670

His Ile Lys Leu Thr Asp Phe Gly Leu Cys Thr Gly Phe Arg Trp Thr
            675                 680                 685

His Asp Ser Lys Tyr Tyr Gln Ser Gly Asp His Pro Arg Gln Asp Ser
690                 695                 700

Met Asp Phe Ser Asn Glu Trp Gly Asp Pro Ser Asn Cys Arg Cys Gly
705                 710                 715                 720

Asp Arg Leu Lys Pro Leu Glu Arg Arg Ala Ala Arg Gln His Gln Arg
            725                 730                 735

Cys Leu Ala His Ser Leu Val Gly Thr Pro Asn Tyr Ile Ala Pro Glu
            740                 745                 750

Val Leu Leu Arg Thr Gly Tyr Thr Gln Leu Cys Asp Trp Trp Ser Val
            755                 760                 765

Gly Val Ile Leu Cys Glu Met Leu Val Gly Gln Pro Pro Phe Leu Ala
770                 775                 780

Gln Thr Pro Leu Glu Thr Gln Met Lys Val Ile Ile Trp Gln Thr Ser
785                 790                 795                 800

Leu His Ile Pro Pro Gln Ala Lys Leu Ser Pro Glu Ala Ser Asp Leu
            805                 810                 815

Ile Ile Lys Leu Cys Arg Gly Pro Glu Asp Arg Leu Gly Lys Asn Gly
            820                 825                 830

Ala Asp Glu Ile Lys Ala His Pro Phe Phe Lys Thr Ile Asp Phe Ser
835                 840                 845

Ser Asp Leu Arg Gln Gln Ser Ala Ser Tyr Ile Pro Lys Ile Thr His
850                 855                 860

Pro Thr Asp Thr Ser Asn Phe Asp Pro Val Asp Pro Asp Lys Leu Trp
865                 870                 875                 880

Ser Asp Gly Ser Glu Glu Asn Ile Ser Asp Thr Leu Ser Gly Trp
            885                 890                 895

Tyr Lys Asn Gly Lys His Pro Glu His Ala Phe Tyr Glu Phe Thr Phe
            900                 905                 910

Arg Arg Phe Phe Asp Asp Asn Gly Tyr Pro Tyr Asn Tyr Pro Lys Pro
            915                 920                 925

Ile Glu Tyr Glu Tyr Ile His Ser Gln Gly Ser Glu Gln Gln Ser Asp
            930                 935                 940

Glu Asp Asp Gln His Thr Ser Ser Asp Gly Asn Asn Arg Asp Leu Val
945                 950                 955                 960

Tyr Val (2) INFORMATION FOR SEQ ID NO:7:

(i) SEQUENCE CHARACTERISTICS:
        (A) LENGTH: 3154 amino acids
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..2943
```

(xi) SEQUENCE DESCRIPTION: SEQ ID NO:7:

```
ATG AGA GCC ACC CCG AAG TTT GGA CCT TAT CAA AAA GCT CTC AGG GAA      48
Met Arg Ala Thr Pro Lys Phe Gly Pro Tyr Gln Lys Ala Leu Arg Glu
 1               5                  10                  15

ATC CGA TAT TCC CTC CTG CCT TTT GCC AAC GAG TCA GGC ACT TCG GCA      96
Ile Arg Tyr Ser Leu Leu Pro Phe Ala Asn Glu Ser Gly Thr Ser Ala
                20                  25                  30

GCT GCA GAG GTG AAC CGG CAG ATG CTT CAG GAG TTG GTG AAT GCG GCA     144
Ala Ala Glu Val Asn Arg Gln Met Leu Gln Glu Leu Val Asn Ala Ala
            35                  40                  45

TGT GAC CAG GAG ATG GCT GGC AGA GCG CTC ACG CAG ACG GGC AGT AGG     192
Cys Asp Gln Glu Met Ala Gly Arg Ala Leu Thr Gln Thr Gly Ser Arg
        50                  55                  60

AGT ATC GAA GCT GCC TTG GAG TAC ATC AGT AAG ATG GGC TAC CTG GAC     240
Ser Ile Glu Ala Ala Leu Glu Tyr Ile Ser Lys Met Gly Tyr Leu Asp
 65                  70                  75                  80

CCC AGG AAT GAG CAG ATT GTG CGA GTC ATC AAG CAG ACC TCC CCA GGA     288
Pro Arg Asn Glu Gln Ile Val Arg Val Ile Lys Gln Thr Ser Pro Gly
                85                  90                  95

AAG GGC CTG GCG TCC ACC CCG GTG ACT CGG CGG CCC AGT TTC GAG GGC     336
Lys Gly Leu Ala Ser Thr Pro Val Thr Arg Arg Pro Ser Phe Glu Gly
               100                 105                 110

ACA GGG GAA GCA CTC CCA TCC TAC CAC CAG CTG GGT GGT GCA AAC TAC     384
Thr Gly Glu Ala Leu Pro Ser Tyr His Gln Leu Gly Gly Ala Asn Tyr
           115                 120                 125

GAG GGC CCC GCC GCA CTG GAG GAG ATG CCG CGG CAA TAT TTA GAC TTT     432
Glu Gly Pro Ala Ala Leu Glu Glu Met Pro Arg Gln Tyr Leu Asp Phe
       130                 135                 140

CTC TTC CCT GGA GCC GGA GCC GGC ACC CAC GGT GCC CAG GCT CAC CAG     480
Leu Phe Pro Gly Ala Gly Ala Gly Thr His Gly Ala Gln Ala His Gln
145                 150                 155                 160

CAT CCT CCC AAA GGG TAC AGC ACA GCA GTA GAG CCA AGT GCG CAC TTT     528
His Pro Pro Lys Gly Tyr Ser Thr Ala Val Glu Pro Ser Ala His Phe
                165                 170                 175

CCG GGC ACA CAC TAT GGT CGT GGT CAT CTA CTA TCG GAG CAG TCT GGG     576
Pro Gly Thr His Tyr Gly Arg Gly His Leu Leu Ser Glu Gln Ser Gly
            180                 185                 190

TAT GGG GTG CAG CGC AGT TCC TCC TTC CAG AAC AAG ACG CCA CCA GAT     624
Tyr Gly Val Gln Arg Ser Ser Ser Phe Gln Asn Lys Thr Pro Pro Asp
        195                 200                 205

GCC TAT TCC AGC ATG GCC AAG GCC CAG GGT GGC CCT CCC GCC AGC CTC     672
Ala Tyr Ser Ser Met Ala Lys Ala Gln Gly Gly Pro Pro Ala Ser Leu
    210                 215                 220

ACC TTT CCT GCC CAT GCT GGG CTG TAC ACT GCC TCG CAC CAC AAG CCG     720
Thr Phe Pro Ala His Ala Gly Leu Tyr Thr Ala Ser His His Lys Pro
225                 230                 235                 240

GCG GCT ACC CCA CCT GGG GCC CAC CCA TTA CAT GTG TTG GGC ACC CGG     768
Ala Ala Thr Pro Pro Gly Ala His Pro Leu His Val Leu Gly Thr Arg
                245                 250                 255

GGT CCC ACG TTT ACT GGC GAA AGC TCT GCA CAG GCT GTG CTG GCA CCG     816
Gly Pro Thr Phe Thr Gly Glu Ser Ser Ala Gln Ala Val Leu Ala Pro
            260                 265                 270

TCC AGG AAC AGC CTC AAT GCT GAC TTG TAC GAG CTG GGC TCC ACG GTG     864
Ser Arg Asn Ser Leu Asn Ala Asp Leu Tyr Glu Leu Gly Ser Thr Val
        275                 280                 285

CCC TGG TCT GCA GCT CCA CTG GCA CGC CGC GAC TCG CTG CAG AAG CAG     912
Pro Trp Ser Ala Ala Pro Leu Ala Arg Arg Asp Ser Leu Gln Lys Gln
    290                 295                 300

GGT CTA GAA GCC TCG CGG CCG CAT GTG GCT TTT CGG GCT GGC CCC AGC     960
```

-continued

| | | | | | | | | | | | | | | |
|---|---|---|---|---|---|---|---|---|---|---|---|---|---|---|
|Gly|Leu|Glu|Ala|Ser|Arg|Pro|His|Val|Ala|Phe|Arg|Ala|Gly|Pro|Ser|
|305| | | |310| | | |315| | | |320| | |

| AGG | ACC | AAC | TCC | TTC | AAC | AAC | CCA | CAA | CCT | GAG | CCC | TCA | CTG | CCC | GCC | 1008 |
|---|---|---|---|---|---|---|---|---|---|---|---|---|---|---|---|---|
| Arg | Thr | Asn | Ser | Phe | Asn | Asn | Pro | Gln | Pro | Glu | Pro | Ser | Leu | Pro | Ala | |
| | | | 325 | | | | | 330 | | | | | 335 | | | |

| CCC | AAC | ACG | GTC | ACC | GCC | GTG | ACG | GCC | GCA | CAC | ATC | CTT | CAC | CCT | GTG | 1056 |
|---|---|---|---|---|---|---|---|---|---|---|---|---|---|---|---|---|
| Pro | Asn | Thr | Val | Thr | Ala | Val | Thr | Ala | Ala | His | Ile | Leu | His | Pro | Val | |
| | | | 340 | | | | | 345 | | | | | 350 | | | |

| AAG | AGC | GTG | CGT | GTG | CTG | CGG | CCC | GAG | CCC | CAG | ACA | GCC | GTG | GGG | CCC | 1104 |
|---|---|---|---|---|---|---|---|---|---|---|---|---|---|---|---|---|
| Lys | Ser | Val | Arg | Val | Leu | Arg | Pro | Glu | Pro | Gln | Thr | Ala | Val | Gly | Pro | |
| | | 355 | | | | | 360 | | | | | 365 | | | | |

| TCG | CAC | CCC | GCC | TGG | GTG | GCT | GCG | CCC | ACA | GCA | CCT | GCC | ACT | GAG | AGC | 1152 |
|---|---|---|---|---|---|---|---|---|---|---|---|---|---|---|---|---|
| Ser | His | Pro | Ala | Trp | Val | Ala | Ala | Pro | Thr | Ala | Pro | Ala | Thr | Glu | Ser | |
| | | 370 | | | | | 375 | | | | | 380 | | | | |

| CTG | GAG | ACG | AAG | GAG | GGC | AGC | GCA | GGC | CCA | CAC | CCG | CTG | GAT | GTG | GAC | 1200 |
|---|---|---|---|---|---|---|---|---|---|---|---|---|---|---|---|---|
| Leu | Glu | Thr | Lys | Glu | Gly | Ser | Ala | Gly | Pro | His | Pro | Leu | Asp | Val | Asp | |
| 385 | | | | | 390 | | | | | 395 | | | | | 400 | |

| TAT | GGC | GGC | TCC | GAG | CGC | AGG | TGC | CCA | CCG | CCT | CCG | TAT | CCA | AAG | CAC | 1248 |
|---|---|---|---|---|---|---|---|---|---|---|---|---|---|---|---|---|
| Tyr | Gly | Gly | Ser | Glu | Arg | Arg | Cys | Pro | Pro | Pro | Pro | Tyr | Pro | Lys | His | |
| | | | | 405 | | | | | 410 | | | | | 415 | | |

| TTG | CTG | CTG | CCC | AGT | AAG | TCT | GAG | CAG | TAC | AGC | GTG | GAC | CTG | GAC | AGC | 1296 |
|---|---|---|---|---|---|---|---|---|---|---|---|---|---|---|---|---|
| Leu | Leu | Leu | Pro | Ser | Lys | Ser | Glu | Gln | Tyr | Ser | Val | Asp | Leu | Asp | Ser | |
| | | | | 420 | | | | | 425 | | | | | 430 | | |

| CTG | TGC | ACC | AGT | GTG | CAG | CAG | AGT | CTG | CGA | GGG | GGC | ACT | GAT | CTA | GAC | 1344 |
|---|---|---|---|---|---|---|---|---|---|---|---|---|---|---|---|---|
| Leu | Cys | Thr | Ser | Val | Gln | Gln | Ser | Leu | Arg | Gly | Gly | Thr | Asp | Leu | Asp | |
| | | 435 | | | | | 440 | | | | | 445 | | | | |

| GGG | AGT | GAC | AAG | AGC | CAC | AAA | GGT | GCG | AAG | GGA | GAC | AAA | GCT | GGC | AGA | 1392 |
|---|---|---|---|---|---|---|---|---|---|---|---|---|---|---|---|---|
| Gly | Ser | Asp | Lys | Ser | His | Lys | Gly | Ala | Lys | Gly | Asp | Lys | Ala | Gly | Arg | |
| | | 450 | | | | | 455 | | | | | 460 | | | | |

| GAC | AAA | AAG | CAG | ATT | CAG | ACC | TCC | CCG | GTG | CCT | GTC | CGC | AAG | AAT | AGC | 1440 |
|---|---|---|---|---|---|---|---|---|---|---|---|---|---|---|---|---|
| Asp | Lys | Lys | Gln | Ile | Gln | Thr | Ser | Pro | Val | Pro | Val | Arg | Lys | Asn | Ser | |
| 465 | | | | | 470 | | | | | 475 | | | | | 480 | |

| AGA | GAT | GAA | GAG | AAG | AGA | GAG | TCT | CGC | ATC | AAG | AGT | TAC | TCC | CCT | TAT | 1488 |
|---|---|---|---|---|---|---|---|---|---|---|---|---|---|---|---|---|
| Arg | Asp | Glu | Glu | Lys | Arg | Glu | Ser | Arg | Ile | Lys | Ser | Tyr | Ser | Pro | Tyr | |
| | | | | 485 | | | | | 490 | | | | | 495 | | |

| GCC | TTC | AAA | TTC | TTC | ATG | GAG | CAA | CAC | GTG | GAG | AAT | GTC | ATC | AAA | ACC | 1536 |
|---|---|---|---|---|---|---|---|---|---|---|---|---|---|---|---|---|
| Ala | Phe | Lys | Phe | Phe | Met | Glu | Gln | His | Val | Glu | Asn | Val | Ile | Lys | Thr | |
| | | | 500 | | | | | 505 | | | | | 510 | | | |

| TAC | CAG | CAG | AAG | GTC | AGC | CGG | AGG | CTA | CAG | CTG | GAG | CAG | GAA | ATG | GCC | 1584 |
|---|---|---|---|---|---|---|---|---|---|---|---|---|---|---|---|---|
| Tyr | Gln | Gln | Lys | Val | Ser | Arg | Arg | Leu | Gln | Leu | Glu | Gln | Glu | Met | Ala | |
| | | 515 | | | | | 520 | | | | | 525 | | | | |

| AAA | GCT | GGG | CTC | TGT | GAG | GCC | GAG | CAG | GAG | CAG | ATG | AGG | AAG | ATC | CTC | 1632 |
|---|---|---|---|---|---|---|---|---|---|---|---|---|---|---|---|---|
| Lys | Ala | Gly | Leu | Cys | Glu | Ala | Glu | Gln | Glu | Gln | Met | Arg | Lys | Ile | Leu | |
| | | 530 | | | | | 535 | | | | | 540 | | | | |

| TAC | CAG | AAG | GAG | TCT | AAC | TAC | AAC | CGG | CTG | AAG | AGG | GCC | AAG | ATG | GAC | 1680 |
|---|---|---|---|---|---|---|---|---|---|---|---|---|---|---|---|---|
| Tyr | Gln | Lys | Glu | Ser | Asn | Tyr | Asn | Arg | Leu | Lys | Arg | Ala | Lys | Met | Asp | |
| 545 | | | | | 550 | | | | | 555 | | | | | 560 | |

| AAG | TCC | ATG | TTT | GTG | AAA | ATC | AAG | ACT | CTA | GGC | ATC | GGT | GCC | TTT | GGG | 1728 |
|---|---|---|---|---|---|---|---|---|---|---|---|---|---|---|---|---|
| Lys | Ser | Met | Phe | Val | Lys | Ile | Lys | Thr | Leu | Gly | Ile | Gly | Ala | Phe | Gly | |
| | | | | 565 | | | | | 570 | | | | | 575 | | |

| GAA | GTG | TGC | CTC | GCT | TGT | AAG | CTG | GAC | ACT | CAC | GCT | CTG | TAC | GCC | ATG | 1776 |
|---|---|---|---|---|---|---|---|---|---|---|---|---|---|---|---|---|
| Glu | Val | Cys | Leu | Ala | Cys | Lys | Leu | Asp | Thr | His | Ala | Leu | Tyr | Ala | Met | |
| | | | 580 | | | | | 585 | | | | | 590 | | | |

| AAG | ACT | CTC | AGG | AAG | AAG | GAT | GTC | CTG | AAC | CGG | AAT | CAA | GTG | GCC | CAT | 1824 |
|---|---|---|---|---|---|---|---|---|---|---|---|---|---|---|---|---|
| Lys | Thr | Leu | Arg | Lys | Lys | Asp | Val | Leu | Asn | Arg | Asn | Gln | Val | Ala | His | |
| | | | 595 | | | | | 600 | | | | | 605 | | | |

| GTC | AAG | GCT | GAG | AGG | GAC | ATC | CTG | GCT | GAA | GCA | GAC | AAT | GAG | TGG | GTG | 1872 |
|---|---|---|---|---|---|---|---|---|---|---|---|---|---|---|---|---|
| Val | Lys | Ala | Glu | Arg | Asp | Ile | Leu | Ala | Glu | Ala | Asp | Asn | Glu | Trp | Val | |
| | | 610 | | | | | 615 | | | | | 620 | | | | |

| GTC | AAA | CTC | TAC | TAC | TCC | TTC | CAG | GAC | AAG | GAC | AGC | CTG | TAC | TTT | GTG | 1920 |
|---|---|---|---|---|---|---|---|---|---|---|---|---|---|---|---|---|

-continued

| | | | | | | | | | | | | | | |
|---|---|---|---|---|---|---|---|---|---|---|---|---|---|---|
|Val|Lys|Leu|Tyr|Tyr|Ser|Phe|Gln|Asp|Lys|Asp|Ser|Leu|Tyr|Phe|Val|
|625| | | | |630| | | |635| | | |640| |

```
ATG GAC TAC ATA CCA GGC GGG GAT ATG ATG AGC CTG CTG ATC AGG ATG        1968
Met Asp Tyr Ile Pro Gly Gly Asp Met Met Ser Leu Leu Ile Arg Met
            645                 650                 655

GAG GTC TTC CCT GAG CAC CTG GCC CGC TTC TAC ATT GCA GAG TTG ACC        2016
Glu Val Phe Pro Glu His Leu Ala Arg Phe Tyr Ile Ala Glu Leu Thr
            660                 665                 670

CTG GCC ATT GAA AGT GTC CAC AAG ATG GGC TTT ATC CAC CGG GAC ATC        2064
Leu Ala Ile Glu Ser Val His Lys Met Gly Phe Ile His Arg Asp Ile
            675                 680                 685

AAG CCT GAC AAC ATA CTC ATC GAC CTG GAT GGT CAT ATT AAG CTG ACA        2112
Lys Pro Asp Asn Ile Leu Ile Asp Leu Asp Gly His Ile Lys Leu Thr
            690                 695                 700

GAT TTT GGC CTC TGC ACT GGA TTC AGG TGG ACT CAC AAT TCC AAG TAC        2160
Asp Phe Gly Leu Cys Thr Gly Phe Arg Trp Thr His Asn Ser Lys Tyr
705                 710                 715                 720

TAC CAG AAA GGG AAC CAC ATG AGA CAG GAC AGC ATG GAG CCC GGT GAC        2208
Tyr Gln Lys Gly Asn His Met Arg Gln Asp Ser Met Glu Pro Gly Asp
                725                 730                 735

CTC TGG GAC GAT GTT TCC AAC TGT CGC TGT GGA GAC AGG TTA AAG ACC        2256
Leu Trp Asp Asp Val Ser Asn Cys Arg Cys Gly Asp Arg Leu Lys Thr
                740                 745                 750

CTG GAG CAG AGG GCG CAG AAG CAG CAC CAG AGG TGC CTG GCA CAT TCT        2304
Leu Glu Gln Arg Ala Gln Lys Gln His Gln Arg Cys Leu Ala His Ser
            755                 760                 765

CTT GTC GGG ACA CCA AAT TAC ATC GCT CCG GAG GTG CTT CTC CGC AAA        2352
Leu Val Gly Thr Pro Asn Tyr Ile Ala Pro Glu Val Leu Leu Arg Lys
            770                 775                 780

GGG TAC ACG CAG CTC TGT GAC TGG TGG AGC GTC GGT GTG ATT CTC TTT        2400
Gly Tyr Thr Gln Leu Cys Asp Trp Trp Ser Val Gly Val Ile Leu Phe
785                 790                 795                 800

GAG ATG CTG GTT GGG CAG CCG CCT TTC TTG GCC CCC ACC CCC ACA GAG        2448
Glu Met Leu Val Gly Gln Pro Pro Phe Leu Ala Pro Thr Pro Thr Glu
                805                 810                 815

ACG CAG CTG AAG GTG ATC AAC TGG GAG AGC ACG CTG CAT ATC CCT ACG        2496
Thr Gln Leu Lys Val Ile Asn Trp Glu Ser Thr Leu His Ile Pro Thr
            820                 825                 830

CAG GTG AGG CTC AGC GCT GAG GCC CGA GAC CTC ATC ACG AAG CTG TGC        2544
Gln Val Arg Leu Ser Ala Glu Ala Arg Asp Leu Ile Thr Lys Leu Cys
            835                 840                 845

TGC GCG GCT GAC TGC CGC CTG GGC AGG GAT GGG GCA GAT GAC CTC AAG        2592
Cys Ala Ala Asp Cys Arg Leu Gly Arg Asp Gly Ala Asp Asp Leu Lys
            850                 855                 860

GCA CAC CCG TTC TTC AAC ACC ATC GAC TTT TCC CGT GAC ATC CGA AAG        2640
Ala His Pro Phe Phe Asn Thr Ile Asp Phe Ser Arg Asp Ile Arg Lys
865                 870                 875                 880

CAG GCT GCA CCC TAC GTC CCC ACC ATC AGC CAC CCC ATG GAC ACC TCC        2688
Gln Ala Ala Pro Tyr Val Pro Thr Ile Ser His Pro Met Asp Thr Ser
                885                 890                 895

AAT TTT GAC CCG GTG GAT GAA GAA AGC CCC TGG CAC GAG GCC AGC GGA        2736
Asn Phe Asp Pro Val Asp Glu Glu Ser Pro Trp His Glu Ala Ser Gly
                900                 905                 910

GAG AGC GCC AAG GCC TGG GAC ACG CTG GCC TCC CCC AGC AGC AAG CAT        2784
Glu Ser Ala Lys Ala Trp Asp Thr Leu Ala Ser Pro Ser Ser Lys His
            915                 920                 925

CCA GAG CAC GCC TTC TAT GAG TTC ACC TTC CGC AGG TTC TTC GAT GAC        2832
Pro Glu His Ala Phe Tyr Glu Phe Thr Phe Arg Arg Phe Phe Asp Asp
930                 935                 940

AAC GGC TAT CCC TTC CGG TGC CCG AAG CCC TCA GAG CCC GCA GAG AGT        2880
```

```
Asn Gly Tyr Pro Phe Arg Cys Pro Lys Pro Ser Glu Pro Ala Glu Ser
945                 950                 955                 960

GCA GAC CCA GGG GAT GCG GAC TTG GAA GGT GCG GCC GAG GGC TGC CAG    2928
Ala Asp Pro Gly Asp Ala Asp Leu Glu Gly Ala Ala Glu Gly Cys Gln
                    965                 970                 975

CCG GTG TAC GTG TAA GCCTCAGTTA ACCACAACTC GAGGAAACCC AAAATGAGAT    2983
Pro Val Tyr Val
            980

TTCTTTTCAG AAGACAAACT CAAGCTTAGG AATCCTTCAT TTTTAGTTCT GGTAAATGGG  3043

CAACAGGAAG AGTCAACATG ATTTCAAATT AGCCCTCTGA GGACCTTCAC TGCATTAAAA  3103

CAGTATTTTT TAAAAAATTA GTACAGTATG GAAAGAGCAC TTATTTTGGG GG          3155

(2) INFORMATION FOR SEQ ID NO:8:

(i) SEQUENCE CHARACTERISTICS:
        (A) LENGTH: 980 amino acids
        (B) TYPE: amino acid
        (D) TOPOLOGY: unknown (ii) MOLECULE TYPE: protein (xi) SEQUENCE DESCRIPTION: SEQ ID NO:8:

Met Arg Ala Thr Pro Lys Phe Gly Pro Tyr Gln Lys Ala Leu Arg Glu
1               5                   10                  15

Ile Arg Tyr Ser Leu Leu Pro Phe Ala Asn Glu Ser Gly Thr Ser Ala
                20                  25                  30

Ala Ala Glu Val Asn Arg Gln Met Leu Gln Glu Leu Val Asn Ala Ala
            35                  40                  45

Cys Asp Gln Glu Met Ala Gly Arg Ala Leu Thr Gln Thr Gly Ser Arg
        50                  55                  60

Ser Ile Glu Ala Ala Leu Glu Tyr Ile Ser Lys Met Gly Tyr Leu Asp
65                  70                  75                  80

Pro Arg Asn Glu Gln Ile Val Arg Val Ile Lys Gln Thr Ser Pro Gly
                85                  90                  95

Lys Gly Leu Ala Ser Thr Pro Val Thr Arg Arg Pro Ser Phe Glu Gly
            100                 105                 110

Thr Gly Glu Ala Leu Pro Ser Tyr His Gln Leu Gly Gly Ala Asn Tyr
        115                 120                 125

Glu Gly Pro Ala Ala Leu Glu Glu Met Pro Arg Gln Tyr Leu Asp Phe
    130                 135                 140

Leu Phe Pro Gly Ala Gly Ala Gly Thr His Gly Ala Gln Ala His Gln
145                 150                 155                 160

His Pro Pro Lys Gly Tyr Ser Thr Ala Val Glu Pro Ser Ala His Phe
                165                 170                 175

Pro Gly Thr His Tyr Gly Arg Gly His Leu Leu Ser Glu Gln Ser Gly
            180                 185                 190

Tyr Gly Val Gln Arg Ser Ser Ser Phe Gln Asn Lys Thr Pro Pro Asp
        195                 200                 205

Ala Tyr Ser Ser Met Ala Lys Ala Gln Gly Gly Pro Ala Ser Leu
    210                 215                 220

Thr Phe Pro Ala His Ala Gly Leu Tyr Thr Ala Ser His His Lys Pro
225                 230                 235                 240

Ala Ala Thr Pro Pro Gly Ala His Pro Leu His Val Leu Gly Thr Arg
                245                 250                 255

Gly Pro Thr Phe Thr Gly Glu Ser Ser Ala Gln Ala Val Leu Ala Pro
            260                 265                 270
```

-continued

```
Ser Arg Asn Ser Leu Asn Ala Asp Leu Tyr Glu Leu Gly Ser Thr Val
    275                 280                 285

Pro Trp Ser Ala Ala Pro Leu Ala Arg Arg Asp Ser Leu Gln Lys Gln
290                 295                 300

Gly Leu Glu Ala Ser Arg Pro His Val Ala Phe Arg Ala Gly Pro Ser
305                 310                 315                 320

Arg Thr Asn Ser Phe Asn Asn Pro Gln Pro Glu Pro Ser Leu Pro Ala
                325                 330                 335

Pro Asn Thr Val Thr Ala Val Thr Ala Ala His Ile Leu His Pro Val
                340                 345                 350

Lys Ser Val Arg Val Leu Arg Pro Glu Pro Gln Thr Ala Val Gly Pro
                355                 360                 365

Ser His Pro Ala Trp Val Ala Ala Pro Thr Ala Pro Ala Thr Glu Ser
370                 375                 380

Leu Glu Thr Lys Glu Gly Ser Ala Gly Pro His Pro Leu Asp Val Asp
385                 390                 395                 400

Tyr Gly Gly Ser Glu Arg Arg Cys Pro Pro Pro Tyr Pro Lys His
                405                 410                 415

Leu Leu Leu Pro Ser Lys Ser Glu Gln Tyr Ser Val Asp Leu Asp Ser
                420                 425                 430

Leu Cys Thr Ser Val Gln Gln Ser Leu Arg Gly Gly Thr Asp Leu Asp
        435                 440                 445

Gly Ser Asp Lys Ser His Lys Gly Ala Lys Gly Asp Lys Ala Gly Arg
450                 455                 460

Asp Lys Lys Gln Ile Gln Thr Ser Pro Val Pro Val Arg Lys Asn Ser
465                 470                 475                 480

Arg Asp Glu Glu Lys Arg Glu Ser Arg Ile Lys Ser Tyr Ser Pro Tyr
                485                 490                 495

Ala Phe Lys Phe Phe Met Glu Gln His Val Glu Asn Val Ile Lys Thr
                500                 505                 510

Tyr Gln Gln Lys Val Ser Arg Arg Leu Gln Leu Glu Gln Glu Met Ala
                515                 520                 525

Lys Ala Gly Leu Cys Glu Ala Glu Gln Glu Gln Met Arg Lys Ile Leu
                530                 535                 540

Tyr Gln Lys Glu Ser Asn Tyr Asn Arg Leu Lys Arg Ala Lys Met Asp
545                 550                 555                 560

Lys Ser Met Phe Val Lys Ile Lys Thr Leu Gly Ile Gly Ala Phe Gly
                565                 570                 575

Glu Val Cys Leu Ala Cys Lys Leu Asp Thr His Ala Leu Tyr Ala Met
                580                 585                 590

Lys Thr Leu Arg Lys Lys Asp Val Leu Asn Arg Asn Gln Val Ala His
                595                 600                 605

Val Lys Ala Glu Arg Asp Ile Leu Ala Glu Ala Asp Asn Glu Trp Val
610                 615                 620

Val Lys Leu Tyr Tyr Ser Phe Gln Asp Lys Asp Ser Leu Tyr Phe Val
625                 630                 635                 640

Met Asp Tyr Ile Pro Gly Gly Asp Met Met Ser Leu Leu Ile Arg Met
                645                 650                 655

Glu Val Phe Pro Glu His Leu Ala Arg Phe Tyr Ile Ala Glu Leu Thr
                660                 665                 670

Leu Ala Ile Glu Ser Val His Lys Met Gly Phe Ile His Arg Asp Ile
                675                 680                 685

Lys Pro Asp Asn Ile Leu Ile Asp Leu Asp Gly His Ile Lys Leu Thr
690                 695                 700
```

```
Asp Phe Gly Leu Cys Thr Gly Phe Arg Trp Thr His Asn Ser Lys Tyr
705                 710                 715                 720

Tyr Gln Lys Gly Asn His Met Arg Gln Asp Ser Met Glu Pro Gly Asp
            725                 730                 735

Leu Trp Asp Asp Val Ser Asn Cys Arg Cys Gly Asp Arg Leu Lys Thr
                740                 745                 750

Leu Glu Gln Arg Ala Gln Lys Gln His Gln Arg Cys Leu Ala His Ser
            755                 760                 765

Leu Val Gly Thr Pro Asn Tyr Ile Ala Pro Glu Val Leu Leu Arg Lys
        770                 775                 780

Gly Tyr Thr Gln Leu Cys Asp Trp Trp Ser Val Gly Val Ile Leu Phe
785                 790                 795                 800

Glu Met Leu Val Gly Gln Pro Pro Phe Leu Ala Pro Thr Pro Thr Glu
                805                 810                 815

Thr Gln Leu Lys Val Ile Asn Trp Glu Ser Thr Leu His Ile Pro Thr
                820                 825                 830

Gln Val Arg Leu Ser Ala Glu Ala Arg Asp Leu Ile Thr Lys Leu Cys
            835                 840                 845

Cys Ala Ala Asp Cys Arg Leu Gly Arg Asp Gly Ala Asp Asp Leu Lys
850                 855                 860

Ala His Pro Phe Phe Asn Thr Ile Asp Phe Ser Arg Asp Ile Arg Lys
865                 870                 875                 880

Gln Ala Ala Pro Tyr Val Pro Thr Ile Ser His Pro Met Asp Thr Ser
                885                 890                 895

Asn Phe Asp Pro Val Asp Glu Glu Ser Pro Trp His Glu Ala Ser Gly
                900                 905                 910

Glu Ser Ala Lys Ala Trp Asp Thr Leu Ala Ser Pro Ser Ser Lys His
        915                 920                 925

Pro Glu His Ala Phe Tyr Glu Phe Thr Phe Arg Arg Phe Phe Asp Asp
        930                 935                 940

Asn Gly Tyr Pro Phe Arg Cys Pro Lys Pro Ser Glu Pro Ala Glu Ser
945                 950                 955                 960

Ala Asp Pro Gly Asp Ala Asp Leu Glu Gly Ala Ala Glu Gly Cys Gln
                965                 970                 975

Pro Val Tyr Val
        980

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO:9:

Asp Leu Lys Pro Glu Asn
1               5

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide
```

(ix) FEATURE:
            (A) NAME/KEY: Peptide
            (B) LOCATION: 2
            (D) OTHER INFORMATION: /label= A
                /note= "X at the second position can be either Threonine
                or Serine."

(ix) FEATURE:
            (A) NAME/KEY: Peptide
            (B) LOCATION: 5
            (D) OTHER INFORMATION: /label= B
                /note= "X at the fifth position can either be Tyrosine or
                Phenylalanine."

(xi) SEQUENCE DESCRIPTION: SEQ ID NO:10:

Gly Xaa Xaa Xaa Xaa Xaa Ala Pro Glu
1               5

(2) INFORMATION FOR SEQ ID NO:11:

(i) SEQUENCE CHARACTERISTICS:
         (A) LENGTH: 620 amino acids
         (B) TYPE: amino acid
         (D) TOPOLOGY: unknown (ii) MOLECULE TYPE: protein (xi) SEQUENCE DESCRIPTION: SEQ ID NO:11:

Met Asp Asn Thr Asn Arg Pro His Leu Asn Leu Gly Thr Asn Asp Thr
1               5                   10                  15

Arg Met Ala Pro Asn Asp Arg Thr Tyr Pro Thr Thr Pro Ser Thr Phe
            20                  25                  30

Pro Gln Pro Val Phe Pro Gly Gln Gln Ala Gly Gly Ser Gln Gln Tyr
        35                  40                  45

Asn Gln Ala Tyr Ala Gln Ser Gly Asn Tyr Tyr Gln Gln Asn His Asn
    50                  55                  60

Asp Pro Asn Thr Gly Leu Ala His Gln Phe Ala His Gln Asn Ile Gly
65                  70                  75                  80

Ser Ala Gly Arg Ala Ser Pro Tyr Gly Ser Arg Gly Pro Ser Pro Ala
                85                  90                  95

Gln Arg Pro Arg Thr Ser Gly Asn Ser Gly Gln Gln Gln Thr Tyr Gly
            100                 105                 110

Asn Tyr Leu Ser Ala Pro Met Pro Ser Asn Thr Gln Thr Glu Phe Ala
        115                 120                 125

Pro Leu Pro Ser Gly Thr Pro Thr Asn Met Ala Pro Met Pro Thr Thr
    130                 135                 140

Thr Arg Arg Ser Ala His Ser Trp Pro Leu Thr Ser Leu Arg Thr Ala
145                 150                 155                 160

Ser Ser Ala Pro Gly Ser Ala Thr Arg Gly Glu Cys Cys Ser Asp Ala
                165                 170                 175

Leu Leu Pro Leu His Pro Ala Val Ile Gly Ala Asp Thr Leu Phe Arg
            180                 185                 190

Gln Ser Glu Met Glu Gln Lys Leu Gly Glu Thr Asn Asp Ala Arg Arg
        195                 200                 205

Arg Glu Ser Ile Trp Ser Thr Ala Gly Arg Lys Glu Gly Gln Tyr Leu
    210                 215                 220

Arg Phe Leu Arg Thr Lys Asp Lys Pro Glu Asn Tyr Gln Thr Ile Lys
225                 230                 235                 240

Ile Ile Gly Lys Gly Ala Phe Gly Glu Val Lys Leu Val Gln Lys Lys
                245                 250                 255

Ala Asp Gly Lys Val Tyr Ala Met Lys Ser Leu Ile Lys Thr Glu Met

```
                   260                 265                 270
Phe Lys Lys Asp Gln Leu Ala His Val Arg Ala Glu Arg Asp Ile Leu
                275                 280                 285
Ala Glu Ser Asp Ser Pro Trp Val Val Lys Leu Tyr Thr Thr Phe Gln
290                 295                 300
Asp Ala Asn Phe Leu Tyr Met Leu Met Glu Phe Leu Pro Gly Gly Asp
305                 310                 315                 320
Leu Met Thr Met Leu Ile Lys Tyr Glu Ile Phe Ser Glu Asp Ile Thr
                325                 330                 335
Arg Phe Tyr Ile Ala Glu Ile Val Leu Ala Ile Asp Ala Val His Lys
                340                 345                 350
Leu Gly Phe Ile His Arg Asp Ile Lys Pro Asp Asn Ile Leu Leu Asp
                355                 360                 365
Arg Gly His Val Lys Leu Thr Asp Phe Gly Leu Ser Thr Gly Phe
370                 375                 380
His Lys Leu His Asp Asn Tyr Tyr Thr Gln Leu Leu Gln Gly Lys
385                 390                 395                 400
Ser Asn Lys Pro Arg Asp Asn Arg Asn Ser Val Ala Ile Asp Gln Ile
                405                 410                 415
Asn Leu Thr Val Ser Asn Arg Ala Gln Ile Asn Asp Trp Arg Arg Ser
                420                 425                 430
Arg Arg Leu Met Ala Tyr Ser Thr Val Gly Thr Pro Asp Tyr Ile Ala
435                 440                 445
Pro Glu Ile Phe Thr Gly His Gly Tyr Ser Phe Asp Cys Asp Trp Trp
                450                 455                 460
Ser Leu Gly Thr Ile Met Phe Glu Cys Leu Val Gly Trp Pro Pro Phe
465                 470                 475                 480
Cys Ala Glu Asp Ser His Asp Thr Tyr Arg Lys Ile Val Asn Trp Arg
                485                 490                 495
His Ser Leu Tyr Phe Pro Asp Asp Ile Thr Leu Gly Val Asp Ala Glu
                500                 505                 510
Asn Leu Ile Arg Ser Leu Ile Cys Asn Thr Glu Asn Arg Leu Gly Arg
                515                 520                 525
Gly Gly Ala His Glu Ile Lys Ser His Ala Phe Phe Arg Gly Val Glu
                530                 535                 540
Phe Asp Ser Leu Arg Arg Ile Arg Ala Pro Phe Glu Pro Arg Leu Thr
545                 550                 555                 560
Ser Ala Ile Asp Thr Thr Tyr Phe Pro Thr Asp Glu Ile Asp Gln Thr
                565                 570                 575
Asp Asn Ala Thr Leu Leu Lys Ala Gln Gln Ala Ala Arg Gly Ala Ala
                580                 585                 590
Ala Pro Ala Gln Gln Glu Glu Ser Pro Glu Leu Ser Leu Pro Phe Ile
                595                 600                 605
Gly Tyr Thr Phe Lys Arg Phe Asp Asn Asn Phe Arg
                610                 615                 620

(2) INFORMATION FOR SEQ ID NO:12:

(i) SEQUENCE CHARACTERISTICS:
        (A) LENGTH: 526 amino acids
        (B) TYPE: amino acid
        (D) TOPOLOGY: unknown (ii) MOLECULE TYPE: protein (xi) SEQUENCE DESCRIPTION: SEQ ID NO:12:
```

-continued

```
Met Asp Ser Ala Arg Gly Trp Phe Gln Lys Leu Ser Ser Thr Lys Lys
1               5                   10                  15

Asp Pro Met Ala Ser Gly Arg Glu Asp Gly Lys Pro Val Ser Ala Glu
            20                  25                  30

Glu Ala Ser Asn Ile Thr Lys Gln Arg Val Ala Ala Lys Gln Tyr
        35                  40                  45

Ile Glu Lys His Tyr Arg Glu Gln Met Lys Asn Leu Gln Glu Arg Arg
50                  55                  60

Glu Arg Arg Ile Leu Leu Glu Lys Lys Leu Ala Asp Ala Asp Val Ser
65                  70                  75                  80

Glu Glu Asp Gln Asn Asn Leu Leu Lys Phe Leu Glu Lys Lys Glu Thr
                85                  90                  95

Glu Tyr Met Arg Leu Gln Arg His Lys Met Gly Ala Asp Asp Phe Glu
            100                 105                 110

Leu Leu Thr Met Ile Gly Lys Gly Ala Phe Gly Glu Pro Ile Cys Met
            115                 120                 125

Ile Gly Phe Ser Val Ile Thr Gly Gln Asn Cys Arg Glu Lys Thr Thr
130                 135                 140

Gly Gln Val Tyr Ala Met Lys Lys Leu Lys Lys Ser Glu Met Leu Arg
145                 150                 155                 160

Arg Gly Gln Val Glu His Val Lys Ala Glu Arg Asn Leu Leu Ala Glu
                165                 170                 175

Val Asp Ser Asp Cys Ile Val Lys Leu Tyr Tyr Ser Phe Gln Asp Asp
            180                 185                 190

Asp Tyr Leu Tyr Leu Val Met Glu Tyr Leu Pro Gly Gly Asp Met Met
        195                 200                 205

Thr Leu Leu Met Arg Lys Asp Ile Leu Thr Glu Asp Glu Ala Arg Phe
210                 215                 220

Tyr Val Ala Glu Thr Val Leu Ala Ile Glu Ser Ile His Lys His Asn
225                 230                 235                 240

Tyr Ile His Arg Asp Ile Lys Pro Asp Asn Leu Leu Leu Asp Arg Tyr
                245                 250                 255

Gly His Leu Lys Leu Ser Asp Phe Gly Leu Cys Lys Pro Leu Asp Cys
            260                 265                 270

Ser Thr Leu Glu Glu Lys Asp Phe Ser Val Gly Asp Asn Ala Asn Gly
            275                 280                 285

Gly Ser Arg Ser Asp Ser Pro Pro Ala Pro Lys Arg Thr Gln Gln Glu
290                 295                 300

Gln Leu Glu His Trp Gln Lys Asn Arg Arg Met Leu Ala Tyr Ser Thr
305                 310                 315                 320

Val Gly Thr Pro Asp Tyr Ile Ala Pro Glu Val Leu Leu Lys Lys Gly
                325                 330                 335

Tyr Gly Met Glu Cys Asp Trp Trp Ser Leu Gly Ala Ile Met Tyr Glu
            340                 345                 350

Met Leu Val Gly Tyr Pro Pro Phe Tyr Ser Asp Asp Pro Met Ser Thr
            355                 360                 365

Cys Arg Lys Ile Val Asn Trp Lys Asn His Leu Lys Phe Pro Glu Glu
            370                 375                 380

Ala Lys Leu Ser Pro Glu Ala Lys Asp Ile Ile Ser Arg Leu Leu Cys
385                 390                 395                 400

Asn Val Thr Glu Arg Leu Gly Ser Asn Gly Ala Asp Glu Ile Lys Val
                405                 410                 415

His Ser Trp Phe Lys Gly Ile Asp Trp Asp Arg Ile Tyr Gln Met Glu
            420                 425                 430
```

```
Ala Ala Phe Ile Pro Glu Val Asn Asp Glu Leu Asp Thr Gln Asn Phe
        435                 440                 445

Gln Lys Phe Glu Glu Ser Glu Ser His Ser Gln Ser Gly Ser Arg Ser
        450                 455                 460

Gly Pro Trp Arg Lys Met Leu Ser Ser Lys Asp Ile Asn Phe Val Gly
465                 470                 475                 480

Tyr Thr Tyr Lys Asn Phe Lys Val Val Asn Asp Tyr Gln Val Pro Gly
                485                 490                 495

Met Val Glu Leu Lys Lys Thr Asn Thr Lys Pro Lys Lys Pro Thr Ile
        500                 505                 510

Lys Ser Leu Phe Gly Asp Glu Ser Glu Ala Ser Glu Asp Asn
        515                 520                 525
```

(2) INFORMATION FOR SEQ ID NO:13:

(i) SEQUENCE CHARACTERISTICS:
        (A) LENGTH: 479 amino acids
        (B) TYPE: amino acid
        (D) TOPOLOGY: unknown (ii) MOLECULE TYPE: protein (xi) SEQUENCE DESCRIPTION: SEQ ID NO:13:

```
Arg Lys Leu His Asp Ala Asp Val Ser Glu Glu Asp Gln Asn Asn Leu
1               5                   10                  15

Leu Lys Phe Leu Glu Lys Lys Gly Thr Glu Tyr Met Arg Leu Gln Arg
            20                  25                  30

His Lys Met Gly Ala Asp Asp Phe Glu Leu Leu Thr Met Ile Gly Lys
        35                  40                  45

Gly Ala Phe Gly Glu Val Arg Val Cys Arg Glu Lys Thr Thr Gly His
50                  55                  60

Val Tyr Ala Met Lys Lys Leu Lys Ser Glu Met Leu Arg Arg Gly
65                  70                  75                  80

Gln Val Glu His Val Lys Ala Glu Arg Asn Leu Leu Ala Glu Val Asp
            85                  90                  95

Ser Asn Cys Ile Val Lys Leu Tyr Cys Ser Phe Gln Asp Glu Glu Tyr
            100                 105                 110

Leu Tyr Leu Ile Met Glu Tyr Leu Pro Gly Gly Asp Met Met Thr Leu
        115                 120                 125

Leu Met Arg Lys Asp Thr Leu Thr Glu Asp Glu Ala Arg Phe Tyr Val
        130                 135                 140

Ala Glu Thr Ile Leu Ala Ile Glu Ser Ile His Lys His Asn Tyr Ile
145                 150                 155                 160

His Arg Asp Ile Lys Pro Asp Asn Leu Leu Leu Asp Lys Phe Gly His
                165                 170                 175

Leu Arg Leu Ser Asp Phe Gly Leu Cys Lys Pro Leu Asp Cys Ser Thr
            180                 185                 190

Leu Glu Glu Lys Asp Phe Glu Val Asn Asn Gly Asn Gly Gly Ser Pro
        195                 200                 205

Ser Asn Glu Gly Ser Thr Lys Pro Arg Arg Thr Gln Gln Glu Gln Leu
        210                 215                 220

Gln His Trp Gln Lys Asn Arg Arg Met Leu Ala Tyr Ser Thr Val Gly
225                 230                 235                 240

Thr Pro Asp Tyr Ile Ala Pro Glu Val Leu Leu Lys Lys Gly Tyr Gly
                245                 250                 255

Met Glu Cys Asp Trp Trp Ser Leu Gly Ala Ile Met Tyr Glu Met Leu
```

```
                    260                 265                 270
Val Gly Tyr Pro Pro Phe Tyr Ser Asp Asp Pro Met Ser Thr Cys Arg
            275                 280                 285

Lys Ile Val Asn Trp Arg Thr His Leu Lys Phe Pro Glu Glu Ala Lys
290                 295                 300

Leu Ser Pro Glu Ala Lys Asp Leu Ile Ser Lys Leu Leu Cys Asn Val
305                 310                 315                 320

Thr Gln Arg Leu Gly Ser Asn Gly Ala His Glu Ile Lys Leu His Pro
                325                 330                 335

Trp Phe Asn Gly Ile Asp Trp Glu Arg Ile Tyr Gln Met Glu Ala Ala
                340                 345                 350

Phe Ile Pro Glu Val Asn Asp Glu Leu Asp Thr Gln Asn Phe Glu Lys
                355                 360                 365

Phe Glu Glu Ala Asp Asn Ser Ser Gln Ser Thr Ser Lys Ala Gly Pro
            370                 375                 380

Trp Arg Lys Met Leu Ser Ser Lys Asp Leu Asn Phe Val Gly Tyr Thr
385                 390                 395                 400

Tyr Lys Asn Phe Glu Ile Val Asn Asp Tyr Gln Val Pro Gly Ile Ala
                405                 410                 415

Glu Leu Lys Lys Lys Asp Thr Lys Pro Lys Arg Pro Ser Ile Lys Ser
                420                 425                 430

Leu Phe Glu Asp Glu Ser Ser Asp Ser Ser Glu Ala Ala Thr Ser Gly
            435                 440                 445

Asp Gln Ser Val Gln Gly Ser Phe Leu Asn Leu Pro Pro Gln Leu
            450                 455                 460

Glu Val Ser Gln Thr Gln Thr Glu Val Pro Pro Pro Lys Phe Thr
465                 470                 475

(2) INFORMATION FOR SEQ ID NO:14:

(i) SEQUENCE CHARACTERISTICS:
        (A) LENGTH: 500 amino acids
        (B) TYPE: amino acid
        (D) TOPOLOGY: unknown (ii) MOLECULE TYPE: protein (xi) SEQUENCE DESCRIPTION: SEQ ID NO:14:

Met Glu Lys Val Lys Ala Ala Lys Lys Phe Ile Glu Asn His Tyr Arg
1               5                   10                  15

Ser Gln Met Lys Asn Ile Gln Glu Arg Lys Glu Arg Arg Trp Val Leu
                20                  25                  30

Glu Lys Gln Leu Ala Ser Ser Asp Val Pro Glu Glu Gln Met Ser
            35                  40                  45

Leu Ile Lys Asp Leu Glu Arg Lys Glu Thr Glu Phe Met Arg Leu Lys
        50                  55                  60

Arg Asn Arg Ile Cys Val Asn Asp Phe Glu Leu Leu Thr Ile Ile Gly
65                  70                  75                  80

Arg Gly Ala Tyr Gly Glu Val Gln Leu Cys Arg Glu Lys Lys Ser Glu
                85                  90                  95

Asn Ile Tyr Ala Met Lys Lys Leu Lys Lys Ser Glu Met Leu Ser Arg
                100                 105                 110

Gly Gln Val Glu His Val Arg Ala Glu Arg Asn Leu Leu Ala Glu Val
            115                 120                 125

Asp Ser His Cys Ile Val Lys Leu Phe Tyr Ser Phe Gln Asp Ala Glu
        130                 135                 140
```

```
Tyr Leu Tyr Leu Ile Met Glu Tyr Leu Pro Gly Gly Asp Met Met Thr
145                 150                 155                 160

Leu Leu Met Arg Glu Asp Ile Leu Thr Glu Lys Val Ala Lys Phe Tyr
            165                 170                 175

Ile Ala Gln Ser Val Leu Ala Ile Glu Ser Ile His Lys His Asn Tyr
            180                 185                 190

Ile His Arg Asp Ile Lys Pro Asp Asn Leu Leu Leu Asp Lys Asn Gly
            195                 200                 205

His Met Lys Leu Ser Asp Phe Gly Leu Cys Lys Pro Leu Asp Cys Ala
            210                 215                 220

Thr Leu Ser Thr Ile Lys Glu Asn Glu Ser Met Asp Asp Val Ser Lys
225                 230                 235                 240

Asn Ser Met Asp Ile Asp Ala Ser Leu Pro Asp Ala Gly Asn Gly His
            245                 250                 255

Ser Trp Arg Ser Ala Arg Glu Gln Leu Gln His Trp Gln Arg Asn Arg
            260                 265                 270

Arg Lys Leu Ala Phe Ser Thr Val Gly Thr Pro Asp Tyr Ile Ala Pro
            275                 280                 285

Glu Val Leu Leu Lys Lys Gly Tyr Gly Met Glu Cys Asp Trp Trp Ser
290                 295                 300

Leu Gly Ala Ile Met Tyr Glu Met Leu Val Gly Tyr Pro Pro Phe Tyr
305                 310                 315                 320

Ser Asp Asp Pro Ile Thr Thr Cys Arg Lys Ile Val His Trp Arg His
            325                 330                 335

Tyr Leu Lys Phe Pro Asp Asp Ala Lys Leu Thr Phe Glu Ala Arg Asp
            340                 345                 350

Leu Ile Cys Arg Leu Leu Cys Asp Val Glu His Arg Leu Gly Thr Gly
            355                 360                 365

Gly Ala Glu Gln Ile Lys Val His Ala Trp Phe Lys Asp Val Glu Trp
370                 375                 380

Asp Arg Leu Tyr Glu Thr Asp Ala Ala Tyr Lys Pro Gln Val Asn Gly
385                 390                 395                 400

Glu Leu Asp Thr Gln Asn Phe Met Lys Phe Asp Glu Ala Asn Pro Pro
            405                 410                 415

Thr Pro Ser Arg Ser Gly Ser Gly Pro Ser Arg Lys Met Leu Thr Ser
            420                 425                 430

Lys Asp Leu Ser Phe Val Gly Tyr Thr Tyr Lys Asn Phe Asp Ala Val
            435                 440                 445

Lys Gly Leu Lys His Ser Phe Asp Arg Lys Gly Ser Thr Ser Pro Lys
            450                 455                 460

Arg Pro Ser Leu Asp Ser Met Phe Asn Glu Asn Gly Met Asp Tyr Thr
465                 470                 475                 480

Ala Lys His Ala Glu Glu Met Asp Val Gln Met Leu Thr Ala Asp Asp
            485                 490                 495

Cys Met Ser Pro
            500
```

(2) INFORMATION FOR SEQ ID NO:15:

(i) SEQUENCE CHARACTERISTICS:
        (A) LENGTH: 564 amino acids
        (B) TYPE: amino acid
        (D) TOPOLOGY: unknown (ii) MOLECULE TYPE: protein (xi) SEQUENCE DESCRIPTION: SEQ ID NO:15:

```
Met Phe Ser Arg Ser Asp Arg Glu Val Asp Asp Leu Ala Gly Asn Met
 1               5                  10                  15

Ser His Leu Gly Phe Tyr Asp Leu Asn Ile Pro Lys Pro Thr Ser Pro
                 20                  25                  30

Gln Ala Gln Tyr Arg Pro Ala Arg Lys Ser Glu Asn Gly Arg Leu Thr
             35                  40                  45

Pro Gly Leu Pro Arg Ser Tyr Lys Pro Cys Asp Ser Asp Asp Gln Asp
 50                  55                  60

Thr Phe Lys Asn Arg Ile Ser Leu Asn His Ser Pro Lys Lys Leu Pro
 65                  70                  75                  80

Lys Asp Phe His Glu Arg Ala Ser Gln Ser Lys Thr Gln Arg Val Val
                 85                  90                  95

Asn Val Cys Gln Leu Tyr Phe Leu Asp Tyr Tyr Cys Asp Met Phe Asp
                100                 105                 110

Tyr Val Ile Ser Arg Arg Gln Arg Thr Lys Gln Val Leu Arg Tyr Leu
                115                 120                 125

Glu Gln Gln Arg Ser Val Lys Asn Val Ser Asn Lys Val Leu Asn Glu
                130                 135                 140

Glu Trp Ala Leu Tyr Leu Gln Arg Glu His Glu Val Leu Arg Lys Arg
145                 150                 155                 160

Arg Leu Lys Pro Lys His Lys Asp Phe Gln Ile Leu Thr Gln Val Gly
                165                 170                 175

Gln Gly Gly Tyr Gly Gln Val Tyr Leu Ala Lys Lys Asp Ser Asp
                180                 185                 190

Glu Ile Cys Ala Leu Lys Ile Leu Asn Lys Lys Leu Leu Phe Lys Leu
                195                 200                 205

Asn Glu Thr Asn His Val Leu Thr Glu Arg Asp Ile Leu Thr Thr Thr
                210                 215                 220

Arg Ser Asp Trp Leu Val Lys Leu Leu Tyr Ala Phe Gln Asp Pro Glu
225                 230                 235                 240

Ser Leu Tyr Leu Ala Met Glu Phe Val Pro Gly Gly Asp Phe Arg Thr
                245                 250                 255

Leu Leu Ile Asn Thr Arg Ile Leu Lys Ser Gly His Ala Arg Phe Tyr
                260                 265                 270

Ile Ser Glu Met Phe Cys Ala Val Asn Ala Leu His Glu Leu Gly Tyr
                275                 280                 285

Thr His Arg Asp Leu Lys Pro Glu Asn Phe Leu Ile Asp Ala Thr Gly
                290                 295                 300

His Ile Lys Leu Thr Asp Phe Gly Leu Ala Ala Gly Thr Val Ser Asn
305                 310                 315                 320

Glu Arg Ile Glu Ser Met Lys Ile Arg Leu Glu Val Lys Asn Leu
                325                 330                 335

Gln Phe Pro Ala Phe Thr Glu Ser Ile Glu Asp Arg Ser Lys Ile
                340                 345                 350

Tyr His Asn Met Arg Lys Thr Glu Ile Asn Tyr Ala Asn Ser Met Val
                355                 360                 365

Gly Ser Pro Asp Tyr Met Ala Leu Glu Val Leu Glu Gly Lys Lys Tyr
370                 375                 380

Asp Phe Thr Val Asp Tyr Trp Ser Leu Gly Cys Met Leu Phe Glu Ser
385                 390                 395                 400

Leu Val Gly Tyr Thr Pro Phe Ser Gly Ser Ser Thr Asn Glu Thr Tyr
                405                 410                 415

Glu Asn Leu Arg Tyr Trp Lys Lys Thr Leu Arg Arg Pro Arg Thr Glu
```

```
                        420                 425                 430
Asp Arg Arg Ala Ala Phe Ser Asp Arg Thr Trp Asp Leu Ile Thr Arg
            435                 440                 445
Leu Ile Ala Asp Pro Ile Asn Arg Val Arg Ser Phe Glu Gln Val Arg
450                 455                 460
Lys Met Ser Tyr Phe Ala Glu Ile Asn Phe Glu Thr Leu Arg Thr Ser
465                 470                 475                 480
Ser Pro Pro Phe Ile Pro Gln Leu Asp Asp Glu Thr Asp Ala Gly Tyr
                485                 490                 495
Phe Asp Asp Phe Thr Asn Glu Glu Asp Met Ala Lys Tyr Ala Asp Val
            500                 505                 510
Phe Lys Arg Gln Asn Lys Leu Ser Ala Met Val Asp Asp Ser Ala Val
            515                 520                 525
Asp Ser Lys Leu Val Gly Phe Thr Phe Arg His Arg Asp Gly Lys Gln
530                 535                 540
Gly Ser Ser Gly Ile Leu Tyr Asn Gly Ser Glu His Ser Asp Pro Phe
545                 550                 555                 560
Ser Thr Phe Tyr (2) INFORMATION FOR SEQ ID NO:16:

(i) SEQUENCE CHARACTERISTICS:
        (A) LENGTH: 561 amino acids
        (B) TYPE: amino acid
        (D) TOPOLOGY: unknown (ii) MOLECULE TYPE: protein (xi) SEQUENCE DESCRIPTION: SEQ ID NO:16:

Met Ala Gly Asn Met Ser Asn Leu Ser Phe Asp Gly His Gly Thr Pro
1               5                   10                  15
Gly Gly Thr Gly Leu Phe Pro Asn Gln Asn Ile Thr Lys Arg Arg Thr
                20                  25                  30
Arg Pro Ala Gly Ile Asn Asp Ser Pro Ser Pro Val Lys Pro Ser Phe
            35                  40                  45
Phe Pro Tyr Glu Asp Thr Ser Asn Met Asp Ile Asp Glu Val Ser Gln
50                  55                  60
Pro Asp Met Asp Val Ser Asn Ser Pro Lys Lys Leu Pro Pro Lys Phe
65                  70                  75                  80
Tyr Glu Arg Ala Thr Ser Asn Lys Thr Gln Arg Val Val Ser Val Cys
                85                  90                  95
Lys Met Tyr Phe Leu Glu Tyr Tyr Cys Asp Met Phe Asp Tyr Val Ile
                100                 105                 110
Ser Arg Arg Gln Arg Thr Lys Gln Val Leu Glu Tyr Leu Gln Gln Gln
            115                 120                 125
Ser Gln Leu Pro Asn Ser Asp Gln Ile Lys Leu Asn Glu Glu Trp Ser
        130                 135                 140
Ser Tyr Leu Gln Arg Glu His Gln Val Leu Arg Lys Arg Leu Lys
145                 150                 155                 160
Pro Lys Asn Arg Asp Phe Glu Met Ile Thr Gln Val Gly Gln Gly Gly
                165                 170                 175
Tyr Gly Gln Val Tyr Leu Ala Arg Lys Lys Asp Thr Lys Glu Val Cys
                180                 185                 190
Ala Leu Lys Ile Leu Asn Lys Lys Leu Leu Phe Lys Leu Asn Glu Thr
            195                 200                 205
Lys His Val Leu Thr Glu Arg Asp Ile Leu Thr Thr Thr Arg Ser Glu
```

```
                  210                 215                 220
Trp Leu Val Lys Leu Leu Tyr Ala Phe Gln Glu Leu Gln Ser Leu Tyr
225                 230                 235                 240

Leu Ala Met Glu Phe Val Pro Gly Gly Asp Phe Arg Thr Leu Leu Ile
                245                 250                 255

Asn Thr Arg Cys Leu Lys Ser Gly His Ala Arg Phe Tyr Ile Ser Glu
                260                 265                 270

Met Phe Cys Ala Val Asn Ala Leu His Asp Leu Gly Tyr Thr His Arg
            275                 280                 285

Asp Leu Lys Pro Glu Asn Phe Leu Ile Asp Ala Lys Gly His Ile Lys
            290                 295                 300

Leu Thr Asp Phe Gly Leu Ala Ala Gly Thr Ile Ser Asn Glu Arg Ile
305                 310                 315                 320

Glu Ser Met Lys Ile Arg Leu Glu Lys Ile Lys Asp Leu Glu Phe Pro
                325                 330                 335

Ala Phe Thr Glu Lys Ser Ile Glu Asp Arg Arg Lys Met Tyr Asn Gln
                340                 345                 350

Leu Arg Glu Lys Glu Ile Asn Tyr Ala Asn Ser Met Val Gly Ser Pro
                355                 360                 365

Asp Tyr Met Ala Leu Glu Val Leu Glu Gly Lys Lys Tyr Asp Phe Thr
            370                 375                 380

Val Asp Tyr Trp Ser Leu Gly Cys Met Leu Phe Glu Ser Leu Val Gly
385                 390                 395                 400

Tyr Thr Pro Phe Ser Gly Ser Ser Thr Asn Glu Thr Tyr Asp Asn Leu
                405                 410                 415

Arg Arg Trp Lys Gln Thr Leu Arg Arg Pro Arg Gln Ser Asp Gly Arg
                420                 425                 430

Ala Ala Phe Ser Asp Arg Thr Trp Asp Leu Ile Thr Arg Leu Ile Ala
            435                 440                 445

Asp Pro Ile Asn Arg Leu Arg Ser Phe Glu His Val Lys Arg Met Ser
            450                 455                 460

Tyr Phe Ala Asp Ile Asn Phe Ser Thr Leu Arg Ser Met Ile Pro Pro
465                 470                 475                 480

Phe Thr Pro Gln Leu Asp Ser Glu Thr Asp Ala Gly Tyr Phe Asp Asp
                485                 490                 495

Phe Thr Ser Glu Ala Asp Met Ala Lys Tyr Ala Asp Val Phe Lys Arg
                500                 505                 510

Gln Asp Lys Leu Thr Ala Met Val Asp Asp Ser Ala Val Ser Ser Lys
            515                 520                 525

Leu Val Gly Phe Thr Phe Arg His Arg Asn Gly Lys Gln Gly Ser Ser
            530                 535                 540

Gly Ile Leu Phe Asn Gly Leu Glu His Ser Asp Pro Phe Ser Thr Phe
545                 550                 555                 560

Tyr
```

NUCLEOTIDE AND PROTEIN SEQUENCES OF LATS GENES AND METHODS BASED THEREON

TABLE OF CONTENTS
1. INTRODUCTION
2. BACKGROUND OF THE INVENTION
3. SUMMARY OF THE INVENTION
   3.1. DEFINITIONS
4. DESCRIPTION OF THE FIGURES
5. DETAILED DESCRIPTION OF THE INVENTION
   5.1. ISOLATION OF THE LATS GENES
   5.2. EXPRESSION OF THE LATS GENE
   5.3. IDENTIFICATION AND PURIFICATION OF THE LATS GENE PRODUCTS
   5.4. STRUCTURE OF THE LATS GENE AND PROTEIN
      5.4.1. GENETIC ANALYSIS
      5.4.2. PROTEIN ANALYSIS
   5.5. GENERATION OF ANTIBODIES TO LATS PROTEINS AND DERIVATIVES THEREOF
   5.6. LATS PROTEINS, DERIVATIVES AND ANALOGS
      5.6.1. DERIVATIVES OF LATS CONTAINING ONE OR MORE DOMAINS OF THE PROTEIN
   5.7. ASSAYS OF LATS PROTEINS, DERIVATIVES AND ANALOGS
   5.8. THERAPEUTIC USES
      5.8.1. TREATMENT AND PREVENTION OF DISORDERS INVOLVING OVERPROLIFERATION OF CELLS
         5.8.1.1. MALIGNANCIES
         5.8.1.2. PREMALIGNANT CONDITIONS
         5.8.1.3. HYPERPROLIFERATIVE AND DYSPROLIFERATIVE DISORDERS
         5.8.1.4. GENE THERAPY
      5.8.2. TREATMENT AND PREVENTION OF DISORDERS IN WHICH CELL PROLIFERATION IS DESIRED
         5.8.2.1. ANTISENSE REGULATION OF LATS EXPRESSION
            5.8.2.1.1. LATS ANTISENSE NUCLEIC ACIDS
            5.8.2.1.2. THERAPEUTIC USE OF LATS ANTISENSE NUCLEIC ACIDS
   5.9. DEMONSTRATION OF THERAPEUTIC OR PROPHYLACTIC UTILITY
   5.10. THERAPEUTIC/PROPHYLACTIC ADMINISTRATION AND COMPOSITIONS
   5.11. ADDITIONAL USE OF INHIBITION OF LATS FUNCTION TO PROMOTE INCREASED GROWTH
   5.12. DIAGNOSIS AND SCREENING
   5.13. SCREENING FOR LATS AGONISTS AND ANTAGONISTS
   5.14. ANIMAL MODELS
   5.15. METHODS OF IDENTIFYING TUMOR SUPPRESSOR GENES AND OTHER GENES WITH IDENTIFIABLE PHENOTYPES
6. IDENTIFYING TUMOR SUPPRESSORS IN GENETIC MOSAICS: THE DROSOPHILA LATS GENE ENCODES A PUTATIVE PROTEIN KINASE
   6.1. MATERIALS AND METHODS
   6.2. RESULTS
   6.3. DISCUSSION
7. ISOLATION AND CHARACTERIZATION OF MAMMALIAN LATS HOMOLOGS
   7.1. ISOLATION AND CHARACTERIZATION OF MOUSE LATS HOMOLOGS
   7.2. ISOLATION AND CHARACTERIZATION OF HUMAN LATS HOMOLOGS
8. CONSERVATION OF SEQUENCES AND DOMAIN STRUCTURE AMONG LATS HOMOLOGS OF DIFFERENT SPECIES
9. FUNCTIONAL INTERCHANGEABILITY OF THE HUMAN AND DROSOPHILA LATS HOMOLOGS
   9.1. OVEREXPRESSION OF HUMAN LATS OR OF DROSOPHILA LATS CAUSES A SMALLER, ROUGH EYE IN DROSOPHILA
   9.2. HUMAN H-LATS GENE CAN REPLACE THE DROSOPHILA HOMOLOG TO PREVENT DEATH IN DROSOPHILA ANIMALS HAVING MUTANT DROSOPHILA LATS
10. HUMAN LATS EXPRESSION IS FOUND IN ALL NORMAL TISSUES TESTED AND IS ABSENT IN A LARGE NUMBER OF TUMOR CELL LINES
    10.1. HUMAN LATS EXPRESSION IN NORMAL TISSUES
    10.2. HUMAN LATS EXPRESSION IN VARIOUS TUMOR CELL LINES
11. DEPOSIT OF MICROORGANISM

1. INTRODUCTION

The present invention relates to tumor suppressor genes, in particular to "lats" genes (large tumor suppressor) and their encoded protein products, as well as derivatives and analogs thereof. Production of lats proteins, derivatives, and antibodies is also provided. The invention further relates to therapeutic compositions and methods of diagnosis and therapy.

2. BACKGROUND OF THE INVENTION

Tumorigenesis in humans is a complex process involving activation of oncogenes and inactivation of tumor suppressor genes (Bishop, 1991, Cell 64:235–248). Tumor suppressor genes in humans have been identified through studies of genetic changes occurring in cancer cells (Ponder, 1990, Trends Genet. 6:213–218; Weinberg, 1991, Science 254:1138–1146). In Drosophila, tumor suppressor genes have been previously identified by recessive overproliferation mutations that cause late larval and pupal lethality (Gateff, 1978, Science 200:1448–1459; Gateff and Mechler, 1989, CRC Crit. Rev. Oncogen 1:221–245; Bryant, 1993, Trends Cell Biol. 3:31–35; Török et al., 1993, Genetics 135:71–80). Mutations of interest were identified when dissection of dead larvae and pupae revealed certain overproliferated tissues. Several genes identified in homozygous mutants have been cloned including l(1)discs large-1(dlg; Woods and Bryant, 1991, Cell 66:451–464; Woods and Bryant, 1993, Mechanisms of Development 44:85–89), fat (Mahoney et al., 1991, Cell 67:853–868), l(2)giant larvae (lgl. Lützelschwab et al., 1987, EMBO J. 6:1791–1797; Jacob et al., 1987, Cell 50:215–225), expanded (ex; Boedigheimer and Laughon, 1993, Development 118:1291–1301; Boedigheimer et al., 1993, Mechanisms of Development 44:83–84), hyperplastic discs (hyd; Mansfield et al., 1994, Developmental Biology 165:507–526) and the gene encoding the S6 ribosomal protein (Watson et al., 1992, Proc. Natl. Acad. Sci. USA 89:11302–11306; Stewart and Denell, 1993, Mol. Cell. Biol. 13:2524–2535).

Although examining homozygous mutant animals has allowed the successful identification of overproliferation mutations that cause late larval and pupal lethality, mutations that cause lethality at early developmental stages are unlikely to be recovered by this approach. The present invention solves this problem by providing a method for identifying tumor suppressor genes that does not exclude genes that when mutated cause lethality in early developmental stages, and provides genes thus identified with a fundamental role in regulation of cell proliferation.

Citation of references hereinabove shall not be construed as an admission that such references are prior art to the present invention.

3. SUMMARY OF THE INVENTION

The present invention relates to nucleotide sequences of lats genes (Drosophila, human, and mouse lats and lats homologs of other species), and amino acid sequences of their encoded proteins, as well as derivatives (e.g., fragments) and analogs thereof. Nucleic acids hybridizable to or complementary to the foregoing nucleotide sequences are also provided. In a specific embodiment, the lats protein is a human protein.

The invention also relates to.a method of identifying tumor suppressor genes that does not exclude from identification genes that cause lethality at early developmental stages, thus overcoming the limitations of prior art methods. The method thus allows the identification of genes that regulate cell proliferation and that act at early developmental stages. The genes which thus can be identified play a fundamental role in regulation of cell proliferation such that their dysfunction (e.g., by lack of expression or mutation) leads to overproliferation and cancer.

Lats is a gene provided by the present invention, identified by the method of the invention, that acts to inhibit cell proliferation, and that plays a crucial role throughout development.

The invention also relates to lats derivatives and analogs of the invention which are functionally active, i.e., they are capable of displaying one or more known functional activities associated with a full-length (wild-type) lats protein. Such functional activities include but are not limited to kinase activity, antigenicity [ability to bind (or compete with lats for binding) to an anti-lats antibody], immunogenicity (ability to generate antibody which binds to lats), and ability to bind (or compete with lats for binding) to a receptor/ligand for lats (e.g., a SH3 domain-containing protein).

The invention further relates to fragments (and derivatives and analogs thereof) of lats which comprise one or more domains of a lats protein.

Antibodies to lats, and lats derivatives and analogs, are additionally provided.

Methods of production of the lats proteins, derivatives and analogs, e.g., by recombinant means, are also provided.

The present invention also relates to therapeutic and diagnostic methods and compositions based on lats proteins and nucleic acids. Therapeutic compounds of the invention include but are not limited to lats proteins and analogs and derivatives (including fragments) thereof; antibodies thereto; nucleic acids encoding the lats proteins, analogs, or derivatives; and lats antisense nucleic acids.

The invention provides for treatment of disorders of overproliferation (e.g., cancer and hyperproliferative disorders) by administering compounds that promote lats activity (e.g., lats, an agonist of lats; nucleic acids that encode lats).

The invention also provides methods of treatment of disorders involving deficient cell proliferation (growth) or in which cell proliferation is otherwise desired (e.g., degenerative disorders, growth deficiencies, lesions, physical trauma) by administering compounds that antagonize, (inhibit) lats function (e.g., antibodies, antisense nucleic acids).

Antagonizing lats function can also be done to grow larger animals and plants, e.g., those used as food or material sources.

Animal models, diagnostic methods and screening methods for predisposition to disorders, and methods to identify lats agonists and antagonists, are also provided by the invention.

3.1. DEFINITIONS

As used herein, underscoring or italicizing the name of a gene shall indicate the gene, in contrast to its encoded protein product which is indicated by the name of the gene in the absence of any underscoring or italicizing. For example, "lats" shall mean the lats gene, whereas "lats" shall indicate the protein product of the lats gene.

4. DESCRIPTION OF THE FIGURES

FIG. 1. Identifying overproliferation mutations in mosaic flies. (A) Although animals that are homozygous for a lethal mutation could die at an early developmental stage, mosaic flies carrying clones of cells that are homozygous for the same mutation could live. One can identify potential tumor suppressors by generating and examining clones of overproliferated mutant cells in mosaic animals. The genetic constitution of these mosaic flies is similar to the mosaicism of the tumor patients. (B) Genetic scheme. The P-element insertions carrying the FLP recombinase (hsFLP; Golic and Lindquist, 1989, Cell 59:499–509), its target site, FRT (solid arrows, Xu and Rubin, 1993, Development 117:1223–1237), the yellow$^+$ and mini-white$^+$ marker genes (y$^+$ and mini-w$^+$, open arrows) are indicated. Mutagenized males were crossed to females to produce heterozygous embryos. Clones of cells homozygous for the induced mutations were generated in developing first-instar larvae by mitotic recombination at the FRT sites induced with the FLP recombinase. Mosaic adults were examined for overproliferated mutant patches (w$^-$, y$^-$). Individuals carrying clones of interest were then mated to recover the mutations of interest in the next generation (Xu and Rubin, 1993, Development 117:1223–1237; Xu and Harrison, 1994; Methods in Cell Biology 44:655–682). Clones of ommatidia derived from fast proliferating mutant cells were identified since they were larger than their darkly pigmented wt (wild-type) twin-spot clones (mini-w$^+$/mini-w$^+$).

FIG. 2. Mutant phenotypes. (A) A clone of unpatterned, overproliferated lats mutant cells in the eye. (B) Induced at the same stage, the 93B mutant cells formed a less overproliferated clone. (C) A third instar lats$^{e26-1}$ larva (right) was much larger than a wt sibling (left; at 18° C.). (D) Wing discs from the larva in (C) (wt, top; lats$^{e26-1}$, bottom). (E) Dissected central nervous systems (wt, top; lats$^{e26-1}$, bottom). (F) A SEM (scanning electron microscope) view of a lats clone near the eye. (G) A closer view of a region in (F) showing the irregularity of the sizes and shapes of the mutant cells. (H) A plastic section of a mutant clone similar to the one in (F). Cells seem to be "budding" out of the surface to form new proliferating lobes (arrows). (I) A lats clone on the back. The boxed area is shown in (J). The bristles in the mutant clone are short, bent and often split (arrows). (K) A closer view of the hairs in a lats clone on the body showing enlarged bases and bent tips. (L) A section of a lats clone on the back showing extra cuticle deposits (arrows). All the mutant clones were induced with lats$^{x1}$ unless stated differently.

Figure 3:
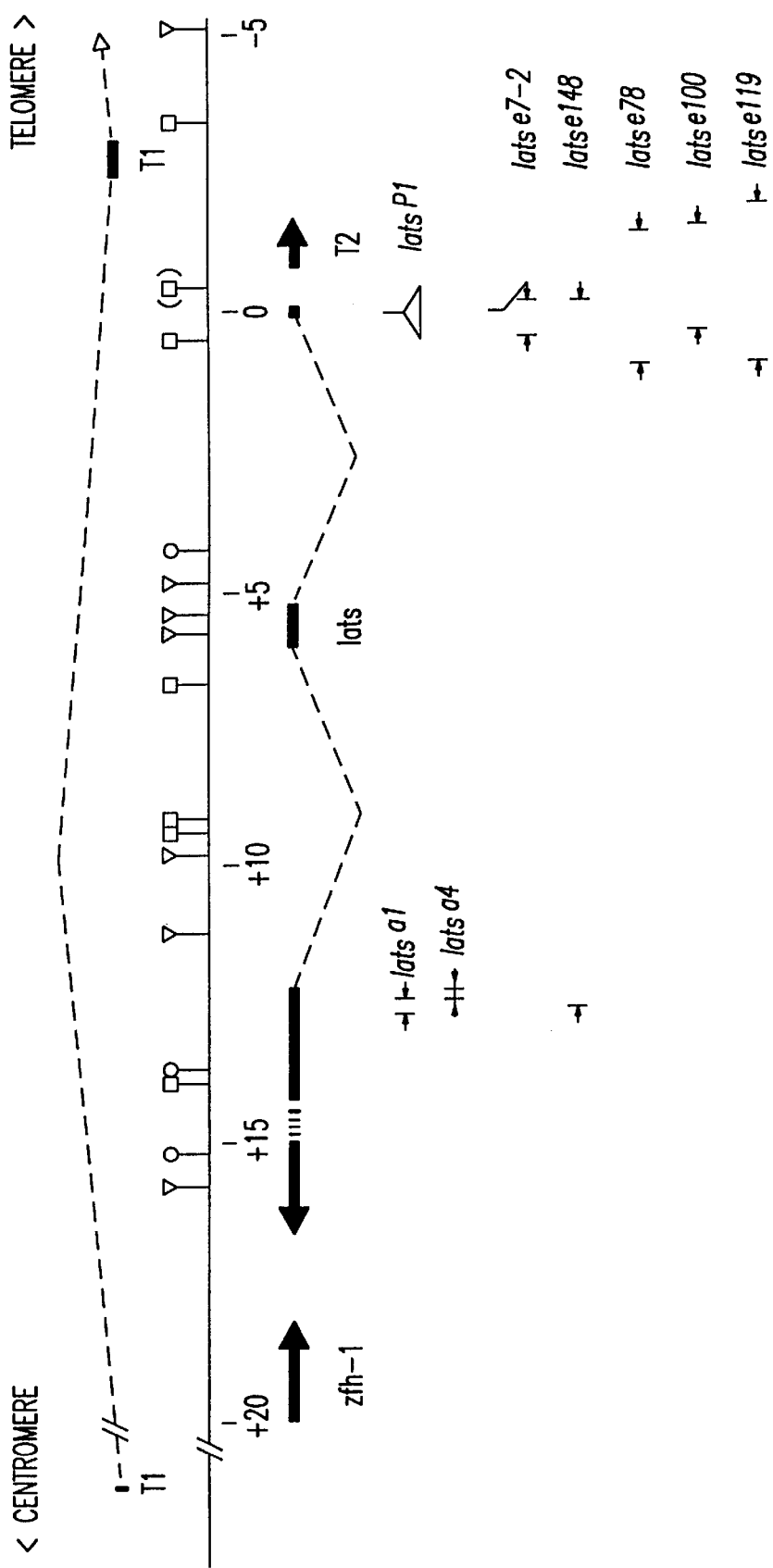

FIG. 3. Organization of the Drosophila lats gene. The genomic restriction map of the lats region is aligned with the lats 5.7 kb transcript unit. The direction of transcription is indicated with large arrows. The sizes of the lats introns are as follows: intron 1 (5.0 kb), intron 2 (5.8 kb), intron 3 (68 bp), intron 4 (63 bp), intron 5 (64 bp), intron 6 (61 bp), intron 7 (62 bp). The genomic DNA from +7.5 (BglII) to −4.2 (EcoRI) was used to screen a total imaginal disc cDNA library, which isolated three groups of cDNAs: lats, T1, T2. The introns in the T2 transcript are not labeled. Only parts of the zfh-1 (Fortini et al., 1991, Mechan. Dev. 34:113–122) and T1 transcripts are indicated. The locations of the P-element insertion (lats$^{P1}$), the deletions in the five excision alleles (lats$^{e7-2,\ e78,\ e100,\ e119,\ e148}$) and in lats$^{a1}$, lats$^{a4}$ are indicated at the bottom. The slash indicates a gap in the genomic map. Restriction sites: EcoRI (small open arrow), BglII (open box) and BamHI (open circle). The BglII site at the −0.5 position of the CLT-52 clone is not present in other genomic DNA. A scale is labeled under the restriction map.

Figure 4:
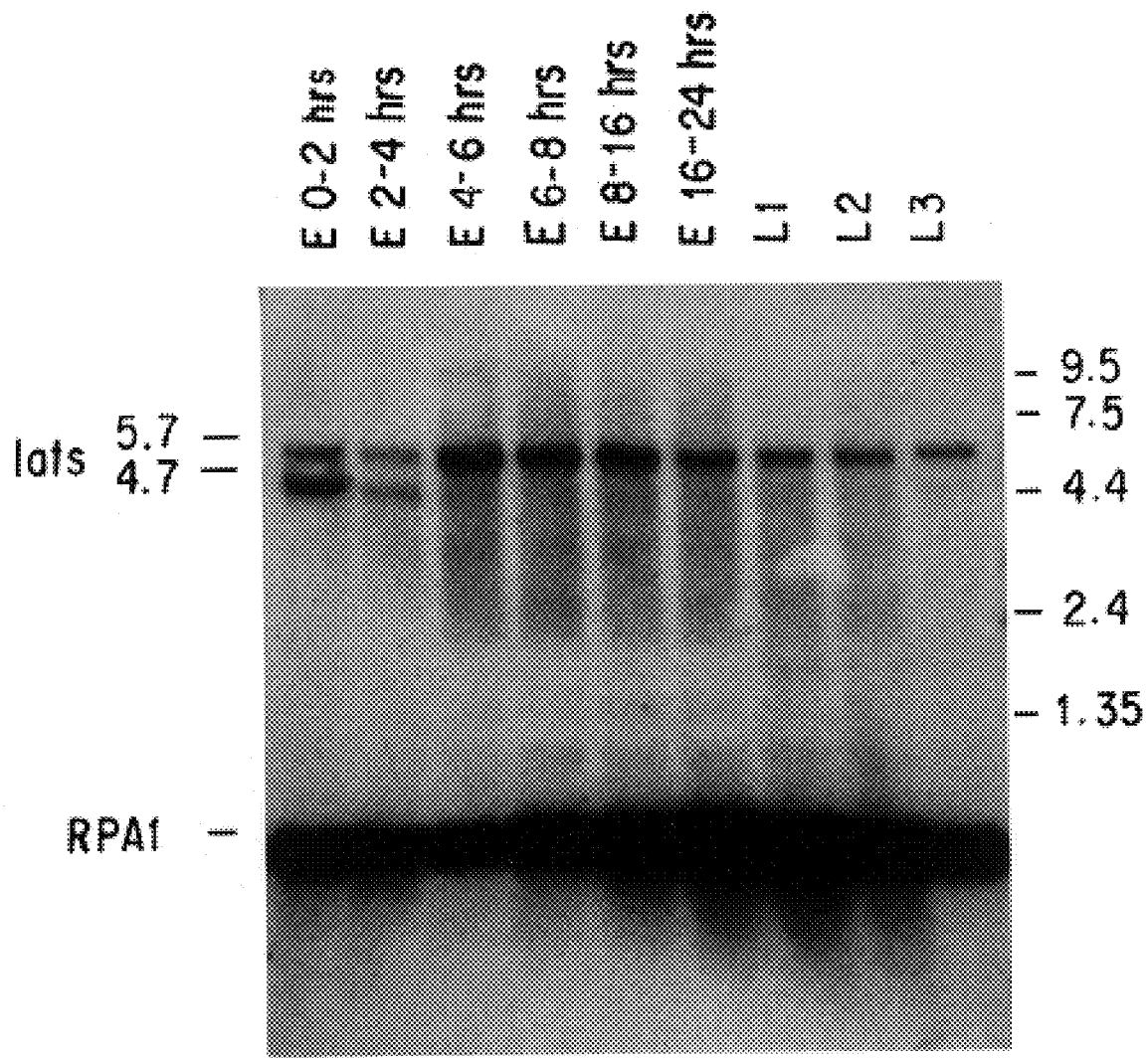

FIG. 4. RNA blot analysis of the Drosophila lats mRNA. Five μg of poly(A)$^+$ RNA isolated from various developmental stages was separated on a 1% agarose gel, and hybridized with $^{32}$P-labeled 5' end 1 kb probe from the Drosophila lats cDNA. E0–2 hrs, E2–4 hrs, E4–6 hrs, E6–8 hrs, E8–16 hrs and E16–24 hrs indicate the age of the embryos in hours. RNA from first, second and third instar larvae is denoted by L1, L2, and L3, respectively. The numbers and arrows on the right correspond to the size and location of the RNA standards. A 5.7 kb RNA was found in all the developmental stages, whereas a 4.7 kb RNA was predominantly present in 0 to 4 hour old embryos. The blot was also hybridized with DNA from the ribosomal protein gene, RNA1.

FIG. 5. Composite cDNA sequence of the Drosophila lats gene. The entire cDNA sequence (SEQ ID NO:1) corresponding to the 5.7 kb lats RNA is shown. This nucleotide sequence is a composite of two cDNA clones (nucleotide 1–191 from cDNA 9 and the rest from cDNA A2). The sequence of the corresponding genomic DNA has been determined and is identical to the cDNA sequence except where indicated (above the cDNA sequence). The predicted amino acid sequence (SEQ ID NO:2) is shown below the cDNA sequence.

The opa repeat is indicated by the heavy bar. The location of the putative SH3 binding site and the RERDQ peptides are designated by dashed lines. The two sites that match the polyadenylation signal consensus sequence are underlined. The second site is located at 12 bp away from the 3' end of the cDNA. The locations of the introns are indicated by vertical arrows. The underlined 141 bp sequence at the 3' end of the lats transcript is identical to the 5' end untranslated sequence of the class I transcript of the Drosophila phospholipase C gene, plc-21. The location of the 446 bp deletion in the lats$^{a1}$ allele is also indicated.

Figure 6A:
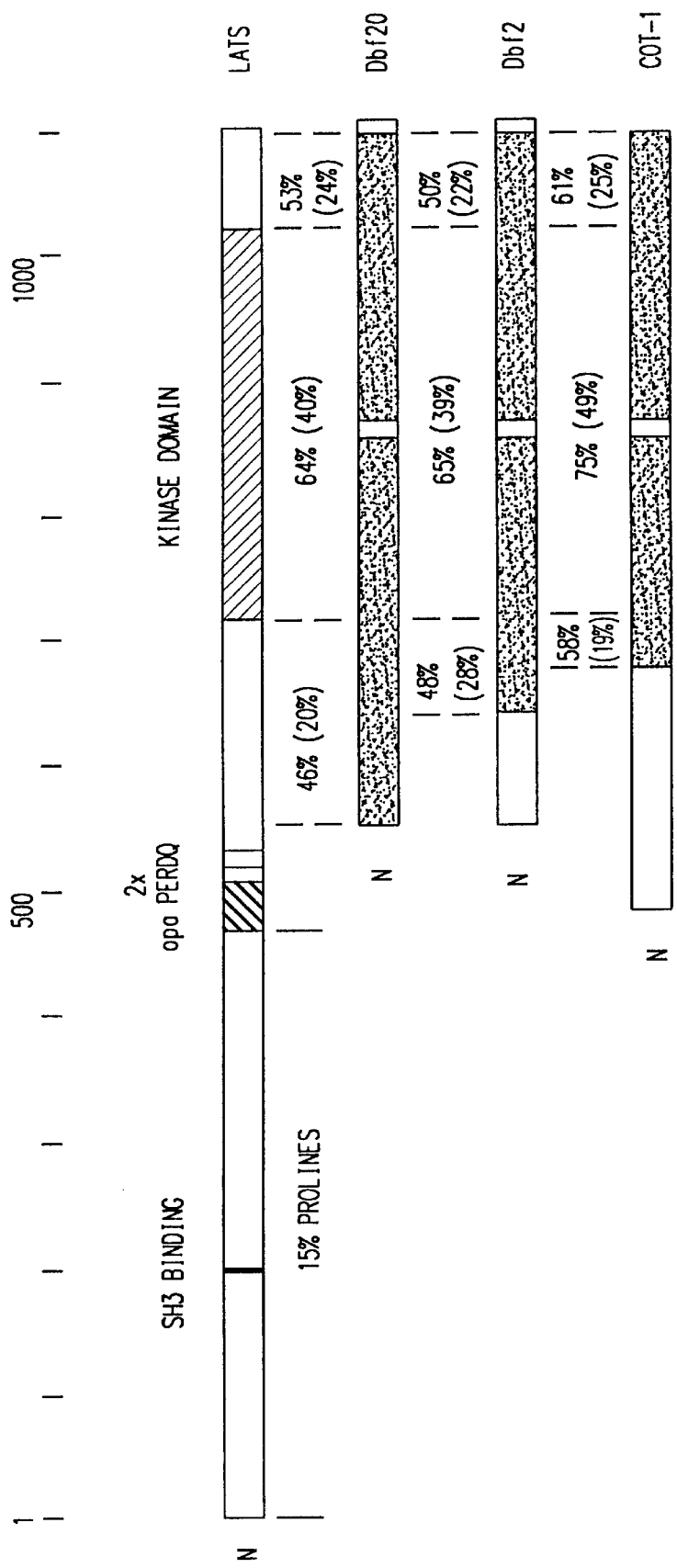
Figure 6B:
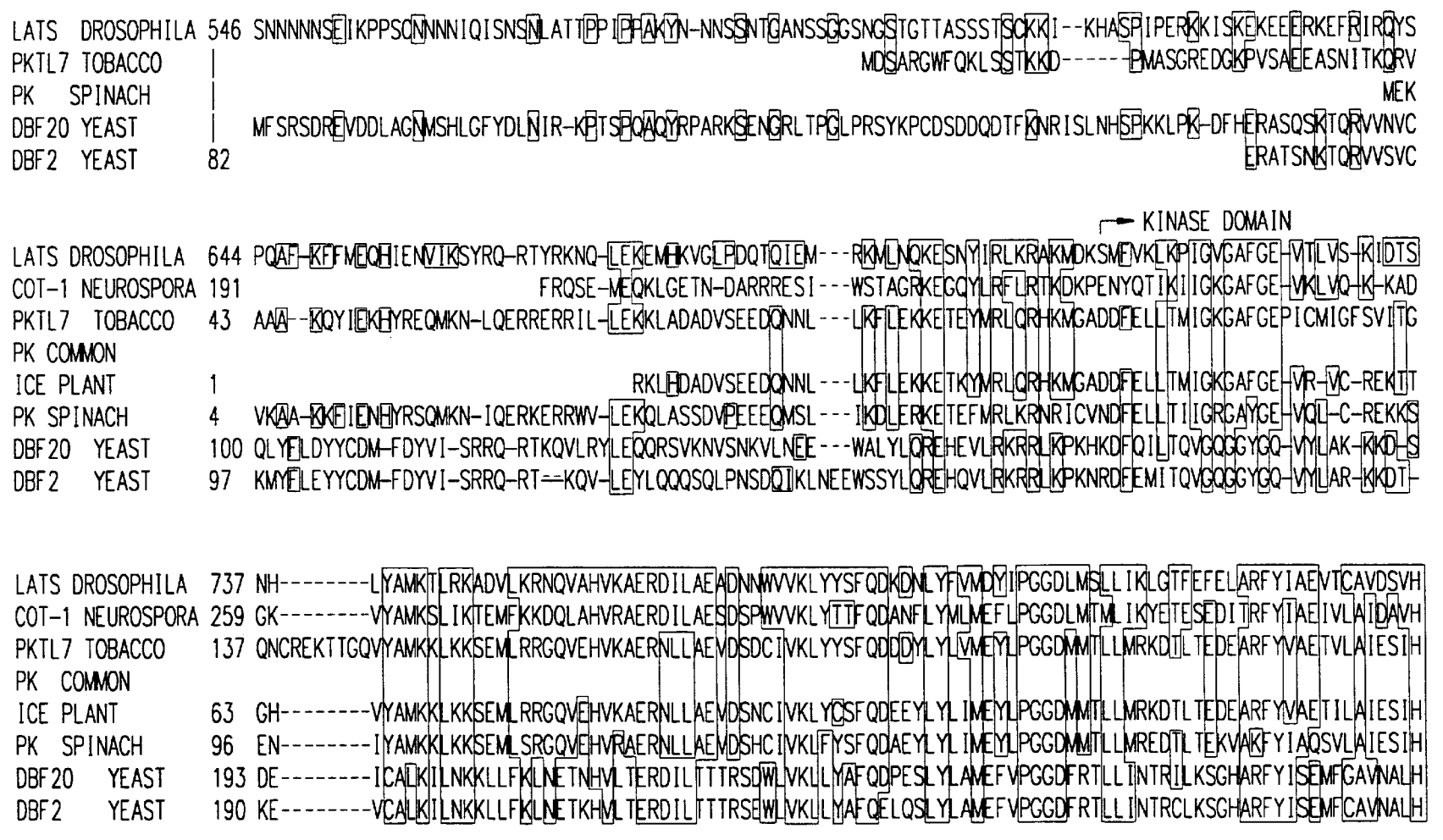

FIGS. 6A and 6B. Schematic of the Drosophila lats predicted protein (SEQ ID NO:2) and the related proteins (A) and sequence comparison of the proteins homologous to lats (B).

In FIG. 6A, solid, hatched, open and shaded boxes denote putative SH3 binding site, opa repeat, RERDQ peptide and kinase domain in the lats protein, respectively. The Dbf20, Dbf2 and COT-1 proteins are illustrated at the bottom. The regions that are homologous to lats are indicated by shaded boxes. The degrees of sequence similarity (percentage of identical sequences inside parentheses; percentage of identical or conservative substitutions outside parentheses) between lats and the three related proteins are indicated above the corresponding regions of these proteins. In FIG. 6B, the carboxy-terminal half of lats is compared to the six most related proteins that are revealed.by blastp (a software program that searches for protein sequence homologies) search as of Sep. 1, 1994. Neurospora cot-1 (SEQ ID NO:11); tobacco PKTL7 (SEQ ID NO:12); common ice plant protein kinase (SEQ ID NO:13); spinach protein kinase (SEQ ID NO:14); yeast Dbf-20 (SEQ ID NO:15); yeast Dbf2 (SEQ ID NO:16). Amino acid residues identical to lats are highlighted. Numbers at the beginning of every sequence refer to the position of that amino acid within the total protein sequence. The boundary of the kinase domain is defined according to Hanks et al. (1988, Science 241:42–52). The location of a region of about 40 amino acid residues that is not conserved among the proteins is indicated by the heavy bar above the sequence. The sequence of PKTL7 from tobacco, *Nicotiana tabacum*, was submitted to Genbank by Huang,Y. (X71057). Both the sequence of the protein kinase from spinach, *Spinacia oleracea*, and the sequence of the protein kinase from common ice plant, *Mesembryanthemum crystallinum*, were submitted to Genbank by Baur, B., Winter, K., Fischer, K. and Dietz, K. (Z30329 and Z30330).

FIG. 7. cDNA sequence (SEQ ID NO:5) and deduced protein sequence (SEQ ID NO:6) of a mouse lats homolog, m-lats.

FIG. 8. cDNA sequence (SEQ ID NO:7) and deduced protein sequence (SEQ ID NO:8) of a mouse lats homolog, m-lats2.

FIG. 9. cDNA sequence (SEQ ID NO:3) and deduced protein sequence (SEQ ID NO:4) of a human lats homolog, h-lats.

Figure 10:
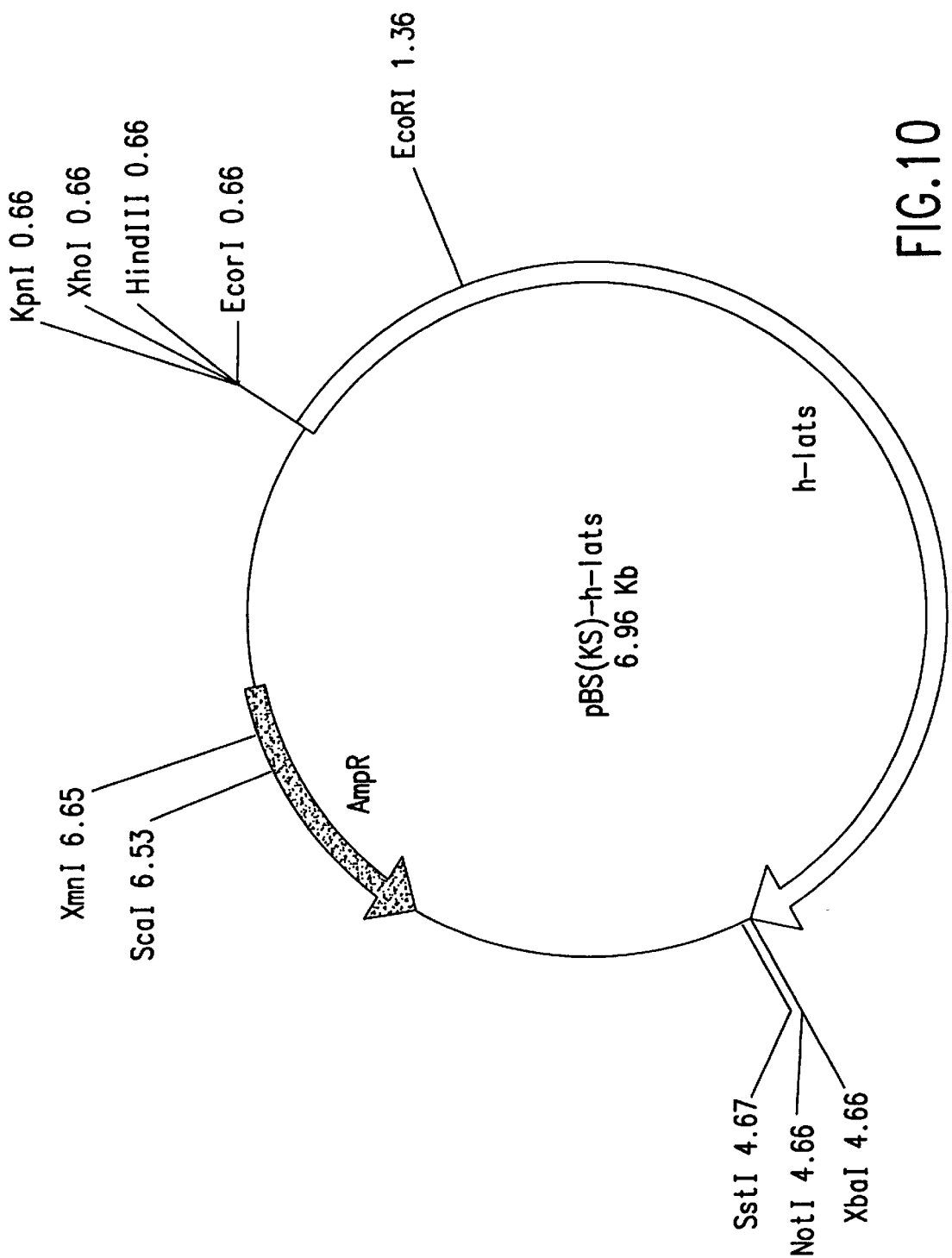

FIG. 10. Schematic diagram of plasmid pBS(KS)-h-lats, containing the full length coding sequence of the h-lats cDNA.

FIG. 11. Alignment of the h-lats protein sequence (SEQ ID NO:4) (upper case letters) with the m-lats protein sequence (SEQ ID NO:6) (lower case letters). A dot indicates amino acid identity; a dash indicates a.deletion relative to the sequence on the line above. The amino-terminal portion of the m-lats protein is not shown due to the missing 5' end of the m-lats cDNA coding region.

FIG. 12. Alignment of the h-lats protein sequence (SEQ ID NO:4) (upper case letters) with the m-lats2 protein sequence (SEQ ID NO:8) (lower case letters). A dot indicates amino acid identity; a dash indicates a deletion relative to the sequence on the line above. The amino-terminal portion of the m-lats2 protein is not shown due to the missing 5' end of the m-lats2 cDNA coding region.

FIG. 13. Alignment of the h-lats protein sequence (SEQ ID NO:4) (upper case letters) with the Drosophila lats protein sequence (SEQ ID NO:2) (lower case letters). A dot indicates amino acid identity; a dash indicates a deletion relative to the sequence on the line above. Insertions in the Drosophila sequence relative to the human sequence are indicated below the sequence line. Conserved domains are indicated. LSD2=lats split domain 2; LSD2a=LSD2 anterior portion; LSD2p=LSD2 posterior portion. The putative SH3-binding domain and the kinase domain are shown. LSD1= lats split domain 1; LSD1a=LSD1 anterior portion; LSD1p= LSD1 posterior portion. LFD=lats flanking domain. LCD1= lats C-terminal domain 1; LCD2=lats C-terminal domain 2; LCD3=lats C-terminal domain 3.

Figure 14:
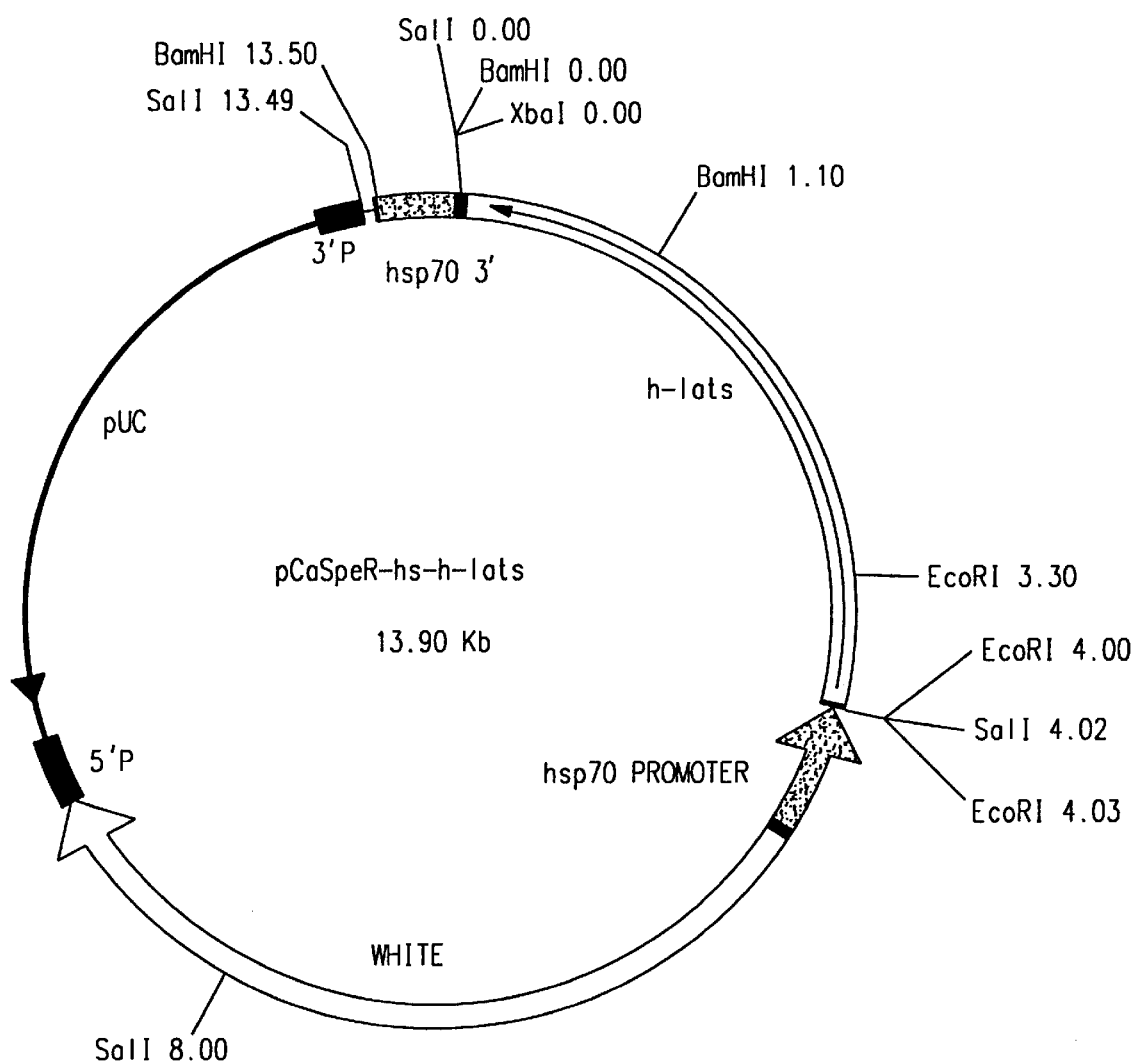

FIG. 14. Schematic diagram of plasmid pCaSpeR-hs-h-lats, an expression vector containing the full length coding sequence of the h-lats cDNA.

Figure 15:
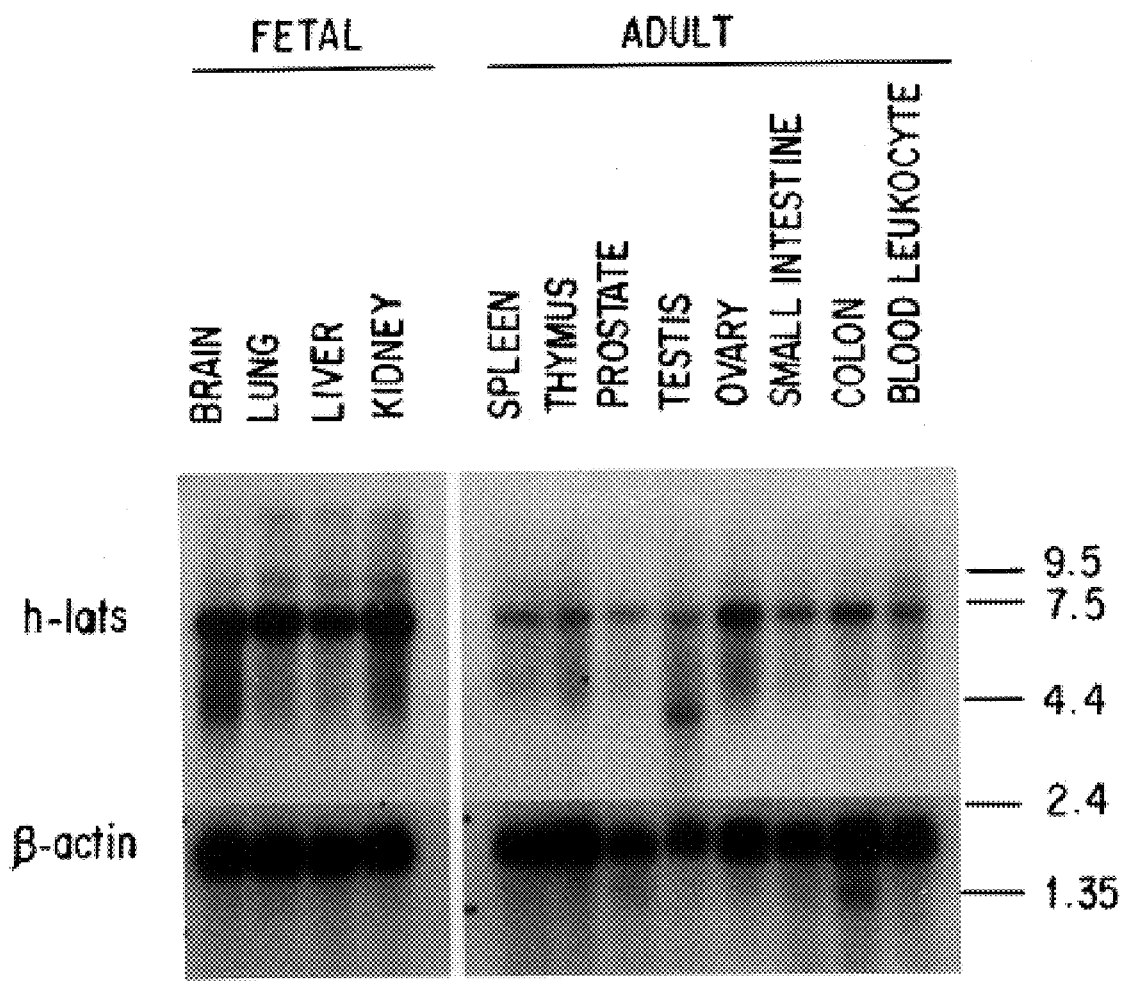

FIG. 15. Northern blot analysis of h-lats expression in normal human tissues. A $^{32}$P-labeled BamHI fragment of h-lats was used as a probe for hybridization to polyA$^+$ RNA from the normal human fetal and adult tissues indicated for each lane. The positions of standard molecular weight markers are shown at right. The positions of the h-lats RNA and of β-actin RNA (used as a standard) are shown.

5. DETAILED DESCRIPTION OF THE INVENTION

The present invention relates to nucleotide sequences of lats genes, and amino acid sequences of their encoded proteins. The invention further relates to fragments and other derivatives, and analogs, of lats proteins. Nucleic acids encoding such fragments or derivatives are also within the scope of the invention. The invention provides lats genes and their encoded proteins of many different species. The lats genes of the invention include Drosophila, human, and mouse lats and related genes (homologs) in other species. In specific embodiments, the lats genes and proteins are from vertebrates, or more particularly, mammals. In a preferred embodiment of the invention, the lats genes and proteins are of human origin. Production of the foregoing proteins and derivatives, e.g., by recombinant methods, is provided.

The invention also relates to a method of identifying tumor suppressor genes that does not exclude from identification genes that cause lethality at early developmental stages, thus overcoming the limitations of prior art methods. The method thus allows the identification of genes that regulate cell proliferation and that act at early developmental stages. The genes which thus can be identified play a fundamental role in regulation of cell proliferation such that their dysfunction (e.g., due to lack of expression or mutation) leads to overproliferation and cancer.

Lats is a gene provided by the present invention, identified by the method of the invention, that acts to inhibit cell proliferation, and that plays a crucial role throughout development.

The invention also relates to lats derivatives and analogs of the invention which are functionally active, i.e., they are capable of displaying one or more known functional activities associated with a full-length (wild-type) lats protein. Such functional activities include but are not limited to kinase activity, antigenicity [ability to bind (or compete with lats for binding) to an anti-lats antibody], immunogenicity (ability to generate antibody which binds to lats), ability to bind (or compete with lats for binding) to an SH3-domain-containing protein or other ligand, ability to inhibit cell proliferation, tumor inhibition, etc.

The invention further relates to fragments (and derivatives and analogs thereof) of lats which comprise one or more domains of the lats protein.

Antibodies to lats, its derivatives and analogs, are additionally provided.

The present invention also relates to therapeutic and diagnostic methods and compositions based on lats proteins and nucleic acids and anti-lats antibodies. The invention provides for treatment of disorders of overproliferation (e.g., cancer and hyperproliferative disorders) by administering compounds that promote lats activity (e.g., lats proteins and functionally active analogs and derivatives (including fragments) thereof; nucleic acids encoding the lats proteins, analogs, or derivatives, agonists of lats).

The invention also provides methods of treatment of disorders involving deficient cell proliferation or in which cell proliferation (growth) is otherwise desirable (e.g., growth deficiencies, degenerative disorders, lesions, physical trauma) by administering compounds that antagonize, or inhibit, lats function (e.g., antibodies, lats antisense nucleic acids, lats derivatives that are dominant-negative protein kinases).

Inhibition of lats function can also be done to grow larger farm animals and plants.

Animal models, diagnostic methods and screening methods for predisposition to disorders are also provided by the invention.

The invention is illustrated by way of examples infra which disclose, inter alia, the cloning and characterization of D. melanogaster lats (Section 6); the cloning and characterization of mouse and human lats homologs (Section 7); the sequence and domain conservation among the lats homologs (Section 8); the functional interchangeability of the human and Drosophila lats homologs (Section 9); and the differentially decreased expression of human lats in human tumor cell lines (Section 10).

For clarity of disclosure, and not by way of limitation, the detailed description of the invention is divided into the subsections which follow.

5.1. ISOLATION OF THE LATS GENES

The invention relates to the nucleotide sequences of lats nucleic acids. In specific embodiments, lats nucleic acids comprise the cDNA sequences of SEQ ID NO:1, 3, 5, or 7, or the coding regions thereof, or nucleotide sequences acids encoding a lats protein (e.g., a protein having the sequence of SEQ ID NO:2, 4, 6, or 8). The invention provides purified nucleic acids consisting of at least 8 nucleotides (i.e., a hybridizable portion) of a lats sequence; in other embodiments, the nucleic acids consist of at least 25 (continuous) nucleotides, 50 nucleotides, 100 nucleotides, 150 nucleotides, or 200 nucleotides of a lats sequence, or a full-length lats coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of a lats gene. In a specific embodiment, a nucleic acid which is hybridizable to a lats nucleic acid (e.g., having sequence SEQ ID NO:3 or 7), or to a nucleic acid encoding a lats derivative, under conditions of low stringency is provided. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in absolution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film.

Other conditions of low stringency which may be used are well known in the art (e.g., as employed for cross-species hybridizations).

In another specific embodiment, a nucleic acid which is hybridizable to a lats nucleic acid under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–°×10cpm of $^{32}$P-labeled probe. Washing of filters is done at 37° C. for 1 h in a solution containing 2×SSC, 0.01 PVP, 0.01 Ficoll, and 0.01% BSA. This is followed by a wash in 0.1×SSC at 50° C. for 45 min before autoradiography. Other conditions of high stringency which may be used are well known in the art.

In another specific embodiment, a nucleic acid, which is hybridizable to a lats nucleic acid under conditions of moderate stringency is provided (see, e.g., Section 7.2).

Nucleic acids encoding derivatives and analogs of lats proteins (see Sections 5.6 and 5.6.1), and lats antisense nucleic acids (see Section 5.8.2.2.1) are additionally provided. As is readily apparent, as used herein, a "nucleic acid encoding a fragment or portion of a lats protein" shall be construed as referring to a nucleic acid encoding only the recited fragment or portion of the lats protein and not the other contiguous portions of the lats protein as a continuous sequence.

Fragments of lats nucleic acids comprising regions conserved between (with homology to) other lats nucleic acids, of the same or different species, are also provided. Nucleic acids encoding one or more lats domains are provided.

Specific embodiments for the cloning of a lats gene, presented as a particular example but not by way of limitation, follows:

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed lats product. In one embodiment, anti-lats antibodies can be used for selection.

In another embodiment, polymerase chain reaction (PCR) is used to amplify the desired sequence in a genomic or cDNA library, prior to selection. Oligonucleotide primers representing known lats sequences can be used as primers in PCR. In a preferred aspect, the oligonucleotide primers represent at least part of the lats conserved segments of strong homology between lats of different species (e.g., LCD1, LCD2, kinase domain, LFD, SH3 binding domain, LSD1, and LSD2 domains; see, e.g., Section 8 infra.) The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known lats nucleotide sequence and the nucleic acid homolog being isolated. For cross species hybridization, low stringency conditions are preferred. For same species hybridization, moderately stringent conditions are preferred. After successful amplification of a segment of a lats homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding lats proteins and lats analogs may be identified.

The above-methods are not meant to limit the following general description of methods by which clones of lats may be obtained.

Any eukaryotic cell potentially can serve as the nucleic acid source for the molecular cloning of the lats gene. The nucleic acid sequences encoding lats can be isolated from vertebrate, mammalian, human, porcine, bovine, feline, avian, equine, canine, as well as additional primate sources, insects, plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a lats (of any species) gene or its specific RNA, or a fragment thereof (see Section 5.6), is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Such a procedure is presented by way of example in Section 7 infra. Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, kinase activity, inhibition of cell proliferation activity, substrate binding activity, or antigenic properties as known for lats. If an antibody to lats is available, the lats protein may be identified by binding of labeled antibody to the putatively lats synthesizing clones, in an ELISA (enzyme-linked immunosorbent assay)-type procedure.

The lats gene can also be identified by mRNA selection by nucleic acid hybridization followed by in vitro translation. In this procedure, fragments are used to isolate complementary mRNAs by hybridization. Such DNA fragments may represent available, purified lats DNA of another species (e.g., Drosophila, mouse, human). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against lats protein. A radiolabelled lats cDNA can be synthesized using the selected mRNA (from the adsorbed polysomes) as a template. The radiolabelled mRNA or cDNA may then be used as a probe to identify the lats DNA fragments from among other genomic DNA fragments.

Alternatives to isolating the lats genomic DNA include, but are not limited to, chemically synthesizing the gene sequence itself from a known sequence or making cDNA to the mRNA which encodes the lats protein. For example, RNA for cDNA cloning of the lats gene can be isolated from cells which express lats. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and lats gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated lats gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The lats sequences provided by the instant invention include those nucleotide sequences encoding substantially the same amino acid sequences as found in native lats proteins, and those encoded amino acid sequences with functionally equivalent amino acids, as well as those encoding other lats derivatives or analogs, as described in Sections 5.6 and 5.6.1 infra for lats derivatives and analogs.

5.2. EXPRESSION OF THE LATS GENES

The nucleotide sequence coding for a lats protein or a functionally active analog or fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native lats gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In specific embodiments, the human lats gene is expressed, or a sequence encoding a functionally active portion of human lats. In yet another embodiment, a fragment of lats comprising a domain of-the lats protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a lats protein or peptide fragment may be regulated by a second nucleic acid sequence so that the lats protein or peptide is expressed in a host transformed with the recombinant DNA molecule. For example, expression of a lats protein may be controlled by any promoter/enhancer element known in the art. Promoters which may be used to control lats expression include, but are not limited to, the SV40 early promoter region (Bernoist and Chambon, 1981, Nature 290:304–310), the.promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 35 78:1441–1445), the regulatory sequences of the metallothionein gene (Brinster et al., 1982, Nature 296:39–42); prokaryotic expression vectors such as the $\beta$-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to a lats-encoding nucleic acid, one or more origins of replication, and, optionally, one or more selectable markers (e.g., an antibiotic resistance gene).

In a specific embodiment, an expression construct is made by subcloning a lats coding sequence into the EcoRI restriction site of each of the three pGEX vectors (Glutathione S-Transferase expression vectors; Smith and Johnson, 1988, Gene 7:31–40). This allows for the expression of the lats protein product from the subclone in the correct reading frame.

Expression vectors containing lats gene inserts can be identified by three general approaches: (a) nucleic acid hybridization, (b) presence or absence of "marker" gene functions, and (c) expression of inserted sequences. In the first approach, the presence of a lats gene inserted in an expression vector can be detected by nucleic acid hybridization using probes comprising sequences that are homologous to an inserted lats gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a lats gene in the vector. For example, if the lats gene is inserted within the marker-gene sequence of the vector, recombinants containing the lats insert can be identified by the absence of the marker gene function. In the third approach, recombinant expression vectors can be identified by assaying the lats product expressed by the recombinant. Such assays can be based, for example, on the physical or functional properties of the lats protein in in vitro assay systems, e.g., kinase activity, binding with anti-lats antibody, inhibition of cell proliferation.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered lats protein may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the lats protein, fragment, analog, or derivative may be expressed as a fusion, or chimeric protein product (comprising the protein, fragment, analog, or derivative joined via a peptide bond to a heterologous protein sequence (of a different protein)).

Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.3. IDENTIFICATION AND PURIFICATION OF THE LATS GENE PRODUCTS

In particular aspects, the invention provides amino acid sequences of lats, preferably human lats, and fragments and derivatives thereof which comprise an antigenic determinant (i.e., can be recognized by an antibody) or which are otherwise functionally active, as well as nucleic acid sequences encoding the foregoing. "Functionally active" lats material as used herein refers to that material displaying one or more known functional activities associated with a full-length (wild-type) lats protein, e.g., kinase activity, inhibition of cell proliferation, tumor inhibition, binding to an SH3-domain, binding to a lats substrate or lats binding partner, antigenicity (binding to an anti-lats antibody), immunogenicity, etc.

In specific embodiments, the invention provides fragments of a lats protein consisting of at least 6 amino acids, 10 amino acids, 50 amino acids, or of at least 75 amino acids. In other embodiments, the proteins comprise or consist essentially of a lats carboxy (C)-terminal domain 3 (LCD3), lats C-terminal domain 2 (LCD2), lats C-terminal domain 1 (LCD1), kinase domain, kinase subdomains, lats flanking domain (amino-terminal to the kinase domain), lats split domain 1 (LSD1), lats split domain 2 (LSD2), SH3-binding domain, and opa repeat domain (see Section 8 infra), or any combination of the foregoing, of a lats protein. Fragments, or proteins comprising fragments, lacking some or all of the foregoing regions of a lats protein are also provided. Nucleic acids encoding the foregoing are provided.

Once a recombinant which expresses the lats gene sequence is identified, the gene product can be analyzed.

This is achieved by assays based on the physical or functional properties of the product, including radioactive labelling of the product followed by analysis by gel electrophoresis, immunoassay, etc.

Once the lats protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once a lats protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In another alternate embodiment, native lats proteins can be purified from natural sources, by standard methods such as those described above (e.g., immunoaffinity purification).

In a specific embodiment of the present invention, such lats proteins, whether produced by recombinant DNA techniques or by chemical synthetic methods or by purification of native proteins, include but are not limited to those containing, as a primary amino acid sequence, all or part of the amino acid sequence substantially as depicted in FIG. 9 (SEQ ID NO:4), as well as fragments and other derivatives, and analogs thereof, including proteins homologous thereto.

5.4. STRUCTURE OF THE LATS GENE AND PROTEIN

The structure of the lats gene and protein can be analyzed by various methods known in the art.

5.4.1. GENETIC ANALYSIS

The cloned DNA or cDNA corresponding to the lats gene can be analyzed by methods including but not limited to Southern hybridization (Southern, E. M., 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, T., 1982, Molecular Cloning, A Laboratory, Cold Spring Harbor, N.Y.), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a lats-specific probe can allow the detection of the lats gene in DNA from various cell types. Methods of amplification other than PCR are commonly known and can also be employed. In one embodiment, Southern hybridization can be used to determine the genetic linkage of lats. Northern hybridization analysis can be used to determine the expression of the lats gene. Various cell types, at various states of development or activity can be tested for lats expression. The stringency of the hybridization conditions for both Southern and Northern hybridization can be manipulated to ensure detection of nucleic acids with the desired degree of relatedness to the specific lats probe used. Modifications of these methods and other methods commonly known in the art can be used.

Restriction endonuclease mapping can be used to roughly determine the genetic structure of the lats gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. PROTEIN ANALYSIS

The amino acid sequence of the lats protein can be derived by deduction from the DNA sequence, or alternatively, by direct sequencing of the protein, e.g., with an automated amino acid sequencer.

The lats protein sequence can-be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the lats protein and the corresponding regions of the gene sequence which encode such regions.

Secondary, structural analysis (Chou, P. and Fasman, G., 1974, Biochemistry 13:222) can also be done, to identify regions of lats that assume specific secondary structures.

Manipulation, translation, and secondary structure prediction, open reading frame prediction and plotting, as well as determination of sequence homologies, can also be accomplished using computer software programs available in the art.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. GENERATION OF ANTIBODIES TO LATS PROTEINS AND DERIVATIVES THEREOF

According to the invention, lats protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to a human lats protein are produced. In another embodiment, antibodies to a domain (e.g., the SH3-binding domain) of a lats protein are produced. In a specific embodiment, fragments of a lats protein identified as hydrophilic are used as immunogens for antibody production.

Various procedures known in the art may be used for the production of polyclonal antibodies to a lats protein or derivative or analog. In a particular embodiment, rabbit polyclonal antibodies to an epitope of a lats protein encoded by a sequence of SEQ ID NOS:2, 4, 6 or 8, or a subsequence thereof, can be obtained. For the production of antibody, various host animals can be immunized by injection with the native lats protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a lats protein sequence or analog thereof, any technique which provides for the production of antibody molecules by continuous cell lines in culture may be used.

For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for lats together with genes from a human antibody molecule of appropriate biological activity can be used; such antibodies are within the scope of this invention.

According to the invention, techniques described for the production of single chain antibodies (U.S. Pat. No. 4,946,778) can be adapted to produce lats-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for lats proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a lats protein, one may assay generated hybridomas for a product which binds to a lats fragment containing such domain. For selection of an antibody that specifically binds a first lats homolog but which does not specifically bind a different lats homolog, one can select on the basis of positive binding to the first lats homolog and a lack of binding to the second lats homolog.

Antibodies specific to a domain of a lats protein are also provided.

The foregoing antibodies can be used in methods known in the art relating to the localization and activity of the lats protein sequences of the invention, e.g., for imaging these proteins, measuring levels thereof in appropriate physiological samples, in diagnostic methods, etc.

In another embodiment of the invention (see infra), anti-lats antibodies and fragments thereof containing the binding domain are Therapeutics.

5.6. LATS PROTEINS, DERIVATIVES AND ANALOGS

The invention further relates to lats proteins, and derivatives (including but not limited to fragments) and analogs of lats proteins. Nucleic acids encoding lats protein derivatives and protein analogs are also provided. In one embodiment, the lats proteins are encoded by the lats nucleic acids described in Section 5.1 supra. In particular aspects, the proteins, derivatives, or analogs are of lats proteins of animals, e.g., fly, frog, mouse, rat, pig, cow, dog, monkey, human, or of plants.

The production and use of derivatives and analogs related to lats are within the scope of the present invention. In a specific embodiment, the derivative or analog is functionally active, i.e., capable of exhibiting one or more functional activities associated with a full-length, wild-type lats protein. As one-example, such derivatives or analogs which have the desired immunogenicity or antigenicity can be used, for example, in immunoassays, for immunization, for inhibition of lats activity, etc. As another example, such derivatives or analogs which have the desired kinase activity, or which are phosphorylated or dephosphorylated, are provided. Derivatives or analogs that retain, or alternatively lack or inhibit, a desired lats property of interest (e.g., binding to an SH3-domain-containing protein or other lats binding partner, kinase activity, inhibition of cell proliferation, tumor inhibition), can be used as inducers, or inhibitors, respectively, of such property and its physiological correlates. A specific embodiment relates to a lats fragment that can be bound by an anti-lats antibody. Derivatives or analogs of lats can be tested for the desired activity by procedures known in the art, including but not limited to the assays described in Sections 5.7 and 5.9.

In particular, lats derivatives can be made by altering lats sequences by substitutions, additions or deletions that provide for functionally equivalent molecules. Due to the degeneracy of nucleotide coding sequences, other DNA sequences which encode substantially the same amino acid sequence as a lats gene may be used in the practice of the present invention. These include but are not limited to nucleotide sequences comprising all or portions of lats genes which are altered by the substitution of different codons that encode a functionally equivalent amino acid residue within the sequence, thus producing a silent change. Likewise, the lats derivatives of the invention include, but are not limited to, those containing, as a primary amino acid sequence, all or part of the amino acid sequence of a lats protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a lats protein consisting of at least 10 (continuous) amino acids of the lats protein is provided. In other embodiments, the fragment consists of at least 20 or 50 amino acids of the lats protein. In specific embodiments, such fragments are not larger than 35, 100 or 200 amino acids. Derivatives or analogs of lats include but are not limited to those molecules comprising regions that are substantially homologous to lats or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding lats sequence, under stringent, moderately stringent, or nonstringent conditions.

The lats derivatives and analogs of the invention can be produced by various methods known in the art. The manipulations which result in their production can occur at the gene or protein level. For example, the cloned lats gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of lats, care should be taken to ensure that the modified gene remains within the same translational reading frame as lats, uninterrupted by translational stop signals, in the gene region where the desired lats activity is encoded.

Additionally, the lats-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), etc.

Manipulations of the lats sequence may also be made at the protein level. Included within the scope of the invention are lats protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of lats can be chemically synthesized. For example, a peptide corresponding to a portion of a lats protein which comprises the desired domain (see Section 5.6.1), or which mediates the desired activity in vitro, can be synthesized by use of a peptide synthesizer. Furthermore, if desired, nonclassical amino acids or chemical amino acid analogs can be introduced as a substitution or addition into the lats sequence. Nonclassical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the lats derivative is a chimeric, or fusion, protein comprising a lats protein or fragment thereof (preferably consisting of at least a domain or motif of the lats protein, or at least 10 amino acids of the lats protein) joined at its amino- or carboxy-terminus via a peptide bond to an amino acid sequence of a different protein. In one embodiment, such a chimeric protein is produced by recombinant expression of a nucleic acid encoding the protein (comprising a lats-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of lats fused to any heterologous protein-encoding sequences may be constructed. A specific embodiment relates to a chimeric protein comprising a fragment of lats of at least six amino acids.

In another specific embodiment, the lats derivative is a molecule comprising a region of homology with a lats protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a lats domain (see Section 5.6.1) or a portion thereof.

Other specific embodiments of-derivatives and analogs are described in the subsection below and examples sections infra.

5.6.1. DERIVATIVES OF LATS CONTAINING ONE OR MORE DOMAINS OF THE PROTEIN

In a specific embodiment, the-invention relates to lats derivatives and analogs, in particular lats fragments and derivatives of such fragments, that comprise, or alternatively consist of, one or more domains of a lats protein, including but not limited to a lats C-terminal domain 3 (LCD3), lats C-terminal domain 2 (LCD2), lats C-terminal domain 1 (LCD1), kinase domain, kinase subdomains, lats flanking domain (LFD) (amino-terminal to the kinase domain), lats split domain 1 (LSD1), lats split domain 2 (LSD2), SH3-binding domain, and opa repeat domain, functional (e.g., binding) fragments of any of the foregoing, or any combination of the foregoing. In particular examples relating to the human, mouse and Drosophila lats proteins, such domains are identified in Examples Sections 6 and 8, and in FIGS. 6A, 6B, and 13.

A specific embodiment relates to molecules comprising specific fragments of lats that are those fragments in the respective lats protein most homologous to specific fragments of a human or mouse lats protein. A fragment comprising a domain of a lats homolog can be identified by protein analysis methods as described in Sections 5.3.2 or 6.

In a specific embodiment, a lats protein, derivative or analog is provided that has a kinase domain and has a phosphorylated serine situated within 20 residues upstream of an Ala-Pro-Glu consensus in subdomain eight of its kinase domain. In another embodiment, a lats protein derivative or analog is provided with a kinase domain and with a dephosphorylated serine situated within 20 residues upstream of an Ala-Pro-Glu consensus in-subdomain eight of its kinase domain, or in which the serine situated within 20 residues upstream of that consensus has been deleted or substituted by another amino acid. In a specific embodiment, the invention provides various phosphorylated and dephosphorylated forms of the lats protein, derivative, or analog that are active kinase forms. Both phosphorylation and dephosphorylation of lats at different residues could potentially activate lats. In another specific embodiment, the invention provides various phosphorylated and dephosphorylated forms of the lats protein, derivative or analog that are inactive kinase forms. Phosphorylation can be carried out by any methods known in the art, e.g., by use of a kinase. Dephosphorylation can be carried out by use of any methods known in the art, e.g., by use of a phosphatase.

Another specific embodiment relates to a derivative or analog of a lats protein that is a dominant-active protein kinase. Such a derivative or analog comprises a lats kinase domain that has been mutated so as to be dominantly active (exhibit constitutively active kinase activity). It is known that acidic residues such as Glu and Asp sometimes mimic a phosphorylated residue, and changing the phosphorylatable Ser or Thr residue in subdomain eight into a Glu or Asp residue has been previously used to produce constitutively active kinases (Mansour et al., 1994, Science 265:966–970). Thus, changing a serine or threonine residue situated within 20 residues upstream of an Ala-Pro-Glu consensus in subdomain eight of a lats kinase domain into another residue (e.g., Glu, Asp) may be used to make a dominant-active lats protein kinase. For example, changing Ser914 in Drosophila lats, or changing Ser909 in h-lats, into a Glu residue could produce a dominant active lats kinase.

Another specific embodiment relates to a derivative or analog of lats that is a dominant-negative protein kinase. Protein kinases can be mutated into dominant negative forms. Expression of a dominant negative protein kinase can suppress the activity of the wild-type form of the same kinase. Dominant negative forms of protein kinases are often obtained by expressing an inactive form of a kinase (Milarski and Saltiel, 1994, J. Biol. Chem. 269(33):21239–21243) or by expressing a noncatalytic domain of a kinase (Lu and Means, 1994, EMBO J. 12:2103–2113; Yarden et al., 1992, EMBO J. 25 11:2159–2166). Thus, a lats dominant-negative kinase can be obtained by mutating the kinase domain so as to be inactive (e.g., by deletion and/or point mutation). By way of example, a lats derivative that is a dominant-negative kinase is a lats protein that lacks a kinase domain but comprises one or more of the other domains of the lats protein; e.g., a lats protein derivative truncated at about the beginning of the kinase domain (i.e., a lats fragment containing only sequences amino-terminal to the kinase domain). By way of another example, a lats derivative that is a dominant-negative kinase is a lats protein in which one of the residues conserved among serine/threonine kinases (see Hanks et al., 1988, Science 241:42–52) is mutated (deleted or substituted by a different residue).

In another specific embodiment, a molecule is provided that comprises one or more domains (or functional portion thereof) of a lats protein but that also lacks one or more domains (or functional portion thereof) of a lats protein. In particular examples, lats protein derivatives are provided that lack an opa repeat domain. By way of another example, such a protein may also lack all or a portion of the kinase domain, but retain at least the SH3-binding domain of a lats protein. In another embodiment, a molecule is provided that comprises one or more domains (or functional portion thereof) of a lats protein, and that has one or more mutant (e.g., due to deletion or point mutation(s)) domains of a lats protein (e.g., such that the mutant domain has decreased function). By way of example, the kinase domain may be mutant so as to have reduced, absent, or increased kinase activity.

5.7. ASSAYS OF LATS PROTEINS, DERIVATIVES AND ANALOGS

The functional activity of lats proteins, derivatives and analogs can be assayed by various methods.

For example, in one embodiment, where one is assaying for the ability to bind or compete with wild-type lats for binding to anti-lats antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where a lats-binding protein is identified, the binding can be assayed, e.g., by means well-known in the art. In another embodiment, physiological correlates of lats binding to its substrates (signal transduction) can be assayed.

In another embodiment, kinase assays can be used to measure lats kinase activity. Such assays can be carried out by methods well known in the art. By way of example, a lats protein is contacted with a substrate (e.g., a known substrate of serine/threonine kinases) in the presence of a $^{32}$P-labeled phosphate donor, and any phosphorylation of the substrate is detected or measured.

In another embodiment, in insect or other model systems, genetic studies can be done to study the phenotypic effect of a lats mutant that is a derivative or analog of wild-type lats (see Section 6, infra).

In addition, assays that can be used to detect or measure the ability to inhibit, or alternatively promote, cell proliferation are described in Section 5.9.

Other methods will be known to the skilled artisan and are within the scope of the invention.

5.8. THERAPEUTIC USES

The invention provides for treatment or prevention of various diseases and disorders by administration of a therapeutic compound (termed herein "Therapeutic"). Such "Therapeutics" include but are not limited to: lats proteins and analogs and derivatives (including fragments) thereof (e.g., as described hereinabove); antibodies thereto (as described hereinabove); nucleic acids encoding the lats proteins, analogs, or derivatives (e.g., as described hereinabove); lats antisense nucleic acids, and lats agonists and antagonists. Disorders involving cell overproliferation are treated or prevented by administration of a Therapeutic that promotes lats function. Disorders-in which cell proliferation is deficient or is desired are treated or prevented by administration of a Therapeutic that antagonizes (inhibits) lats function. The above is described in detail in the subsections below.

Generally, administration of products of a species origin or species reactivity (in the case of antibodies) that is the same species as that of the patient is preferred. Thus, in a preferred embodiment, a human lats protein, derivative, or analog, or nucleic acid, or an antibody to a human lats protein, is therapeutically or prophylactically administered to a human patient.

Additional descriptions and sources of Therapeutics that can be used according to the invention are found in Sections 5.1 through 5.7 herein.

5.8.1. TREATMENT AND PREVENTION OF DISORDERS INVOLVING OVERPROLIFERATION OF CELLS

Diseases and disorders involving cell overproliferation are treated or prevented by administration of a Therapeutic that promotes (i.e., increases or supplies) lats function. Examples of such a Therapeutic include but are not limited to lats proteins, derivatives, or fragments that are functionally active, particularly that are active in inhibiting cell proliferation (e.g., as demonstrated in in vitro assays or in animal models or in Drosophila), and nucleic acids encoding a lats protein or functionally active derivative or fragment thereof (e.g., for use in gene therapy). Other Therapeutics that can be used, e.g., lats agonists, can be identified using in vitro assays or animal models, or assays in Drosophila, examples of which are described infra.

In specific embodiments, Therapeutics that promote lats function are administered therapeutically (including prophylactically): (1) in diseases or disorders involving an absence or decreased (relative to normal or desired) level of lats protein or function, for example, in patients where lats protein is lacking, genetically defective, biologically inactive or underactive, or underexpressed; or (2) in diseases or disorders wherein in vitro (or in vivo) assays (see infra) indicate the utility of lats agonist administration. The absence or decreased level in lats protein or function can be readily detected, e.g., by obtaining a patient tissue sample (e.g., from biopsy tissue) and assaying it in vitro for RNA or protein levels, structure and/or activity of the expressed lats RNA or protein. Many methods standard in the art can be thus employed, including but not limited to kinase assays, immunoassays to detect and/or visualize lats protein (e.g., Western blot, immunoprecipitation followed by sodium dodecyl sulfate polyacrylamide gel electrophoresis, immunocytochemistry, etc.) and/or hybridization assays to detect lats expression by detecting and/or visualizing lats mRNA (e.g., Northern assays, dot blots, in situ hybridization, etc.), etc.

Diseases and disorders involving cell overproliferation that can be treated or prevented include but are not limited to malignancies, premalignant conditions (e.g., hyperplasia, metaplasia, dysplasia), benign tumors, hyperproliferative disorders, benign dysproliferative disorders, etc. Examples of these are detailed below.

In a specific embodiment, the Therapeutic used, that promotes lats function, is a lats protein, derivative or analog comprising a lats kinase domain (and optionally also a lats LFD, or the remainder of the lats sequence) in which a serine within 20 residues upstream of the Ala-Pro-Glu consensus in subdomain eight of the kinase domain is phosphorylated or substituted by another residue (e.g., Glu, Asp).

In another specific embodiment, the Therapeutic used, that promotes lats function, is a-derivative or analog comprising a kinase domain of a lats protein that has been mutated so as to be dominantly active.

5.8.1.1. MALIGNANCIES

Malignancies and related disorders that can be treated or prevented by administration of a Therapeutic that promotes lats function include but are not limited to those listed in Table 1 (for a review of such disorders, see Fishman et al., 1985, *Medicine*, 2d Ed., J. B. Lippincott Co., Philadelphia):

TABLE 1

MALIGNANCIES AND RELATED DISORDERS

Leukemia
  acute leukemia
    acute lymphocytic leukemia
    acute myelocytic leukemia
      myeloblastic
      promyelocytic
      myelomonocytic
      monocytic
      erythroleukemia
  chronic leukemia
    chronic myelocytic (granulocytic) leukemia
    chronic lymphocytic leukemia
Polycythemia vera
Lymphoma
  Hodgkin's disease
  non-Hodgkin's disease
Multiple myeloma
Waldenstrom's macroglobulinemia
Heavy chain disease
Solid tumors
  sarcomas and carcinomas
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
    pancreatic cancer
    breast cancer
    ovarian cancer
    prostate cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma TABLE 1-continued

MALIGNANCIES AND RELATED DISORDERS hepatoma
    bile duct carcinoma
    choriocarcinoma
    seminoma
    embryonal carcinoma
    Wilms' tumor
    cervical cancer
    uterine cancer
    testicular tumor
    lung carcinoma
    small cell lung carcinoma
    bladder carcinoma
    epithelial carcinoma
    glioma
    astrocytoma
    medulloblastoma
    craniopharyngioma
    ependymoma
    pinealoma
    hemangioblastoma
    acoustic neuroma
    oligodendroglioma
    menangioma
    melanoma
    neuroblastoma
    retinoblastoma In specific embodiments, malignancy or dysproliferative changes (such as metaplasias and dysplasias), or hyperproliferative disorders, are treated or prevented in the bladder, breast, colon, lung, melanoma, pancreas, or uterus. In other specific embodiments, sarcoma, or leukemia is treated or prevented.

5.8.1.2. PREMALIGNANT CONDITIONS

The Therapeutics of the invention that promote lats activity can also be administered to treat premalignant conditions and to prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic that promotes lats function. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W.B. Saunders Co., Philadelphia, pp. 112–113) etc.)

In another specific embodiment, a Therapeutic of the invention is administered to a human patient to prevent progression to breast, colon, lung, pancreatic, or uterine cancer, or melanoma or sarcoma.

5.8.1.3. HYPERPROLIFERATIVE AND DYSPROLIFERATIVE DISORDERS

In another embodiment of the invention, a Therapeutic that promotes lats activity is used to treat or prevent hyperproliferative or benign dysproliferative disorders. Specific embodiments are directed to treatment or prevention of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

5.8.1.4. GENE THERAPY

In a specific embodiment, nucleic acids comprising a sequence encoding a lats protein or functional derivative thereof, are administered to promote lats function, by way of gene therapy. Gene therapy refers to therapy performed by the administration of a nucleic acid to a subject. In this embodiment of the invention, the nucleic acid produces its encoded protein that mediates a therapeutic effect by promoting lats function.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215). Methods commonly known in the art of recombinant DNA technology which can be used are described in Ausubel et al. (eds.), 1993, Current Protocols in Molecular Biology, John Wiley & Sons, New York; and Kriegler, 1990, Gene Transfer and Expression, A Laboratory Manual, Stockton Press, New York.

In a preferred aspect, the Therapeutic comprises a lats nucleic acid that is part of an expression vector that expresses a lats protein or fragment or chimeric protein thereof in a suitable host. In particular, such a nucleic acid has a promoter operably linked to the lats coding region, said promoter being inducible or constitutive, and, optionally, tissue-specific. In another particular embodiment, a nucleic acid molecule is used in which the lats coding sequences and any other desired sequences are flanked by regions that promote homologous recombination at a desired site in the genome, thus providing for intrachromosomal expression of the lats nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the lats nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The lats nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdrl gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

Adeno-associated virus (AAV) has also been proposed for use in gene therapy (Walsh et al., 1993, Proc. Soc. Exp. Biol. Med. 204:289–300.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a lats nucleic acid is introduced into the cells such that it is expressible by the cells or their progeny, and the recombinant cells are then administered in vivo for therapeutic effect. In a specific embodiment, stem or progenitor cells are used. Any stem-and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, 1992, Cell 71:973–985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a lats protein or functional derivative thereof are described in Section 5.8.2.2.2.

5.8.2. TREATMENT AND PREVENTION OF DISORDERS IN WHICH CELL PROLIFERATION IS DESIRED

Diseases and disorders involving a deficiency in cell proliferation (growth) or in which cell proliferation is otherwise desirable for treatment or prevention, are treated or prevented by administration of a Therapeutic that antagonizes (inhibits) lats function (in particular, lats-mediated inhibition of cell proliferation). Therapeutics that can be used include but are not limited to anti-lats antibodies (and fragments and derivatives thereof containing the binding region thereof), lats derivatives or analogs that are dominant-negative kinases, lats antisense nucleic acids, and lats nucleic acids that are dysfunctional (e.g., due to a heterologous (non-lats sequence) insertion within the lats coding sequence) that are used to "knockout" endogenous lats function by homologous recombination (see, e.g., Capecchi, 1989, Science 244:1288–1292). In a specific embodiment of the invention, a nucleic acid containing a portion of a lats gene in which lats sequences flank (are both 5' and 3' to) a different gene sequence, is used, as a lats antagonist, to promote lats inactivation by homologous recombination (see also Koller and Smithies, 1989, Proc. Natl. Acad. Sci. USA 86:8932–8935; Zijlstra et al., 1989, Nature 342:435–438). Other Therapeutics that inhibit lats function can be identified by use of known convenient in vitro assays, e.g., based on their ability to inhibit binding of lats to another protein (e.g., an SH3-domain containing protein), or inhibit any known lats function, as preferably assayed in vitro or in cell culture, although genetic assays (e.g., in Drosophila) may also be employed. Preferably, suitable in vitro or in vivo assays, are utilized to determine the effect of a specific Therapeutic and whether its administration is indicated for treatment of the affected tissue.

In specific embodiments, Therapeutics that inhibit lats function are administered therapeutically (including prophylactically): (1) in diseases or disorders involving an increased (relative to normal or desired) level of lats protein or function, for example, in patients where lats protein is overactive or overexpressed; or (2) in diseases or disorders wherein in vitro (or in vivo) assays (see infra) indicate the utility of lats antagonist administration. The increased levels in lats protein or function can be readily detected, e.g., by quantifying protein and/or RNA, by obtaining a patient tissue sample (e.g., from biopsy tissue) and assaying it in vitro for RNA or protein levels, structure and/or activity of the expressed lats RNA or protein. Many methods standard in the art can be thus employed, including but not limited to kinase assays, immunoassays to detect and/or visualize lats protein (e.g., Western blot, immunoprecipitation followed by sodium dodecyl sulfate polyacrylamide gel electrophoresis, immunocytochemistry, etc.) and/or hybridization assays to detect lats expression by detecting and/or visualizing respectively lats mRNA (e.g., Northern assays, dot blots, in situ hybridization, etc.), etc.

Diseases and disorders involving a deficiency in cell proliferation or in which cell proliferation is desired for treatment or prevention, and that can be treated or prevented by inhibiting lats function, include but are not limited to degenerative disorders, growth deficiencies, hypoproliferative disorders, physical trauma, lesions, and wounds; for example, to promote wound healing, or to promote regeneration in degenerated, lesioned or injured tissues, etc. In a specific embodiment, nervous system disorders are treated. In another specific embodiment, a disorder that is not of the nervous system is treated.

Lesions which may be treated according to the present invention include but are not limited to the following lesions:

(i) traumatic lesions, including lesions caused by physical injury or associated with surgery;

(ii) ischemic lesions, in which a lack of oxygen results in cell injury or death, e.g., myocardial or cerebral infarction or ischemia, or spinal cord infarction or ischemia;

(iii) malignant lesions, in which cells are destroyed or injured by malignant tissue;

(iv) infectious lesions, in which tissue is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which tissue is destroyed or injured as a result of a degenerative process, including but not limited to nervous system degeneration associated with Parkinson's disease, Alzheimer's disease, Huntington's chorea, or amyotrophic lateral sclerosis;

(vi) lesions associated with nutritional diseases or disorders, in which tissue is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) lesions associated with systemic diseases including but not limited to diabetes or systemic lupus erythematosus;

(viii) lesions caused by toxic substances including alcohol, lead, or other toxins; and (ix) demyelinated lesions of the nervous system, in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Nervous system lesions which may be treated in a patient (including human and non-human mammalian patients) according to the invention include but are not limited to the lesions of either the central (including spinal cord, brain) or peripheral nervous systems.

Therapeutics which are useful according to this embodiment of the invention for treatment of a disorder may be selected by testing for biological activity in promoting the survival or differentiation of cells (see also Section 5.9). For example, in a specific embodiment relating to therapy of the nervous system, a Therapeutic which elicits one of the following effects may be useful according to the invention:

(i) increased sprouting of neurons in culture or in vivo;

(ii) increased production of a neuron-associated molecule in culture or in vivo, e.g., choline acetyltransferase or acetylcholinesterase with respect to motor neurons; or (iii) decreased symptoms of neuron dysfunction in vivo.

Such effects may be measured by any method known in the art. In preferred, non-limiting embodiments, increased sprouting of neurons may be detected by methods set forth in Pestronk et al. (1980, Exp. Neurol. 70:65–82) or Brown et al. (1981, Ann. Rev. Neurosci. 4:17–42); and increased production of neuron-associated molecules may be measured by bioassay, enzymatic assay, antibody binding, Northern blot assay, etc., depending on the molecule to be measured.

5.8.2.1. ANTISENSE REGULATION OF LATS EXPRESSION

In a specific embodiment, lats function is inhibited by use of lats antisense nucleic acids. The present invention provides the therapeutic or prophylactic use of nucleic acids of at least six nucleotides that are antisense to a gene or cDNA encoding lats or a portion thereof. A lats "antisense" nucleic acid as used herein refers to a nucleic acid capable of hybridizing to a portion of a lats RNA (preferably mRNA) by virtue of some sequence complementarity. The antisense nucleic acid may be complementary to a coding and/or noncoding region of a lats mRNA. Such antisense nucleic acids have utility as Therapeutics that inhibits lats function, and can be used in the treatment or prevention of disorders as described supra in Section 5.8.2 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the lats antisense nucleic acids provided by the instant invention can be used to promote regeneration or wound healing or to promote growth (larger size).

The invention further provides pharmaceutical compositions comprising an effective amount of the lats antisense nucleic acids of the invention in a pharmaceutically acceptable carrier, as described infra.

In another embodiment, the invention is directed to methods for inhibiting the expression of a lats nucleic acid sequence in a prokaryotic or eukaryotic cell comprising providing the cell with an effective amount of a composition comprising an lats antisense nucleic acid of the invention.

Lats antisense nucleic acids and their uses are described in detail below.

5.8.2.1.1. LATS ANTISENSE NUCLEIC ACIDS

The lats antisense nucleic acids are of at least six nucleotides and are preferably oligonucleotides (ranging from 6 to about 50 oligonucleotides). In specific aspects, the oligonucleotide is at least 10 nucleotides, at least nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a lats antisense oligonucleotide is provided, preferably of single-stranded DNA. In a most preferred aspect, such an oligonucleotide comprises a sequence antisense to the sequence encoding an SH3 binding domain or a kinase domain of a lats protein, most preferably, of a human lats protein. The oligonucleotide may be modified at any position on its structure with substituents generally known in the art.

The lats antisense oligonucleotide may comprise at least one modified base moiety which is-selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, the lats antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the lats antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the lats antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the lats antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a lats gene, preferably a human lats gene.

However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded lats antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a lats RNA it may contain and still form a stable duplex (or triplex, as the case may be). One skilled in the art can ascertain a tolerable degree of mismatch by use of standard procedures to determine the melting point of the hybridized complex.

5.8.2.1.2. THERAPEUTIC USE OF LATS ANTISENSE NUCLEIC ACIDS

The lats antisense nucleic acids can be used to treat (or prevent) disorders of a cell type that expresses, or preferably overexpresses, lats. In a specific embodiment, such a disorder is a growth deficiency. In a preferred embodiment, a single-stranded DNA antisense lats oligonucleotide is used.

Cell types which express or overexpress lats RNA can be identified by various methods known in the art. Such methods include but are not limited to hybridization with a lats-specific nucleic acid (e.g. by Northern hybridization, dot blot hybridization, in situ hybridization), observing the ability of RNA from the cell type to be translated in vitro into lats, immunoassay, etc. In a preferred aspect, primary tissue from a patient can be assayed for lats expression prior to treatment, e.g., by immunocytochemistry or in situ hybridization.

Pharmaceutical compositions of the invention (see Section 5.10), comprising an effective amount of a lats antisense nucleic acid in a pharmaceutically acceptable carrier, can be administered to a patient having a disease or disorder which is of a type that expresses or overexpresses lats RNA or protein.

The amount of lats antisense nucleic acid which will be effective in the treatment of a-particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising lats antisense nucleic acids are administered via liposomes, microparticles, or microcapsules. In various embodiments of the invention, it may be useful to use such compositions to achieve sustained release of the lats antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

Additional methods that can be adapted for use to deliver a lats antisense nucleic acid are described in Section 5.8.1.4.

5.9. DEMONSTRATION OF THERAPEUTIC OR PROPHYLACTIC UTILITY

The Therapeutics of the invention are preferably tested in vitro, and then in vivo for the desired therapeutic or prophylactic activity, prior to use in humans. For example, In vitro assays which can be used to determine whether administration of a specific Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.8.1 through 5.8.3 infra.

In another specific embodiment, a Therapeutic is indicated for use in treating cell injury or a degenerative disorder (see Section 5.8.2) which exhibits in vitro promotion of growth/proliferation of cells of the affected patient type. Regarding nervous system disorders, see also Section 5.8.2.1 for assays that can be used.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, *General Virology*, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the cell type upon which an effect is desired, according to the present invention.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.10. THERAPEUTIC/PROPHYLACTIC ADMINISTRATION AND COMPOSITIONS

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described in Sections 5.8.1.4 and 5.8.2.2 above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a.liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun;

Biolistic, Dupont), or coating with lipids or cell-surface receptors or transfecting agents, or by.administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.11. ADDITIONAL USE OF INHIBITION OF LATS FUNCTION TO PROMOTE INCREASED GROWTH

Inhibition of lats function (e.g., by administering a compound that inhibits lats function as described in Sections 5.8.2 through 5.8.2.1.2 above), has utility that is not limited to therapeutic or prophylactic applications. For example, lats function can be inhibited in order to increase growth of animals (e.g., cows, horses, pigs, goats, deer, chickens) and plants (particularly edible plants, e.g., tomatoes, melons, lettuce, carrots, potatoes, and other vegetables), particularly those that are food or material sources. For example, antisense inhibition (preferably where the lats antisense nucleic acid is under the control of a tissue-specific promoter) can be used in plants or animals to increase growth where desired (e.g., in the fruit or muscle). For example, a lats antisense nucleic acid under the control of a temperature-sensitive promoter can be administered to a plant or animal, and the desired portion of the (or the entire) plant or animal can be subjected to heat in order to induce antisense nucleic acid production, resulting lats inhibition, and resulting cell proliferation. In other embodiments, chemical mutagenesis, or homologous recombination with an insertionally inactivated lats gene (see Capecchi, 1989, Science 244:1288–1292 and Section 5.14 infra) can be carried out to reduce or destroy endogenous lats function, in order to achieve increased growth. Suitable methods, modes of administration and compositions, that can be used to inhibit lats function are described in Sections 5.8.2 through 5.8.2.1.2, above. Methods to make plants recombinant are commonly known in the art and can be used. Regarding methods of plant transformation (e.g., for transformation with a lats antisense nucleic acid or with a sequence encoding a lats derivative that is a dominant-negative kinase), see e.g., Valvekens et al., 1988, Proc. Natl. Acad. Sci. USA 85:5536–5540. Regarding methods of targeted gene inactivation in plants (e.g., to inactivate lats), see e.g., Miao and Lam, 1995, The Plant J. 7:359–365.

Inhibition of lats function can also have uses in vitro, e.g., to expand cells in vitro, including but not limited to stem cells, progenitor cells, muscle cells, fibroblasts, liver cells, etc., e.g., to grow cells/tissue in vitro prior to administration to a patient (preferably a patient from which the cells were derived), etc.

5.12. DIAGNOSIS AND SCREENING

Lats proteins, analogues, derivatives, and subsequences thereof, lats nucleic acids (and sequences complementary thereto), anti-lats antibodies, have uses in diagnostics. Such molecules can be used in assays, such as immunoassays, to detect, prognose, diagnose, or monitor various conditions, diseases, and disorders affecting lats expression, or monitor the treatment thereof. In particular, such an immunoassay is carried out by a.method comprising contacting a sample derived from a patient with an anti-lats antibody under conditions such that immunospecific binding can occur, and detecting or measuring the amount of any immunospecific binding by the antibody. In a specific aspect, such binding of antibody, in tissue sections, can be used to detect aberrant lats localization or aberrant (e.g., low or absent) levels of lats. In a specific embodiment, antibody to lats can be used to assay in a patient tissue or serum sample for the presence of lats where an aberrant level of lats is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Lats genes and related nucleic acid sequences and subsequences, including complementary sequences, can also be used in hybridization assays. Lats nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in lats expression and/or activity as described supra. In particular, such a hybridization assay is carried out by a method comprising contacting a sample containing nucleic acid with a nucleic acid probe capable of hybridizing to lats DNA or RNA, under conditions such that hybridization can occur, and detecting or measuring any resulting hybridization.

In specific embodiments, diseases and disorders involving overproliferation of cells can be diagnosed, or their suspected presence can be screened for, or a predisposition to develop such disorders can be detected, by detecting decreased levels of lats protein, lats RNA, or lats functional activity (e.g., kinase activity, SH3 domain-binding activity, etc.), or by detecting mutations in lats RNA, DNA or protein (e.g., translocations in lats nucleic acids, truncations in the lats gene or protein, changes in nucleotide or amino acid sequence relative to wild-type lats) that cause decreased expression or activity of lats. Such diseases and disorders include but are not limited to those described in Section 5.8.1 and its subsections. By way of example, levels of lats protein can be detected by immunoassay, levels of lats RNA can be detected by hybridization assays (e.g., Northern blots, dot blots), lats kinase activity can be measured by kinase assays commonly known in the art, lats binding to an SH3 domain-containing protein can be done by binding assays commonly known in the art, translocations and point mutations in lats nucleic acids can be detected by Southern blotting, RFLP analysis, PCR using primers that preferably generate a fragment spanning at least most of the lats gene, sequencing of the lats genomic DNA or cDNA obtained from the patient, etc.

In a preferred embodiment, levels of lats mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting increased levels of lats protein, lats RNA, or lats functional activity (e.g., kinase activity, SH3 domain binding activity, etc.), or by detecting mutations in lats RNA, DNA or protein (e.g., translocations in lats nucleic acids, truncations in the gene or protein, changes in nucleotide or amino acid sequence relative to wild-type lats) that cause increased expression or activity of lats. Such diseases and disorders include but are not limited to those described in Section 5.8.2 and its subsections. By way of example, levels of lats protein, levels of lats RNA, lats kinase activity, lats binding activity, and the presence of translocations or point mutations can be determined as described above.

In a specific embodiment, levels of lats mRNA or protein in a patient sample are detected or measured, in which increased levels indicate that the subject has, or has a predisposition to developing, a growth deficiency or degenerative or hypoproliferative disorder; in which the increased levels are relative to the levels present in an analogous sample from a portion of the body or from a subject not having the growth deficiency, degenerative, or hypoproliferative disorder, as the case may be.

Kits for diagnostic use are also provided, that comprise in one or more containers an anti-lats antibody, and, optionally, a labeled binding partner to the antibody.

Alternatively, the anti-lats antibody can be labeled (with a detectable marker, e.g., a chemiluminescent, enzymatic, fluorescent, or radioactive moiety). A kit is also provided that comprises in one or more containers a nucleic acid probe capable of hybridizing to lats RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a lats nucleic acid. A kit can optionally further comprise in a container a predetermined amount of a purified lats protein or nucleic acid, e.g., for use as a standard or control.

5.13. SCREENING FOR LATS AGONISTS AND ANTAGONISTS

Lats nucleic acids, proteins, and derivatives also have uses in screening assays to detect molecules that specifically bind to lats nucleic acids, proteins, or derivatives and thus have potential use as agonists or antagonists of lats, in particular, molecules that thus affect cell proliferation. In a preferred embodiment, such assays are performed to screen for molecules with potential utility as anti-cancer drugs or lead compounds for drug development. The invention thus provides assays to detect molecules that specifically bind to lats nucleic acids, proteins, or derivatives. For example, recombinant cells expressing lats nucleic acids can be used to recombinantly produce lats proteins in these assays, to screen for molecules that bind to a lats protein. Molecules (e.g., putative binding partners of lats) are contacted with the lats protein (or fragment thereof) under conditions conducive to binding, and then molecules that specifically bind to the lats protein are identified. Similar methods can be used to screen for molecules that bind to lats derivatives or nucleic acids. Methods that can be used to carry out the foregoing are commonly known in the art.

By way of example, diversity libraries, such as random or combinatorial peptide or nonpeptide libraries can be screened for molecules that specifically bind to lats. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but re not limited to those described in PCT Publication No. WO 91/05058 dated April 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and PCT Publication No. WO 94/18318.

In a specific embodiment, screening can be carried out by contacting the library members with a lats protein (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to a lats protein or derivative.

In addition, Drosophila can be used as a model system in order to detect genes that phenotypically interact with lats. For example, overexpression of lats in Drosophila eye leads to a smaller and rougher eye. Mutagenesis of the fly genome can be performed, followed by selecting flies in which the mutagenesis has resulted in suppression or enhancement of the small rough eye phenotype; the mutated genes in such flies are likely to encode proteins that interact/bind with lats.

5.14. ANIMAL MODELS

The invention also provides animal models.

In one embodiment, animal models for diseases and disorders involving cell overproliferation (e.g., as described in Section 5.8.1) are provided. Such an animal can be initially produced by promoting homologous recombination between a lats gene in its chromosome and an exogenous lats gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated lats gene, such that homologous recombination occurs, followed by injecting the ES cells into a blastocyst, and implanting the blastocyst into a foster mother, followed by the birth of the chimeric animal ("knockout animal") in which a lats gene has been inactivated (see Capecchi, 1989, Science 244:1288–1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving cell overproliferation (e.g., malignancy) and thus can have use as animal models of such diseases and disorders, e.g., to screen for or test molecules (e.g., potential anti-cancer therapeutics) for the ability to inhibit overproliferation (e.g., tumor formation) and thus treat or prevent such diseases or disorders.

In a different embodiment of the invention, transgenic animals that have incorporated and express a functional lats gene have use as animal models of diseases and disorders involving deficiencies in cell proliferation or in which cell proliferation is desired. Such animals can be used to screen for or test molecules for the ability to promote proliferation and thus treat or prevent such diseases and disorders.

5.15. METHODS OF IDENTIFYING TUMOR SUPPRESSOR GENES AND OTHER GENES WITH IDENTIFIABLE PHENOTYPES

The invention also provides methods of identifying a tumor suppressor gene (or potential tumor suppressor gene) comprising identifying an overproliferation phenotype in a genetic mosaic, and isolating a gene that is mutated in cells exhibiting the overproliferation phenotype. The genetic mosaic is achieved by induction of somatic cells in an animal that is hetreozygous for an induced mutation to become homozygous for the mutation, at any desired developmental stage. The mutation can be induced by any known method, e.g., X-ray exposure or chemical mutation exposure or insertion of a transposable element (e.g., P-element). A genetic mosaic is produced by induction of homozygosity by mitotic recombination between homologous arms of both parental chromosomes, which is achieved using a site-specific recombination system [a sequence capable of expressing a site-specific recombinase; and its target sites (sequences at which the recombinase promotes recombination)], that have been inserted in the homozygous arms of both parental chromosomes. The target sites are preferably inserted close to the centromere on each chromosome arm (the closer to the centromere, the more preferred), so that mitotic recombination events will result in cells being homozygous for the mutation located on the chromosome arm distal to the insertion of the target site. For example, an FLP recombinase can be used with FRT target sites; Cre recombinase can be used with lox target sites. The recombinase coding sequence, used to express recombinase, preferably, but need not be, intrachromosomally situated. For at least one chromosome, the target sites are intrachromosomally inserted on the homologous arms of both parental (maternal and paternal) chromosomes.

The genetic mosaic can be an animal, e.g., mouse, hamster, sheep, pig, cow, Drosophila, etc., and is preferably a non-human mammal.

In a specific embodiment relating to the production of a non-human mammal that is a genetic mosaic, a recombinase target site is introduced onto one arm of a chromosome in an embryo-derived stem cell (ES). The target site can be introduced into the cell by homologous recombination (by use of flanking sequences from the desired site of intrachromosomal integration) or by random integration resulting from cell transformation (e.g., by transfection, electroporation), etc. This ES is then injected into a blastocyst, the blastocyst is implanted-into a foster mother, followed by birth of the recombinant animal. This mammal is bred to a wild-type female, to produce siblings. Siblings carrying the target site insertion are mated, and offspring carrying the target site on the homologous arms of both parental chromosomes are isolated ("the target strain"). A target strain member is then mutagenized and mated with a non-mutagenized target strain member of the opposite sex (preferably also carrying a recombinant nucleic acid encoding and capable of expressing a recombinase that promotes recombination at the target sites), to obtain a target strain member that is heterozygous for the mutation. Provision of the recombinase (by expression) in mitotically active cells of a developing animal or an adult animal promotes mitotic recombination between the homologous arms of the parental chromosomes, resulting in a cell that is homozygous for the mutation. Cells that display a mutant phenotype by virtue of their being homozygous for the mutation are then detected, and the mutant gene can be genetically mapped by any known method, and can be isolated.

In a Drosophila animal, a site-specific recombination system can be introduced by use of P-element-mediated insertions.

In one embodiment, target sites are introduced onto homologous arms of both of a set of parental chromosomes, for one chromosome. In another embodiment, target sites are introduced onto homologous arms of both of a set of parental chromosomes, for a plurality of chromosomes.

The recombinase can be under the control of a constitutive (e.g., phosphorylated kinase promoter) or inducible (e.g., heat shock promoter) or tissue-specific promoter. The recombinase can be expressed episomally (e.g., from a plasmid) or chromosomally. Once the recombination system is introduced into the animal, genetic mosaicism is produced by the activity of the recombinase (which promotes recombination at the target sites).

In a specific embodiment, an animal is used that contains a recombinant nucleic acid encoding an FLP recombinase (Broach and Hicks, 1980, Cell 21:501–508) such that it is expressible by a cell of the animal, and intrachromosomal insertions of an FRT site on the homologous arms of both parental chromosomes; and genetic mosaicism is produced by inducing mitotic recombination between the FRT sites on the homologous chromosome arms after FLP recombinase expression (e.g., by heat shock, when expression of the FLP recombinase is under the control of a heat shock promoter).

In another specific embodiment, an animal is used that contains a recombinant nucleic acid encoding a Cre recombinase (Sauer and Henderson, 1988, Proc. Natl. Acad. Sci. USA 85:5166–5170) such that it is expressible by a cell of the animal, and intrachromosomal insertions of a lox site on homologous arms of both parental chromosomes; and genetic mosaicism is produced by inducing mitotic recombination between the lox sites on the homologous chromosome arms after Cre recombinase expression.

The animal may optionally further comprise intrachromosomal insertions of marker genes (comprising a sequence encoding a protein containing a reporter group such as an epitope tag), to facilitate confirmation and/or monitoring of recombination events. For example, in a non-human mammal, a marker gene (e.g., lacZ) operably linked to a constitutive promoter can be inserted, on the same chromosome arm as that carrying the target site and the induced mutation.

In a specific embodiment, the-overproliferation phenotype is the formation of overproliferated outgrowth tissue in a non-position-dependent fashion. In another specific embodiment, the overproliferation phenotype is the formation of a normal structure of larger than normal size.

The above-described genetic mosaics have uses not only in identifying tumor suppressor genes, but, more generally, in identifying genes with an identifiable phenotype, i.e., those genes which in mutated form cause an observable mutant phenotype to be displayed in the genetic mosaic.

In another embodiment, the invention provides a method of identifying genes with an observable mutant phenotype by use of human (or other animal) tissue culture cells that have incorporated a site-specific recombination system such as described above. The site-specific recombination system can be introduced by methods such as described above, so as to introduce a recombinant source of recombinase and effect intrachromosomal insertions of the recombinase target sites on the homologous arms of both of a set of parental chromosomes, for one or more chromosomes. In a preferred aspect relating to this use of culture cells, the recombinase target sites are ligated to a selectable marker (e.g., an antibiotic resistance gene), and cells are obtained that have the target sites on each of the homologous chromosome arms, by selecting under selection conditions of relatively high stringency (e.g., by increasing the antibiotic concentration in the cell medium), As with the use of genetic mosaics as described above, once mitotic recombination is induced between the target sites on the homologous chromosome arms, one then identifies cells displaying a mutant phenotype, and recovers a gene mutated in cells exhibiting the mutant phenotype. For example, a potential tumor suppressor gene can be identified by isolating a gene that is mutated in cultured cells exhibiting a transformed phenotype.

6. IDENTIFYING TUMOR SUPPRESSORS IN GENETIC MOSAICS: THE DROSOPHILA LATS GENE ENCODES A PUTATIVE PROTEIN KINASE

We have identified recessive overproliferation mutations by screening and examining clones of mutant cells in genetic mosaics of the fruitfly Drosophila melanogaster (FIG. 1A). Flies that carry small groups of somatic cells mutated for negative regulators of cell proliferation or tumor suppressors are viable, yet the overproliferated mutant tissues can be readily identifiable.

Figure 1B:
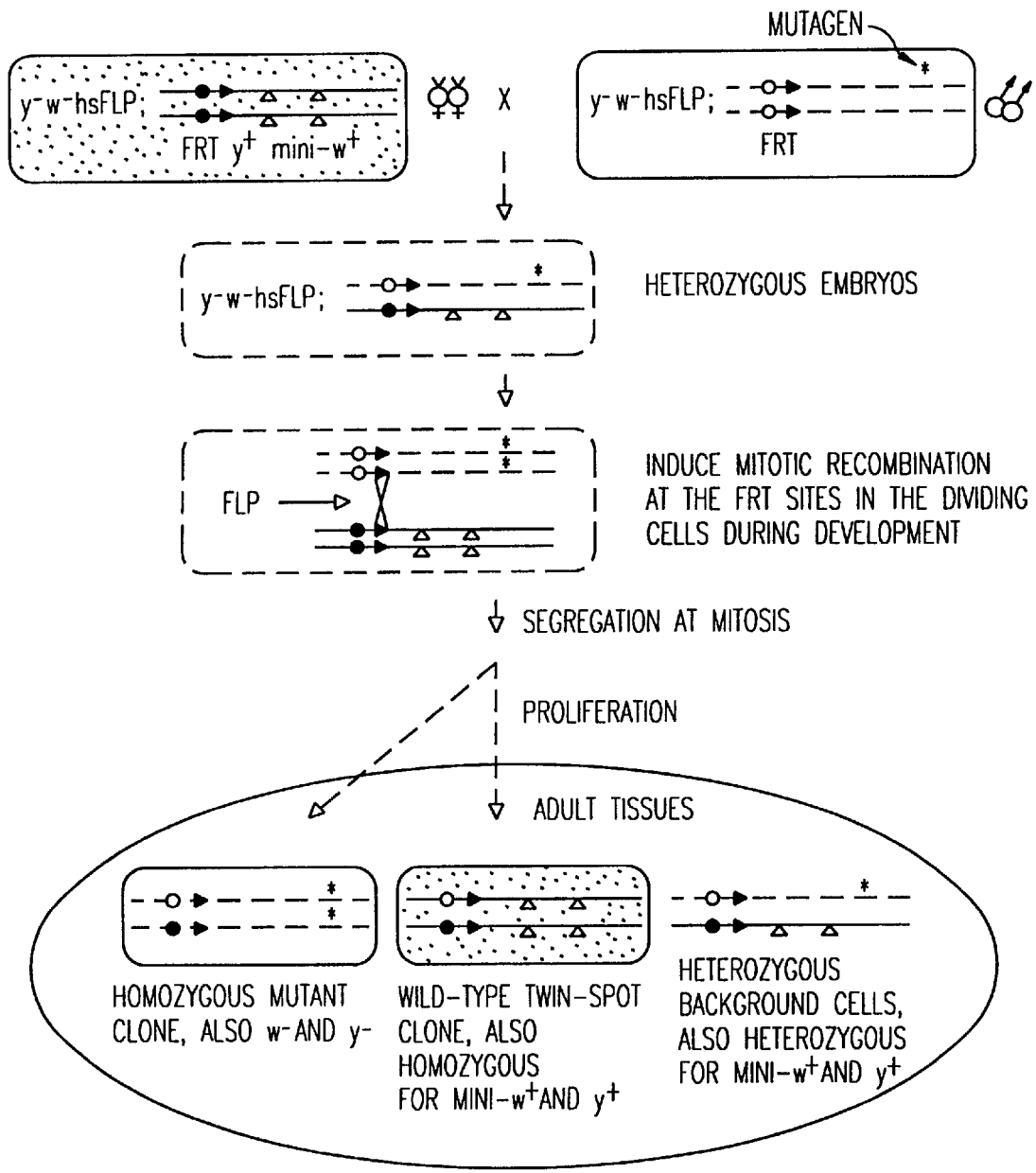

One way to generate mosaic animals is to induce mitotic recombination in developing heterozygous individuals (FIG. 1B). Recently, it was found that the site-specific recombination system from yeast, the FLP recombinase and its target site FRT, can be used to induce high frequency of mitotic recombination in Drosophila (Golic and Lindquist, 1989, Cell 59:499–509; Golic, 1991, Science 252:958–961). To produce and analyze genetic mosaics, a series of special Drosophila strains were constructed, containing the FLP/FRT recombination system on genetically marked chromosomes (Xu and Rubin, 1993, Development 117:1223–1237). Using these strains, high frequencies of mosaicism can be produced for more than 95% of the Drosophila genes. We have used these strains to identify overproliferation mutations in mosaic animals.

Our results show that screening for overproliferation mutations in mosaic animals is a powerful way to identify negative regulators of cell proliferation and potential tumor suppressor genes. One of the identified genes, large tumor suppressor (lats), has been cloned, and encodes a predicted novel protein kinase. Mutations in lats cause dramatic overproliferation phenotypes and various developmental defects in both mosaic animals and homozygous mutants.

6.1. MATERIALS AND METHODS
Genetics

Fly stocks and crosses were grown on standard medium at 25° C. unless otherwise indicated. The F1 mosaic screens were modified from the one described in Xu and Rubin (1993, Development 117:1223–1237) and in Xu and Harrison (1994, Methods in Cell Biology 44:655–682). Briefly, the F1 mosaic individuals were produced from three crosses: Mutagenized y w hsFLP1; P[ry$^+$; hs-neo; FRT]40A males were mated to the y w hsFLP1; P[ry$^+$; y$^+$]25F, P[mini-w$^+$; hs-NM]31E, P[ry$^+$; hs-neo; FRT]40A females. Mutagenized y w hsFLP1; P[ry$^+$; hs-neo; FRT]42D males were mated to the y w hsFLP1; P[ry$^+$; hs-neo; FRT]42D, P[ry$^+$; y$^+$]44B, P[mini-w$^+$; hs-NM]46F/CyO females. Finally, mutagenized y w hsFLP1; P[ry$^+$; hs-neo; FRT]82B males were mated to the y w hsFLP1; P[ry$^+$; hs-neo; FRT]82B, P[mini-w$^+$; hs-πM]87E, Sb$^{63b}$, P[ry$^+$; y$^+$]96E females. The male parents were irradiated with X-rays (4000 r) and were removed from the crosses after four days of mating. The eggs from the crosses were collected for every 12 hours and aged for another 30 hours before being incubated in a 38° C. water bath for 60 minutes. The $F_1$ animals were then returned to normal culture conditions until eclosion. About 25,000 $F_1$ adults from these crosses were examined. Each P-induced lethal mutation was recombined onto one of the FRT-carrying arms using the neo$^R$ and w$^-$ double selection as described in Xu and Harrison (1994, Methods in Cell Biology 44:655–682) before examining its clonal phenotype.

The lats$^{x1}$ mutation was meiotically mapped to the right of claret. It was further localized to the 100A1-5 region since it complemented Df(3R)tll$^e$(100A2-5; 100C2-3) and failed to complement Df(3R)tll$^{Pgx}$(100A1-2; 100B4-5) and Df(3R))tll$^{20}$ (100A1-3; 100B1-2). A saturation genetic screen had previously been performed for this interval, and three lethal complementation groups, l(3)100Aa, l(3)100Ab and the zfh-1, were isolated (Lai et al., 1993, Proc. Natl. Acad. Sci. USA 90:4122–4126). The lats$^{x1}$ mutation failed to complement the EMS-induced mutations in l(3)100Aa (lats$^{a1-a15}$), but complement mutations in 1(3)100Ab and zfh-1. The clonal phenotypes were examined for lats$^{x1, P1, a1, a2, a6,}$ and $_{a10}$ induced either with the FLP/FRT-marker system or X-ray irradiation.

The lats$^{P1}$ allele was recovered from a mosaic male produced from the cross of y w hsFLP1; P[ry$^+$; hs-neo; FRT]82B x y w P[lacZ; w$^+$]5; P[ry$^+$; hs-neo; FRT]82B/delta2-3, Sb. The mutant chromosome was cleaned up before performing complementation tests and an excision screen (Robertson et al., 1988, Genetics 118:461–470). Two hundred and fifteen excision lines were established that had lost the w$^+$ gene in the P[lacZ; w$^+$] element (Bier et al., 1989, Genes Dev. 3:1273–1287). In about 50% of these lines, the pupal lethality had been reverted completely to wild type, indicating the mutant phenotype is caused by the P-element insertion. Five lines were found to cause lethality at late embryonic and/or early first instar larval stages. The remaining lines were found to cause lethality at larval and pupal stages or to produce viable mutant animals. All of these mutant excision lines (except one which is located outside the 100A1-5 region) failed to complement lats$^{x1}$ and lats$^{P1}$, but do complement mutations in the zfh-1 and l(3)100Ab loci.

The insert in lats cDNA A2 was cloned into the pCaSpeR-hs vector (Thummel and Pirrotta, 1992, Drosophila Inform. Service 71:150) for germ line transformation. Three of the transformed lines were tested and were able to rescue the lethality of the lats$^{a1}$/lats$^{x1}$, lats$^{P1}$ and lats$^{e26-1}$ animals after one hour heat shock for every 24 hours during larval and pupal development.

Histology

Fixation and sectioning (2 mm) of adult Drosophila tissues were performed as described (Tomlinson and Ready, 1987, Dev. Biol. 123:264–275). Scanning electron microscopy was performed as described (Xu and Artavanis-Tsakonas, 1990, Genetics 126:665–677).

Nucleic Acid Manipulation

A P1 genomic clone (DS02640) mapped in the 100A1-7 region was obtained from the Berkeley Drosophila Genome Center (personal communication; Hartl et al., 1994, Proc. Natl. Acad. Sci. USA 91:6824–6829). DNA fragments from this P1 clone and genomic DNA obtained by plasmid rescue from the lats$^{P1}$ mutant (Bier et al., 1989, Genes Dev. 3:1273–1287) were used to isolate several overlapping cosmids including CLT-52 from the genomic library prepared by J. Tamkun. Genomic DNA from +7.5 (BglII) to −4.2 (EcoRI; FIG. 3) was used to screen a total imaginal disc cDNA library prepared by A. Cowman. Screening approximately 2 million phage.yielded three groups of cDNAs (five lats cDNAs; fifteen T1 cDNAs; fourteen T2 cDNAs). The sizes of the inserts in the lats cDNAs are as follows: 5.6 kb in A2; 5.1 kb in B1; 1.1 kb in 9 and 4; and 0.9 kb in B3.

Genomic DNA from lats$^{x1}$/TM6B, lats$^{a1-15}$/TM6B, lats$^{P1}$/TM6B, lats$^{e7-2}$/TM6B, lats$^{e78}$/TM6B, lats$^{e100}$/TM6B, lats$^{e119}$/TM6B and lats$^{e148}$/TM6B flies was digested with a combination of the EcoRI, BamHI, BglII and XhoI restriction enzymes for Southern analysis.

DNA Sequencing

DNA sequence was determined by the dideoxy chain termination method (Sanger et al., 1977, Proc. Natl. Acad. Sci. USA 74:5463–5467) using Taq polymerase (Perkin Elmer) and Sequenase (U.S. Biochemical Corp.). The sequences of lats cDNAS were determined from both strands using templates generated from plasmids containing EcoRI fragments inserted into the pBlueScriptII vector. Templates generated from DNase 1 deletion subclones were also used. The complete sequences of cDNAs A2 and 9 were determined; partial sequences were determined for cDNAs B1 and 4. Templates of genomic DNA were generated from plasmids containing EcoRI fragments and were sequenced on one strand using synthetic oligonucleotide primers. Mutant DNA from the latsal allele was amplified with PCR reactions using synthetic oligonucleotide primers and cloned in the pBlueScript II vector for sequencing.

6.2. RESULTS

Screening for Overproliferation Mutations in Mosaic Animals

We have screened individuals carrying clones of cells that were homozygous for either X-ray or P-element induced mutations for overproliferation phenotypes. (FIG. 1B; Materials and Methods). Two types of overproliferation phenotypes were sought: a) Clones of mutant cells formed overproliferated, outgrowth tissues in a non-position-dependent fashion; b) Clones of mutant cells formed normal structures, but proliferated faster than wild-type cells such that the sizes of the mutant clones were larger than their wt twin-spot clones. Three independent mutations were identified that caused the first type of phenotype (FIGS. 2A–2E). A mutation which was allelic to one of the original mutations was later found to cause the second type of phenotype (see below). All three mutations in the first class caused embryonic and/or early larval lethality and they represented single alleles of different loci since they had different chromosome locations. One of them was identified among 215 randomly chosen lethal mutations in which each were caused by a P-element insertion in a different essential gene (Karpen and Spradling, 1992, Genetics 132:737–753; Berkeley Drosophila Genome Center, personal communication). In addition to these overproliferation mutations, one P-induced mutation was found to cause both unpatterned outgrowth and duplications of patterned structures in mosaic animals, suggesting that this mutation may not directly affect cell proliferation.

Figure 2A:
Figure 2B:

The lats Locus Is Defined by a Single Complementation Group of Mutations That Cause Defects Throughout Development The mutations caused different levels of overproliferation. One mutation (lats$^{x1}$) produced much more dramatic overproliferated clones than the ones produced by the other mutations (FIGS. 2A, 2B). The lats mutant clones induced in first instar larvae can be as large as ⅕ of the body size. Tumorous outgrowth caused by lats$^{x1}$ was found in all the tissues that had been examined including eyes, legs, wings, heads, notums, antenna, and abdominal cuticles. The lats$^{x1}$ mutation was genetically mapped in the 100A1-5 region and the locus was further defined by a single complementation group of over fifty alleles including mutations induced by X-ray, EMS, P-element insertion and imprecise excision of the P-element (Table 2; Materials and Methods).

TABLE 2

The alleles of the *lats* locus*

| Alleles | Phenotypes of homozygous animals | Phenotypes of mutant clones | Representative alleles | No. of alleles |
|---|---|---|---|---|
| Strong | Late embryonic and early 1st instar larval lethal | Large outgrowth | lats$^{x1}$, lats$^{a1}$ lats$^{a4}$ | 14 |
| Medium | Late larval and pupal lethal, normal size of animals | Large outgrowth | lats$^{P1}$, lats$^{e124}$ | 16 |
| | Pupal lethal, giant animals | Large outgrowth | lats$^{e26-1}$ | 3 |

TABLE 2-continued

The alleles of the *lats* locus*

| Alleles | Phenotypes of homozygous animals | Phenotypes of mutant clones | Representative alleles | No. of alleles |
|---------|----------------------------------|-----------------------------|------------------------|----------------|
| Weak | Semi-viable and viable: rough eye outgrowth on head, wing held-out, sterile | Mutant clones larger or normal in size | $lats^{a10}$, $lats^{e53-2}$ | 17 |

*The various alleles of the *lats* gene are classified into three main groups as indicated in the left column. Their phenotypes, displayed in either homozygous mutant animals or clones of mutant cells in mosaic animals, are listed in the next two columns respectively. For a given viable or semi-viable allele the homozygous mutant animals display one, two, three, or all four of the listed phenotypes. Representative alleles and the numbers of alleles for each group are given in the two right columns. The origins of these alleles are described in the Material and Methods.

Removing the P-element insertion reverted the lethal chromosome into wild type, indicating the P-element insertion is responsible for the mutant phenotype. Furthermore, five of the imprecise excision lines caused late embryonic and early larval lethality which were stronger than the pupal lethality phenotype caused by the $lats^{P1}$ mutation. These five excision lines failed to complement $lats^{x1}$, but complemented the mutations in two other complementation groups (l(3)100Ab and zfh-1) in the 100A1-5 region, indicating that these two genes were not affected by the excision alleles.

Figure 2C:

The lats alleles can be classified into three main groups (Table 2). Strong alleles caused homozygous animals to die at a late embryonic stage or shortly after hatching with no obvious cuticular defect. Mutations in the group of medium alleles cause lethality at different times in larval and pupal development. This group was further divided into two subgroups because three of the excision alleles not only caused pupal lethality, but the sizes of the homozygous mutant animals were also significantly larger than wt animals (FIG. 2C). The weak mutations caused either one or a combination of the following phenotypes: held out wings with broadened blades, rough eye with ventral outgrowth, outgrowth on the dorsal-anterior region of the head and partial to complete sterility (Table 2).

Figure 2D:
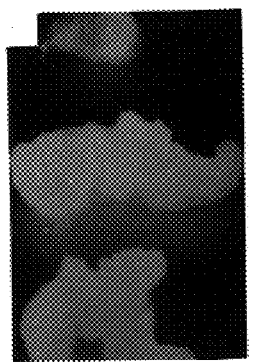
Figure 2E:
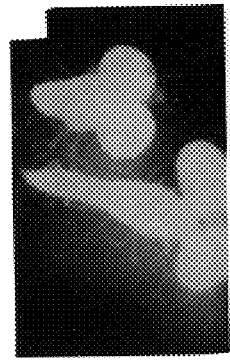
Figure 2F:
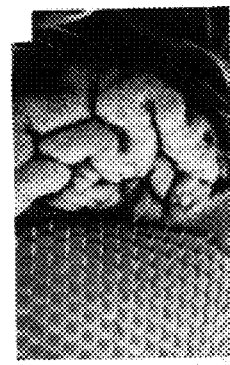
Figure 2G:
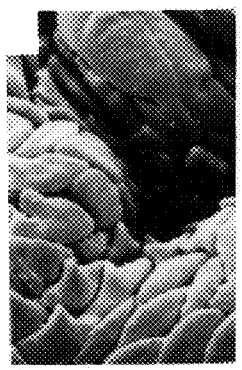
Figure 2H:
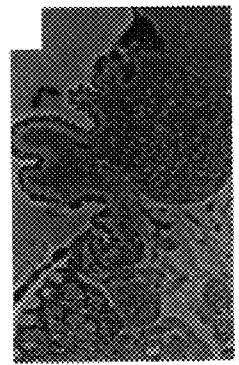
Figure 2I:
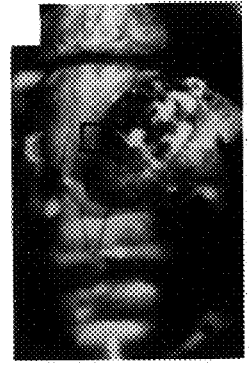
Figure 2J:
Figure 2K:
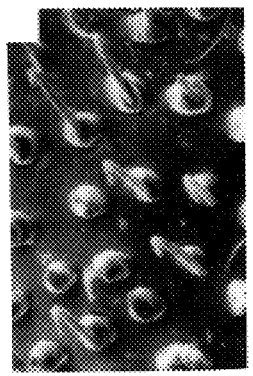
Figure 2L:
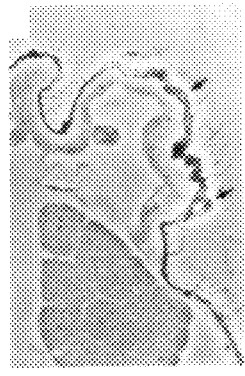

Proliferation defects were observed in both mutant clones in mosaic animals and homozygous mutants. Clones of cells on the head that were homozygous for strong or medium alleles formed unpatterned, overproliferated tissues with many lobes or folds. The mutant cells seemed to be "budding out" of the surface to form new proliferation centers or lobes (FIGS. 2A, 2F, 2H). The sizes and the shapes of these mutant cells were very irregular. Cells several times larger than their neighbors were often seen in mutant clones, indicating problematic cell division (FIGS. 2F, 2G). Furthermore, lats mutant clones behaved differently from clones mutant for the previously identified Drosophila tumor suppressor genes such as dlg, lgl and hyd. The dlg, lgl or hyd mutant cells proliferated slower than wt cells and thus, the mutant clones induced in first instar larvae were competed away during growth and did not form detectable clones in the adults (Bryant, 1987, Experimental and genetic analysis of growth and cell proliferation in Drosophila imaginal discs, in "Genetic Regulation of Development," A. R. Liss, New York, pp. 339–372; Woods and Bryant, 1989; Dev. Biol. 134:222–235; Mansfield et al., 1994, Dev. Biol. 165:507–526; Allen Shearn, personal communication). In contrast, the lats mutant clones induced at similar developmental stages formed dramatic overproliferated tissues, suggesting the mutant cells proliferated faster than wt cells. Consistent with this notion, clones of cells mutant for a weak lats allele ($lats^{a10}$) produced normal looking tissues, but the mutant clones were significantly larger than their wt twin-spot clones. In homozygous nimals, the imaginal discs and the central nervous system in any of the pupal lethal mutants were dramatically verproliferated (FIGS. 2D, 2E). The discs lost the single layer of epithelial structure and formed multi-layer, deformed tissues. The lats overproliferation phenotype was ot caused by prevention of differentiation. Cells in the verproliferated mutant clones on the body differentiated and roduced bristles and hairs, although the morphologies of these structures were not wild type (FIGS. 2I–2L). Careful examination of multiple mutant clones confirmed that lats caused mutant cells ($w^-$ cells in the eye, $y^-$ bristles and enlarged-base hairs on the body) to overproliferate and did not affect the surrounding wt tissues. Finally, the frequency of overproliferated clones was similar to wt clonal frequency induced with the same FRT element, indicating that loss of the lats function alone is sufficient to initiate the overproliferation process.

Cloning of the lats Gene

Genomic DNA from the 100A1-5 region was isolated using probes mapped to this region (Materials and Methods). A restriction map of the relevant genomic region is illustrated in FIG. 3. Genomic DNA flanking the P-insertion site (+7.5 to −4.2) was used to screen a total imaginal disc cDNA library. A group of cDNAs corresponding to a 5.7 kb transcript (lats) was found to contain sequence from the region where the P-element was inserted (FIG. 3). Two other groups of cDNAs were also isolated (T1 and T2). The 5.7 kb transcript was located in an intron of the T1 gene (FIG. 3). The intron-exon structure of the 5.7 transcription unit was determined by Southern and sequence analysis of the cDNA clones and the corresponding genomic DNA (Materials and Methods). The zfh-1 gene was found to be located at the left side of the 5.7 kb transcription unit (FIG. 3; Fortini et al., 1991, Mechanisms of Development 34:113–122).

In addition to $lats^{P1}$, genomic DNA from the five strong excision alleles was analyzed. All of them deleted exon sequences from the 5.7 kb transcript and, in addition, three of them also deleted sequences in the next transcript (T2; FIG. 3). Furthermore, DNA from the X-ray and EMS induced mutants was analyzed with cDNA probes made from the 5.7 kb, T2 and T1 transcripts. In two cases alterations were detected in the 5.7 kb transcription unit: a 0.4 kb and a 0.3 kb deletions associated with $lats^{a1}$ and $lats^{a4}$, respectively (FIG. 3). The 446 bp deletion in $lats^{a1}$ was revealed by sequencing. It removed codons 92 to 238 of the open reading frame and caused a frame shift from codon 239 (FIG. 5). Finally, transformants containing a cDNA corresponding to the 5.7 transcript driving by the hsp7o promoter rescued the lethality of both strong and medium lats alleles. These findings indicate that the 5.7 kb transcription unit which correspond to the lats gene and strong lats alleles including $lats^{a1}$ were either amorphic or nearly amorphic alleles.

The lats Gene Encodes a Putative Protein-Serine/Threonine Kinase

The 5.7 kb lats transcript was detected throughout development (FIG. 4) and in both adult males and females (data not shown). In addition, probes from the 5.7 kb transcript also detected a second transcript, which is about 1 kb shorter (4.7 kb), in young embryos (0–4 hrs; FIG. 4) and in adult males and females. Northern analysis showed there was more maternally deposited 4.7 kb transcripts than 5.7 kb transcripts in young embryos (0–2 hrs; FIG. 4). The 5.7 kb transcript became the dominant message at the embryonic stage (4–6 hrs), known to have zygotic gene expression (FIG. 4). No effort was made to isolate cDNA clones corresponding to the 4.7 kb transcript; thus the exact sequence of this short transcript is not known. However, a polyadenylation signal consensus sequence was found at nucleotide position 4655–4660 in the 5.7 kb transcript and in the corresponding genomic DNA (FIG. 5) and a 0.51 kb probe from the 3' end of the 5.7 kb transcript did not hybridize to the 4.7 kb transcript while a 1 kb probe from the 5' untranslated region of the 5.7 kb transcript hybridized to both the 5.7 kb and 4.7 kb transcripts. This suggests that the 4.7 kb transcript may be a truncated version of the 5.7 kb transcript. The genomic and cDNA sequence corresponding to the 5.7 kb transcript was determined (Materials and Methods). The entire 5720 bp cDNA sequence, which is interrupted by seven introns, and the putative lats product (lats), deduced from the long open reading frame, are illustrated in FIG. 5. An interesting feature of the 5.7 kb transcript is the existence of a 141 bp segment located in the 3' untranslated region (FIG. 5), which is identical to the first 141 bp of the 5' untranslated region of the class I transcript from the Drosophila phospholipase C gene, plc-21 (Shortridge et al., 1991, J. Biol. Chem. 266:12474–12480). The functional significance of this sequence motif is unknown. It could be a regulatory target sequence that is shared by both genes.

Figure 6C:
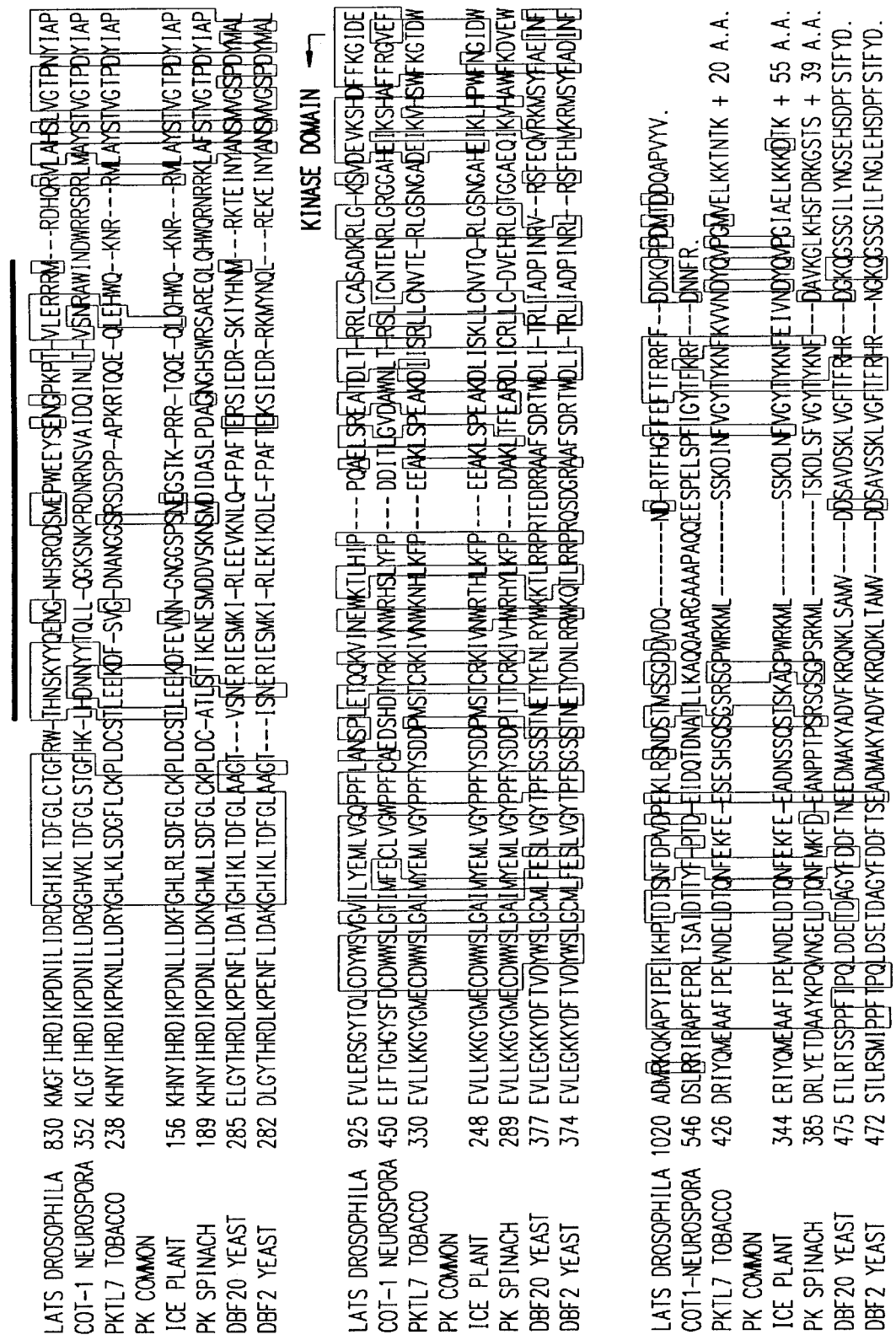

There are 34 differences between the lats cDNA and genomic sequences and 31 of them do not affect the deduced amino acid sequence. In the remaining three differences, one changes the serine 206 in cDNA into a cysteine. The second change in the genomic sequence adds an additional glutamine in the poly-glutamine opa repeat (FIG. 6; Wharton et al., 1985, Cell 40:55–62). The third is the addition of a fifteen bp sequence in the genomic DNA after the nucleotide 2644 of the cDNA. This sequence could be translated into another copy of the Arg-Glu-Arg-Asp-Gln (part of SEQ ID NO:2) peptide. However, this sequence is not present in the two independent cDNA clones that were sequenced.

The predicted lats product contains 1099 amino acid residues. The kinase domain of lats is more similar to protein-serine/threonine kinases than to protein-tyrosine kinases, especially in the sequences of the domains VI and VIII defined by Hanks et al. (1988, Science 241:42–52); protein-serine/threonine kinase consensus in domain VI: Asp-Leu-Lys-Pro-Glu-Asn (SEQ ID NO:9). Lats sequence in domain VI: Arg-Asp-Ile-Lys-Pro-Asp-Asn (836–842) (part of SEQ ID NO:2); protein-serine/threonine kinase consensus in domain VIII: Gly-Thr/Ser-X-X-Tyr/Phe-X-Ala-Pro-Glu (SEQ ID NO:10). Lats sequence in domain VIII: Gly-Thr-Pro-Asn-Tyr-Ile-Ala-Pro-Glu (917–925) (part of SEQ ID NO:2). The C-terminal half of lats shares extensive sequence similarity with a group of six proteins including the Dbf20 and Dbf2 cell cycle protein-ser/thr kinases from *Saccharomyces cerevisiae* (Johnston et al., 1990, Mol. Cell. Biol. 10:1358–1366; Toyn et al., 1991, Gene 104:63–70; Toyn and Johnston, 1994, EMBO J. 13:1103–1113), and the COT-1 putative protein kinase from *Neurospora crassa* (Yarden et al., 1992; EMBO J. 11:2159–2166) (FIGS. 6A, 6B). The sequence similarity between the kinase domains of lats and these proteins (39–49% identity) is much higher than the sequence similarity observed between the different subgroups of protein-ser/thr kinases (20–25% identity; Hanks et al., 1988, Science 241:42–52). However, there is an insertion of about 40 amino acid residues within the kinase domains of these proteins, sharing little sequence similarity (denoted by a black bar in FIG. 6B). The human myotonic dystrophy protein kinases (MDPK) also have significant similarity with the C-terminal region of lats (Brook et al., 1992, Cell 68:799–808; Fu et al., 1993; Science 260:235–238, Mahadevan et al., 1993, Hum. Mol. Genet. 2:299–304), but their kinase domains do not contain this ~40 amino acid insertion. In addition, lats and these proteins also share significant levels of sequence similarity in the two regions (each contains ~100–150 amino acids) flanking the kinase domain (20–28% identity; FIG. 6A, 6B). In the case of Dbf20, its entire sequence except for the 20 C-terminal most residues can be aligned with lats, indicating lats is a close relative of Dbf20. A poly-glutamine opa repeat is located near the middle of the protein (FIG. 5; Wharton et al., 1985, Cell 40:55–62). The N-terminal half of lats contains many short homopolymeric runs including poly-proline which makes up about 15% of the residues. At least one of the proline-rich stretches closely matches the consensus of SH3-binding sites (FIG. 3B; Ren et al., 1993, Science 259:1157–1161), raising the possibility that it may interact with SH3-containing proteins. No putative signal sequence appears in the lats protein, indicating that it is an intracellular t rotein.

6.3. DISCUSSION

Screening for Mutations in Mosaic Animals to Identify and Study Potential Tumor Suppressors The comparison between mosaic flies and tumor patients is simplistic yet u seful. Tumor patients contain wt tumor suppressor genes in most of their cells and only small groups of cells sustain mutations in tumor suppressors. We have searched for recessive overproliferation mutations in mosaic is animals. Flies that carry somatic cells mutated for tumor suppressors or negative regulators of cell proliferation are viable, yet the overproliferation mutant phenotype is readily identifiable. Therefore, mosaic flies, which are in a fashion analogous to tumor patients, provide a mean to screen for potential tumor suppressors. Three overproliferation mutations were identified in our screen. They were not identified as "interesting" mutations in screens for embryonic lethal mutations. Identifying overproliferation mutations in homozygous mutant larvae and pupae is not only biased against embryonic lethals, but also laborious, since it requires establishment of individual lines before examining the potential phenotypes. Further screens for overproliferation mutations in mosaic animals will allow us to identify other important players in pathways that negatively regulate cell proliferation.

The overproliferation phenotypes that we observed were caused by loss of function in a single gene. In humans, it was suggested that most retinoblastomas are caused by defects in a single tumor suppressor (Knudson, 1971, Proc. Natl. Acad. Sci. USA 68:820–823). On the other hand, evidence indicates that tumorigenesis in other human tissues (e.g., colon cancer) is a multistep process which involves inactivation of more than one gene (Fearon and Vogelstein, 1990, Cell 61:759–767; Vogelstein and Kinzler, 1993, Trends Genet. 9:138–141). Overproliferation caused by defects in multiple genes is unlikely to be detected in our screens unless these genes are located on the same chromosome arm.

To identify this type of gene, one could perform a modified mosaic screen which induces clones of cells to become homozygous for more than one mutagenized chromosome arm.

lats Affects Many Tissues Throughout Development

The lats gene is genetically defined by a single complementation group that consists of various alleles causing a wide range of defects. Different alleles were found to cause lethality at almost every stage during development: embryo, early larvae, late larvae, early pupae, late pupae and pharate-adult. The embryonic lethality occurs in the pharate first instar stage. The early embryonic requirements for lats could well be masked by the wt products that are maternally deposited in the egg. Weak lats alleles produce viable animals with phenotypes ranging from rough eye to sterility. The lats transcripts were detected throughout development up to adult stage, consistent with the observation that lats mutants affect all these stages. Although mutations at lats cause many defects, affecting cell proliferation could cause most of the phenotypes including overproliferation in mutant clones, lethality at the various stages, tissue over-proliferation on the head, broadened wing blade, and sterility in homozygous mutants. However, phenotypes such as extra cuticle deposits and malformed bristles and hairs are evidence of defects in differentiation.

The different behavior of the lats mutant clones and clones mutant for other previously identified Drosophila tumor suppressors is interesting. Cells mutant for dlg, lgl or hyd seem to fail to receive growth regulation signals. They proliferated slower than wt cells during larval stages when the cells were instructed to proliferate, and they failed to terminate proliferation in late larval and pupal stages when the wt cells have ceased proliferation. on the other hand, the lats mutant clones induced during the larval stages were overproliferated, and later the mutant cells on the body were differentiated to form adult cuticular structures. Thus, lats could be a neg ative regulator that monitors the rate of proliferation.

The lats gene is located in a complex region. The 5' end of the lats 5.7 kb transcript (cDNA) is only about 550 bp away from the T2 transcript and its 3' end is about 1.5 kb away from the zfh-1 transcript. Furthermore, all three of these closely located transcripts are located in an intron of the T1 transcription unit. Thus, a sizable deletion in the 5.7 kb transcription unit could affect the function of any of the genes in the region, which ma kes it difficult to determine which transcript is responsible for the lats phenotype. The fact that P-element transform lines carrying a cDNA from the 5.7 kb transcript under the hsp70 promoter rescued all types of lats alleles demonstrated that the 5.7 kb transcription unit is the lats gene.

The lats Putative Protein-Ser/Thr Kinase Shares Homology With Proteins That Are Involved in Regulation of Cell Cycle and Growth in Budding Yeast and Neurospora All 11 subdomains of the kinase domain that are found in previously identified protein kinases (Hanks et al., 1988, Science 241:42–52) are conserved in lats. This predicts that lats is a protein kinase. Furthermore, the sequence comparisons suggest lats to be a ser/thr kinase as the lats kinase domain is more similar to protein-ser/thr kinases than to protein-tyr kinases. The C-terminal half of lats shares extensive sequence similarity with a group of six proteins. Mutations are known for three of these genes and in each case they affect either cell cycle or growth; The cot-1 (colonial temperature sensitive-1) gene of Neurospora was identified by a temperature sensitive mutant that causes compact colony growth (Mitchell and Mitchell, 1954, Proc. Natl. Acad. Sci. USA 40:436–440; Galsworthy, 1966, Diss. Abstr. 26:6348). Wild-type filamentous ascomycete Neurospora grows on solid media by continuous hyphal elongation and branching to form spreading colonies. Strains lacking functional cot-1 gene are viable, but their hyphae branch extensively, resulting in compact colonial growth (Yarden et al., 1992, EMBO J. 11:2159–2166). This extensive branching phenotype is somewhat similar to the growth property of the lats mutant clones: the lats mutant cells continue to "bud" out of the surface to form new proliferation lobes. Another homologous gene, the DBF2 gene of the budding yeast, was identified in a genetic screen for mutations causing defects in DNA synthesis (Johnston and Thomas, 1982, Mol. Gen. Genet. 186:439–444). The temperature sensitive alleles of DBF2 were found to both delay the initiation of S phase and also to arrest the cell cycle during nuclear division (Johnston et al., 1990, Mol. Cell. Biol. 10:1358–1366). The DBF20 gene was identified through cross hybridization with DBF2 DNA (Toyn et al., 1991, Gene 104:63–70). Strains carrying deletions for either DBF2 or DBF20 are viable; however, deleting both genes in the same strain causes lethality. The kinase activities of both proteins have been shown to be specific for serine/threonine residues and are regulated during the cell cycle (Toyn and Johnston, 1994, EMBO J. 13:1103–1113). In the case of Dbf20, its entire sequence except the 20 most C-terminal residues can be aligned with lats. The mutant phenotype of lats and its sequence homology with the cell cycle protein kinases is consistent with the notion that lats might be directly involved in regulation of the cell cycle. The N-terminal half of lats contains many proline-rich stretches and at least one of them closely matches the consensus sequence of SH3 binding sites (Ren et al., 1993, Science 259:1157–1161), raising the possibility that this region could be a regulatory domain for the lats kinase, which binds to SH3 omain-containing proteins.

In recent years, many protein kinases have been identified to be involved in regulation of the cell cycle and cell proliferation. While Wee1 is an inhibitor of the Cdc2 kinase (Russell and Nurse, 1987, Cell 49:559–567; Featherstone and Russell, 1991, Nature 349:808–811), all other previously identified protein kinases are positive regulators of cell proliferation. They are either required for completion of the cell cycle or for signalling cells to proliferate. Lats is the first predicted protein-ser/thr kinase that has been shown to cause overproliferation when its function is removed. Studies of lats and other overproliferation mutations in Drosophila will provide a better understanding of how cell proliferation is regulated during development and how mutations could lead to abnormal growth.

7. ISOLATION AND CHARACTERIZATION OF MAMMALIAN LATS HOMOLOGS

As described herein, we have cloned and sequenced both mouse and human lats homologs.

7.1. ISOLATION AND CHARACTERIZATION OF MOUSE LATS HOMOLOGS cDNA clones for two different lats homologs in mice were obtained as follows.

Screening of Mouse Homologs:

| | |
|---|---|
| Probe: | A 2.2 kb BamHI fragment containing the kinase domain of the *Drosophila lats* gene was labeled with $^{32}$P by random labeling |
| Library: | Newborn mouse brain lambda ZAP cDNA library from Stratagene |
| Hybridization Condition: | 45° C., overnight in 6× SSC<br>5× Denhart's<br>0.5% SDS (sodium dodecyl sulfate)<br>100 μg/ml salmon sperm DNA |
| Wash: | 50° C., 30 min. × 4, in 2× SSC<br>0.1% SDS |
| Results: | Three positive clones were identified. (M41 clone for the m-*lats* gene, and M51 and M31 clones for the m-*lats*2 gene.) |

Two different mouse lats homologs, termed m-lats and m-lats2, respectively, were isolated and sequenced. Both the m-lats and m-lats2 clones are missing a small amount of the 5' end of their respective genes. The cDNA sequence (SEQ ID NO:5) and deduced protein sequence (SEQ ID NO:6) of m-lats are shown in FIG. 7. The cDNA sequence (SEQ ID NO:7) and deduced protein sequence (SEQ ID NO:8) of m-lats2 are shown in FIG. 8.

Portions of both the m-lats and m-lats2 cDNAs were used as probes to screen a mouse genomic library, under standard hybridization conditions. Genomic clones for both m-lats and m-lats2 have been isolated that contain most of the coding regions of these genes.

7.2. ISOLATION AND CHARACTERIZATION OF HUMAN LATS HOMOLOGS cDNA clones for at least one human lats homolog were obtained as follows.

Screening of Human Homologs (moderately stringent conditions):

| | |
|---|---|
| Probe: | A 2.1 kb PstI fragment containing the kinase domain of the m-*lats* gene was labeled with $^{32}$P by random labeling |
| Library: | Fetal human brain lambda gt10 cDNA library from Clontech |
| Hybridization Condition: | 55° C., overnight in 6× SSC<br>5× Denhart's<br>0.5% SDS<br>100 µg/ml salmon sperm DNA |
| Wash: | 60° C., 30 min. × 2, in 1× SSC<br>0.1% SDS |
| Results: | About 20 positive clones were identified for the h-*lats* gene. |

One human lats homolog, termed h-lats, was isolated and sequenced. The cDNA sequence (SEQ ID NO:3) and deduced protein sequence (SEQ ID NO:4) of h-lats are shown in FIG. 9. The deduced protein sequence is full-length. The complete coding sequence of the h-lats cDNA was inserted into a bacterial cloning vector (derived from Bluescript (KS)-vector; Stratagene) to form plasmid pBS (KS)-h-lats (FIG. 10). The total size of pBS(KS)-h-lats is 6.96 kb.

A h-lats cDNA fragment was used as a probe under conditions of moderate stringency to screen a human genomic cosmid library. Genomic h-lats clones were isolated. Over 70 kb of the genomic h-lats sequence has been isolated; the isolated sequences include all of the h-lats coding sequence (but not all the exon sequences).

An m-lats2 cDNA fragment was used as a probe to screen a human genomic phage library under the conditions described above, except that hybridization was carried out at 50° C., and washing was carried out at 55° C. with 2×SSC, 0.1% SDS. Two genomic h-lats clones have been isolated that specifically hybridize to m-lats2 cDNA probes and do not hybridize to m-lats and h-lats cDNA probes.

8. CONSERVATION OF SEQUENCES AND DOMAIN STRUCTURE AMONG LATS HOMOLOGS OF DIFFERENT SPECIES

Comparison of the sequences of Drosophila lats, h-lats, m-lats, and m-lats2 showed a startlingly high degree of sequence conservation, both overall and within domains of the lats protein. An alignment of the h-lats (SEQ ID NO:4) and m-lats (SEQ ID NO:6) protein sequences is shown in FIG. 11. The overall amino acid sequence identity between h-lats and m-lats is 93%. An alignment of the h-lats (SEQ ID NO:4) and m-lats2 (SEQ ID NO:8) protein sequences is shown in FIG. 12.

Homologous domains (i.e., domains conserved) between the different lats homologs were identified. FIG. 13 presents an alignment of the h-lats protein sequence (SEQ ID NO:4) and the Drosophila lats protein sequence (SEQ ID NO:2), and indicates the domains identified as conserved among the lats homologs from the various species.

The identified domains were as follows:

(1) Lats C-terminal domain 3 (LCD3)

The last three amino acids (VYV) are completely conserved in all four homologs including Drosophila lats, h-lats, m-lats, and m-lats2.

(2) Lats C-terminal domain 2 (LCD2)

| | amino acid residues |
|---|---|
| h-*lats* | 1077–1086 |
| Drosophila *lats* | 1075–1084 |

This domain is completely conserved in all four homologs including Drosophila lats, h-lats, m-lats, and m-lats2 (10/10 identical residues).

(3) Lats C-terminal domain 1 (LCD1)

| | amino acid residues |
|---|---|
| h-*lats* | 1032–1043 |
| Drosophila *lats* | 1035–1047 |

This domain is completely conserved among Drosophila lats, h-lats, and m-lats (12/12 identical), and is highly conserved between any of the foregoing and m-lats2 (11/12 identical).

(4) Kinase domain

| | amino acid residues |
|---|---|
| h-*lats* | 703–1014 |
| Drosophila *lats* | 711–1018 |

This domain is highly conserved among the four homologs (76% identical between Drosophila lats and h-lats; 99% identical between h-lats and m-lats; 83% identical between h-lats and m-lats2).

A potential phosphorylation residue in Drosophila lats and the mammalian homologs that could lead to the activation of the lats kinases after phosphorylation was identified.

Activities of protein kinases are often regulated by varying the phosphorylation state of specific serine, threonine, and tyrosine residues. Phosphorylation of a serine or threonine within twenty residues upstream of an Ala-Pro-Glu consensus in subdomain eight of the kinase domain, is often required for catalytic activities of many protein-ser/thr kinases (Hanks et al., 1988, Science 241:42–52). For example, Thr167 and Thr197 are phosphorylated in Cdc2 of fission yeast and in the cardiac muscle adenosine 3',5'-phosphate dependent protein kinase, respectively (Ducommun et al., 1991, EMBO J. 10:3311–3319; Gould et al., 1991, EMBO J. 10:3297–3309; Shoji et al., 1983, Biochem. 22:3702–3709). A ser residue in a similar position of the lats kinase domain is conserved in Drosophila lats, h-lats, m-lats, and m-lats2 (Ser914 in Drosophila lats; Ser909 in h-lats). Thus, the activities of Drosophila lats and its mammalian homologs may be regulated by phosphorylation of this ser residue.

(5) Lats flanking domain (LFD)

|                | amino acid residues |
| -------------- | ------------------- |
| h-*lats*       | 607–702             |
| Drosophila *lats* | 612–710          |

LFD is a domain that flanks and is amino-terminal to the kinase domain. This domain is highly conserved between Drosophila lats and h-lats (68% identical) and is also highly conserved between h-lats and m-lats2 (71% identical). This domain is completely conserved between h-lats and m-lats (100% identical).

(6) Lats split domain 1 (LSD1)

|                                  | amino acid residues |
| -------------------------------- | ------------------- |
| LSD1 Drosophila-*lats*           | 365–392             |
| LSD1 anterior (LSD1a) h-*lats*   | 328–334             |
| LSD1 posterior (LSD1p) h-*lats*  | 498–518             |

Certain lats domains have been termed split domains because the amino- (anterior) and carboxy- (posterior) portions of the domain appear separated from each other in at least one of the lats homologs. Split domains may constitute discontinuous binding/functional regions (e.g., brought together by tertiary structure). The LSD1a subdomain is completely conserved among Drosophila lats, h-lats, and m-lats (7/7 identical), and is not conserved in m-lats. The LSD1p subdomain is conserved between the four homologs (14/21 identical among Drosophila lats, h-lats, and m-lats; 13/21 identical between h-lats and m-lats2). The LSD1a and LSD1p subdomains are adjacent to each other in Drosophila lats and are separated in the mammalian homologs.

(7) Lats split domain 2 (LSD2)

|                                  | amino acid residues |
| -------------------------------- | ------------------- |
| LSD2 Drosophila-*lats*           | 536–544             |
| LSD2 anterior (LSD2a) h-*lats*   | 28–31               |
| LSD2 posterior (LSD2p) h-*lats*  | 555–559             |

Both the LSD2a and LSD2p subdomains are completely conserved among the four homologs. However, the two subdomains are adjacent to each other in Drosophila lats and are separated in the mammalian homologs.

(8) Putative SH3-binding domain (SH3-binding)

|                   | amino acid residues |
| ----------------- | ------------------- |
| h-*lats*          | 247–268             |
| Drosophila *lats* | 196–217             |

This domain is highly conserved among Drosophila lats, h-lats, and m-lats (10/22 identical), and does not exist in m-lats2.

The opa domain does not appear in the mammalian lats homologs.

9. FUNCTIONAL INTERCHANGEABILITY OF THE HUMAN AND DROSOPHILA LATS HOMOLOGS

9.1. OVEREXPRESSION OF HUMAN LATS OR OF DROSOPHILA LATS CAUSES A SMALLER, ROUGH EYE IN DROSOPHILA

Overexpression of lats and h-lats in the developing Drosophila eye was carried out. The Drosophila lats cDNA and h-lats cDNA were each cloned into the pGMR P-element vector. This vector was constructed by Bruce Hay and Gerald M. Rubin at the University of California at Berkeley, and will direct the expression of a cDNA of interest in the posterior region of the developing third instar larval eye imaging disc of Drosophila. Ten independent transformant lines for each of the pGMR-lats and pGMR-h-lats constructs were generated. The adult eyes of all these lines displayed a small-rough eye phenotype (eyes smaller than normal, with irregular, rough appearance). This indicates that both lats and h-lats genes have the same biological effect when they are overexpressed in the developing Drosophila eye.

9.2. HUMAN H-LATS GENE CAN REPLACE THE DROSOPHILA HOMOLOG TO PREVENT DEATH IN DROSOPHILA ANIMALS HAVING MUTANT DROSOPHILA LATS

The Drosophila lats cDNA was cloned into the pCaSpeR-hs vector (Thummel and Pirrotta, 1992, Drosophila Inform. Service 71:150) for germ line transformation of Drosophila. Three of the transformed lines were tested and were able to rescue the lethality of the $lats^{a1}/lat^{x1}, lats^{P1}$ and $lats^{e26-1}$ animals after one hour heat shock for every 24 hours during larval and pupal development. The human h-lats cDNA (in a XhoI (blunted)-XbaI fragment) from pBS(SK)-h-lats (FIG. 10) was cloned into the HpaI-XbaI sites of the pCaSpeR-hs vector, to produce plasmid pCaSpeR-hs-h-lats (FIG. 14). Plasmid pCaSpeR-hs-h-lats was used for germ line transformant. Three of the pCaSpeR-hs-h-lats transformant lines were tested and were able to rescue the lethality of the $lats^{P1}$ and $lats^{e26-1}$ animals under the same conditions used in rescuing experiments for the Drosophila gene.

10. HUMAN LATS EXPRESSION IS FOUND IN ALL NORMAL TISSUES TESTED AND IS ABSENT IN A LARGE NUMBER OF TUMOR CELL LINES

10.1. HUMAN LATS EXPRESSION IN NORMAL TISSUES

The expression of human lats RNA was investigated in various adult tissues. A 1.2 kb BamHI fragment of the h-lats cDNA was used as a $^{32}$P-labeled probe for Northern analysis. Hybridization was to a nylon-membrane containing polyA$^+$ RNA from various human fetal and adult tissues, obtained from Clontech. The Northern analysis was carried out according to the recommended instructions of the manufacturer (Clontech). The results are shown in FIG. 15. h-lats was expressed in every tissue tested (fetal brain, fetal lung, fetal liver, fetal kidney, adult spleen, adult thymus, adult prostate, adult testis, adult ovary, adult small intestine, adult colon, and adult blood leukocytes). Expression was higher in fetal tissues than in adult tissues.

10.2. HUMAN LATS EXPRESSION IN VARIOUS TUMOR CELL LINES

The $^{32}$P-labeled BamHI fragment of h-lats was used as a probe for Northern analysis, for hybridization to total RNAs isolated from 42 different human tumor cell lines (obtained from the American Type Culture Collection, Rockville, Md.). No h-lats expression was detected in 20 of the tumor lines (48%). The name and tissue origin of the tumor cell lines tested, and the results of the Northern analysis are presented in Table 3.

TABLE 3

| Name of tumor lines | Tumor Origin | Expression detected by Northern analyses YES | Expression detected by Northern analyses NO |
|---|---|---|---|
| 5637 | Bladder | | X |
| RT4 | Bladder | ±* | |
| HT-1376 | Bladder | | X |
| HT-1197 | Bladder | | X |
| BT-20 | Breast | X | |
| BT-474 | Breast | X | |
| ZR-75-1 | Breast | | X |
| ZR-75-30 | Breast | X | |
| BT-549 | Breast | | X |
| MDA-MB-453 | Breast | | X |
| MDA-MB-435S | Breast | | X |
| HBL-100 | Breast | | X |
| LoVo | Colon | | X |
| HT-29 | Colon | X | |
| HCT116 | Colon | X | |
| LS 180 | Colon | | X |
| DLD-1 | Colon | X | |
| WiDr | Colon | X | |
| SW480 | Colon | X | |
| Caco-2 | Colon | ± | |
| HEL 92.1.7 | Erythroleukemia | X | |
| MOLT-4 | Leukemia | X | |
| CEM-CM3 | Leukemia | X | |
| K-562 | Leukemia | X | |
| Jurkat | Leukemia | | X |
| HUT 78 | Lymphoma | X | |
| SK-LU-1 | Lung | | X |
| A-427 | Lung | | X |
| Calu-1 | Lung | X | |
| NCI-H69 | Lung | X | |
| SK-MEL-3 | Melanoma | | X |
| SK-MEL-28 | Melanoma | | X |
| SK-MEL-31 | Melanoma | | X |
| MIA PaCa-2 | Pancreas | | X |
| BxPC-3 | Pancreas | | X |
| Hs 700T | Pancreas | X | |
| Hs 766T | Pancreas | X | |
| RD | Sarcoma | | X |
| A-204 | Sarcoma | | X |
| AN3 CA | Uterine | X | |
| SK-UT-1 | Uterine | X | |
| HEC-1-A | Uterine | ± | |

*: weak signal

Thus, 48% of the tumor cell lines tested had no detectable h-lats expression, whereas 100% of the normal tissues tested had detectable h-lats expression. It should be noted that the 48% figure may be an underestimate of the actual number of tumor cell lines that had decreased lats protein level or activity relative to normal tissue, since while lack of lats RNA (i.e., a transcriptional block) allows the conclusion that no lats protein is made, tumor cells that expressed the lats RNA may still have had no or low lats protein levels and/or activity due to the possible existence of a translational block or the presence of mutation(s) in an expressed lats protein.

11. DEPOSIT OF MICROORGANISM

Bacteria strain *E. coli* TG2 containing plasmid pBS(KS)-h-lats was deposited on Mar. 24, 1995 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 69769.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A purified protein that is (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS.

2. The protein of claim 1 which is a human protein.

3. The protein of claim 1 which is a D. melanogaster protein.

4. The protein of claim 1 which is a mouse protein.

5. The protein of claim 1 which is a mammalian protein.

6. The protein of claim 1 that has a phosphorylated serine within 20 residues upstream of the amino acid sequence Ala-Pro-Glu in a subdomain eight of a kinase domain of said protein.

7. The protein of claim 1 that has a dephosphorylated serine within 20 residues upstream of the amino acid sequence Ala-Pro-Glu in a subdomain eight of a kinase domain of said protein.

8. The protein of claim 1 in which a threonine or serine residue within 20 residues upstream of the amino acid sequence Ala-Pro-Glu in a subdomain eight of a kinase domain of said protein has been deleted or substituted with a glutamate or an aspattate residue.

9. The protein of claim 1 in which said first nucleic acid is hybridizable under conditions of moderate stringency to said second nucleic acid, said moderate stringency conditions consisting of hybridization for 12–18 hours at 55° C. in a solution containing 6×SSC, 5×Denhardt's solution, 0.5% SDS and 100 μg/ml denatured salmon sperm DNA; and washing twice for 30 minutes at 60° C. in a solution containing 1×SSC and 0.1% SDS.

10. A purified protein encoded by a nucleic acid hybridizable under conditions of low stringency to the lats DNA sequence in plasmid pBS (KS)-h-lats as deposited with the ATCC and assigned accession number 69769, which protein is able to be bound by an antibody induced by immunization with at least an immunogenic fragment of a polypeptide; the sequence of which polypeptide consists of SEQ ID NO:2, SEQ ID NO:4, SEQ ID NO:6 or SEQ ID NO:8, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon siperm DNA, hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS.

11. The protein of claim 10 in which said nucleic acid is hybridizable under conditions of moderate stringency to said lats DNA sequence, said conditions of moderate stringency consisting of hybridization for 12–18 hours at 55° C. in a solution containing 6×SSC, 5×Denhardt's solution, 0.5% SDS and 100 μg/ml denatured salmon sperm DNA; and washing twice for 30 minutes at 60° C. in a solution containing 1×SSC and 0.1% SDS.

12. A purified protein encoded by a nucleic acid hybridizable under conditions of low stringency to the lats DNA sequence in plasmid pBS (KS)-h-lats as deposited with the ATCC and assigned accession number 69769, which protein (a) has kinase activity, and (b) is encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS.

13. A purified protein that is (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS, which protein is capable of rescuing a lethal lats mutation.

14. A purified protein encoded by a nucleic acid hybridizable under conditions of low stringency to a DNA consisting of a sequence complementary to the coding region of SEQ ID NO:3, which protein is capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8, said low stringency conditions consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS.

15. The protein of claim 14 in which said nucleic acid is hybridizable under conditions of moderate stringency to said DNA consisting of a sequence complementary to the coding region of SEQ ID NO:3, said conditions of moderate stringency consisting of hybridization for 12–18 hours at 55° C. in a solution containing 6×SSC, 5×Denhardt's solution. 0.5% SDS and 100 μg/ml denatured salmon sperm DNA; and washing twice for 30 minutes at 60° C. in a solution containing 1×SSC and 0.1% SDS.

16. A purified protein encoded by a nucleic acid hybridizable under conditions of low stringency to a DNA consisting of a sequence complementary to the coding region of SEQ ID NO:7, which protein is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS.

17. A purified fragment of a protein, which fragment lacks a kinase domain; said protein being (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA, hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate, and washing twice for 1.5 hours at 55° C. in a wash solution containing 2×SSC, 25 mM Tris-HCl (1H 7.4), 5 mM EDTA, and 0.1% SDS.

18. A purified first protein comprising an amino acid sequence that has at least 90% identity to a domain of a second protein, said second protein consisting of a sequence of SEQ ID NO:2, SEQ ID NO:4, SEQ ID NO:6, or SEQ ID NO:8, said domain being selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain, in which the percentage identity is determined over an amino acid sequence of identical size to the domain.

19. A purified product of a process of producing a protein, said process comprising growing a recombinant cell containing a recombinant first nucleic acid comprising a nucleotide sequence encoding a protein such that the encoded protein is expressed by the cell; and purifying the expressed protein; wherein the protein is capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8, and said first nucleic acid is hybridizable under conditions of low stringency to a second nucleic acid having a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containin 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a wash solution containing 2×SSC, 25 mM Tris-HCl (pH 7.4) 5 mM EDTA, and 0.1% SDS.

20. The product of the process of claim 19 in which the second nucleic acid consists of the sequence complementary to the sequence of SEQ ID NO:3.

21. A purified molecule, which molecule comprises 20 contiguous amino acids of a protein encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS, and which molecule is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8.

22. The molecule of claim 21, which inhibits proliferation of a cell.

23. A purified protein that is (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of high stringency to a second nucleic acid consisting of a sequence complementary to a sequence selected from the group consisting of SEQ ID NO:1, SEQ ID NO:3, SEQ ID NO:5, and SEQ ID NO:7, said conditions of high stringency consisting of pretreatment for 8 to 12 hours at 65° C. in a solution containing 6×SSC, 50 mM Tris-HCl (pH 7.5), 1 mM EDTA, 0.02% PVP, 0.02% Ficoll, 0.02% BSA, and 500 μg/ml denatured salmon sperm DNA; hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 μg/ml denatured salmon sperm DNA; washing for 1 hour at 37° C. in a solution containing 2×SSC, 0.01% PVP, 0.01% Ficoll, and 0.01% SDS and a second washing for 45 minutes at 50° C. in a solution containing 0.1×SSC.

24. The purified protein of claim 23 wherein said purified protein is a human protein.

25. A purified protein which comprises the amino acid sequence as set forth in SEQ ID NO:2.

26. A purified protein which comprises the amino acid sequence as set forth in SEQ ID NO:4.

27. A purified protein which comprises the amino acid sequence as set forth in SEQ ID NO:6.

28. A purified protein which comprises the amino acid sequence as set forth in SEQ ID NO:8.

29. A purified protein which comprises the amino acid sequence as set forth in SEQ ID NO:4 with the exception that the serine residue at amino acid number 909 of SEQ ID NO:4, as depicted in FIG. 9, is a glutamate residue.

30. A purified protein which comprises the amino acid sequence as set forth in SEQ ID NO:2 with the exception that the serene residue at amino acid number 914 of SEQ ID NO:2, as depicted in FIG. 5, is a glutamate residue.

31. A purified human lats protein which is encoded by plasmid pBS(KS)-h-lats as deposited with the ATCC and assigned accession number 69769.

32. A purified fragment of a protein, which protein (a) is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) is encoded by a first nucleic acid that is hybridizable under low stringency conditions to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5) 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS; said fragment comprising a domain of the protein selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain.

33. A purified product of a process of producing a protein, said process comprising growing a recombinant cell containing a recombinant nucleic acid comprising a nucleotide sequence encoding a first protein such that the encoded first protein is expressed by the cell; and purifying the expressed first protein; in which said first protein comprises an amino acid sequence that has at least 90% identity to a domain of a second protein, said second protein consisting of the sequence of SEQ ID NO:2, SEQ ID NO:4, SEQ ID NO:6, or SEQ ID NO:8, said domain being selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain, in which the percentage identity is determined over an amino acid sequence of identical size to the domain.

34. A purified product of a process of producing a fragment, said process comprising growing a recombinant cell containing a recombinant nucleic acid comprising a nucleotide sequence encoding a fragment of a protein such that the encoded fragment is expressed by the cell; and purifying the expressed fragment; in which the protein is (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) is encoded by a first nucleic acid that is hybridizable under low stringency conditions to a second nucleic acid consisting of a sequence complementary to a sequence selected from the group consisting of SEQ ID NO:1, SEQ ID NO:3, SEQ ID NO:5, and SEQ ID NO:7, which fragment comprises a domain of the lats protein, said domain selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain, and said low stringency conditions consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS.

35. A purified fragment of a protein, which protein is (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) is encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, which fragment lacks at least one domain of the protein, said domain being selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain, and said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS.

36. A purified molecule, which molecule comprises 20 contiguous amino acids of a protein encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS, and which molecule has kinase activity.

37. A purified molecule comprising a fragment of a protein, which protein (a) is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) is encoded by a first nucleic acid that is hybridizable under low stringency conditions to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS; and which fragment comprises a domain of the protein selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain.

38. A purified fragment of a protein, said fragment containing only sequences of the protein amino terminal to a kinase domain of the protein, said protein being (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7; said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a wash solution containing 2×SSC, 25 mM Tris-HCl (pH 7.4), 5 mM EDTA, and 0.1% SDS.

39. A purified fragment of a protein, which protein consists of the amino acid sequence as set forth in SEQ ID NO:4, which fragment contains only sequences of the protein amino terminal to a kinase domain of the protein.

40. A purified fragment of a protein, said protein consisting of the sequence set forth in SEQ ID NO:2, SEQ ID NO:4, SEQ ID NO:6, or SEQ ID NO:8, wherein the fragment consists of at least 20 contiguous amino acids of the protein.

41. A purified fragment of a protein, said protein consisting of the sequence set forth in SEQ ID NO:2, SEQ ID NO:4, SEQ ID NO:6, or SEQ ID NO:8, wherein the fragment is capable of being bound to an antibody induced by immunization with at least an immunogenic fragment of a polypeptide, the sequence of which polypeptide consists of SEQ ID NO:2, SEQ ID NO:4, SEQ ID NO:6, or SEQ ID NO:8.

42. A purified fragment of a protein, said protein consisting of the sequence set forth in SEQ ID NO:2, SEQ ID NO:4, SEQ ID NO:6, or SEQ ID NO:8, wherein the fragment comprises at least one domain of the protein, said domain being selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain.

43. A purified fragment of a protein, said protein consisting of the sequence set forth in SEQ ID NO:2, SEQ ID NO:4, SEQ ID NO:6, or SEQ ID NO:8, wherein the fragment lacks at least one domain of the protein.

44. A purified protein comprising 20 contiguous amino acids of the amino acid sequence set forth in SEQ ID NO:4.

45. A purified fragment of a protein, which protein consists of the amino acid sequence as set forth in SEQ ID NO:4, said fragment comprising a domain of the protein selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain.

46. A chimeric protein comprising a fragment of a first protein, said first protein being (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, which fragment consists of at least 20 contiguous amino acids of said first protein, said fragment being fused via a covalent bond to an amino acid sequence of a second protein, in which the second protein is not a lats protein, said conditions of low stringency consisting of pretreatment for 6 hours at 40° C. in a solution containing 35% formamide, 5×SSC, 50 mM Tris-HCl (pH 7.5) 5 mM EDTA, 0.1% PVP, 0.1% Ficoll, 1% BSA, and 500 μg/ml denatured salmon sperm DNA, hybridization for 18–20 hours at 400C in a solution containing 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS.

47. A chimeric protein comprising a fragment of a first protein, which first protein is (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of high stringency to a second nucleic acid consisting of a sequence complementary to a sequence selected from the group consisting of SEQ ID NO:1, SEQ ID NO:3, SEQ ID NO:5, and SEQ ID NO:7, said conditions of high stringency consisting of pretreatment for 8 to 12 hours at 65° C. in a solution containing 6×SSC, 50 mM Tris-HCl (pH 7.5), 1 mM EDTA, 0.02% PVP, 0.02% Ficoll, 0.02% BSA, and 500 μg/ml denatured salmon sperm DNA; hybridization for 48 hours at 65° C. in a solution containing 6×SSC, 50 mM Tris-HCl (pH 7.5), 1 mM EDTA, 0.02% PVP, 0.02% Ficoll, 0.2% BSA, and 100 μg/ml denatured salmon sperm DNA; washing for 1 hour at 37° C. in a solution containing 2×SSC, 0.01% PVP, 0.01% Ficoll, and 0.01% SDS and a second washing for 45 minutes at 50° C. in a solution containing 0.1×SSC, which fragment consists of at least 20 contiguous amino acids of said first protein fused via a covalent bond to an amino acid sequence of a second protein, in which the second protein is not said first protein.

48. A composition comprising a pharmaceutically acceptable carrier; and a purified protein that is (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5) 5 mM EDTA, 0.02% PVP, 0.02% Ficoll, 0.2% BSA, 100 µg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS.

49. The composition of claim 48 in which the protein is a human protein.

50. A composition comprising a purified fragment of a protein, and a pharmaceutically acceptable carrier, in which said protein (a) is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) is encoded by a first nucleic acid that is hybridizable under low stringency conditions to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS; and said fragment comprising a domain of the protein selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1). lats split domain 2 (LSD2), SH3-binding domain, and opa repeat domain.

51. A composition comprising a purified first protein, and a pharmaceutically acceptable carrier, in which said first protein comprises an amino acid sequence that has at least 90% identity to a domain of a second protein, said second protein consisting of a sequence of SEQ ID NO:2, SEQ ID NO:4, SEQ ID NO:6, or SEQ ID NO:8, and said domain being selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain, in which the percentage identity is determined over an amino acid sequence of identical size to the domain.

52. A composition comprising a chimeric protein, and a pharmaceutically acceptable carrier, which chimeric protein comprises a fragment of a first protein, said first protein being (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, which fragment consists of at least 20 contiguous amino acids of said first protein, said fragment being fused via a covalent bond to an amino acid sequence of a second protein, in which the second protein is not a lats protein, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA and 0.1% SDS.

53. A composition comprising a purified protein, and a pharmaceutically acceptable carrier, which protein is encoded by a nucleic acid hybridizable under conditions of low stringency to the lats DNA sequence in plasmid pBS (KS)-h-lats as deosited with the ATCC and assigned accession number 69769, which protein is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA, hybridization for 18–20 hours at 40° C. in a solution containing 35% formamide, 5×SSC, 50 mM Tris-HCl (pH 7.5), 5 mm EDTA, 0.02% PVP, 0.02% Ficoll, 0.2% BSA, 100 µg/ml denatured salmon sperm DNA, and 10% (wt./vol.) dextran sulfate, and washing twice for 1.5 hours at 55° C. in a solution containing 2×SSC, 25 mM Tris-HCl (pH7.4), 5 mM EDTA and 0.1% SDS.

54. A composition comprising a purified protein, which protein is encoded by plasmid PBS(KS)-h-lats as deposited with the ATCC and assigned accession number 69769; and a pharmaceutically acceptable carrier.

55. A composition comprising a purified molecule; and a pharmaceutically acceptable carrier; which molecule comprises 20 contiguous amino acids of a protein encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt./vol.) dextran sulfate; and washing twice for 1.5 hours at 55° C. in a wash solution containing 2×SSC, 25 mM Tris-HCl (pH 7.4), 5 mM EDTA, and 0.1% SDS, and which molecule is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8.

56. A composition comprising a purified protein, which protein comprises the amino acid sequence as set forth in SEQ ID NO:4; and a pharmaceutically acceptable carrier.

57. A composition comprising a purified protein, which protein comprises the amino acid sequence as set forth in SEQ ID NO:6; and a pharmaceutically acceptable carrier.

58. A kit comprising in a container a purified molecule, which molecule comprises 20 contiguous amino acids of a protein encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA, hybridization for 18–20 hours at 40° C. in a solution containing 35% formamide, 5×SSC, 50 mM Tris-HCl (pH 7.5) 5 mM EDTA, 0.02% PVP, 0.02% Ficoll, 0.2% BSA, 100 µg/ml denatured salmon sperm DNA, and 10% (wt./vol.) dextran sulfate; and washing twice for 1.5 hours at 55° C. in a wash solution containing 2×SSC, 25 mM Tris-HCl (pH 7.4), 5 mM EDTA, and 0.1% SDS; and which molecule is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8.

59. A kit comprising in a container a purified fragment of protein, which protein (a) is able to be bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) is encoded by a first nucleic acid that is hybridizable under low stringency conditions to a second nucleic acid consisting of a sequence complementary to a sequence selected from the group consisting of SEQ ID NO:1, SEQ ID NO:3, SEQ ID NO:5, and SEQ ID NO:7, said conditions of low stringency consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS; in which said fragment comprises a domain of the protein selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain.

60. A kit comprising in a container a purified first protein, said first protein comprising an amino acid sequence that has at least 90% identity to a domain of a second protein, said second protein consisting of a sequence of SEQ ID NO:2, SEQ ID NO:4, SEQ ID NO:6, or SEQ ID NO:8, said domain being selected from the group consisting of a lats C-terminal domain 3 (LCD3), lats C-terminal domain 2 (LCD2), lats C-terminal domain 1 (LCD1), kinase domain, lats flanking domain (LFD), lats split domain 1 (LSD1), lats split domain 2 (LSD2), SH3-binding domain, and opa repeat domain, in which the percentage identity is determined over an amino acid sequence of identical size to the domain.

61. A kit comprising in a container the purified protein of claim 10.

62. A kit comprising in a container the purified protein of claim 26.

63. A kit comprising in a container the purified protein of claim 27.

64. A kit comprising in a container the purified protein of claim 31.

65. A kit comprising in a container the chimeric protein of claim 46.

66. A kit comprising in a container a protein that is (a) capable of being bound by an antibody induced by immunization with at least an immunogenic fragment of a polypeptide, the sequence of which polypeptide consists of SEQ ID NO:2, SEQ ID NO:4, SEQ ID NO:6 or SEQ ID NO:8; and (b) encoded by a first nucleic acid that is hybridizable under conditions of low stringency to a second nucleic acid consisting of a sequence complementary to a sequence selected from the group consisting of SEQ ID NO:1, SEQ ID NO:3, SEQ ID NO:5, and SEQ ID NO:7, said low stringency conditions consisting of pretreatment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 hours at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt./vol.) dextran sulfate; and washing twice for 1.5 hours at 55° C. in a solution containing 2×SSC, 25 mM Tris-HCl (pH 7.4), 5 mM EDTA, and 0.1% SDS.

67. The kit of claim 66 in which the protein is a human protein.

* * * * *